United States Patent
Pecker et al.

(10) Patent No.: US 6,664,105 B1
(45) Date of Patent: *Dec. 16, 2003

(54) POLYNUCLEOTIDE ENCODING A POLYPEPTIDE HAVING HEPARANASE ACTIVITY AND EXPRESSION OF SAME IN GENETICALLY MODIFIED CELLS

(75) Inventors: Iris Pecker, Rishon le Zion (IL); Israel Vlodavsky, Mevaseret Zion (IL); Elena Feinstein, Rehovot (IL)

(73) Assignees: Insight Strategy & Marketing Ltd., Rehovot (IL); Hadasit Medical Research Services and Development Ltd., Jerusalem (IL)

(*) Notice: Subject to any disclaimer, the term of this patent is extended or adjusted under 35 U.S.C. 154(b) by 0 days.

This patent is subject to a terminal disclaimer.

(21) Appl. No.: 09/435,739

(22) Filed: Nov. 8, 1999

Related U.S. Application Data

(63) Continuation of application No. 09/258,892, filed on Mar. 1, 1999, now abandoned, which is a continuation-in-part of application No. PCT/US98/17954, filed on Aug. 31, 1998, which is a continuation of application No. 08/922,170, filed on Sep. 2, 1997, now Pat. No. 5,968,822.

(51) Int. Cl.$^7$ .................... C12Q 1/68; C12P 19/34; C07H 21/02; C07H 21/04; C12N 15/00
(52) U.S. Cl. .................... 435/320.1; 435/6; 435/91.1; 536/23.1; 536/24.1; 536/24.5; 536/23.5
(58) Field of Search ................ 536/23.1, 24.1, 536/24.5; 514/44; 435/320.1, 455; 530/350

(56) References Cited

U.S. PATENT DOCUMENTS 5,968,822 A * 10/1999 Pecker et al. ............... 435/325
6,177,545 B1 * 1/2001 Pecker et al. ............ 530/387.3

OTHER PUBLICATIONS

Sudhir Agrawal, Antisense oligonucleotides: towards clinical trials, TIBTECH, vol. 14, Oct. 1996, pp. 376–387.*
Alan M. Gewirtz et al., Facilitating oligonucleotide delivery: Helping antisense deliver on its promise. PROC. NATL. ACAD SCI. USA, vol. 93, pp. 3161–3163 1996.*
Douglas W. Green et al., Antisense Oligonucleotides: An Evolving Technology for the Modulation of Gene Expression in Human Disease, J. AM. COLL. SURG., pp. 93–105 2000.*

* cited by examiner

Primary Examiner—Ram R. Shukla
Assistant Examiner—Joe Zara
(74) Attorney, Agent, or Firm—G. E. Ehrlich (1995) Ltd.

(57) ABSTRACT

A polynucleotide (hpa) encoding a polypeptide having heparanase activity, vectors including same, genetically modified cells expressing heparanase, a recombinant protein having heparanase activity and antisense oligonucleotides and constructs for modulating heparanase expression are provided.

5 Claims, 34 Drawing Sheets

```
   1 CTAGAGCTTTCGACTCTCCGCTGCGCGGCAGCTGGCGGGGGGAGCAGCCAGGTGAGCCCA

61 AGATGCTGCTGCGCTCGAAGCCTGCGCTGCCGCCGCCGCTGATGCTGCTGCTCCTGGGGC
      M  L  L  R  S  K  P  A  L  P  P  P  L  M  L  L  L  L  G  P

121 CGCTGGGTCCCCTCTCCCCTGGCGCCCTGCCCCGACCTGCGCAAGCACAGGACGTCGTGG
      L  G  P  L  S  P  G  A  L  P  R  P  A  Q  A  Q  D  V  V  D

181 ACCTGGACTTCTTCACCCAGGAGCCGCTGCACCTGGTGAGCCCCTCGTTCCTGTCCGTCA
      L  D  F  F  T  Q  E  P  L  H  L  V  S  P  S  F  L  S  V  T

241 CCATTGACGCCAACCTGGCCACGGACCCGCGGTTCCTCATCCTCCTGGGTTCTCCAAAGC
      I  D  A  N  L  A  T  D  P  R  F  L  I  L  L  G  S  P  K  L

301 TTCGTACCTTGGCCAGAGGCTTGTCTCCTGCGTACCTGAGGTTTGGTGGCACCAAGACAG
      R  T  L  A  R  G  L  S  P  A  Y  L  R  F  G  G  T  K  T  D

361 ACTTCCTAATTTTCGATCCCAAGAAGGAATCAACCTTTGAAGAGAGAAGTTACTGGCAAT
      F  L  I  F  D  P  K  K  E  S  T  F  E  E  R  S  Y  W  Q  S

421 CTCAAGTCAACCAGGATATTTGCAAATATGGATCCATCCCTCCTGATGTGGAGGAGAAGT
      Q  V  N  Q  D  I  C̲  K  Y  G  S  I  P  P  D  V  E  E  K  L

481 TACGGTTGGAATGGCCCTACCAGGAGCAATTGCTACTCCGAGAACACTACCAGAAAAAGT
      R  L  E  W  P  Y  Q  E  Q  L  L  R  E  H  Y  Q  K  K  F

541 TCAAGAACAGCACCTACTCAAGAAGCTCTGTAGATGTGCTATACACTTTTGCAAACTGCT
      K  N  S  T  Y  S  R  S  S  V  D  V  L  Y  T  F  A  N  C̲  S

601 CAGGACTGGACTTGATCTTTGGCCTAAATGCGTTATTAAGAACAGCAGATTTGCAGTGGA
      G  L  D  L  I  F  G  L  N  A  L  L  R  T  A  D  L  Q  W  N

661 ACAGTTCTAATGCTCAGTTGCTCCTGGACTACTGCTCTTCAAGGGGTATAACATTTCTT
      S  S  N  A  Q  L  L  L  D  Y  C̲  S  S  K  G  Y  N  I  S  W

721 GGGAACTAGGCAATGAACCTAACAGTTTCCTTAAGAAGGCTGATATTTTCATCAATGGGT
      E  L  G  N  E  P  N  S  F  L  K  K  A  D  I  F  I  N  G  S
                       (T)
 781 CGCAGTTAGGAGAAGATTATATTCAATTGCATAAACTTCTAAGAAAGTCCACCTTCAAAA
      Q  L  G  E  D  Y  I  Q  L  H  K  L  L  R  K  S  T  F  K  N
                    (F)
 841 ATGCAAAACTCTATGGTCCCTGATGTTGGTCAGCCTCGAAGAAAGACGGCTAAGATGCTGA
      A  K  L  Y  G  P  D  V  G  Q  P  R  R  K  T  A  K  M  L  K

901 AGAGCTTCCTGAAGGCTGGTGGAGAAGTGATTGATTCAGTTACATGGCATCACTACTATT
      S  F  L  K  A  G  G  E  V  I  D  S  V  T  W  H  H  Y  Y  L

961 TGAATGGACGGACTGCTACCAGGGAAGATTTTCTAAACCCTGATGTATTGGACATTTTTA
      N  G  R  T  A  T  R  E  D  F  L  N  P  D  V  L  D  I  F  I

1021 TTTTCATCTGTGCAAAAAGTTTTCCAGGTGGTTGAGAGCACCAGGCCTGGCAAGAAGGTCT
      S  S  V  Q  K  V  F  Q  V  V  E  S  T  R  P  G  K  K  V  W

1081 GGTTAGGAGAAACAAGCTCTGCATATGGAGGCGGAGCGCCCTTGCTATCCGACACCTTTG
      L  G  E  T  S  S  A  Y  G  G  G  A  P  L  L  S  D  T  F  A

1141 CAGCTGGCTTTATGTGGCTGGATAAATTGGGCCTGTCAGCCCGAATGGGAATAGAAGTGG
      A  G  F  M  W  L  D  K  L  G  L  S  A  R  M  G  I  E  V  V

1201 TGATGAGGCAAGTATTCTTTGGAGCAGGAAACTACCATTTAGTGGATGAAAACTTCGATC
      M  R  Q  V  F  F  G  A  G  N  Y  H  L  V  D  E  N  F  D  P

1261 CTTTACCTGATTATTGGCTATCTCTTCTGTTCAAGAAATTGGTGGGCACCAAGGTGTTAA
      L  P  D  Y  W  L  S  L  L  F  K  K  L  V  G  T  K  V  L  M

1321 TGGCAAGCGTGCAAGGTTCAAAGAGAAGGAAGCTTCGAGTATACCTTCATTGCACAAACA
      A  S  V  Q  G  S  K  R  R  K  L  R  V  Y  L  H  C̲  T  N  T

1381 CTGACAATCCAAGGTATAAAGAAGGAGATTTAACTCTGTATGCCATAAACCTCCATAACG
      D  N  P  R  Y  K  E  G  D  L  T  L  Y  A  I  N  L  H  N  V

1441 TCACCAAGTACTTGCGGTTACCCTATCCTTTTTCTAACAAGCAAGTGGATAAATACCTTC
      T  K  Y  L  R  L  P  Y  P  F  S  N  K  Q  V  D  K  Y  L  L

1501 TAAGACCTTTGGGACCTCATGGATTACTTTCCAAATCTGTCCAACTCAATGGTCTAACTC
      R  P  L  G  P  H  G  L  L  S  K  S  V  Q  L  N  G  L  T  L

1561 TAAAGATGGTGGATGATCAAACCTTGCCACCTTTAATGGAAAAACCTCTCCGGCCAGGAA
      K  M  V  D  D  Q  T  L  P  P  L  M  E  K  P  L  R  P  G  S

1621 GTTCACTGGGCTTGCCAGCTTTCTCATATAGTTTTTTTGTGATAAGAAATGCCAAAGTTG
      S  L  G  L  P  A  F  S  Y  S  F  F  V  I  R  N  A  K  V  A
                                                               *
1681 CTGCTTGCATCTGAAAATAAAATATACTAGTCCTGACACTG
      A  C̲  I
```

FIG. 1

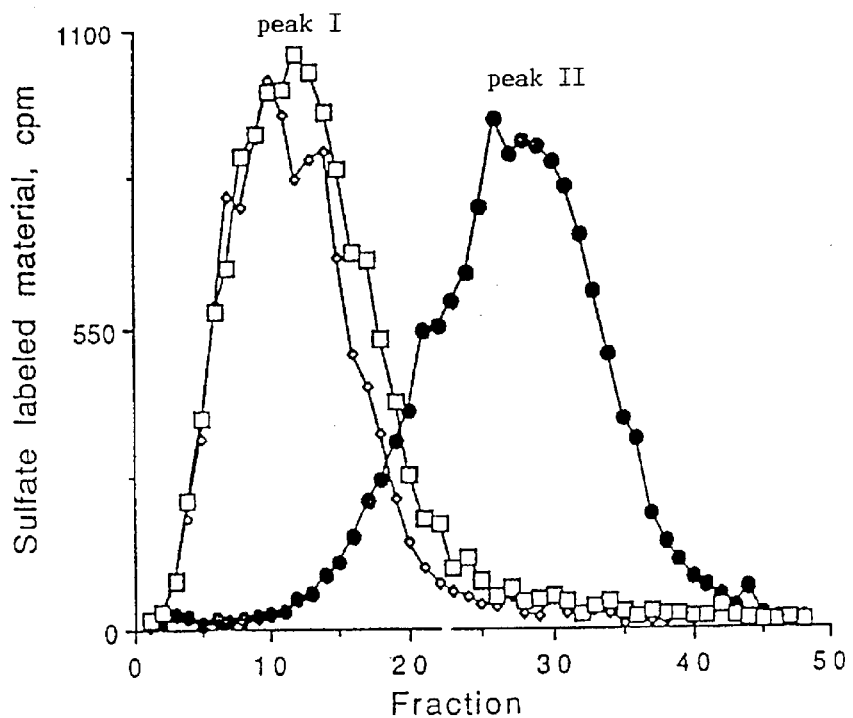
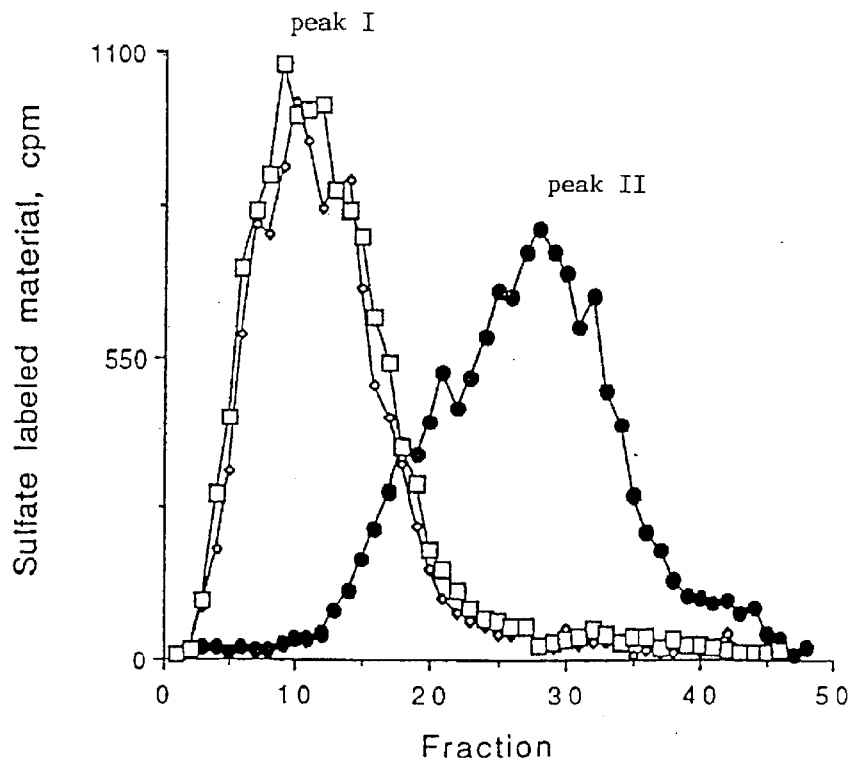

Fig. 13

```
mouse  CTGGCAAGAAGGTCTGGTTGGGAGAGACGAGCTCAGCTTACGGTGGCGGT 50
       |||||||||||||||||| ||||| || ||||| || || || |||||
human  CTGGCAAGAAGGTCTGGTTAGGAGAAACAAGCTCTGCATATGGAGGCGGA 1115 mouse  GCACCCTTGCTGTCCAACACCTTTGCAGCTGGCTTTATGTGGCTGGATAA 100
       || ||||||||| ||| ||||||||||||||||||||||||||||||||
human  GCGCCCTTGCTATCCGACACCTTTGCAGCTGGCTTTATGGCTGGATAA 1165 mouse  ATTGGGCCTGTCAGCCCAGATGGGCATAGAAGTCGTGATGAGGCAGGTGT 150
       |||||||||||||||||| ||||| ||||||||| |||||||||| || |
human  ATTGGGCCTGTCAGCCCGAATGGGAATAGAAGTGGTGATGAGGCAAGTAT 1215 mouse  TCTTCGGAGCAGGCAACTACCACTTAGTGGATGAAAACTTTGAGCCTTTA 200
       |||| |||||||| |||||||| |||||||||||||||||| || ||||||
human  TCTTTGGAGCAGGAAACTACCATTTAGTGGATGAAAACTTCGATCCTTTA 1265 mouse  CCTGATTACTGGCTCTCTCTTCTGTTCAAGAAACTGGTAGGTCCCAGGGT 250
       |||||||| ||||| |||||||||||||||||| ||||| || ||| |||
human  CCTGATTATTGGCTATCTCTTCTGTTCAAGAAATTGGTGGGCACCAAGGT 1315 mouse  GTTACTGTCAAGAGTGAAAGGCCCAGACAGGAGCAAACTCCGAGTGTATC 300
       |||| || |||| ||| |||| || | || || || || || ||||| || |
human  GTTAATGGCAAGCGTGCAAGGTTCAAAGAGAAGGAAGCTTCGAGTATACC 1365 mouse  TCCACTGCACTAACGTCTATCACCCACGATATCAGGAAGGAGATCTAACT 350
       | || ||||| ||| | | |||| | ||| | ||||||||| |||||
human  TTCATTGCACAAACACTGACAATCCAAGGTATAAAGAAGGAGATTTAACT 1415 mouse  CTGTATGTCCTGAACCTCCATAATGTCACCAAGCACTTGAAGGTACCGCC 400
       ||||||| | | ||||||||||| |||||||||| ||||| ||||| | || |
human  CTGTATGCCATAAACCTCCATAACGTCACCAAGTACTTGCGGTTACCCTA 1465 mouse  TCCGTTGTTCAGGAAACCAGTGGATACGTACCTTCTGAAGCCTTCGGGGC 450
       ||| || | | || | |||||||| |||||||| | |||| ||| |
human  TCCTTTTTCTAACAAGCAAGTGGATAAATACCTTCTAAGACCTTTGGGAC 1515 mouse  CGGATGGATTACTTTCCAAATCTGTCCAACTGAACGGTCAAATTCTGAAG 500
       | |||||||||||||||||||||||||||||| || |||| || ||| |||
human  CTCATGGATTACTTTCCAAATCTGTCCAACTCAATGGTCTAACTCTAAAG 1565 mouse  ATGGTGGATGAGCAGACCCTGCCAGCTTTGACAGAAAACCTCTCCCCGC 550
       |||||||||| || ||| ||||| |||| | ||||||||||||| |
human  ATGGTGGATGATCAAACCTTGCCACCTTTAATGGAAAACCTCTCCGGCC 1615 mouse  AGGAAGTGCACTAAGCCTGCCTGCCTTTTCCTATGGTTTTTTTGTCATAA 600
       ||||||| |||| || |||| || || || ||| |||||||||| ||||
human  AGGAAGTTCACTGGGCTTGCCAGCTTTCTCATATAGTTTTTTTGTGATAA 1665 mouse  GAAATGCCAAAATCGCTGCTTGTATATGAAAATAAAA 637
       |||||||||| | ||||||||| || ||||||||||||
human  GAAATGCCAAAGTTGCTGCTTGCATCTGAAAATAAAA 1702
```

| | |
|---|---|
| ggatcttggctcactgcaatctctgcctcccatgcaattcttatgcatca | 50 |
| gcctcctgagtagcttggattataggtctgcgccaccactcctggctaca | 100 |
| ccatgttgcccaggctggtcttgaactcttgggctctagtgatccacccg | 150 |
| ccttggcctcccaaagtgctgggattacaggtgtgagccatcacacccgg | 200 |
| cccccgtttccatattagtaactcacatgtagaccacaaggatgcacta | 250 |
| tttagaaaacttgcaatggtccacttttcaaatcacccaaacatgttaaa | 300 |
| gaaattggtatgactgggcatggcacagtggctcatgcctgcaatcctag | 350 |
| cattttgtgaggctgagacgggcagatcacgagtcaggagattgagacc | 400 |
| atcctgacagacatggtgaaatcccatctctactaaaaatacaaaacaat | 450 |
| tagccggggtgatggcaggccctgtagtcccagctactcgggaggctg | 500 |
| aggcaggagaatggcgtgaatccaggaggcagagcttgcagtgagccgag | 550 |
| atggtgccactgcactccagcctgggcgacagagcgagactccgtctcaa | 600 |
| aaaaaaaaaaagaaagaaattggtatgactgttgactcacaacaggag | 650 |
| tcaggggcatggggtggggtgtaagattaatgtcatgacaaatgtggaaa | 700 |
| agaaacttctgtttttccaactccacgtctgctaccatattattacactc | 750 |
| ttctggtagtgtggtgtttatgtgtgaattttttttcatatgtatacagt | 800 |
| aattgtaggatatgaacctgattctagttgcaaaactcactatgagctta | 850 |
| gcttttaagttgcttaagaataggtagatctatgcaaataatgataatta | 900 |
| ttattatttttaagagagggtctcactttgtcacccaggctggagtgc | 950 |
| agtggtgtgattaagggtcactgcaacctccacctcccaggctcaaataa | 1000 |
| acctcccacctcagcctcccagtagctggaaccacaggcacgggccacc | 1050 |
| acgcctggctaatttttttgtattttttgtagagatggggttcatcatgt | 1100 |
| tgcccaggctgttcttgaattcctcggctcaagcaatcctcccaccttgg | 1150 |
| cctcccaaaatgctggcatcacaggcatgatggcatcactggcatcacat | 1200 |
| accatgcctggcctgatttatgcaaattagatatgcatttcaaaataatc | 1250 |
| tatttttatttgttgccttattggtggtacaatctcaagtggaaaaatct | 1300 |
| aagggttttggtgttatttgcttactcaaccaatatttattagactctta | 1350 |
| ctaagcaccaacatgatcacatgcctgagctatggctagcatagcgtgtg | 1400 |
| agacaaacttaatctctgttttggtggagcatataatctagtagatgaag | 1450 |
| ccaatgttgagcaacatcacaataacaaattgaggatgctacgagag | 1500 |
| tgtctaacaaattgaggatgctacgagagtgtctaacaaattgaggatgc | 1550 |
| tatgagagtgtgtcatggagagctgcctggagattgagagaaagcttcct | 1600 |
| tgagggaagttacatttcagctgaaacacactgccatctgctcgaggttt | 1650 |
| tgtaactgcattcacatcccgattctgacacttcacatcccgattctgac | 1700 |
| acttcacccagttactgtctcagagcttgggtccgcatgtgtaaaacaag | 1750 |
| gacagtatgcacttggcagggttgtgagaagggaagagaacacaagtaaa | 1800 |
| gcacctgtatcaggcatacagtaggcactaagcgtgcgatgcttgctatg | 1850 |
| attatacatcagtgtaagcatcaaggaaaagctgaagaaaagtctgacca | 1900 |
| acagcgaaagataaatgcgcagaggagaaatttggcaaaggctccaaatt | 1950 |
| cagggcagtccgtactctacactttgtatggggcttcaggtcctgagt | 2000 |
| tccagacattggagcaactaaccctttaagattgctaaatattgtcttaa | 2050 |
| tgagaagttgataaagaattttgggtggttgatctctttccagctgcagt | 2100 |
| ttagcgtatgctgaggccagatttttttcaagcaaaagtaaaatcctgag | 2150 |
| aaactgcctggccagaggacaatcagattttggctggctcaagtgacaag | 2200 |
| caagtgtttataagctagatgggagaggaagggatgaatactccattgga | 2250 |
| ggttttactcgagggtcagagggatacccggcgccatcagaatgggatct | 2300 |
| gggagtcggaaacgctgggttccacgagagcgcgcagaacacgtgcgtc | 2350 |
| aggaagcctggtccgggatgcccagcgctgctccccgggcgctcctcccc | 2400 |
| gggcgctcctcccaggcctcccgggcgcttggatcccggccatctccgc | 2450 |
| acccttcaagtgggtgtgggtgatttcgtaagtgaacgtgaccgccaccg | 2500 |
| aggggaaagcgagcaaggaagtaggagagagccgggcaggcggggcgggg | 2550 |
| ttggattgggagcagtgggagggatgcagaagaggagtgggagggatgga | 2600 |
| gggcgcagtgggaggggtgaggaggcgtaacgggGCGGAGGAAAGGAGAA | 2650 |
| AAGGGCGCTGGGGCTCGGCGGGAGGAAGTGCTAGAGCTCTCGACTCTCCG | 2700 |
| CTGCGCGGCAGCTGGCGGGGGGAGCAGCCAGGTGAGCCCAAGATGCTGCT | 2750 |
|                                              M  L  L | |
| GCGCTCGAAGCCTGCGCTGCCGCCGCCGCTGATGCTGCTGCTCCTGGGGC | 2800 |
|  R  S  K  P  A  L  P  P  P  L  M  L  L  L  G | |
| CGCTGGGTCCCCTCTCCCCTGGCGCCCTGCCCCGACCTGCGCAAGCACAG | 2850 |

| |
|---|
| Fig. 16 a |
| Fig. 16 b |
| Fig. 16 c |
| Fig. 16 d |
| Fig. 16 e |
| Fig. 16 f |
| Fig. 16 g |
| Fig. 16 h |
| Fig. 16 i |
| Fig. 16 j |
| Fig. 16 k |
| Fig. 16 l |
| Fig. 16 m |
| Fig. 16 n |
| Fig. 16 o |
| Fig. 16 p |

```
       P  L  G  P  L  S  P  G  A  L  P  R  P  A  Q  A  Q
      GACGTCGTGGACCTGGACTTCTTCACCCAGGAGCCGCTGCACCTGGTGAG       2900
       D  V  V  D  L  D  F  F  T  Q  E  P  L  H  L  V  S
      CCCCTCGTTCCTGTCCGTCACCATTGACGCCAACCTGGCCACGGACCCGC       2950
       P  S  F  L  S  V  T  I  D  A  N  L  A  T  D  P
      GGTTCCTCATCCTCCTGGGgtaagcgccagcctcctggtcctgtcccctt       3000
       R  F  L  I  L  L  G
      tcctgtcctcctgacacctatgtctgcccgccagcggctctccttcttt        3050
      tgcgcggaaacaacttcacaccggaacctccccgcctgtctctccccacc       3100
      ccacttcccgcctctcattctccctctccctcccttactctcagacccca      3150
      aaccgcttttggggggtatcatttaaaaaatagatttaggggttacaag       3200
      tgcagttctgttccatgggtatattgcattgtggtggcatctgggctctt      3250
      agtgtaactgtcacccgaatgttgtacattgtatctaataggtaatttct      3300
      catccctcatccctctcccacctcccaccttttggagtctccagtgtct       3350
      actattccactaagtccatgtgtacacattgtttagcgcccactctaaat      3400
      gagcctttttgtttcattcattctgtaagtgttgaataggcaccacctaa      3450
      ggtcaggtataagtggaaatttgaaaaagaaactgcccacttgccccagt      3500
      actccctagccaagaggagggaaaccaggcaggtgcacctgaaggcctg       3550
      tgagtgcttgatttgctgtgcagtgtaggacaagtaagattgtgcatagc      3600
      cttctgtatttaagactgtgttaggaagatttctctttcttttcttttct      3650
      ttttcttttttctttcttttttttttttaggcagatgaaaagggcgtca      3700
      cagaacaggaataaaaatctaaatattcaataaatgagacctaggagact      3750
      actgcagtgacttacaaagtcctaataaaaagatgtctctccaaaatggg      3800
      gctgcaaaatgtggtgctgccttatcagctctaagttttttccttacctg      3850
      agaaagaaggaacctgatgcaggttcagggctcctgccccatgaatgcag      3900
      gctgactccaagatgggagctacagggacaatcccaggtcttctaggcc      3950
      tcttatttaggccctgggagcctccagagatggccacatcttgaccagcc      4000
      cagatagagggaaagatcaccattatctcacctctgtgtcaaatacctag      4050
      atgctgtcctccctgagcccacactatagttgccagcgctaatttaatgg      4100
      gtagtgtactggttaagagatggacagaccatcctggcttgactctcagc      4150
      tctggcaaagatgagtgacttggttttttccatatctcttggccacaccaa      4200
      ccttgatttcttcagctgtagaatggaatttctcaagcttgcctcaagga      4250
      ttattgcccgaggatttgatgatatggtaagagcttctcagtgttttgacc      4300
      catagtaagtgtttgacgtttcaaacgaattgttctcttttctaggacatgg     4350
      tgagcatttggtagccattcaccggttttctgtttctttggatcatagtt      4400
      aacctctcctttctccttctggcactacaatttctggtggggaagaatcc      4450
      ttactttctgcccttcccttaaggataggaagctgatactaggcagcaa       4500
      ctagttgggggataggaagattgttccagagaaatgctgaaccataggc      4550
      tccagatcacaggaccccagtcttagcttgctgggtgtgggtgggggg       4600
      gggcggttactgaacatgggtatgaagtagatgtccatttactgaaatgt      4650
      gaggacctgaggcctcttctattgctgtagccagcatattccccaacctc      4700
      tccccaagaaaggacagatggggttccccccctggagtaacaggtccaaa      4750
      agaaaaaacatacagtgggacttccaggatctgggcctgatcacccagca      4800
      gtcaagctcccccgcaattgactaacaccccctaacacgtagaaattcca      4850
      atctgcaatttagtgaggatgatacctttattcttcttaaatacatctct      4900
      tcatttcccagagcaccctttttttcccctcctctgcacctttttgttaaa      4950
      gactggagtataatgaaataccaagagagcataacatgtgatacataaaa      5000
      cttttttctggtttacaaaacagttcattcttgtccatacgtgcttctc       5050
      tccaaggctggctgctgtctgttccagcccgcttcgcttggagaggccat      5100
      ctgccatacctgctcccagacgcatcgacaagcacacccagagtgttat      5150
      ctgctaagacctaaaagaggggaggaaccccctctcctcatctaagaccta      5200
      gcttctaaattagagtgtgagggtccatctccccaggagggcacagggc      5250
      ccaaacagcccagccatctcagaagacaacactaagctttgtaggggtcc      5300
      acagtagaggagagtaagacgcctgttgtttaatttattacagttcctca      5350
      aaagtgaagatgtgtgggcgggatggcaagagctgagcagacgaaagctg      5400
      aaggaataaggaagagaggaggacacaaacagctgacacttcctcagtt      5450
      cttgtcatttgcctggccctgttctaagcaccttctaggtattaatccat      5500
      ttagtcttggctacaacactgtgagtaactagttttgtcaccccccatttt      5550
      aaaaatgaagaaagtgaggctcagggaggttaagtaacttggccacagtt      5600
      tgaaactagactctgatcacatgagataatagtgcccataaaaagggaaa      5650
      gcagattatattttttaaaggaagagagtaggatatggtagaaaaagat       5700
```

Fig. 16 b

```
tgtttggaaaggaattgagagattgatataatgaaaagaagcattcacat      5750
gagagtaacagtatcagggccaaaccttcatctaaggtacttcaaagag      5800
gcctaagcaaacttagtcactggcgtggttctagtctccatgatggcaaa     5850
tacattgtgtacagcccaactccacacaaaacttaaataccaatgataga     5900
gcaatctaaaatttgaaagaaaaaatctttcaatttgtcgtcttcccaga     5950
gggacttaatcaagaaaccaatcaaaatacttcctaagcctaactgtgtg     6000
cagaactccaaagagagccgagccctaaatcaaactgtccaatggaaat      6050
ataatataatgtgggcctcatatgcaaggtcatatgtaattttaaatttt     6100
ctagtagccatattaaaaaggtaaaagaaacaagtgaaattaattttaa      6150
taattttatttagttcaatagatccaaaatgttttctcagcatgtaatca     6200
atataaaaatattaatgaggtatttattattccttttctcaaaccaagtc     6250
tattctataatctggcgtgtattatttacagcacttctcagactatattt     6300
ctttctttcttttttttttccgagacaattttgctcttgtcacccaagct     6350
agagtacaatggcgttacctcggctcactgcaacctccgcctcccgggtt     6400
caagttattctcctgcctcagtctcccaagtagctgggactagaggcatg     6450
caccaccacgcctggctaattgtgtattttagtagagacagggtttcac     6500
catgttggccaggctaatctcaaactcctgagctcaggtgatatgcccac     6550
ctcggcctcccaaagtgttgggattacaggcgtgagccactgcacccggc     6600
ctcagattaactatatttcaagcgttcagtagccacatgtagctagtgct     6650
atggtagtggacagtacagatctgcatttcaattaagacacgtatacaag     6700
catagttcactaatgcacggtaaaaaaagtatagtgctgagtcggtggt     6750
agaaatcctaaatactgcagagcaaaagtggtacgaacagcaatctcagt     6800
gataatgcaaccatgcttgcttttcattgcaatttgcttattttccttca     6850
gcaaagttcatccattttgccaattcaataaatatttactgataaaaac     6900
tttcaatattagattcttgcatcttcatagacagagttgcttttcacatt     6950
tagaaaattacttatcaatgttaaacacacgttttgataaccagtgttgg     7000
aaagaggtgcagactcccatgtgcctattgatggcagaaatattcacag     7050
ccaaagggaaacaaagggctggggacaatcacacacctcatgtctcctaa     7100
ctcctgggaagtgctgtccctctgattgagctcttattattgccttcccc     7150
actaaccctgtccactgtgcctggagcccttgcagggttacctgctct      7200
gtcctcctcacagaatatctcctctacctcctgtccaagctacaacttg     7250
gctattctctgatgacactgtcttccctgtagccttttgagtaatggct     7300
gcatattctcccatagtccagttcttttcctgttctccagtctggcttct     7350
ggatgacagcccactagtttgaactccatactgctatagttcaagtccct     7400
tttgacttgttaccttgggcaaattacctccttttgttcaggttccttgt     7450
ttgtaaaatgacgataataatgccatttgcttcagtgggttattttgaaa     7500
ttgagtgaaagaaggcgggtagcttccctacacgctcagtgtagactagc     7550
ctgatgtgcattacgggtgatgccatgactcagtgtgttttcctcatctc     7600
cacatctggctctcatccagtgctcctgcttacggcactctgtcccctc     7650
ttacttactccccttattaactgaagactggcactgatctcacagtttc     7700
ctctccacttcctagtctcaccatcatcctagatgacttcaagtcaccta     7750
gataaactgtctcagtttcttcactcacatttttttataacagataatgt     7800
tacactcaagttgtaacagaaccagcttatccagctcatgaaatgtatgc     7850
atttcatctcaactctgtattcagtgacatcctgtgggtatctggaaatc     7900
agccatggtgagaatatttaccatggaaattggcaaatactaaaaagcag     7950
agcaccttttttctgagagccagaccatagctcttctactccatagcac     8000
ccatcataacaattttaaatacctccactgaacagcttcttcctctctc     8050
tacttcttccatatctgatttgagcttcttaatttatcatgtgaaccact     8100
cttgtaataataaccccaaatccctgttccattgttcttcctgctaaaat     8150
actaaacctggttagtccaaccatatttctctctttggaatctacagg     8200
gtggcccaaaaacctggaaatggaaaaatattacttattaattttaatgt     8250
atattaataagccattttaatgcttcatttccagtctcagtggccaccct     8300
gtatagctgggctattgagctcttgcgggaggagggagtggacagtctcc     8350
cagccacacagactgatgttgcaccaaacatttttagcttccagacttc     8400
cctggcccttagtgttaccctaactctccattctctgcctttcacatt      8450
ctctacttttaaaaatctctgactccaccttcaccttatcattcttagc     8500
acatgaccatacttctgcttcccaaagaaaatgagcaattacttccttt     8550
cctttcctcctgtcatcaaatctgcagacatgtcatgcctaagtccagc     8600
tttcctcctttctctgatctcagtctgcttcttccatttctgccctgaat     8650
cccgtccctcccaaccccaaggacttcgctctatcagtcacctcttc     8700
cctctcctgtatcttcaactcctcccatttactggcttcttcctcaagc     8750
```

Fig. 16 c

```
ctttcccaagcctttcccatctcaattacctcctgcacatgcctctgc      8800
agaaaccacccgtttcttccctccctcggcagcctgttcttcctgttc      8850
tgccctcatgatggcaccatcattgtgtcactaaaatcaatctctccgac    8900
atcatcaatggccttccttgttgggaaacctaataaacacttatctta      8950
tttggtcttgttatgggttgaatgaggttaccccgaaatccatattaga     9000
agtcctaaccccagtacctcagaatgtgactttatttgggaatagggtc     9050
attgcagacgttattagttaggatgaggtcatactggaatgtgatgggct    9100
gcttatctaatatgactgatgtccttataacaaggagaaatttggagaca    9150
gacacgcacataggagaataccatgtgatgacaggagttatggagttgg     9200
agtcaaaaagctatgggaacttaggagaaagacctggaacaaatcctttc    9250
ctgcgcctagagagggagtatggccctgccactaccttgaattcaacgtt    9300
tcggcttttcaaaactgtaagacaatacatttctgttgttcaaaccaatt    9350
agtttgcagtactctgcgactgcagccctaacaaactaatacagtctctt    9400
ggaggcatttggcaaggttgacaatggaagcactttcttaccccctttagg   9450
tctgtcgcctttcttgttgggggtgttttctaacaattcctctccatct     9500
ctctctctagtttgtcttaaacattggtgttcttcagacttctgacct      9550
aggccttcttttcacttcacatattccctgggtggtctcacccacttcc     9600
agaaattacttaaattactgctcatgcagtactgtgctggaaactgttta    9650
acaactggctctctgggaagaggggagactggttgatggtttttgctgat    9700
ttctgtggtgtaaatactccctccatggccaattccaaactgccaacagt    9750
ttaacaactggctcacaaattttctccaaatttaacatttggcttttcaca   9800
ggccaacaacgtggtacagccaactccagcacacctctgcttttgtgtca    9850
gagagaagtaacttattttttgtacaaaaggtaaaataaaaacacctgcag   9900
gccccctttttttccttaacaaactgctctagaaatagaatagctgaagc    9950
ttcttttatgcattcatctgttatttccatgtcactgtggtggtgggatt    10000
attttttcctttattttcttgtatatggttgaaatactgtaccttgatc     10050
agtttagttttatggcatgttttgcacccatattaaatctagttttttgt    10100
cagagggcgtcaatattatttctcaaaacaagaaaatatttcattgcaa     10150
aggagacaaacaaaaggtccttaataccaaaactttgaaatgtgatttc     10200
ttgtacttggcagtgtccaagtggtaaacccaaacagtattgggtttta     10250
ttttgttcaggaaagtctttgtctggcagcgacttacccttacatcaggc    10300
gggccttgctcattcattcacttaagtatttattaaacaccagcggtgtg    10350
ccaagtacttatctaggtatcgggtagattctgataagtcagtcaggtcc    10400
ctgctctcaggagcttgcagcagagatgggggctgcaatagagagtaag     10450
ccaaggaaatgaaaaaggaagttgatttcagagagtgatgaatgctatga    10500
agaaaatgaaggcagcgcagtgtgatggagagtgacccaaggtggtacag    10550
tttgtacctctaaggaccagactgtgacccaggtcactcacagatgcccg    10600
tcatgtgatgccacagcaacttttccaggtgctcgtttcctcccacttcc    10650
cagtctcttgcccagccgcgactgcttacaaatacagctagaggaatcta    10700
aatgaggttcctctatcatcaaacccaatcaaaatgccaaggaacagaat    10750
cagtgcctggctgaaggcagtggaacagggccagcctggagtggttctct    10800
ctgaggaagttcctcatcttggttttagggccatacctttgtgacctgtga   10850
gctaggggttgccagtccctgacatttctactgaggactcgcctgtctat    10900
attcccggcctgtatgtgtctcctgagttccagacacacagggcgaagcg    10950
cctgatggatggaagtatgttttttggtgttccattggtatctcaaattc    11000
tacaaaacttagtgccccttctcctccctgttcctccccatcttcagtct    11050
atcacctgttcctcatccagcaaatgatattaccatcttccaaggagctt    11100
cccaggagtaatccttgactcctcctcaacatccaattaataatcaaatc    11150
taggccaggtacaatagctcacgcctataatcccagcactttgggaggct    11200
gaggcaggtggatcatttgaggccaggagttcaagaccagcctggccaac    11250
aaggtgaaacctgtctcatttaaaaaagttattttaaaaactcaaatct     11300
attatttctacctctaagtgtgtcttgaatttatccatctctctccatct    11350
ctgagctgttaccttacctcagtccatcacgttttgtctacgttaacatg    11400
accagagtcttgttcttagtctggtgaggtcactccagctgcttcagatc    11450
cttccatggctcaccgttgccctcatataagttggcactcctggacatg    11500
tggcttacgggccctccgtgatgtggccctatttgcttctccattctgt    11550
tctctcccagcctctctgccccatctctaggcaccaaccacacccttct    11600
gctcgtcaatggtgccagcttctcttctatctctggtctttggacagact   11650
tttcccttcacctggaatgctttcttcaatcctaccccactctctttaat    11700
ctagataaggtttattctttttgaatgtctagcagtgaaaccatttcccc    11750
tgaaaaaccttctctaaccaaccccctaccctcagcccaaggtctagatt    11800
```

Fig. 16 d

```
aggagtccctctgaatgtttccatagcattttaaagaattgcctattta    11850
cttgttcgtatctatcactaaactacaaattgtatgagaacagccactat    11900
ctctgcctggttcaccattcatctccagcaactagcataatgcctggcag    11950
agtcagcctgcaacaaatatttgttgaataaattaacagatggctttatc    12000
tccttaagtaaatcttgcttttttcacctattaaaacagacgcacaggcc    12050
aggtgtggtggcccatgcctgtaatcccagcactttggcaggctgaggtg    12100
ggcggatcacctgaggtcaggagttcaagaccagcctggccaacatggtg    12150
aaaccccatctctaataaaaatacaaaaattagctgggcatggtggtggg    12200
tgcgtatagtcccagctactagggaggctgaggcaagagaatcgcttgaa    12250
cccaggaggcagaggtggcagtgagccgagatcatgccactgtactccag    12300
cctggatgacagagaccctgtctcaaaacacacacacacacacacacaca    12350
cacacacacacacacacacacacacaccaagttgtataatttaaaata    12400
taacgtgcttgttatggaacacttgtaaaatacaggaaagtaatgaaaaa    12450
gtctaccatctagctcaccacataatgaccattgctatcatcctggcata    12500
attctctcctgtatataaatatatattcttttattgttaaaattacacta    12550
tgagtactatttatttattttactgtggcaaaatgcgcaaaacataaaat    12600
cttgccatttaaggtatgcagtttggtgcattcaccacactcacattgt    12650
tgtgcaaatatcaccactatctatctcagaacttcttcgtcttcccaaac    12700
tgaaactctgtacccattaaacaatagtgcatcctctgtttttcccctccc    12750
tacaattttatttttatttgggtttgtaccaaactgaaaatagctgcttct    12800
tccttacttagttcagattagcatttccatttatttagccgtggttttga    12850
ggatgccatgacagatgccatccttcctagagctctttggggctgtcagg    12900
tatttcagtcagggtgaattcggttgataacattttaaaatctcacttt    12950
attctgaggttcctagtgtcagagcccaccgtatttttagggactcccaa    13000
gttacaaacaaaaatatggtgaggaggaatcactgaagtttaacacaag    13050
agacttacattttgttcaattctatcttttagtttatttcctaagcata    13100
aagaaatactttgaaaattttacatagcattatacatatttaattaagca    13150
tgagcacatcttaaaactttaaattttagatcagatctttaattcctagg    13200
atattaagaggtactggcaatttggccaggtgtggtggttcacgcctata    13250
atcccaacactttgggagggtgaagtgggcgaattgctagagcccaggag    13300
gtggaggctgcaatggcctgagatcacgccatcgtactccagcctggatg    13350
atgagaatgaaatcctgtctcaaaaaaaaaaaaaaaaaaaaaagaagaa    13400
gaagaagtattggcaatcagtgctccaggaataattcctgacttgaaat    13450
aaacctacatgtagacaaactaattaggccattccaagagttgctagcat    13500
tggtttaatatgttttcagagcattccaggaagcagtgtggccagcattg    13550
catgtttgatacttcagaaatgtatgacaggtgttttctcttacccaggtc    13600
ttctgttttcttagttttgctcatgtaaatatttatgaacatcctcatct    13650
ttttgagggaagggattatagatcattctaattccattttctagcatttg    13700
gtaccattctaagcacatgataggcacccatttggagcatttttggcttg    13750
acagaatatgcatttagaattgttcaaattagaggtgtcagtgatgggaa    13800
ttagaatactatataattctaagtcatttgacttaaatacaaaagaatga    13850
ttttccttggtggggaatggtgaagggaggcaggagttaagaagaggaga    13900
agagatcctaagtcatttataaacttctctggaagacaggtgtgtgaag    13950
acttttaaaaagtcattcaccaaattgtgtgtgtgtgtgtgtgtgtgtt    14000
ttaaatagactttatttttagagcagtttaggttcacagcaaaattga    14050
atgcaaggacagagatttcccataaacccctgcccacacacatgcatag    14100
cctccctcattatcaacatcccaccagagaggtgtttgttctagttgat    14150
gaacctacactgacacatcattatcacccaaagtccatagttcacggcag    14200
ggttcactgtcggtgtacattctatgggtttgagcaaatgtataatgaca    14250
tgtatccaccattatagtaacatacagagtattttcagtgccctgcaaat    14300
ccctgttctccacctattcatccctctctgcatttccaccccag    14350
cccctggtaaccgctgatctttttactgtcccatagtttcggacgatcta    14400
ttttcagacagacacagagctgtctttcccttagtttctattctatcat    14450
ttcttttctcccatccatcataaaaggctatgagttttttttaagtgttg    14500
aacaccatcctacttgtcaagttaaaacataagctcctggctgggtacag    14550
tggctcatgcctgtaatctcagcatttgggaggctgtggcagaagcatc    14600
acttgaagccagaagtttgagaccagcctgggcaacatagcaagacccca    14650
tccctccacacacaaacacacacacacacacacacacacacacacacaca    14700
cacacacacacaaaaacaagctcttgccagaattagagctacaaattg    14750
ccctcaggttcctagaagatcagtccttcaattagattcagattgagatg    14800
cttcctcttttaaacaatgattcccttttctatcatgcccaataagaaaac    14850
```

Fig. 16 e

```
aaataaaaattaaacaatactgcctgtaatctcagctacccaggaggcag      14900
aagcagaactgcttcaacccggcaagcagaagttgcagtgaagtgagatc      14950
gcgccactgcactccagcctgggaaacagagcaagattctgtctcaaaaa      15000
caaaacaatgtgattcctcctctaagtcctgcacagggaaatgttaaga      15050
aataggtccaccaggaaagaaggaagtaagaatgtttgactagattgtct      15100
tggaaaaaatagttatactttcttgcttgtcttcctaacagTTCTCCAAA      15150
                                              S  P  K
GCTTCGTACCTTGGCCAGAGGCTTGTCTCCTGCGTACCTGAGGTTTGGTG      15200
  L  R  T  L  A  R  G  L  S  P  A  Y  L  R  F  G
GCACCAAGACAGACTTCCTAATTTTCGATCCCAAGAAGGAATCAACCTTT      15250
  G  T  K  D  F  L  I  F  D  P  K  K  E  S  T  F
GAAGAGAGAAGTTACTGGCAATCTCAAGTCAACCAGGgtgaaaatttta      15300
  E  E  R  S  Y  W  Q  S  Q  V  N  Q
aagattcactctatattttaattaacgtcagtccgtcatgagaatgcttt      15350
gagaaaactgttatttctcacacctaacaattaatgagattaacttcctc      15400
tcccctcatctgacctgtggaggaatctgaacaagaggaggaggcagtgg      15450
gcaggtttccttatcatgatgtttgtcatgttcagtgtgaggcctacaa      15500
aaaaaaaaaaaaaaaaaaaggcgtcctggatataactgagagctcattg      15550
tacagtaaatattaataaaacagtgattgtagctgaaggatagaactgct      15600
tggagggagcaagtgggtagaatcgcgtcaaactaaagagcatttctagc      15650
caaagacacaatgatagattgaaggatatttattctaaatatagaatatg      15700
ggtgaacgagatctgtggacttctgggctccaacgttagattctgatttt      15750
agcaagcttgtcaggggattctgatattgaaaggctgtggccttcacctg      15800
agaaacctgccctagggggccatgaaaatttgtcctgtctttcagaagtg      15850
ctatcagacatcaaatggaagttaaatcgtatcttaacaattactaggat      15900
gggcgcagtgactcacacctgtaatcccaacactttgggaggctgaggca      15950
ggaggatcacttgagcccaggagttcgggaccagcctgggcaacatagag      16000
agacgttgtctctattttttaataatttaaagagaaaaaaatactgaaaa      16050
tattgtatacaccactgaattataataatgtgtatataatgtatatattc      16100
attatgaggaatatttgattatttcatatattatatcttttccttctgtt      16150
tatttatccagttatgaagtatttagaacaattcatcagtaattgggc      16200
taaattgacagaatagtaatcagagaaaatagaaaaagacagatgggtta      16250
tctttgaataccaggttggagttgtttatgggtttgttttttgttttggg      16300
ggcgttttttagacagagtcccactctgttgcccaggctggagtgcagt      16350
ggcacaagcatggcccactgcatccttgacctcttgggctcaagcaatct      16400
tcccaccttagcctcctgagtagctgggaccacaggtgcatgtcaccaca      16450
cccagctaattttttatttttgtagagacagtctttctatgttatcca      16500
ggctgatctcaaactcctgcactcaagtgatccccctgccttggcgtccc      16550
aaagtattgggattataggcatagccaccacacccaacctagtttctatt      16600
tagacttggcccttccccaccagtcatttgtgtccaaaagatctcataaa      16650
tgtagacaggaaactgtcctttgctcatcagttttcttcatcctgtgtct      16700
aggggatggtcggtgggggaaactgggttatgcaagttcctctgaaac      16750
atcctctgtgagcccagggatggatgaggcaccagccgccagcgagtcag      16800
tgtgcagctttccagaaaggaagtcatcagccagtcagccggccctggca      16850
gccagcacccggcaaccctgctgtcttgtgataaagaaatggtctgcctg      16900
acaggatggtgtggattttctttttcttttttttttttttgagacagg      16950
gtctggctctgtcgcccaggctggagtggcgggatcttggctcac      17000
tgcagcctctgcctcccaggctcaaggcatcctcccacctcggtctcccg      17050
agtagctgggaccacaggcacacaccaccgcccaactaagttttcgta      17100
ttttttagtagaggcagggtttactatgttgtccaggctagtctcaaact      17150
cctgagctcaagctatccatctgccttggcctcccaaagagctggaatta      17200
caagcgtgagccactgtgcctgaccagggtggattttttcaagtgcacat      17250
gttgtggtcccagaagctctgatggtaccaaattccaagcgaaaaaaagt      17300
caatggttcccacccatcctacctcccatgatggcaagaggaaatcacca      17350
cactgcagatacagtccatgtaaaacaaattgctatggattttgaaagtg      17400
aaccttaagagaactgcactatgttttcttcattagagttctctggtaat      17450
ttccagcttttttttttttttttagacagtgtctcgctttgtcgccc      17500
agtgtcacccaggctggagtgcagtgacgtgatctcggctcactgcaacc      17550
tccgcctcgtgggttgaagtgattctcctgcctcagcctcctgagtagct      17600
gtattttagtagagacgaggtttcaccatttggccaggctggtctcgaac      17650
tcctgacctcaagtgattcgcccatctcagcctcccaaagtgctgggatt      17700
```

Fig. 16 f

```
acaggtgtgagccactgcaccggccagtaatttcaagcttctgaggagc      17750
ccttttgaattgttaaatacttgtagctatgtccaacatatccatgttca     17800
gtgtatgttcgatatttcttaggaaacctgccctggttgttttcttgt       17850
ggtaatcatgagccggcaaatttgacatgttacagaatatacctttt        17900
ctctgtctcctacctcataaccagaacttaattatcctgctttagtcac      17950
ataaatagctaactaaataaatatatgagatttcagtctgctcactgtga     18000
aaatagaccttctaaatgatctcttccacttgcagATATTTGCAAATATG     18050
                                    D  I  C  K  Y
GATCCATCCCTCCTGATGTGGAGGAGAAGTTACGGTTGGAATGGCCCTAC     18100
 G  S  I  P  P  D  V  E  E  K  L  R  L  E  W  P  Y
CAGGAGCAATTGCTACTCCGAGAACACTACCAGAAAAAGTTCAAGAACAG     18150
 Q  E  Q  L  L  L  R  E  H  Y  Q  K  K  F  K  N  S
CACCTACTCAAgtaagaaatgaaaggcacctagagatgttccagccca       18200
 T  Y  S
aagatatttgaataggttggactcgggcaccaatctagcaagtcctacgg     18250
aagttgtataaagctgaaaatactgaagcatttcccaaatgggaaatcct     18300
aaactcaaaacttgcttttttggttttttgtttgtttgtttttcttcat      18350
ctgacattgctagtagtcacagaatgaaagataaatcaatcattcatga     18400
tctaacaatgaccttcagtgctctaaaaaactacggagtcaaggaaaaca     18450
tgaatatattcctcatgtaaaattaaaatacagacatataaagggcaaaa     18500
catgaacatcattcataccttgaggtccgtcccctcccagaaataaccc      18550
ccagtatgccttggtttagagcattaagcaggagggccctgagtcactcc     18600
agacagtcttgaccaccaagcagcattctcttttgtttcctctgtggct      18650
tttgcaaatacagggctagctcagctaccattagtatgttttcagtcac      18700
taaaacagtcttccagtcttcaaattaggatgacattgtcacatggggct     18750
ttaaagcaagtgaaacaagaacccccttttttttttttttgagatgga      18800
atctcactcttgtcgcccagcctggagtgcaatggcgcaatcttggctca     18850
ctgcaacctccacctcccaggttcaagagattctcctgccttagcctcct     18900
attcattatgaggaatatttgattattcagttcctgtagggtaaagatat     18950
taccccgatcatattattgattattgagtagctgagattacaggtgcct     19000
gccaccacgaccggctaatttttgtatttttagtagagacagggtttc      19050
accatgttggccaggctccaggctcgtctcgaactcctgacctcaggtga     19100
tccacccacctcagcctcccaaagttctgggattacaggcgtgagccacc     19150
actcctggccacaatccttttttaactatgaaatatattttatctgaag     19200
tttgatgttatacccaactgagggatgatgttcccatatctcagtttaaa     19250
gaaataacctgctcagatacttcaagctcttcttttgacttttgaaaata     19300
aatgatcttgaagttactatactttgtttgggttagttaacattatttaa     19350
agtatattattttaattaattatcttgtaagattttactgtatactacc     19400
tggagttcaatgtatcagatggatttcaaattatgtacatttttatgt     19450
atatggtacagaaaaaaatgtgatccataagaaatcagaaaatagcgcat     19500
atgctaatagctaatgttgtcctctaaaaaacttattttgcattttaa      19550
gagggggatatactctgacactttaataagtgtaattaattattgactgg     19600
aattggcatgaggcagggccatttcagatcccattaaaggaatgacaca     19650
taccagagaaccacagaagtaaggccacatttgtaataaatcattataqc     19700
tctgctaggagaagaccccagttgtattaggtaattaatggatttgctctt     19750
aaaacacatgtcccggaagatataggtgagtcttggggggccgcattaaa     19800
cattataccaatgtatcttacatttctaagaaagttttactactttacag     19850
gatcttctgttaccaaaatggaaggtttccaactccaggacttggcttt     19900
catagttcctacaccaggggaaatgccttcctttgctaactatgcaacca     19950
ggttagttagtgtaagtccagccaccctgttggcaatgctaaaaggtaca     20000
acaaacacagaattttatttgcatttgtaaacatttgatttctggctcga     20050
aattttcagtttcatgggcacgtcatggaaacagaaatcttctgtgttt      20100
agtttgggcacctactcattgtagtgacaaatatttcagaagccaatagg     20150
ggattccacaaattgttctgaacctgtggctgagactggtaatggctgag     20200
tgacatggggacataccacaaagaagaggtagcaaaggctgctgagat      20250
aaggacatgttcattgcttagctagtggcctgcaccttaaaacacatgt     20300
cccaggctggtgctgtggctcacgcctgtaatcccagcactttgggagg     20350
ctgaggcgggtggattacctgaggtcaggagttcgagaccaacctggca     20400
acatagtgaaaccctcatttctactaaaaatacaaaaattagccaggcatg     20450
gtggcgggcgcctgtagtcccagctactcaggaggcaggcaggagaatta     20500
cttgaatctgggaggcagaggttgtggtgagccgagattgcgccaccgca     20550
```

Fig. 16 g

```
cgctagcctgggcgacaaagtgagactctgtctcaaaaaaacaaaaacaa      20600
aaaacaaacaaacaaaaacaacaacaacaaaaaacgggtatcccagaa        20650
gatacaggtaagtttttctaacacaggtcctcttgtatggtgcgttccact     20700
taagtagaagatgacaaaaacattgtcatgagaatatagactcacattt       20750
taaacctgttttgagcaggaaaaggaagcaatgttacagatgtaattctgg     20800
gtgtgactgcagaaaggatgactcccttattaaagtagtcatcctgagtg      20850
agctaactctttgtacttcctcttctcctcctgttcccctcatccccca       20900
ttcttccgttgcctacacccaggcccacattggatgctgacatagactta      20950
catggtacagtccaagggaaagatctgccattttttttcaatgtgtcatct     21000
tggttatcttcattccaaggatctctccactctttatacagtaagaatg       21050
agagtctggaaaggattgggaataagataatgaattgtaagttttaaatt      21100
gttcttcgtatttgggggaaggagtaggctaggtggtccttctgtttttt      21150
ttttgtttttttttttaaagtagatgtggccagacgtggtggctcacgcc      21200
tgtaatcccagcactttgagaggctgaggcaggtggatcacttgatgtca     21250
ggagttcaagaccagcctggccaacacagtgaaacccccgtctttactaaa     21300
aatacaaaaactagccgggcttggtggcgtccacctgtagtcccagctac      21350
tgcagaggtggaggcaggagaatcacttgaacccgggaggtggaggttgc      21400
agtgagccaagatcatgccattgtactccagcctgggcgacagaacaata     21450
ctctgtctcaaaaaaaagagaaaagaaaagaaaaaagaatggatttga       21500
actcagtcgtcaatagcctctattccaggagatgttacagttgattatgt     21550
tataggggtgtataatagaatttcgagctatgtaaattccaagtgcatt      21600
tggaagaatgaagaaatggaggaagggtaaagtatgagtgcaagcattcc      21650
aggttttttgaaaatgctataatctttgttcagggctagtacaaagtgct     21700
attagctgtaaggttttttgtgatttacagacagttttcacatgtgtc       21750
atttcaaccttggttttatggcgaaggcatgtgatggtgcttgtcccagg    21800
actttagatccatatctgaggttcctgtcgggcaaagatattaccccctga    21850
tcatattatagtctataagtgggagagttgtgcctggagctcaagtctta     21900
tgattttctgatccagggcacttcctacaacatgattttgcaatataaaag    21950
cctataatgtgtgactaaagcaggtcactcaccccttgtaacagactcta     22000
gtaatggtactgccaccaaacggctgcgtgatattgggcaaagacttacc    22050
ttatttgaatctcagtttcctcctagaaaaatgagggtggaggttaagca    22100
taggctgatgatcctaaagcctccatactgccctaaactgtggctctaag     22150
atccagtagaatgctgggtcacaggactctagggagcttttcaaacccaa     22200
atgtctgtcattccttgatggtaggcagcagtttatggaagtgggcgaca    22250
cagcaaatatcaaaatacctaaagcagcttgcaagagttgtttctgccta    22300
gtggtctttatagttaatattaaatagttaattttttttttttttgagac     22350
agagtcttgctctgttacccaggctgcagtgcagtggcacaatctcggct    22400
cactgcaacctccacctcccgggtttgagcaattctgtctcagcctccca    22450
agtagctgggactacaggtgcatgccactgcacccagctaattttttgtat    22500
ttttagtagagacgggtttttccaccatattgggcaggctggtctcgaactc    22550
ttgacctcaggtgatccacctgcctcagcctcccaaagtgctgggattac    22600
aggcatgagccactgcacccagcttaaatagctaatatttaatattattc     22650
tatagttattcaagtaattcaggccaaagacttagaaacaaaacaaaaag     22700
ccacttttaaggagaaagggtgtaagtttgccagatagatagagatcttt     22750
ctttttaactacaagagttcaggaatgaattactctttaacaaacgact     22800
atagatatacatgaaaattggaaggacttattatgcatatgataatcaat    22850
ttaaagacaacacttaaaattatattgttgccactctcaaaaagtggtaa     22900
tagaacagctaatggtttaaaaagcagagtacagaagttcccaaacttat     22950
ggcaccttaatatcgcagaaaacttttttaaagcatgcctaggccacaaaa    23000
aatacctgtattttgattattaaattgtaaggtctacacaacctaatagt    23050
aataggtccaatagtaatgctgtccaatagatgttgatgttttttttcctt    23100
gcaaacttaaaagatcctacagtgcctctgtaaatagcactgcctggtta    23150
gagttgaatttcagataaataatttttttcatgttaattattttttctttt     23200
ctttacttttttttttgttttttttgttttttttttgagaca             23250
gggtctcattctgttgcccaggctgctgtgcaatggcatgatcatggctc    23300
actgcagccttgacctccctgggctcaggtgatcctcccacctcagcctc    23350
ccaagtagctagctgggactacaggtgcttaccatcatgcccggctaatt    23400
tttgtgtttttttgtagagatgtggttttgccatgttgcccaggctggtct    23450
tgaactcctgggctcaagtgatccgcccgcctcggcctcccaaagtgcta    23500
ggatgacaggcatgagccactgcacctggcccctgggcgaagtatttctt    23550
aatggttacataggacatacactaaacattatttattgtctatatgaagt    23600
```

Fig. 16 h

```
tcaagtttaactaggtgccctgcacttttagttgctaaatcctgtagctg    23650
taccoatgcattcactggtgctcccagcttgccttgcacagagtttgga    23700
aaccatagtcctataactctaggccaattttttaatgtaaaatttgattc    23750
attttaaattaataaataataacaggaattttttaaaaattgttttaaa    23800
tataattaaaattatcaaaatattttttaactgaacttgtgactagagat    23850
atttagattatgaagagtgggggtttatgctaactaatgacagtctggcta    23900
tgcatgtggagcactgagctataaattgtggcttccccaattctcctgat    23950
gtcacttgaacaaaacctaagtgtcagaccagagcttctggtatcttcca    24000
tgggatttcattcaacagctggagcaaatgaagtcagattgattttttt    24050
aatttgtccaattttgttgtctcaaaaacataattataatcatttattag    24100
aactagaatttcttcagtttaacaacagaaatagttattcattatgaaaa    24150
gcgaatctggaggccttcattgtggtgccaatctaaccattaaattgtga    24200
cgttttttcttttagGAAGCTCTGTAGATGTGCTATACACTTTTGCAAACT    24250
                 R   S   S   V   D   V   L   Y   T   F   A   N
GCTCAGGACTGGACTTGATCTTTGGCCTAAATGCGTTATTAAGAACAGCA    24300
C   S   G   L   D   L   I   F   G   L   N   A   L   L   R   T   A
GATTTGCAGTGGAACAGTTCTAATGCTCAGTTGCTCCTGGACTACTGCTC    24350
 D   L   Q   W   N   S   S   N   A   Q   L   L   D   Y   C   S
TTCCAAGGGTATAACATTTCTTGGGAACTAGGCAATGgtgagtaccca    24400
S   K   G   Y   N   I   S   W   E   L   G   N
gggaacaattcattaataaggagattccccactagcattatttctttct    24450
tttcttttctttctttttttttttttgagacagagtctcgcactgc    24500
tgcccaggctggagtgcagtggcgccacctcggctcacttgaagctctgc    24550
ctcccaaaacgccattctcctgcctcagcctcccgagtagctgggactac    24600
aggcacccgccaccgcgccggctaattttttttttttttttttttttt    24650
tttttttgcatttttagtagagacggggtttcaccgtgttagccaggatg    24700
gtcttgatctcctgacctcgtgatctgccctcctcggcctcccaaagtgc    24750
tgggattacaggcgtgagccacaggcccggctagcattatttcttatga    24800
cactttttttttttttttgagacggagtctcgctctgtcgcccaggctgg    24850
agtgcagtggcgccatctcggctcactgcaagctccacctcccaggttca    24900
cgccattctcctgcctcagcctcccgagtagctgggactacacgcacccg    24950
ccaccacgccggctaattttttttgtattttagtagagacgggggtttca    25000
ccgtgttagccaggatggtctctatatcctgacccatgatctgcccgcc    25050
tcggcctcccaaagtggtgggattacaggcgtgagccactgcgccggcc    25100
aacactcttttattattagcaaatatacttctgcctgggcacattcttg    25150
caagtgctcaacaatgcaacttttggaagtgcatgtggcagaaactcctg    25200
ctgtattattccagaacctattattgctaatcccagtttatgttacatt    25250
tgaagtgagaaccagttggagccagcaacgttcccagctccaaagttccc    25300
ttgagattttcagaatcacttaaccctattatgcttggcaacctggactc    25350
agcaaaactgggaagtcagcagtttgttttattcatcccttcctttctca    25400
gtttctcaaatgtgtcagttaatctcagtaaccccattgcaaccttcatt    25450
acctgcccaagcggtctagaacttgccagtatagaatcctacgtgggtca    25500
agctcctgactgtctccttcttcactcttttttttgcaaagaacttgtaaa    25550
ttttaactataagtattcatgattcgccacatttattcaaaacatagagt    25600
gcttttttccacatatcagccaatggaaataaggattaaatgggaaatgaa    25650
atgtagtaataggataagcacaagtcttcttcctgctcaaacttttttttt    25700
ttttttttttcagacaagatcttgctctgttacccaggctggagtgcagt    25750
ggcgtgttcatagctcaatgtaacctccaactcctgggctcatgcaatct    25800
ctcacacctcagcccctgattagctaggactacactatgcctagccaat    25850
ttttttctttttgtctggttgtgttgcccaggctgtctcgatctcctggc    25900
ctcaagtaatcctcctgcctcggccttctaaagtgctgggattataggca    25950
tgagccactgtgcccggtctcaaacctttttttccaaagtaaatgaagtt    26000
attagatatggaatatagtctagttcccagatatccatatccattggttt    26050
attaccctcattattaacttcaaattgtttaatagaccctcatatctcag    26100
ttatacagttaaaattttgttttgtttttctggagtatcttatttataa    26150
ctatgagttttacttttactttatttttattttttgagacagacgcttg    26200
ctctgtcactcaggctggagtgcggttgcgtgatcatggctcactatggc    26250
ctcgaccttctgggctcaagtgatcctctccctcagcctcccaagctgag    26300
actacaggcatgcaccaccacatctagctaattttttttttttcccatgg    26350
aacaaggctttactatgttacccagagtggtctcaaactcctggcctcag    26400
gggatcctcctgtctcagcctaccaaaatgctgggattacaggcatgagc    26450
```

Fig. 16 i

```
catagcgccagacctggttttacttttcttqactttqaattacaaqttttt    26500
tgtaatttggaaaatgttttgttgcttttaaatactgctgtatgtttgct    26550
tttaaatacaacattctcgatatatattttgagaattgctgtctttcag     26600
AACCTAACAGTTTCCTTAAGAAGGCTGATATTTTCATCAATGGGTCGCAG    26650
 E   P   N   S   F   L   K   K   A   D   I   F   I   N   G   S   Q
TTAGGAGAAGATTTTATTCAATTGCATAAACTTCTAAGAAAGTCCACCTT    26700
 L   G   E   D   F   I   Q   L   H   K   L   L   R   K   S   T   F
CAAAAATGCAAAACTCTATGGTCCTGATGTTGGTCAGCCTCGAAGAAAGA    26750
  K   N   A   K   L   Y   G   P   D   V   G   Q   P   R   R   K
CGGCTAAGATGCTGAAGAGgtaggaactagaggatgcagaatcacttac     26800
 T   A   K   M   L   K   S
ttttcttcttttccttttgagacagagtctcactctgtcagccagactg     26850
gagtgcagtggtacaatcatggctcactgcaacttcgacctcccaggctc    26900
aagcaatcctcccatctcagtcccacaaatagctgggactacaggtgcac    26950
atcaccacacctggctactttaaaaaaatttttttgtagagatggggtct    27000
ccctgtgttgcccaggctggtctcttgaattcctgtgctcaagccatcct    27050
tccacctcagcctcccagagtgccaggattacaggcatgagccaccacac    27100
ccagccaccactttttcttaaaaaaaaaaaagattctctctggtagacaa    27150
tcctcaatagtccacatgttattaaacaatctgctgcctgaatacatgat    27200
ttaccaaaaaaggaaatttgacgggttcagaatatcaagggatctgag     27250
gcaaatgtcacctatgataaaatttgctatcaaaattaggaagtttgtgt    27300
ttacctgatcctaaagcagtaaccagcccatttctagggaataaaactct    27350
catgcgtatattgtgcatatatatgtattatatgactgagtgataataaa    27400
attttttttctagCTTCCTGAAGGCTGGTGGAGAAGTGATTGATTCAGTT    27450
             F   L   K   A   G   G   E   V   I   D   S   V
ACATGGCATCAgtaagtatgtctcctattcttaatactaggaaagtaagg    27500
 T   W   H   H
ctagctttatttattacctagtattcaaaaagttagttcatttaactgcc    27550
aattgactgcagttcaaataagaaacaaatagtgtctcaagtagcactgt    27600
actccaattttaatattaataaaaaaaatttttaagttatttttaaataatg    27650
tagtggtttctataaagatcactttatacagaagaacagtgccaattaac    27700
ccatggaacatataagtagctaaaaccaattgcttgccaaagaaccagta    27750
acccaggagtacatgtccttgccactgtgttttttcaagacagagtaact    27800
gatttctagttacttgcatagaatggactcctcctcataactccccttcca    27850
tcttggtctttccctagtagaacttctacctttttttagtaacaggtgag    27900
tgggagaggtaagaaggagaataaggtcagcaattaacctaaaagcagaa    27950
agtaaaatttgttattttttttctgaatattttctgtgtaatttagCTAC    28000
                                                Y
TATTTGAATGGACGGACTGCTACCAGGGAAGATTTTCTAAACCCTGATGT    28050
 Y   L   N   G   R   T   A   T   R   E   D   F   I   N   P   D   V
ATTGGACATTTTTATTTCATCTGTGCAAAAAGTTTTCCAGgtaatagtct    28100
 L   D   I   F   I   S   S   V   Q   K   V   F   Q
ttttaaacttttttaatgtaaaaccagaatccttatttatagtctagcta    28150
gttctaaattctataggtatgtatatttacatgttttctaattttagag    28200
aacaagcactatgacttatccactgttagttttccccttagcattgggtc    28250
ttaccccatgtacgtgattagaaatttgaaatatttccaatagcctttag    28300
tagaattaactcacatagatgataagaatggggttggttcacttcatgttc    28350
cttccacagcctactatttcaataaaaagaaagtttcccaagacctaaatg    28400
actatgaacatatttataactatataggaggggtgggtctaggaataca    28450
aagttttgaatgctgttaatcttcaacaccacagttgaaaccacaggtca    28500
gcttttttgcaattaccatggatacttttctgttctatagGTGGTTGAGA    28550
                                        V   V   E
GCACCAGGCCTGGCAAGAAGGTCTGGTTAGGAGAAACAAGCTCTGCATAT    28600
 S   T   R   P   G   K   K   V   W   L   G   E   T   S   S   A   Y
GGAGGCGGAGCGCCCTTGCTATCCGACACCTTTGCAGCTGGCTTTATgtg    28650
 G   G   A   P   L   L   S   D   T   F   A   A   G   F   M
agtgaagcagcgctggccttaggggtcagagtgcagctcttctccatcct    28700
tctattctgctgaaatagctccccagccaaaaagcagatcaaagaccgtt    28750
tcagtggctgagccccaaaattcatgccagattttgcaagaaaatgattt    28800
actaaagcttgagggacatctttaacaagtgttccaaattaatcactata    28850
aggatgaattgtttcagaaatttttggcctttaattatggcccataaatat    28900
```

Fig. 16j

```
gtcaagtagtccttactctaaagaagtacactgtaaaagaatgcatatag    28950
ccggatatggtagttcctgtaatcccaatactttgggaggccaaggtgg     29000
gaggattgcttgagcccaggagtttgaggctgcagtgagttatgatggtg    29050
ccactgcactctagactgggcaacagagtgagactgtcttttttttccc    29100
ctctgtcacccagactggagggcagtggcacgatctcacctcactgcaac   29150
ctctgcctcccggattgaagcgattctcctgcctcagcgtcctgagtagc   29200
tgggactacaggagtatcaccgcactgggctaattttttgtattttagta   29250
gagacggggttttgacatgttgcccaggctggtctgaaacccatgagctc   29300
aagtgatctgcctacctcagccttccaaaatgctgggattacggacatga   29350
gctaccacgcccggccacaccctgtctcttaaaaaaaaaaaaaatgcaag   29400
ttagagcatattacagctttgtctctcaggaggatacttagtgtatgtag   29450
ctataattcatagattcccaagaagtttagagcctaaagtatgaggtccc   29500
accagaggggctatcattaaatttaaagatttgttaaatcatctcattgt   29550
ccaacaccacaaacttgattgctttaaaatactggtttagttacatttag   29600
taactctattagtgcttttaatctatactgctatatcctcacattgagat   29650
tttttttcttttctcttccatcttcattcttttttctctcatcctcattc   29700
ttataagcctagaatacatcacaaatcctttatgcccatggaagcaagag   29750
gaataaagaatggagatgtttgttttgccattaactaaagatctggggtg   29800
tcggggaaggggggatagagaaggagaagtgggaagaggtgtccataat    29850
agcttaggtgcaattctgcttattttacattttaccccgctgactgcca    29900
cttttttcttcagccctcacacattgtttgtgcagggacctcataggacca   29950
ggaattgtctatagaggtgggaattttgtctcaccctgaaagggatacctc   30000
tagcatggtaatagtcttctaggatttgttatcatatggaaagatgtaaa   30050
gggagggattctgctgctgctgctgctgcatgcagttgccatttcat      30100
ttaaatgacttatttataattgatgacacttttctggcttcctgttaatt   30150
cctccctcaaagatcaataaaccagaaccaggcatggtggcatgcacttg   30200
tggtcctgtaaccacccaacaggttcaccttgcctgctgtctagatagag   30250
ccaattatcaagacaggggaattgcaaaggagaaagagtaatttatgcag   30300
agccagctgtgcaggagaccagagttttattattactcaaatcagtctcc   30350
ccgaacattcgaggatcagagcttttaaggataatttggccggtaggggc   30400
ttaggaagtggagagtgctggttggtcaggttggagatggaatcacaggg   30450
agtggaatgaggttttcttgctgtcttctgttcctggatgggatggcag   30500
aactggttgggccagattaccggtctgggtggtctcaaatgatccaccca   30550
gttcagggtctgcaagatatctcaagcactgatcttaggttttacaacag   30600
tgatgttatcccaggaacaatttggggaggttcagactcttggagccag   30650
aggctgcattatccctaaaccgtaatctctaatgttgtagctaatttgtt   30700
agtcctgcaaaggtagacttgtccccaggcaagaagggggtcttttcaga   30750
aaagggctattatcatttttgtttcagagtcaaaccatgaactgaatttc   30800
ttcccaaagttagttcagcctacacccaggaatgaagaaggacagcttaa   30850
aggttagaagcaagatggagtcaatgaggtctgatctctttcactgtcat   30900
aatttcctcagttataattttgcaaaggcggtttcagtcccagctactt   30950
gggaggctgagacaggaggattaatggagcccaggagtttgaggttgca    31000
agagctatgatcacgccactgcactccagcctgggtgacagagtgagacc   31050
ctgtctctaaataaataaataagtaaataaataaatacataaataaaatc   31100
aagatggtgtgcaattagaattgagcgattttgtttccaaacctcaagaa   31150
agcttggtcttgctctgtcccagGTGGCTGGATAAATTGGGCCTGTCAGC   31200
                        W  L  D  K  L  G  L  S  A
CCGAATGGGAATAGAAGTGGTGATGAGGCAAGTATTCTTTGGAGCAGGAA   31250
  R  M  G  I  E  V  V  M  R  Q  V  F  F  G  A  G
ACTACCATTTAGTGGATGAAAACTTCGATCCTTTACCTgtaagtgaccat   31300
  N  Y  H  L  V  D  E  N  F  D  P  L  P
tattttcctaattctagtggagtagattaaagtcaactcaggacctctgg   31350
tgttaacctcctatgaacagtcagtcctctcagtaactagccaaatcatg   31400
agatgatgaattagaaggagccttagatgcatccaatctaacattttttt   31450
tgtgtgtttgaagagaagaaatcaagagctaggaataacttttttaaaggt   31500
aagccatttgcagtatagtgtggattttgtttaaaagggggataatttgaa   31550
attttatgactcattatacaagacaaaataagttggattttcaaatgttt   31600
tacaaagtaaatcaaagttataattgcctacagtacgcaaagcttcaaaa   31650
cattttttatgttatgaaattgtaatttatttaaccttaaaatgagccag   31700
taccatgtgtttgcttaaaaatctcatgctaagaatttactatgttgtta   31750
ataatcttcaagatatttatgaataaagtcttatttctaatccttcctcc   31800
```

Fig. 16 k

```
tttgtctttgtgtgtacatgtgtttgtgtatgtgtgtgtctaaaagtt    34900
tggctttgagctttgctttgaattcttggatgaacaataaccaagaatac  34950
ttaaactctgatcattcttgacagatatcccctacaggctatggcttttt  35000
gaattgtgtcctccagtgataaaaagcagcaagcacgatactgctctcag  35050
attcatggtggtcacatgtgaggtgaaaaaaaaaaaaagatgaatccta   35100
tttaaatgccccaggataacagtgatactctttgtaggataactatttg   35150
cttgccactggtttcattaaataaggacataagtaaagatctatttttgt  35200
ctcttttctccccaaccaccacaactagGATTATTGGCTATCTCTTCTGTT  35250
                              D  Y  W  L  S  L  F
CAAGAAATTGGTGGGCACCAAGGTGTTAATGGCAAGCGTGCAAGGTTCAA   35300
 K  K  L  V  G  T  K  V  L  M  A  S  V  Q  G  S
AGAGAAGGAAGCTTCGAGTATACCTTCATTGCACAAACACTGACAAgtaa   35350
 K  R  R  K  L  R  V  Y  L  H  C  T  N  T  D  N
gtatgaaacacacccttaccaatcatcaagttttagtgggtaagcctgt   35400
aactttactcaaacaccctgttgcatgtgtctatacattgcataagtata  35450
ggcagttgcaatttagtaaagttttatacaacgattttatttatttat    35500
tttagaagaaaaatgctactttgttgttgttgttttttgagacggggc    35550
ctcgctcgtcacccaggctgagtgcagtggtgcaatctcagctcactgc   35600
aacctcgcctcccgggttcaagtgattcttgaagaggagaacaataata   35650
acaacaatattattttcaaaagttgtgaccgcagtttctggagttgagaa  35700
gacatcgagattttttgtagcctcatactcttgctttaggtagcaaaaaat 35750
gttcctaaatctcaggaatattctctagataggtttcaatctatcattcc  35800
tgataagatgatgctgaaatactaattctagccaaaaaagaccagctacc  35850
atttccgattgttgggactgggaactctggatagtgaggaccccagtag   35900
gaagtagcgagggaatggtttgaatggataaaattcataaaaaatgtcag  35950
tagatttaattttcttatacatttcagtcttttataaggctaggaaaag   36000
ccctgttttatggtttataatttgaattcacatgaacccacaaaattt    36050
gccttttaccttcctatgtctgaaaatggatagtctggctggcctcttaa  36100
caacccagctggcagagctgtgaggatctcagtgtgctctagcccagaca  36150
ttggtagcatgaacggcaacattttaattgtgtttttcaaaataggagca  36200
cactagcggtctaaaacgatcataaaagaaggatactaagagggcccact  36250
gtcattatggatcctaatacttaggatgcattatgagttttcattatgga  36300
tactaatacttaggatcacatttgtaattgagttttttaattgcttaaatt 36350
agatacatattctattaagttaacctctttgcttttagTCCAAGGTATA   36400
                                          P  R  Y
AAGAAGGAGATTTAACTCTGTATGCCATAAACCTCCATAATGTCACCAAG  36450
 K  E  G  D  L  T  L  Y  A  I  N  L  H  N  V  T  K
TACTTGCGGTTACCCTATCCTTTTTCTAACAAGCAAGTGGATAAATACCT  36500
 Y  L  R  L  P  Y  P  F  S  N  K  Q  V  D  K  Y  L
TCTAAGACCTTTGGGACCTCATGGATTACTTTCCAAgtaagtaattttcc   36550
 L  R  P  L  G  P  H  G  L  L  S  K
ttgttcattccaaactttcaataaatttattggtgtttatcagaatagag  36600
agtttggacagggagcaaaagacaaagtcaactatatcaagttctaataa  36650
ttcttaatattcaggaaatttatgtatgaatacttactaatatgagtata  36700
actcatcctaagagtctaaagcaaaaggatgtgaacacaaactagcagtt  36750
atcttagagaataagtttgcatttcaaaataacttgacatatcaagatcc  36800
actcaacgcatttaaattatttactctaaaaagacataattcttggtaac  36850
acattcactaaagcaaaatatacctttatataattgctatcaaaggtatg  36900
tgggttggtataaaatatcataccatgtgagatcagtgtgattcctttac  36950
agcattaatttttattggttagagtaagaaaaagaatagctagagtatat  37000
ttcttaagtagattctcatacactttggtttcaaaaaccaattattgact  37050
acatcttataaaagcctgtattcaatggagtgccaaaaaatgactatgag  37100
tcttaaagagttaggcatataaatattttaaggtttctgttcaatgtatg  37150
ttggaaggagttccttctcatgactattctcatattggagcataaaaag   37200
agtttacaggcttggcgcagtggctcatgcctgtaatcccaatactttgg  37250
gaagctgaagcaggcagatcacttcagcccaggagtttgagaccagcctg  37300
ggcaatatggcaaaactctctctacaaaatataccaaaattagccaggcg  37350
tggtggtgcatgcctgtagtcccagctacttgggaagctgaggtgggagg  37400
attgcttgagcccaggggggtcatggctgcagtgagctgtgatggtgcct  37450
ctgtcacccagcctgggtgacagagtgagaccctgtctcaaaaaaataaa  37500
taaataaaaattaagagtttacaaaattctcaccatctcctcccatctttt 37550
```

Fig. 16 m

```
aatagtat ctggt gctaaat caggaaat gtt tct tccaaaagcct cgt   31850
ggaagat ctgtatgt ct aaat at atgt caggga taat a agat gt agccc   31900
tgcgaagcat gaccttgat ttt tatagtct aaaatgt cat tt gcagatat   31950
ct at ttt ct aagaat aat t ct aaaagaat tat t t gaat gt t gt aggaaa   32000
gct aagaaat tt t gcaaagacgt agt gaaaat at aagct aggct ttt g     32050
tggt t t gt ggatagact t ccaacaaaat tgctt ttt atct atagt gat c    32100
caagct t gt ggaacat at t agt cat ct tt tt t agaaaat t ct t agaaaa   32150
gt gat ct t gcaaaaat ggaat t t at ct tt ccccaagt at at t ct gt cat g  32200
tat agagt t aaact aagcat agt aat tt caccagacaaacat t caaaat c   32250
tact cct gacct t tt t at ct cat ccaaat ttt cccaggggcccagacat a   32300
acct tt gcct t acgaact ct tt gt at at gcact aaat at gct t ct cct t c   32350
aaggt t ct cagt cagct agaaaaat gt gcaagagt aaat ggt accct t ct    32400
cact t gt agat ccaagagaat t agact t aaact cact ct acat gt ct gt g   32450
act t t att t tat t t gcat gacagt cct gt gaggt ggcaaggcaggt at ct  32500
tggat ccat t tt t t agat aaggaagt t caaat t gagaagaggt t gcat ga   32550
t t t acaggaagccat act gt agt cct at gt t act ct t aaaaat cccat t c   32600
aaat cct gct t ct gaggcct gcat act t ct accct accagt cat t gacc    32650
cat gct t at gt ct cct t t gaaaacat t gat t ccact ct t gt ct ccagt ga 32700
aaaagt ggaat t t aagcagagaaacaaaagccat t t gt ct t gt t aagt ct   32750
act t t ccct ct act t t caagaaggaaagt t gggt at gt gt t gaat ggt g   32800
at t t at t t at t t at t tat t tt aaaaat t gat acaaggt ct t act gt a   32850
t t gt gcaggct ggt ct caaact cct gggct caagt gat cat cccacct ca    32900
gcct cccagt gt t gggat t acagcat gaaccat t gt gcccaccaccgat c    32950
cgcagt tt tt t aagaaact tt tact at agaaaat t t aat cat at aca      33000
aaat acagaggaaagt at at gaacccact tt aggagact agaat at gcca     33050
cccaaaat at gccact tt ggcat aaggat t at t t cgagct aaagccaac    33100
t gggaagaaacacat agaagaaaagt t ct ct gt cct t ct ccat t t gcct a   33150
aaagcaggacat gaat ct t aaagt ccccct cct t cct tt ct accagga      33200
aaaacaagagt t aat cact gaagat aact t cagaccct t at cagt gt aga   33250
gat ggcact agaagaat ct at at t acat act cat t t at tt t cct t cccac 33300
aact t gccacccagagact aaaaat cct t tt cct t gt cat gt ct ct t g    33350
t ccaaaaat t t gct ct at aagct ggaat ct aagccacct ct t t gagaat   33400
t act t gt t ccct ggt at t t t ct gt t aacat acat gt at t aat at acat gt 33450
t aacaagct t ct gt t t gt t tt t ct cct gt t tt ct gt ct tgt t acagaggt  33500
ccat cccaact aagaact aaagagt aggaggaaaat at aat t t cct cct g   33550
cat act t t gat ct t gt t aat ccgt aaccct t cccact t tt caact cct a   33600
cct at t agat t act t t gaagcaaat tt cagat at at t act t t at ct at aa 33650
at at t t cagt at gt gct aggt gt ggt ggct cacacct gt aat cccaacac 33700
t t t gggaagct gaggcaggaggat cact t gagcccaggagt t caagacca    33750
gct acggcaacaaaaaat caaaaact t at ct gggcat ggt ggcacat gcc    33800
t gt ggt cccagct acat gagaggct gaggcaggaggat cgct t agccca     33850
ggaggt t gaggct gcagt aagct gcat t cacaccact gcact ccagcct g    33900
ggt gacagagt aagaccat gt ct caaaaaaat acat at t t t agt at gt at  33950
cct t tt t gt aaaaacaat aat ct t t at cat act t t aaat aat aacaat a    34000
at t cct t agt at cacccaaat at t t t gt cagt gt ct cacat tt t cct t at t 34050
gt ct aaaat at t gt t gat agt t at t caaat cagaat ccaaacaaggt cca  34100
tat at t acat t t ggt t gacaagt ct ct t aagt t t gt t cat ct t t aagt t c 34150
t t cct ccct ct ct t t cat ct ct t gt aat t t at t aat gt gaaaaaacaggt 34200
aat t t gt t ct at agt at t t cct acat t at agagt t t gct acat t t at t cc 34250
ct at gat at cat t t agcat gt t cct ct gt ccct gt gt t t cct gt aaact    34300
ggt agt t at acct agaagct t gagt t t at t cagt t t t t aat t gt at t t t   34350
t t t t gcaagaat t ct t t at t at ct gct t ct ggaagcacagaat gt ct ggt  34400
t gt gt ct ggt t t t gat ct t gacagct act gat gaccat t gcct aat cat   34450
t act t t at t gggt gggggaat aaggt t t t aaaat aaat t tt t tt t aaa    34500
gat t t t t t aact gt t at t t t gagacagt gt ct cat t t cgt t t cccagct   34550
t ggagt t gcagt ggcacaat cacggct cact gcagcct t gacct cct ggga  34600
t caggt gat ct t ct cacct cagcct cct gggt acct ggaact acaggt gc   34650
acaccaccacacct ggct aat tt t tt gt at tt t gt gt acagaagggggt t t  34700
cat cat gt t t cccagact ggt ct t gaact cct gggt t caagt gat ct acc   34750
cact t cagct t cccaaaat cct gggat t acact t t ggccaccgt gcct gg   34800
cct aaat gaaat t at t t gt ct ct aaacagacagaagt t tt act t t aaaaa  34850
```

Fig. 16 I

```
gcaaatgccacataagtgatgtgttccaggactattagcctcggaacctg  37600
aggcagtacagtaagcacgctttctccaaagtcctgtccccacagacaa   37650
acattatttacactgggtactgctcttttatttttcccctctatgcttt   37700
attttactataactataatcatataacatgtaataggaaaaaggcagggt  37750
cgggggagagatccagaagtcttcccaagagcctttccaacatagcctct  37800
gtagacatttttctttcttcttttttttttttttttttttctgagaca    37850
gagtctcactctgttgtccaggctagagtgcagtggcgtgatctaggctc  37900
actgcaacctccgcctcctgggttcaagcaattctcccacctcagcctcc  37950
ctagtagctgggattagaggcatgcatcaccacgcctggctaattttttgt 38000
atttttagtagagatgaggtttcaccatgtgggccaggctggtcttgaac  38050
tcctgacctcaagtgatccacctgccttagcctcccaaagtgctaggatt  38100
acacgagtgagccaccgtgccctgcccctattacattctgatcacacatt  38150
tcatgttttataattggaaaactggtgaaattatagacaatgttttgttc  38200
ccctaaattctctttgatgagtatatattacttacactcttctgtcttta  38250
aaattttgcaaaatagtatcctagataagtttatgagtgcacagtctgta  38300
cgcttactcatattaatgacctcggagagttaaacaacagtcaccttta   38350
aaattattactatcattatcattatttttgaggcgggggtctcattctgt  38400
ctcccaggctggagagtagtggtgcggtcacagctcactgcagccaccgc  38450
tacctgggctcaagtgatccttcctcctcagccttctgagtagctgagac  38500
cacaggcttatgctaccacacctggctaatttttttaacttttttgtagaga 38550
cgatgtctcattatgttgcccaggctggtctcaaactcctaagctcaagt  38600
gatcttcctcagcctcccaaagtgctgggattacaggcatgaaaaactgc  38650
acccagccctaaaattattagggtcctgcatagtaagactttaataaat   38700
atttaaatgaacatctggttttttaaaaaaaaaatagagacaaggtctc   38750
actatattgcccaagctggtctcgaactcctggactcacgcaatcctgct  38800
gccttagccgcccaaagtgctgggattacaggcatgacccaccctcatctg 38850
ggctgagtgaacatattttaacataaaggccgtatttatattatctc     38900
atacattttgcccagcatccccatttccgccgaatctgttgcttgctaat  38950
tccttccagcttcatttcatctgaaatttgacaaacatcttctatttctt  39000
tgtcgtcatgttattgacttcagaatataaaataaaacactatacccaaa  39050
ttaaacccacccctcattgccagcctgatgtgaaaataatcagcataca   39100
ttaagcttaccccttgatatatgtgtagcatcttttagataaatatacagc  39150
tgattaagcaatatagcctgatggtataatatcttgcccatgtacctcat  39200
cttatctccagcaggattaattcacagtgatcagatttaccttaaactt   39250
tgtagcaaaatatcctctccaaaagcatatctaaaacttttgtgtgtact  39300
cttgcaagtttcttaatttcatgcagaacaggctcttaccactgttagct  39350
ggagatattttcaagacctattttttgtttgtggtttcctgatgatggtca 39400
tggcatttcccccttcactccatctaaaaattgaggtgatacaggcttt   39450
aaacaaaaccaactcatatagactgagtacaactgcaatgcaggcatgct  39500
aacctctgctacaatcatgggcgtgctattgatatgtcttaagttacaga  39550
acacagggctgagcgtctcattaggtcaaaatgtaaaccagttttctgc   39600
tcactgatgcttaatgaggacagggtgtgagagatttctttaaggaaaac  39650
aaatatataataatgctacatggaaaaatatctaacattagagaattaag  39700
taaataaactaatatactcacaccatggaatcttgtgcagacattaaaat  39750
tatgtagtggatggatgtttaatggtgtgagaaaaagttaggatgtgctg  39800
gggtgggggaagaatcaagttttaagaaaatacagtatacccatactta   39850
agtaaaaaaaaaaaaaaggtatgtacagtcatgtgttgcttaatgatgg   39900
ggatacattccgagaaatgtgtcgataggtgatttcatccttgtgtgaac  39950
atcatagagtgaacttacacaaacctagatggtctagcctactatgtatc  40000
taggctatatgactagcctgttgctcctaggctacaaacctgtaaagcat  40050
gttactgtagcgaatatacaaatacttaacacaatggcaagctatcattg  40100
tgttaagtagttgtgtatctaaacatatctaaaacatagaaaactaatgt  40150
gttgtgctacaatgttacaatgactatgacattgctaggcaataggaatt  40200
ataatttatcctttatggaaccacacttatatatgcggtccatggtgg    40250
accaaaacatcctatgtggcatatgactgtatacatgtacacaaaaaat   40300
agatgaaagaatgaatatacatcaaaatatttaaaatggttataatgact  40350
taggttacttttatttatcttagtaataataatgatgatagataatactt  40400
ttatagtgtttactatataaaagacactgttataagtgttctacatactt  40450
tacatgtattacctaaatgatataaatataactctgacagtaactaatct  40500
tatacgttctctttcttttttttttttttctttttttagacagaatctt   40550
gctctaccaggctggagtgcagggtgcaatctcggctcactgcaacctcc  40600
```

Fig. 16 n

```
gcctcccaggttcaaacgattctcatgtctcagcctcctgagtagctggg       40650
actacaggcacacaccaccatgcccggctaattttgtatttttgggtag         40700
agatggagttttgccatgttggccaggctgatcttgaactcctggcctca        40750
agtgatctgcctgcctcagcctcccaaagtgctgggattacaggtgtgaa        40800
ccactgtgctcggcctaatcttacaagttttcaatatttaaagagtgcta        40850
actttgttgacaatataaaacatatttgagaaaaagagatataagcatct        40900
tatttagaattatgaaaatatcaatagacctacagccgactaaagctttt       40950
cttcataagctcttgcctatattgattcgctcctgtgaatatgcattaat        41000
ttgatttaaataataagtatgtataagaaataacactttccttaatttt        41050
taagaacgttcaacagtttttaatttgaattccaatagtgaaatacatag        41100
aaaatataaattttctgtagtttagccaaattgttttgtttcaccaca          41150
gcattctaccaaaatttcttaataacagtaagaaaatgaatgcatacctc        41200
ctgcaggagagggagttaggcagtttatgggcatagttacaagtgaga          41250
aatttcattggctaccatttacgctaaattcataaaaactgcattcaatt        41300
ctatatatctatttctcttacataaaaaaggtttcaattattggccatta        41350
aataaaatagccaccattccagaagttgtgtcatgttatccttttata         41400
ccaccatcatattgcctattatatagattgtgtgtgttccattttctgta       41450
atgggccagacagtaagtatttctggctttggagtccatatggtctctat       41500
cataactactcatctctgccattgtagcttaaagattatctaggtcaaat        41550
gcctaagtgatatagtgttgaaatacaagttatataatataggctgccac        41600
aaaaaaaatttatttggtctaaaaaagatttcatgacttttgtagcagc         41650
atgggtgggcatgcaccacttggttaactcggtgtatctttctcctttg        41700
cagATCTGTCCAACTCAATGGTCTAACTCTAAAGATGGTGGATGATCAAA        41750
   S  V  Q  L  N  G  L  T  L  K  M  V  D  D  Q CCTTGCCACCTTTAATGGAAAAACCTCTCCGGCCAGGAAGTTCACTGGGC        41800
 T  L  P  P  L  M  E  K  P  L  R  P  G  S  S  L  G TTGCCAGCTTTCTCATATAGTTTTTTTGTGATAAGAAATGCCAAAGTTGC        41850
 L  P  A  F  S  Y  S  F  F  V  I  R  N  A  K  V  A TGCTTGCATCTGAAAATAAAATATACTAGTCCTGACACTGaattttttcaa       41900
 A  C  I  *
gtatactaagagtaaagcaactcaagttataggaaaggaagcagatacct        41950
tgcaaagcaactagtgggtgcttgagagacactgggacactgtcagtgct        42000
agatttagcacagtattttgatctcgctaggtagaacactgctaataata       42050
atagctaataataccttgttccaaatactgcttagcattttgcatgtttt       42100
acttttatctaaagttttgttttgttttattattttatttatttatttatt     42150
ttgagacagaatctctctctgtcacccaggctggagtgccatggtgcgat       42200
cttggctcactgcaactttaagcaattctcctgcctcagcttcctgagta       42250
gctgggattataggcgtgtgccaccacgccagctactttctatattttt         42300
tgtagagatggagtttcgccatattggccagctggtctcgaactcctgt        42350
cctcgaactcctgtcctcaagtgatccaccgcctcagcctctcaaagtg        42400
ctgggattacaggtgtgagccaccacacccagcagtgttttattttgag       42450
acagggtatcattctgttgcccaggcttgagtgcagtggtgcaatcatag        42500
atcactgcagccttttaactcctgggctcaagtcatcctcctgcttagcc        42550
tcccaagtagctaggaccacagacacatgccatcacacttggctatttt        42600
aaaaaattttttgtagagatggggtctcgctatgttacccaaactggtcc       42650
tgaactcctggactcaattgatcctcccaccttggccttccaggtgctgt      42700
gatttctttgggagtacagcatggtacagcaggagatcatttgatgttac       42750
ctctgtgcagtgttgctagtcagcgaaagactataatacctgtggggaca       42800
gcgattagccaccacaaccagtctttatttaaagttattaaaaatggctg        42850
ggcgcagtggctcacacctgtaatcctagcactttgggaggccgaggcag       42900
atggatcacctgacgtgaggaatttgagaccagcctggccaacatggtga       42950
aaccccatctctactaaaaatacaaaaattagctgggtgtggtcctgta        43000
gtcccagctacttgggaggctggggcaggagaattacttgaacccaggag       43050
gcagaggttgcagtgagccgagattgtgccactgcactccagcctgggtg       43100
acagagagagattccatctcaaaaaaacaagttattaaaaatgtatatga      43150
atgctcctaatatggtcaggaagcaaggaagcgaaggatatattatgagt       43200
tttaagaaggtgcttagctgtatatttatctttcaaaatgtattagaaga      43250
ttttagaattctttccttcatgtgccatctctacaggcacccatcagaaa      43300
aagcatactgccgttaccgtgaaactggttgtaaaagagaaactatctat      43350
ttgcaccttaaaagacagctagattttgctgattttcttctttcggtttt     43400
```

Fig. 16 o

```
ctttgtcagcaataatatgtgagaggacagattgttagatatgatagtat    43450
aaaaaatggttaatgacaattcagaggcgaggagattctgtaaacttaaa    43500
attactataaatgaaattgatttgtcaagaggataaatttagaaaacac     43550
ccaatacottataactgtctgttaatgcttgcttttttctctacctttctt   43600
cctgtttcagttgggaagcttttggctgcaagtaacagaaactcctaat     43650
tcaaatggcttaagcaataaggaaatgtatattcccacataactagacgt    43700
tcaaacaggccaggctccagcacttcagtacgtcaccagggatctggtt     43750
cttcccagctctctgctctgccatctttagcgctggcttcattctcagac    43800
tctggtagcatgatggctgtagctgtttcatgggccccttcaaacctcat    43850
agcaaccagaggaagaaaatgagccatttttgagtctccttcatagact     43900
tgaataactcttttcagagcttctcacagcaaacctctcctcatgtctc     43950
ctcatgtcttattgttcagaaatgggtaatgtggccatttcaccagtcac    44000
tgccaacaacaacgaggttcctataattgtctctgagtaacoctttggaa    44050
tggagagggtgttggtcagtctacaaactgaacactgcagttctgcgctt    44100
tttaccagtgaaaaatgtaattatttccctcttaaggattaatattc      44150
ttcaaatgtatgcctgttatggatatagtatctttaaaattttttatttt    44200
aatagctttaggggtacacacttttgcttacaggggtgaattgtgtagt    44250
ggtgaagactcggcttttaatgtacttgtcacctgagtgatgtacattgt    44300
acccaataggtaattttttcatccattaccotccttccgccctcttccctt   44350
ctgagtctccaacatcccttataccactgtgtatgttcttgtgtacctac    44400
agctaagcttccacttataagtgagaacatgcagtatttggttttccatt   44450
cctgagttacttcccttaggataacagcccccagttccgtccaagttgct    44500
gcaaaatacattattcttctttatggctgagtaatagtccatggtacata    44550
tataccacattttctttatccacttatcagttgatggacacttaggttaa    44600
ttccattcaatttcattcaatttaagtatatttgtaaggagctaaagctg   44650
aaaattaaattttagatcttcaatactcttaaatttatatgtaagtgg    44700
tttttatattttcacattgaaataaagtaattttataaccttgatatt    44750
gtatgactattcttttagtaatgtaaagcctacagactcctacatttgga    44800
accactagtgtgttgtttcacccttgttatactatcaggatcctcga      44898
```

Fig. 16 p

|  | | | | | 50 |
|---|---|---|---|---|---|
| human | MLLRSKPALP | PPLMLLLLGP | LGPLSPGALP | RPAQAQDVVD | LDFFTQEPLH |
| mouse | ~~~~~~~~ML | RLLLLWLWGP | LGALAQGAPA | GTAPTDDVVD | LEFYTKRPLR |
| rat | ~~~~~~~~~~ | ~LLLLWLWGR | LRALTQGTPA | GTAPTKDVVD | LEFYTKRLFQ |

|  | | | | | 100 |
|---|---|---|---|---|---|
| human | LVSPSFLSVT | IDANLATDPR | FLILLGSPKL | RTLARGLSPA | YLRFGGTKTD |
| mouse | SVSPSFLSIT | IDASLATDPR | FLTFLGSPRL | RALARGLSPA | YLRFGGTKTD |
| rat | SVSPSFLSIT | IDASLATDPR | FLTFLSSPRL | RALSRGLSPA | YLRFGGTKTD |

|  | | | | | 150 |
|---|---|---|---|---|---|
| human | FLIFDPKKES | TFEERSYWQS | QVNQDICKYG | SIPPDVEEKL | RLEWPYQEQL |
| mouse | FLIFDPDKEP | TSEERSYWKS | QVNHDICRSE | PVSAAVLRKL | QVEWPFQELL |
| rat | FLIFDPNNEP | TSEERSYWQS | QDNNDICGSD | RVSADVL~~~ | ~~~~~~~~~~ |

|  | | | | | 200 |
|---|---|---|---|---|---|
| human | LLREHYQKKF | KNSTYSRSSV | DVLYTFANCS | GLDLIFGLNA | LLRTADLQWN |
| mouse | LLREQYQKEF | KNSTYSRSSV | DMLYSFAKCS | GLDLIFGLNA | LLRTPDLRWN |
| rat | ~~~~~~~~~~ | ~~~~~~~~~~ | ~~~~~~~~~~ | ~~~~~~~~~~ | ~~~~~~~~~~ |

|  | | | | | 250 |
|---|---|---|---|---|---|
| human | SSNAQLLLDY | CSSKGYNISW | ELGNEPNSFL | KKADIFINGS | QLGEDYIQLH |
| mouse | SSNAQLLLDY | CSSKGYNISW | ELGNEPNSFW | KKAHILIDGL | QLGEDFVELH |
| rat | ~~~~~~~~~~ | ~~~~~~~~~~ | ~~~~~~~~~~ | ~~~~~~~~~~ | ~~~~~~~~~~ |

|  | | | | | 300 |
|---|---|---|---|---|---|
| human | KLLRKSTFKN | AKLYGPDVGQ | PRRKTAKMLK | SFLKAGGEVI | DSVTWHHYYL |
| mouse | KLLQRSAFQN | AKLYGPDIGQ | PRGKTVKLLR | SFLKAGGEVI | DSLTWHHYYL |
| rat | ~~~~~~~~~~ | ~~~~~~~~~~ | ~~~~~~~~~~ | ~~~~~~~~~~ | ~~~~~~~~~~ |

|  | | | | | 350 |
|---|---|---|---|---|---|
| human | NGRTATREDF | LNPDVLDIFI | SSVQKVFQVV | ESTRPGKKVW | LGETSSAYGG |
| mouse | NGRIATKEDF | LSSDALDTFI | LSVQKILKVT | KEITPGKKVW | LGETSSAYGG |
| rat | ~~~~~~~~~~ | ~~~~~~~~~~ | ~~~~~~~~~~ | ~~~~~~~~~~ | ~~~~~~~~~~ |

|  | | | | | 400 |
|---|---|---|---|---|---|
| human | GAPLLSDTFA | AGFMWLDKLG | LSARMGIEVV | MRQVFFGAGN | YHLVDENFDP |
| mouse | GAPLLSNTFA | AGFMWLDKLG | LSAQMGIEVV | MRQVFFGAGN | YHLVDENFEP |
| rat | ~~~~~~~~~~ | ~~~~~~~~~~ | ~~~~~~~~~~ | ~~~~~~~~~~ | ~~~~~~~~~~ |

|  | | | | | 450 |
|---|---|---|---|---|---|
| human | LPDYWLSLLF | KKLVGTKVLM | ASVQGSKRRK | LRVYLHCTNT | DNPRYKEGDL |
| mouse | LPDYWLSLLF | KKLVGPRVLL | SRVKGPDRSK | LRVYLHCTNV | YHPRYQEGDL |
| rat | ~~~~~~~~~~ | ~~~~~~~~~~ | ~~~~~~~~~~ | ~~~~~~~~~~ | ~~~~~~~~~~ |

|  | | | | | 500 |
|---|---|---|---|---|---|
| human | TLYAINLHNV | TKYLRLPYPF | SNKQVDKYLL | RPLGPHGLLS | KSVQLNGLTL |
| mouse | TLYVLNLHNV | TKHLKVPPPL | FRKPVDTYLL | KPSGPDGLLS | KSVQLNGQIL |
| rat | ~~~~~~~~~~ | ~~~~~~~~~~ | ~~~~~~~~~~ | ~~~~~~~~~~ | ~~~~~~~~~L |

|  | | | | | 543 |
|---|---|---|---|---|---|
| human | KMVDDQTLPP | LMEKPLRPGS | SLGLPAFSYS | FFVIRNAKVA | ACI~ |
| mouse | KMVDEQTLPA | LTEKPLPAGS | ALSLPAFSYG | FFVIRNAKIA | ACI~ |
| rat | KMVDEQTXPA | LTEKPLPAGS | SLSVPAFSYG | FFVIRNAKIA | ACI~ |

Fig. 17

```
    |MLLRSKPALPPPLMLLLLGPLGPLSPGALPRPAQAQDVVDLDFFTQEPLHLVSPSFLSVT|  60
PHD |         EEEEE              HHH       EEEE      EEE|

|IDANLATDPRFLILLGSPKLRTLARGLSPAYLRFGGKTDFLIFDPKKESTFEERSYWQS| 120
PHD |EEE      EEEEE   HHHHHH   HHHHE      EEEEE         HHHHHH|

|QVNQDICKYGSIPPDVEEKLRLEWPYQEQLLREHYQKKFKNSTYSRSSVDVLYTFANCS| 180
PHD |HHHHHHHH     HHHHHHH    HHHHHHHHHHHHHHHHH     EEEEEEEEEEE    |

|GLDLIFGLNALLRTADLQWNSSNAQLLLDYCSSKGYNISWELGNEPNSFLKKADIFINGS| 240
PHD | HHHHHHHHHHHHHHHHHHHHHHHHHHHHHHHHH    EEEEE    HHHHHHH EEEE  |

|QLGEDYIQLHKLLRKSTFKNAKLYGPDVGQPRRKTAKMLKSFLKAGGEVIDSVTWHHYYL| 300
PHD | HHHHHHHHHHHHHHHHHHH         HHHHHHHHHHHHH    EEEEEEEEEEE |

|NGRTATREDFLNPDVLDIFISSVQKVFQVVESTRPGKKVWLGETSSAYGGAPLLSDTFA| 360
PHD |          HHHHHHHHHHHHEEEEEEE      EEEEEE         HHHHHHH|

|AGFMWLDKLGLSARMGIEVVMRQVFFGAGNYHLVDENFDPLPDYWLSLLFKKLVGTKVLM| 420
PHD |HHHHHHHH    HHHH HHHHHHHHHHHHH     EEEEE     HHHHHHHHHHH  EEEEE|

|ASVQGSKRRKLRVYLHCTNTDNPRYKEGDLTLYAINLHNVTKYLRLPYPFSNKQVDKYLL| 480
PHD |EEE    E  EEEEEEEE       EEEEEE      EEEE      HHHHHHHH|

|RPLGPHGLLSKSVQLNGLTLKMVDDQTLPPLMEKPLRPGSSLGLPAFSYSFFVIRNAKVA| 540
PHD |HH   EEEEEEE   EEEEE                        EEEEEEEE EE |

|ACI|                                                          543
PHD |   |
```

Fig. 19

POLYNUCLEOTIDE ENCODING A POLYPEPTIDE HAVING HEPARANASE ACTIVITY AND EXPRESSION OF SAME IN GENETICALLY MODIFIED CELLS

This is a continuation of U.S. patent application Ser. No. 09/258,892, filed Mar. 1, 1999 now abandoned, which is a continuation-in-part of PCT/US98/17954, filed Aug. 31, 1998, which is a continuation of Ser No. 08/922,170, filed Sep. 2, 1997, U.S. Pat. No. 5,968,822.

FIELD AND BACKGROUND OF THE INVENTION

The present invention relates to a polynucleotide, referred to hereinbelow as hpa, encoding a polypeptide having heparanase activity, vectors (nucleic acid constructs) including same and genetically modified cells expressing heparanase. The invention further relates to a recombinant protein having heparanase activity and to antisense oligonucleotides, constructs and ribozymes for down regulating heparanase activity. In addition, the invention relates to heparanase promoter sequences and their uses.

Heparan sulfate proteoglycans: Heparan sulfate proteoglycans (HSPG) are ubiquitous macromolecules associated with the cell surface and extra cellular matrix (ECM) of a wide range of cells of vertebrate and invertebrate tissues (1–4). The basic HSPG structure includes a protein core to which several linear heparan sulfate chains are covalently attached. These polysaccharide chains are typically composed of repeating hexuronic and D-glucosamine disaccharide units that are substituted to a varying extent with N- and O-linked sulfate moieties and N-linked acetyl groups (1–4). Studies on the involvement of ECM molecules in cell attachment, growth and differentiation revealed a central role of HSPG in embryonic morphogenesis, angiogenesis, neurite outgrowth and tissue repair (1–5). HSPG are prominent components of blood vessels (3). In large blood vessels they are concentrated mostly in the intima and inner media, whereas in capillaries they are found mainly in the subendothelial basement membrane where they support proliferating and migrating endothelial cells and stabilize the structure of the capillary wall. The ability of HSPG to interact with ECM macromolecules such as collagen, laminin and fibronectin, and with different attachment sites on plasma membranes suggests a key role for this proteoglycan in the self-assembly and insolubility of ECM components, as well as in cell adhesion and locomotion. Cleavage of the heparan sulfate (HS) chains may therefore result in degradation of the subendothelial ECM and hence may play a decisive role in extravasation of blood-borne cells. HS catabolism is observed in inflammation, wound repair, diabetes, and cancer metastasis, suggesting that enzymes which degrade HS play important roles in pathologic processes. Heparanase activity has been described in activated immune system cells and highly metastatic cancer cells (6–8), but research has been handicapped by the lack of biologic tools to explore potential causative roles of heparanase in disease conditions.

Involvement of Heparanase in Tumor Cell Invasion and Metastasis: Circulating tumor cells arrested in the capillary beds of different organs must invade the endothelial cell lining and degrade its underlying basement membrane (BM) in order to invade into the extravascular tissue(s) where they establish metastasis (9, 10). Metastatic tumor cells often attach at or near the intercellular junctions between adjacent endothelial cells. Such attachment of the metastatic cells is followed by rupture of the junctions, retraction of the endothelial cell borders and migration through the breach in the endothelium toward the exposed underlying BM (9). Once located between endothelial cells and the BM, the invading cells must degrade the subendothelial glycoproteins and proteoglycans of the BM in order to migrate out of the vascular compartment. Several cellular enzymes (e.g., collagenase IV, plasminogen activator, cathepsin B, elastase, etc.) are thought to be involved in degradation of BM (10). Among these enzymes is an endo-β-D-glucuronidase (heparanase) that cleaves HS at specific intrachain sites (6, 8, 11). Expression of a HS degrading heparanase was found to correlate with the metastatic potential of mouse lymphoma (11), fibrosarcoma and melanoma (8) cells. Moreover, elevated levels of heparanase were detected in sera from metastatic tumor bearing animals and melanoma patients (8) and in tumor biopsies of cancer patients (12).

The control of cell proliferation and tumor progression by the local microenvironment, focusing on the interaction of cells with the extracellular matrix (ECM) produced by cultured corneal and vascular endothelial cells, was investigated previously by the present inventors. This cultured ECM closely resembles the subendothelium in vivo in its morphological appearance and molecular composition. It contains collagens (mostly type III and IV, with smaller amounts of types I and V), proteoglycans (mostly heparan sulfate- and dermatan sulfate-proteoglycans, with smaller amounts of chondroitin sulfate proteoglycans), laminin, fibronectin, entactin and elastin (13, 14). The ability of cells to degrade HS in the cultured ECM was studied by allowing cells to interact with a metabolically sulfate labeled ECM, followed by gel filtration (Sepharose 6B) analysis of degradation products released into the culture medium (11). While intact HSPG are eluted next to the void volume of the column ($K_{av}<0.2$, $M_r\sim0.5\times10^6$), labeled degradation fragments of HS side chains are eluted more toward the $V_t$ of the column ($0.5<k_{av}<0.8$, $M_r=5–7\times10^3$) (11).

The heparanase inhibitory effect of various non-anticoagulant species of heparin that might be of potential use in preventing extravasation of blood-borne cells was also investigated by the present inventors. Inhibition of heparanase was best achieved by heparin species containing 16 sugar units or more and having sulfate groups at both the N and O positions. While O-desulfation abolished the heparanase inhibiting effect of heparin, O-sulfated, N-acetylated heparin retained a high inhibitory activity, provided that the N-substituted molecules had a molecular size of about 4,000 daltons or more (7). Treatment of experimental animals with heparanase inhibitors (e.g., non-anticoagulant species of heparin) markedly reduced (>90%) the incidence of lung metastases induced by B16 melanoma, Lewis lung carcinoma and mammary adenocarcinoma cells (7, 8, 16). Heparin fractions with high and low affinity to anti-thrombin III exhibited a comparable high anti-metastatic activity, indicating that the heparanase inhibiting activity of heparin, rather than its anticoagulant activity, plays a role in the anti-metastatic properties of the polysaccharide is (7).

Heparanase activity in the urine of cancer.patients: In an attempt to further elucidate the involvement of heparanase in tumor progression and its relevance to human cancer, urine samples for heparanase activity were screened (16a). Heparanase activity was detected in the urine of some, but not all, cancer patients. High levels of heparanase activity were determined in the urine of patients with an aggressive metastatic disease and there was no detectable activity in the urine of healthy donors.

Heparanase activity was also found in the urine of 20% of normal and microalbuminuric insulin dependent diabetes mellitus (IDDM) patients, most likely due to diabetic nephropathy, the most important single disorder leading to renal failure in adults.

Possible involvement of heparanase in tumor angiogenesis: Fibroblast growth factors are a family of structurally related polypeptides characterized by high affinity to heparin (17). They are highly mitogenic for vascular endothelial cells and are among the most potent inducers of neovascularization (17, 18). Basic fibroblast growth factor (bFGF) has been extracted from the subendothelial ECM produced in vitro (19) and from basement membranes of the cornea (20), suggesting that ECM may serve as a reservoir for bFGF. Immunohistochemical staining revealed the localization of bFGF in basement membranes of diverse tissues and blood vessels (21). Despite the ubiquitous presence of bFGF in normal tissues, endothelial cell proliferation in these tissues is usually very low, suggesting that bFGF is somehow sequestered from its site of action. Studies on the interaction of bFGF with ECM revealed that bFGF binds to HSPG in the ECM and can be released in an active form by HS degrading enzymes (15, 20, 22). It was demonstrated that heparanase activity expressed by platelets, mast cells, neutrophils, and lymphoma cells is involved in release of active bFGF from ECM and basement membranes (23), suggesting that heparanase activity may not only function in cell migration and invasion, but may also elicit an indirect neovascular response. These results suggest that the ECM HSPG provides a natural storage depot for bFGF and possibly other heparin-binding growth promoting factors (24, 25). Displacement of bFGF from its storage within basement membranes and ECM may therefore provide a novel mechanism for induction of neovascularization in normal and pathological situations.

Recent studies indicate that heparin and HS are involved in binding of bFGF to high affinity cell surface receptors and in bFGF cell signaling (26, 27). Moreover, the size of HS required for optimal effect was similar to that of HS fragments released by heparanase (28). Similar results were obtained with vascular endothelial cells growth factor (VEGF) (29), suggesting the operation of a dual receptor mechanism involving HS in cell interaction with heparin-binding growth factors. It is therefore proposed that restriction of endothelial cell growth factors in ECM prevents their systemic action on the vascular endothelium, thus maintaining a very low rate of endothelial cells turnover and vessel growth. On the other hand, release of bFGF from storage in ECM as a complex with HS fragment, may elicit localized endothelial cell proliferation and neovascularization in processes such as wound healing, inflammation and tumor development (24, 25).

Expression of heparanase by cells of the immune system: Heparanase activity correlates with the ability of activated cells of the immune system to leave the circulation and elicit both inflammatory and autoimmune responses. Interaction of platelets, granulocytes, T and B lymphocytes, macrophages and mast cells with the subendothelial ECM is associated with degradation of HS by a specific heparanase activity (6). The enzyme is released from intracellular compartments (e.g., lysosomes, specific granules, etc.) in response to various activation signals (e.g., thrombin, calcium ionophore, immune complexes, antigens, mitogens, etc.), suggesting its regulated involvement in inflammation and cellular immunity.

Some of the observations regarding the heparanase enzyme were reviewed in reference No. 6 and are listed hereinbelow:

First, a proteolytic activity (plasminogen activator) and heparanase participate synergistically in sequential degradation of the ECM HSPG by inflammatory leukocytes and malignant cells.

Second, a large proportion of the platelet heparanase exists in a latent form, probably as a complex with chondroitin sulfate. The latent enzyme is activated by tumor cell-derived factor(s) and may then facilitate cell invasion through the vascular endothelium in the process of tumor metastasis.

Third, release of the platelet heparanase from α-granules is induced by a strong stimulant (i.e., thrombin), but not in response to platelet activation on ECM.

Fourth, the neutrophil heparanase is preferentially and readily released in response to a threshold activation and upon incubation of the cells on ECM.

Fifth, contact of neutrophils with ECM inhibited release of noxious enzymes (proteases, lysozyme) and oxygen radicals, but not of enzymes (heparanase, gelatinase) which may enable diapedesis. This protective role of the subendothelial ECM was observed when the cells were stimulated with soluble factors but not with phagocytosable stimulants.

Sixth, intracellular heparanase is secreted within minutes after exposure of T cell lines to specific antigens.

Seventh, mitogens (Con A, LPS) induce synthesis and secretion of heparanase by normal T and B lymphocytes maintained in vitro. T lymphocyte heparanase is also induced by immunization with antigen in vivo.

Eighth, heparanase activity is expressed by pre-B lymphomas and B-lymphomas, but not by plasmacytomas and resting normal B lymphocytes.

Ninth, heparanase activity is expressed by activated macrophages during incubation with ECM, but there was little or no release of the enzyme into the incubation medium. Similar results were obtained with human myeloid leukemia cells induced to differentiate to mature macrophages.

Tenth, T-cell mediated delayed type hypersensitivity and experimental autoimmunity are suppressed by low doses of heparanase inhibiting non-anticoagulant species of heparin (30).

Eleventh, heparanase activity expressed by platelets, neutrophils and metastatic tumor cells releases active bFGF from ECM and basement membranes. Release of bFGF from storage in ECM may elicit a localized neovascular response in processes such as wound healing, inflammation and tumor development.

Twelfth, among the breakdown products of the ECM generated by heparanase is a tri-sulfated disaccharide that can inhibit T-cell mediated inflammation in vivo (31). This inhibition was associated with an inhibitory effect of the disaccharide on the production of biologically active TNFα by activated T cells in vitro (31).

Other potential therapeutic applications: Apart from its involvement in tumor cell metastasis, inflammation and autoimmunity, mammalian heparanase may be applied to modulate: bioavailability of heparin-binding growth factors (15); cellular responses to heparin-binding growth factors (e.g., bFGF, VEGF) and cytokines (IL-8) (31a, 29); cell interaction with plasma lipoproteins (32); cellular susceptibility to certain viral and some bacterial and protozoa infections (33, 33a, 33b); and disintegration of amyloid plaques (34). Heparanase may thus prove useful for conditions such as wound healing, angiogenesis, restenosis, atherosclerosis, inflammation, neurodegenerative diseases and viral infections. Mammalian heparanase can be used to neutralize plasma heparin, as a potential replacement of protamine. Anti-heparanase antibodies may be applied for immunodetection and diagnosis of micrometastases, autoimmune lesions and renal failure in biopsy specimens, plasma samples, and body fluids. Common use in basic research is expected.

The identification of the hpa gene encoding for heparanase enzyme will enable the production of a recombinant enzyme in heterologous expression systems. Availability of the recombinant protein will pave the way for solving the protein structure function relationship and will provide a tool for developing new inhibitors.

Viral Infection: The presence of heparan sulfate on cell surfaces have been shown to be the principal requirement for the binding of Herpes Simplex (33) and Dengue (33a) viruses to cells and for subsequent infection of the cells. Removal of the cell surface heparan sulfate by heparanase may therefore abolish virus infection. In fact, treatment of cells with bacterial heparitinase (degrading heparan sulfate) or heparinase (degrading heparan) reduced the binding of two related animal herpes viruses to cells and rendered the cells at least partially resistant to virus infection (33). There are some indications that the cell surface heparan sulfate is also involved in HIV infection (33b).

Neurodegenerative diseases: Heparan sulfate proteoglycans were identified in the prion protein amyloid plaques of Genstmann-Straussler Syndrome, Creutzfeldt-Jakob disease and Scrape (34). Heparanase may disintegrate these amyloid plaques which are also thought to play a role in the pathogenesis of Alzheimer's disease.

Restenosis and Atherosclerosis: Proliferation of arterial smooth muscle cells (SMCs) in response to endothelial injury and accumulation of cholesterol rich lipoproteins are basic events in the pathogenesis of atherosclerosis and restenosis (35). Apart from its involvement in SMC proliferation (i.e., low affinity receptors for heparin-binding growth factors), HS is also involved in lipoprotein binding, retention and uptake (36). It was demonstrated that HSPG and lipoprotein lipase participate in a novel catabolic pathway that may allow substantial cellular and interstitial accumulation of cholesterol rich lipoproteins (32). The latter pathway is expected to be highly atherogenic by promoting accumulation of apoB and apoE rich lipoproteins (i.e. LDL, VLDL, chylomicrons), independent of feed back inhibition by the cellular sterol content. Removal of SMC HS by heparanase is therefore expected to inhibit both SMC proliferation and lipid accumulation and thus may halt the progression of restenosis and atherosclerosis.

Gene therapy:

The ultimate goal in the management of inherited as well as acquired diseases is a rational therapy with the aim to eliminate the underlying biochemical defects associated with the disease rather then symptomatic treatment. Gene therapy is a promising candidate to meet these objectives. Initially it was developed for treatment of genetic disorders, however, the consensus view today is that it offers the prospect of providing therapy for a variety of acquired diseases, including cancer, viral infections, vascular diseases and neurodegenerative disorders.

The gene-based therapeutic can act either intracellularly, affecting only the cells to which it is delivered, or extracellularly, using the recipient cells as local endogenous factories for the therapeutic product(s). The application of gene therapy may follow any of the following strategies: (i) prophylactic gene therapy, such as using gene transfer to protect cells against viral infection; (ii) cytotoxic gene therapy, such as cancer therapy, where genes encode cytotoxic products to render the target cells vulnerable to attack by the normal immune response; (iii) biochemical correction, primarily for the treatment of single gene defects, where a normal copy of the gene is added to the affected or other cells.

To allow efficient transfer of the therapeutic genes, a variety of gene delivery techniques have been developed based on viral and non-viral vector systems. The most widely used and most efficient systems for delivering genetic material into target cells are viral vectors. So far, 329 clinical studies (phase I, I/II and II) with over 2,500 patients have been initiated Worldwide since 1989 (50).

The approach of gene addition pose serious barriers. The expression of many genes is tightly regulated and context dependent, so achieving the correct balance and function of expression is challenging. The gene itself is often quite large, containing many exons and introns. The delivery vector is usually a virus, which can infect with a high efficiency but may, on the other hand, induce immunological response and consequently decreases effectiveness, especially upon secondary administration. Most of the current expression vector-based gene therapy protocols fail to achieve clinically significant transgene expression required for treating genetic diseases. Apparently, it is difficult to deliver enough virus to the right cell type to elicit an effective and therapeutic effect (51).

Homologous recombination, which was initially considered to be of limited use for gene therapy because of its low frequency in mammalian cells, has recently emerged as a potential strategy for developing gene therapy. Different approaches have been used to study homologous recombination in mammalian cells; some involve DNA repair mechanisms. These studies aimed at either gene disruption or gene correction and include RNA/DNA chimeric oligonucleotides, small or large homologous DNA fragments, or adeno-associated viral vectors. Most of these studies show a reasonable frequency of homologous recombination, which warrants further in vivo testing (52). Homologous recombination-based gene therapy has the potential to develop into a powerful therapeutic modality for genetic diseases. It can offer permanent expression and normal regulation of corrected genes in appropriate cells or organs and probably can be used for treating dominantly inherited diseases such as polycystic kidney disease.

Genomic sequencesfunction in regulation of gene expression:

The efficient expression of therapeutic genes in target cells or tissues is an important component of efficient and safe gene therapy. The expression of genes is driven by the promoter region upstream of the coding sequence, although regulation of expression may be supplemented by farther upstream or downstream DNA sequences or DNA in the introns of the gene. Since this important information is embedded in the DNA, the description of gene structure is crucial to the analysis of gene regulation. Characterization of cell specific or tissue specific promoters, as well as other tissue specific regulatory elements enables the use of such sequences to direct efficient cell specific, or developmental stage specific gene expression. This information provides the basis for targeting individual genes and for control of their expression by exogenous agents, such as drugs. Identification of transcription factors and other regulatory proteins required for proper gene expression will point at new potential targets for modulating gene expression, when so desired or required.

Efficient expression of many mammalian genes depends on the presence of at least one intron. The expression of mouse thymidylate synthase (TS) gene, for example, is greatly influenced by intron sequences. The addition of almost any of the introns from the mouse TS gene to an intronless TS minigene leads to a large increase in expression (42). The involvement of intron 1 in the regulation of expression was demonstrated for many other genes. In human factor IX (hFIX), intron 1 is able to increase the expression level about 3 fold mare as compared to that of the HFIX cDNA (43). The expression enhancing activity of intron 1 is due to efficient functional splicing sequences, present in the precursor mRNA. By being efficiently assembled into spliceosome complexes, transcripts with splicing sequences may be better protected in the nucleus from random degradations, than those without such sequences (44).

A forward-inserted intron1-carrying HFIX expression cassette suggested to be useful for directed gene transfer, while for retroviral-mediated gene transfer system, reversely-inserted intron 1-carrying HFIX expression cassette was considered (43).

A highly conserved cis-acting sequence element was identified in the first intron of the mouse and rat c-Ha-ras, and in the first exon of Ha- and Ki-ras genes of human, mouse and rat. This cis-acting regulatory sequence confers strong transcription enhancer activity that is differentially modulated by steroid hormones in metastatic and nonmetastatic subpopulations. Perturbations in the regulatory activities of such cis-acting sequences may play an important role in governing oncogenic potency of Ha-ras through transcriptional control mechanisms (45).

Intron sequences affect tissue specific, as well as inducible gene expression. A 182 bp intron 1 DNA segment of the mouse Col2a1 gene contains the necessary information to confer high-level, temporally correct, chondrocyte expression on a reporter gene in intact mouse embryos, while Col2a1 promoter sequences are dispensable for chondrocyte expression (46). In Col1A1 gene the intron plays little or no role in constitutive expression of collagen in the skin, and in cultured cells derived from the skin, however, in the lungs of young mice, intron deletion results in decrease of expression to less than 50% (47).

A classical enhancer activity was shown in the 2 kb intron fragment in bovine beta-casein gene. The enhancer activity was largely dependent on is the lactogenic hormones, especially prolactin. It was suggested that several elements in the intron-1 of the bovine beta-casein gene cooperatively interact not only with each other but also with its promoter for hormonal induction (48).

Identification and characterization of regulatory elements in genomic non-coding sequences, such as introns, provides a tool for designing and constructing novel vectors for tissue specific, hormone regulated or any other defined expression pattern, for gene therapy. Such an expression cassette was developed, utilizing regulatory elements from the human cytokeratin 18 (K18) gene, including 5' genomic sequences and one of its introns. This cassette efficiently expresses reporter genes, as well as the human cystic fibrosis transmembrane conductance regulator (CFTR) gene, in cultured lung epithelial cells (49).

Alternative splicing:

Alternative splicing of pre mRNA is a powerful and versatile regulatory mechanism that can effect quantitative control of gene expression and functional diversification of proteins. It contributes to major developmental decisions and also to a fine-tuning of gene function. Genetic and biochemical approaches have identified cis-acting regulatory elements and trans-acting factors that control alternative splicing of specific mRNAs.

This mechanism results in the generation of variant isoforms of various proteins from a single gene. These include cell surface molecules such as CD44, receptors, cytokines such as VEGF and enzymes. Products of alternatively spliced transcripts differ in their expression pattern, substrate specificity and other biological parameters.

The FGF receptor RNA undergoes alternative splicing which results in the production of several isoforms, which exhibit different ligand binding specificities. The alternative splicing is regulated in a cell specific manner (53).

Alternative spliced mRNAs are often correlated with malignancy. An increase in specific splice variant of tyrosinase was identified in murine melanomas (54). Multiple splicing variants of estrogen receptor are present in individual human breast tumors. CD44 has various isoform, some are characteristic of malignant tissues.

Identification of tumor specific alternative splice variants provide new tool for cancer diagnostics. CD44 variants have been used for detection of malignancy in urine samples from patients with urothelial cancer by competitive RT-PCR (55). CD44 exon 6 was suggested as prognostic indicator of metastasis in breast cancer (56).

Different enzymes or polypeptides generated by alternative splicing may have different function or catalytic specificity. The identification and characterization of the enzyme forms, which are involved in pathological processes, is crucial for the design of appropriate and efficient drugs.

Modulation of gene expression—Antisense technology:

An antisense oligonucleotide (e.g., antisense oligodeoxyribonucleotide) may bind its target nucleic acid either by Watson-Crick base pairing or Hoogsteen and anti-Hoogsteen base pairing (64). According to the Watson-Crick base pairing, heterocyclic bases of the antisense oligonucleotide form hydrogen bonds with the heterocyclic bases of target single-stranded nucleic acids (RNA or single-stranded DNA), whereas according to the Hoogsteen base pairing, the heterocyclic bases of the target nucleic acid are double-stranded DNA, wherein a third strand is accommodated in the major groove of the B-form DNA duplex by Hoogsteen and anti-Hoogsteen base pairing to form a triple helix structure.

According to both the Watson-Crick and the Hoogsteen base pairing models, antisense oligonucleotides have the potential to regulate gene expression and to disrupt the essential functions of the nucleic acids in cells. Therefore, antisense oligonucleotides have possible uses in modulating a wide range of diseases in which gene expression is altered.

Since the development of effective methods for chemically synthesizing oligonucleotides, these molecules have been extensively used in biochemistry and biological research and have the potential use in medicine, since carefully devised oligonucleotides can be used to control gene expression by regulating levels of transcription, transcripts and/or translation.

Oligodeoxyribonucleotides as long as 100 base pairs (bp) are routinely synthesized by solid phase methods using commercially available, fully automated synthesis machines. The chemical synthesis of oligoribonucleotides, however, is far less routine. Oligoribonucleotides are also much less stable than oligodeoxyribonucleotides, a fact which has contributed to the more prevalent use of oligodeoxyribonucleotides in medical and biological research, directed at, for example, the regulation of transcription or translation levels.

Gene expression involves few distinct and well regulated steps. The first major step of gene expression involves transcription of a messenger RNA (mRNA) which is an RNA sequence complementary to the antisense (i.e., -) DNA strand, or, in other words, identical in sequence to the DNA sense (i.e., +) strand, composing the gene. In eukaryotes, transcription occurs in the cell nucleus.

The second major step of gene expression involves translation of a protein (e.g., enzymes, structural proteins, secreted proteins, gene expression factors, etc.) in which the mRNA interacts with ribosomal RNA complexes (ribosomes) and amino acid activated transfer RNAs (tRNAs) to direct the synthesis of the protein coded for by the mRNA sequence.

Initiation of transcription requires specific recognition of a promoter DNA sequence located upstream to the coding sequence of a gene by an RNA-synthesizing enzyme—RNA polymerase. This recognition is preceded by sequence-specific binding of one or more transcription factors to the promoter sequence. Additional proteins which bind at or close to the promoter sequence may trans upregulate transcription via cis elements known as enhancer sequences. Other proteins which bind to or close to the promoter, but whose binding prohibits the action of RNA polymerase, are known as repressors.

There are also evidence that in some cases gene expression is downregulated by endogenous antisense RNA repressors that bind a complementary mRNA transcript and thereby prevent its translation into a functional protein.

Thus, gene expression is typically upregulated by transcription factors and enhancers and downregulated by repressors.

However, in many disease situation gene expression is impaired. In many cases, such as different types of cancer, for various reasons the expression of a specific endogenous or exogenous (e.g., of a pathogen such as a virus) gene is upregulated. Furthermore, in infectious diseases caused by pathogens such as parasites, bacteria or viruses, the disease progression depends on expression of the pathogen genes, this phenomenon may also be considered as far as the patient is concerned as upregulation of exogenous genes.

Most conventional drugs function by interaction with and modulation of one or more targeted endogenous or exogenous proteins, e.g., enzymes. Such drugs, however, typically are not specific for targeted proteins but interact with other proteins as well. Thus, a relatively large dose of drug must be used to effectively modulate a targeted protein.

Typical daily doses of drugs are from $10^{-5}$–$10^{-1}$ millimoles per kilogram of body weight or $10^{-3}$–10 millimoles for a 100 kilogram person. If this modulation instead could be effected by interaction with and inactivation of mRNA, a dramatic reduction in the necessary amount of drug could likely be achieved, along with a corresponding reduction in side effects. Further reductions could be effected if such interaction could be rendered site-specific. Given that a functioning gene continually produces mRNA, it would thus be even more advantageous if gene transcription could be arrested in its entirety.

Given these facts, it would be advantageous if gene expression could be arrested or downmodulated at the transcription level.

The ability of chemically synthesizing oligonucleotides and analogs thereof having a selected predetermined sequence offers means for downmodulating gene expression. Three types of gene expression modulation strategies may be considered.

At the transcription level, antisense or sense oligonucleotides or analogs that bind to the genomic DNA by strand displacement or the formation of a triple helix, may prevent transcription (64).

At the transcript level, antisense oligonucleotides or analogs that bind target mRNA molecules lead to the enzymatic cleavage of the hybrid by intracellular RNase H (65). In this case, by hybridizing to the targeted mRNA, the oligonucleotides or oligonucleotide analogs provide a duplex hybrid recognized and destroyed by the RNase H enzyme. Alternatively, such hybrid formation may lead to interference with correct splicing (66). As a result, in both cases, the number of the target mRNA intact transcripts ready for translation is reduced or eliminated.

At the translation level, antisense oligonucleotides or analogs that bind target mRNA molecules prevent, by steric hindrance, binding of essential translation factors (ribosomes), to the target mRNA, a phenomenon known in the art as hybridization arrest, disabling the translation of such mRNAs (67).

Thus, antisense sequences, which as described hereinabove may arrest the expression of any endogenous and/or exogenous gene depending on their specific sequence, attracted much attention by scientists and pharmacologists who were devoted at developing the antisense approach into a new pharmacological tool (68).

For example, several antisense oligonucleotides have been shown to arrest hematopoietic cell proliferation (69), growth (70), entry into the S phase of the cell cycle (71), reduced survival (72) and prevent receptor mediated responses (73). For use of antisense oligonucleotides as antiviral agents the reader is referred to reference 74.

For efficient in vivo inhibition of gene expression using antisense oligonucleotides or analogs, the oligonucleotides or analogs must fulfill the following requirements (i) sufficient specificity in binding to the target sequence; (ii) solubility in water; (iii) stability against intra- and extracellular nucleases; (iv) capability of penetration through the cell membrane; and (v) when used to treat an organism, low toxicity.

Unmodified oligonucleotides are impractical for use as antisense sequences since they have short in vivo half-lives, during which they are degraded rapidly by nucleases. Furthermore, they are difficult to prepare in more than milligram quantities. In addition, such oligonucleotides are poor cell membrane penetraters (75).

Thus it is apparent that in order to meet all the above listed requirements, oligonucleotide analogs need to be devised in a suitable manner. Therefore, an extensive search for modified oligonucleotides has been initiated.

For example, problems arising in connection with double-stranded DNA (dsDNA) recognition through triple helix formation have been diminished by a clever "switch back" chemical linking, whereby a sequence of polypurine on one strand is recognized, and by "switching back", a homopurine sequence on the other strand can be recognized. Also, good helix formation has been obtained by using artificial bases, thereby improving binding conditions with regard to ionic strength and pH.

In addition, in order to improve half-life as well as membrane penetration, a large number of variations in polynucleotide backbones have been done, nevertheless with little success.

Oligonucleotides can be modified either in the base, the sugar or the phosphate moiety. These modifications include, for example, the use of methylphosphonates, monothiophosphates, dithiophosphates, phosphoramidates, phosphate esters, bridged phosphorothioates, bridged phosphoramidates, bridged methylenephosphonates, dephospho internucleotide analogs with siloxane bridges, carbonate bridges, carboxymethyl ester bridges, carbonate bridges, carboxyrnethyl ester bridges, acetamide bridges, carbamate bridges, thioether bridges, sulfoxy bridges, sulfono bridges, various "plastic" DNAs, α-anomeric bridges and borane derivatives. For further details the reader is referred to reference 76.

International patent application WO 89/12060 discloses various building blocks for synthesizing oligonucleotide analogs, as well as oligonucleotide analogs formed by joining such building blocks in a defined sequence. The building blocks may be either "rigid" (i.e., containing a ring structure) or "flexible" (i.e., lacking a ring structure). In both cases, the building blocks contain a hydroxy group and a mercapto group, through which the building blocks are said to join to form oligonucleotide analogs. The linking moiety in the oligonucleotide analogs is selected from the group consisting of sulfide (—S—), sulfoxide (—SO—), and sulfone (—SO$_2$—). However, the application provides no data supporting the specific binding of an oligonucleotide analog to a target oligonucleotide.

International patent application WO 92/20702 describe an acyclic oligonucleotide which includes a peptide backbone on which any selected chemical nucleobases or analogs are stringed and serve as coding characters as they do in natural DNA or RNA. These new compounds, known as peptide nucleic acids (PNAs), are not only more stable in cells than their natural counterparts, but also bind natural DNA and RNA 50 to 100 times more tightly than the natural nucleic acids cling to each other (77). PNA oligomers can be synthesized from the four protected monomers containing thymine, cytosine, adenine and guanine by Merrifield solid-phase peptide synthesis. In order to increase solubility in water and to prevent aggregation, a lysine amide group is placed at the C-terminal.

Thus, antisense technology requires pairing of messenger RNA with an oligonucleotide to form a double helix that inhibits translation. The concept of antisense-mediated gene therapy was already introduced in 1978 for cancer therapy. This approach was based on certain genes that are crucial in cell division and growth of cancer cells. Synthetic fragments of genetic substance DNA can achieve this goal. Such molecules bind to the targeted gene molecules in RNA of tumor cells, thereby inhibiting the translation of the genes and resulting in dysfunctional growth of these cells. Other mechanisms has also been proposed. These strategies have been used, with some success in treatment of cancers, as well as other illnesses, including viral and other infectious diseases. Antisense oligonucleotides are typically synthesized in lengths of 13–30 nucleotides. The life span of oligonucleotide molecules in blood is rather short. Thus, they have to be chemically modified to prevent destruction by ubiquitous nucleases present in the body. Phosphorothioates are very widely used modification in antisense oligonucleotide ongoing clinical trials (57). A new generation of antisense molecules consist of hybrid antisense oligonucleotide with a central portion of synthetic DNA while four bases on each end have been modified with 2' O-methyl ribose to resemble RNA. In preclinical studies in laboratory animals, such compounds have demonstrated greater stability to metabolism in body tissues and an improved safety profile when compared with the first-generation unmodified phosphorothioate (Hybridon Inc. news). Dosens of other nucleotide analogs have also been tested in antisense technology.

RNA oligonucleotides may also be used for antisense inhibition as they form a stable RNA-RNA duplex with the target, suggesting efficient inhibition. However, due to their low stability RNA oligonucleotides are typically expressed inside the cells using vectors designed for this purpose. This approach is favored when attempting to target a mRNA that encodes an abundant and long-lived protein (57).

Recent scientific publications have validated the efficacy of antisense compounds in animal models of hepatitis, cancers, coronary artery restenosis and other diseases. The first antisense drug was recently approved by the FDA. This drug Fomivirsen, developed by Isis, is indicated for local treatment of cytomegalovirus in patients with AIDS who are intolerant of or have a contraindication to other treatments for CMV retinitis or who were insufficiently responsive to previous treatments for CMV retinitis (Pharmacotherapy News Network).

Several antisense compounds are now in clinical trials in the United States. These include locally administered antivirals, systemic cancer therapeutics. Antisense therapeutics has the potential to treat many life-threatening diseases with a number of advantages over traditional drugs. Traditional drugs intervene after a disease-causing protein is formed. Antisense therapeutics, however, block mRNA transcription/translation and intervene before a protein is formed, and since antisense therapeutics target only one specific mRNA, they should be more effective with fewer side effects than current protein-inhibiting therapy.

A second option for disrupting gene expression at the level of transcription uses synthetic oligonucleotides capable of hybridizing with double stranded DNA. A triple helix is formed. Such oligonucleotides may prevent binding of transcription factors to the gene's promoter and therefore inhibit transcription. Alternatively, they may prevent duplex unwinding and, therefore, transcription of genes within the triple helical structure.

Another approach is the use of specific nucleic acid sequences to act as decoys for transcription factors. Since transcription factors bind specific DNA sequences it is possible to synthesize oligonucleotides that will effectively compete with the native DNA sequences for available transcription factors in vivo. This approach requires the identification of gene specific transcription factor (57).

Indirect inhibition of gene expression was demonstrated for matrix metalloproteinase genes (MMP-1, -3, and -9), which are associated with invasive potential of human cancer cells. E1AF is a transcription activator of MMP genes. Expression of E1AF antisense RNA in HSC3AS cells showed decrease in mRNA and protein levels of MMP-1, -3, and -9. Moreover, HSC3AS showed lower invasive potential in vitro and in vivo. These results imply that transfection of antisense inhibits tumor invasion by down-regulating MMP genes (58).

Ribozymes:

Ribozymes are being increasingly used for the sequence-specific inhibition of gene expression by the cleavage of mRNAs encoding proteins of interest. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders. Most notably, several ribozyme gene therapy protocols for HIV patients are already in Phase 1 trials (62). More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

Gene disruption in animal models:

The emergence of gene inactivation by homologous recombination methodology in embryonic stem cells has revolutionized the field of mouse genetics. The availability of a rapidly growing number of mouse null mutants has represented an invaluable source of knowledge on mammalian development, cellular biology and physiology, and has provided many models for human inherited diseases. Animal models are required for an effective drug delivery development program and evaluation of gene therapy approach. The improvement of the original knockout strategy, as well as exploitation of exogenous enzymatic systems that are active in the recombination process, has been considerably extended the range of genetic manipulations that can be produced. Additional methods have been developed to provide versatile research tools: Double replacement method, sequential gene targeting, conditional cell type specific gene targeting, single copy integration method, inducible gene targeting, gene disruption by viral delivery, replacing one gene with another, the so called knock-in method and the induction of specific balanced chromosomal translocation. It is now possible to introduce a point mutation as a unique change in the entire genome, therefore allowing very fine dissection of gene function in vivo. Furthermore, the advent of methods allowing conditional gene targeting opens the way for analysis of consequence of a particular mutation in a defined organ and at a specific time during the life of the experimental animal (59).

DNA vaccination:

Observations in the early 1990s that plasmid DNA could directly transfect animal cells in vivo sparked exploration of the use of DNA plasmids to induce immune response by direct injection into animal of DNA encoding antigenic protein. When a DNA vaccine plasmid enters the eukaryotic cell, the protein it encodes is transcribed and translated within the cell. In the case of pathogens, these proteins are presented to the immune system in their native form, mimicking the presentation of antigens during a natural infection. DNA vaccination is particularly useful for the induction of T cell activation. It was applied for viral and bacterial infectious diseases, as well as for allergy and for cancer. The central hypothesis behind active specific immunotherapy for cancer is that tumor cells express unique antigens that should stimulate the immune system. The first DNA vaccine against tumor was carcino-embrionic antigen (CEA). DNA vaccinated animals expressed immunoprotection and immunotherapy of human CEA-expressing syngeneic mouse colon and breast carcinoma (61). In a mouse model of neuroblastoma, DNA immunization with HuD resulted in tumor growth inhibition with no neurological disease (60). Immunity to the brown locus protein, gp75 tyrosinase-related protein-1, associated with melanoma, was investigated in a syngeneic mouse model. Priming with human gp75 DNA broke tolerance to mouse gp75. Immunity against mouse gp75 provided significant tumor protection (60).

Glycosyl hydrolases:

Glycosyl hydrolases are a widespread group of enzymes that hydrolyze the o-glycosidic bond between two or more carbohydrates or between a carbohydrate and a noncarbohydrate moiety. The enzymatic hydrolysis of glycosidic bond occurs by using major one or two mechanisms leading to overall retention or inversion of the anomeric configuration. In both mechanisms catalysis involves two residues: a proton donor and a nucleophile. Glycosyl hydrolyses have been classified into 58 families based on amino acid similarities. The glycosyl hydrolyses from families 1, 2, 5, 10, 17, 30, 35, 39 and 42 act on a large variety of substrates, however, they all hydrolyze the glycosidic bond in a general acid catalysis mechanism, with retention of the anomeric configuration. The mechanism involves two glutamic acid residues, which are the proton donors and the nucleophile, with an aspargine always preceding the proton donor. Analyses of a set of known 3D structures from this group revealed that their catalytic domains, despite the low level of sequence identity, adopt a similar ($\alpha/\beta$) 8 fold with the proton donor and the nucleophile located at the C-terminal ends of strands $\beta 4$ and $\beta 7$, respectively. Mutations in the functional conserved amino acids of lysosomal glycosyl hydrolases were identified in lysosomal storage diseases.

Lysosomal glycosyl hydrolases including $\beta$-glucuronidase, $\beta$-manosidase, $\beta$-glucocerebrosidase, $\beta$-galactosidase and $\alpha$-L iduronidase, are all exo-glycosyl hydrolases, belong to the GH-A clan and share a similar catalytic site. However, many endo-glucanases from various organisms, such as bacterial and fungal xylenases and cellulases share this catalytic domain.

Genomic sequence of hpa gene and its implications:

It is well established that heparanase activity is correlated with cancer metastasis. This correlation was demonstrated at the level of enzymatic activity as well as the levels of protein and hpa cDNA expression in highly metastatic cancer cells as compared with non-metastatic cells. As such, inhibition of heparanase activity is desirable, and has been attempted by several means. The genomic region, encoding the hpa gene and the surrounding, provides a new powerful tool for regulation of heparanase activity at the level of gene expression. Regulatory sequences may reside in noncoding regions both upstream and downstream the transcribed region as well as in intron sequences. A DNA sequence upstream of the transcription start site contains the promoter region and potential regulatory elements. Regulatory factors, which interact with the promoter region may be identified and be used as potential drugs for inhibition of cancer, metastasis and inflammation. The promoter region can be used to screen for inhibitors of heparanase gene expression. Furthermore, the hpa promoter can be used to direct cell specific, particularly cancer cell specific, expression of foreign genes, such as cytotoxic or apoptotic genes, in order to specifically destroy cancer cells.

Cancer and yet unknown related genetic disorders may involve rearrangements and mutations in the heparanase gene, either in coding or non-coding regions. Such mutations may affect expression level or enzymatic activity. The genomic sequence of hpa enables the amplification of specific genomic DNA fragments, identification and diagnosis of mutations.

There is thus a widely recognized need for, and it would be highly advantageous to have genomic, cDNA and composite polynucleotides encoding a polypeptide having heparanase activity, vectors including same, genetically modified cells expressing heparanase and a recombinant protein having heparanase activity, as well as antisense oligonucleotides, constructs and ribozymes which can be used for down regulation heparanase activity.

SUMMARY OF THE INVENTION

Cloning of the human hpa gene which encodes heparanase, and expression of recombinant heparanase by transfected host cells is reported herein, as well as down-regulation of heparanase activity by antisense technology.

A purified preparation of heparanase isolated from human hepatoma cells was subjected to tryptic digestion and microsequencing. The YGPDVGQPR (SEQ ID NO:8) sequence revealed was used to screen EST databases for homology to the corresponding back translated DNA sequence. Two closely related EST sequences were identified and were thereafter found to be identical. Both clones contained an insert of 1020 bp which included an open reading frame of 973 bp followed by a 27 bp of 3' untranslated region and a Poly A tail. Translation start site was not identified.

Cloning of the missing 5' end of hpa was performed by PCR amplification of DNA from placenta Marathon RACE cDNA composite using primers selected according to the EST clones sequence and the linkers of the composite. A 900 bp PCR fragment, partially overlapping with the identified 3' encoding EST clones was obtained. The joined cDNA fragment (hpa), 1721 bp long (SEQ ID NO:9), contained an open reading frame which encodes a polypeptide of 543 amino acids (SEQ ID NO:10) with a calculated molecular weight of 61,192 daltons.

Cloning an extended 5' sequence was enabled from the human SK-hep1 cell line by PCR amplification using the Marathon RACE. The 5' extended sequence of the SK-hep1 hpa cDNA was assembled with the sequence of the hpa cDNA isolated from human placenta (SEQ ID NO:9). The assembled sequence contained an open reading frame, SEQ ID NOs: 13 and 15, which encodes, as shown in SEQ ID NOs:14 and 15, a polypeptide of 592 amino acids with a calculated molecular weight of 66,407 daltons.

The ability of the hpa gene product to catalyze degradation of heparan sulfate in an in vitro assay was examined by expressing the entire open reading frame of hpa in insect cells, using the Baculovirus expression system. Extracts and conditioned media of cells infected with virus containing the hpa gene, demonstrated a high level of heparan sulfate degradation activity both towards soluble ECM-derived HSPG and intact ECM. This degradation activity was inhibited by heparin, which is another substrate of heparanase. Cells infected with a similar construct containing no hpa gene had no such activity, nor did non-infected cells. The ability of heparanase expressed from the extended 5' clone towards heparin was demonstrated in a mammalian expression system.

The expression pattern of hpa RNA in various tissues and cell lines was investigated using RT-PCR. It was found to be expressed only in tissues and cells previously known to have heparanase activity.

A panel of monochromosomal human/CHO and human/mouse somatic cell hybrids was used to localize the human heparanase gene to human chromosome 4. The newly isolated heparanase sequence can be used to identify a chromosome region harboring a human heparanase gene in a chromosome spread.

A human genomic library was screened and the human locus harboring the heparanase gene isolated, sequenced and characterized. Alternatively spliced heparanase mRNAs were identified and characterized. The human heparanase promoter has been isolated, identified and positively tested for activity. The mouse heparanase promoter has been isolated and identified as well. Antisense heparanase constructs were prepared and their influence on cells in vitro tested. A predicted heparanase active site was identified. And finally, the presence of sequences hybridizing with human heparanase sequences was demonstrated for a variety of mammalians and for an avian.

According to one aspect of the present invention there is provided an isolated nucleic acid comprising a genomic, complementary or composite polynucleotide sequence encoding a polypeptide having heparanase catalytic activity.

According to further features in preferred embodiments of the invention described below, the polynucleotide or a portion thereof is hybridizable with SEQ ID NOs: 9, 13, 42, 43 or a portion thereof at 68° C. in 6×SSC, 1% SDS, 5×Denharts, 10% dextran sulfate, 100 µg/ml salmon sperm DNA, and $^{32}$p labeled probe and wash at 68° C. with 3×SSC and 0.1% SDS.

According to still further features in the described preferred embodiments the polynucleotide or a portion thereof is at least 60% identical with SEQ ID NOs: 9, 13, 42, 43 or portions thereof as determined using the Bestfit procedure of the DNA sequence analysis software package developed by the Genetic Computer Group (GCG) at the university of Wisconsin (gap creation penalty—12, gap extension penalty—4).

According to still further features in the described preferred embodiments the polypeptide is as set forth in SEQ ID NOs:10, 14, 44 or portions thereof.

According to still further features in the described preferred embodiments the polypeptide is at least 60% homologous to SEQ ID NOs: 10, 14, 44 or portions thereof as determined with the Smith-Waterman algorithm, using the Bioaccelerator platform developed by Compugene (gapop: 10.0, gapext: 0.5, matrix: blosum62).

According to additional aspects of the present invention there are provided a nucleic acid construct (vector) comprising the isolated nucleic acid described herein and a host cell comprising the construct.

According to a further aspect of the present invention there is provided an antisense oligonucleotide comprising a polynucleotide or a polynucleotide analog of at least 10 bases being hybridizable in vivo, under physiological conditions, with a portion of a polynucleotide strand encoding a polypeptide having heparanase catalytic activity.

According to an additional aspect of the present invention there is provided a method of in vivo downregulating heparanase activity comprising the step of in vivo administering the antisense oligonucleotide herein described.

According to yet an additional aspect of the present invention there is provided a pharmaceutical composition comprising the antisense oligonucleotide herein described and a pharmaceutically acceptable carrier.

According to still an additional aspect of the present invention there is provided a ribozyme comprising the antisense oligonucleotide described herein and a ribozyme sequence.

According to a further aspect of the present invention there is provided an antisense nucleic acid construct comprising a promoter sequence and a polynucleotide sequence directing the synthesis of an antisense RNA sequence of at least 10 bases being hybridizable in vivo, under physiological conditions, with a portion of a polynucleotide strand encoding a polypeptide having heparanase catalytic activity.

According to further features in preferred embodiments of the invention described below, the polynucleotide strand encoding the polypeptide having heparanase catalytic activity is as set forth in SEQ ID NOs: 9, 13, 42 or 43.

According to still further features in the described preferred embodiments the polypeptide having heparanase catalytic activity is as set forth in SEQ ID NOs: 10, 14 or 44.

According to still a further aspect of the present invention there is provided a method of in vivo downregulating heparanase activity comprising the step of in vivo administering the antisense nucleic acid construct herein described.

According to yet a further aspect of the present invention there is provided a pharmaceutical composition comprising the antisense nucleic acid construct herein described and a pharmaceutically acceptable carrier.

According to a further aspect of the present invention there is provided a nucleic acid construct comprising a polynucleotide sequence functioning as a promoter, the polynucleotide sequence is derived from SEQ ID NO:42 and includes at least nucleotides 2535–2635 thereof or from SEQ ID NO:43 and includes at least nucleotides 320–420.

According to a further aspect of the present invention there is provided a method of expressing a polynucleotide sequence comprising the step of ligating the polynucleotide sequence into the nucleic acid construct described above, downstream of the polynucleotide sequence derived from SEQ ID NOs:42 or 43.

According to a further aspect of the present invention there is provided a recombinant protein comprising a polypeptide having heparanase catalytic activity.

According to further features in preferred embodiments of the invention described below, the polypeptide includes at least a portion of SEQ ID NOs:10, 14 or 44.

According to still further features in the described preferred embodiments the protein is encoded by a polynucleotide hybridizable with SEQ ID NOs: 9, 13, 42, 43 or a portion thereof at 68° C. in 6×SSC, 1% SDS, 5×Denharts, 10% dextran sulfate, 100 μg/ml salmon sperm DNA, and $^{32}$p labeled probe and wash at 68° C. with 3×SSC and 0.1% SDS.

According to still further features in the described preferred embodiments the protein is encoded by a polynucleotide at least 60% identical with SEQ ID NOs: 9, 13, 42, 43 or portions thereof as determined using the Bestfit procedure of the DNA sequence analysis software package developed by the Genetic Computer Group (GCG) at the university of Wisconsin (gap creation penalty—12, gap extension penalty—4).

According to a further aspect of the present invention there is provided a pharmaceutical composition comprising, as an active ingredient, the recombinant protein herein described.

According to a further aspect of the present invention there is provided a method of identifying a chromosome region harboring a heparanase gene in a chromosome spread comprising the steps of (a) hybridizing the chromosome spread with a tagged polynucleotide probe encoding heparanase; (b) washing the chromosome spread, thereby removing excess of non-hybridized probe; and (c) searching for signals associated with the hybridized tagged polynucleotide probe, wherein detected signals being indicative of a chromosome region harboring a heparanase gene.

According to a further aspect of the present invention there is provided a method of in vivo eliciting anti-heparanase antibodies comprising the steps of administering a nucleic acid construct including a polynucleotide segment corresponding to at least a portion of SEQ ID NOs:9, 13 or 43 and a promoter for directing the expression of said polynucleotide segment in vivo. Accordingly, there is provided also a DNA vaccine for in vivo eliciting anti-heparanase antibodies comprising a nucleic acid construct including a polynucleotide segment corresponding to at least a portion of SEQ ID NOs:9, 13 or 43 and a promoter for directing the expression of said polynucleotide segment in vivo.

The present invention can be used to develop new drugs to inhibit tumor cell metastasis, inflammation and autoimmunity. The identification of the hpa gene encoding for heparanase enzyme enables the production of a recombinant enzyme in heterologous expression systems. Additional features, advantages, uses and applications of the present invention in biological science and in diagnostic and therapeutic medicine are described hereinafter.

BRIEF DESCRIPTION OF THE DRAWINGS

The invention herein described, by way of example only, with reference to the accompanying drawings, wherein:

FIG. 1 presents nucleotide sequence and deduced amino acid sequence of hpa cDNA (SEQ ID NO: 11). A single nucleotide difference at position 799 (A to T) between the EST (Expressed Sequence Tag) and the PCR amplified cDNA (reverse transcribed RNA) and the resulting amino acid substitution (Tyr to Phe) are indicated above and below the substituted unit, respectively. Cysteine residues and the poly adenylation consensus sequence are underlined. The asterisk denotes the stop codon TGA.

FIGS. 3a–b demonstrate degradation of soluble sulfate labeled HSPG substrate by the culture medium of pFhpa2 and pFhpa4 infected cells. Culture media of High Five cells infected with pFhpa2 (3a) or pFhpa4 (3b) viruses (●), or with control viruses (□) were incubated (18 h, 37° C.) with sulfate labeled ECM-derived soluble HSPG (peak I, ◇). The incubation media were then subjected to gel filtration on Sepharose 6B. Low molecular weight HS degradation fragments (peak II) were produced only during incubation with the hpa gene containing viruses. There was no degradation of the HSPG substrate by the culture medium of cells infected with control viruses.

FIG. 13 presents a comparison between nucleotide sequences of the human hpa and a mouse EST cDNA fragment (SEQ ID NO:12) which is 80% homologous to the 3' end (starting at nucleotide 1066 of SEQ ID NO:9) of the human hpa. The aligned termination codons are underlined.

FIGS. 16a–p presents the nucleotide sequence of the genomic region of the hpa gene (SEQ ID NO: 42). Exon sequences appear in upper case and intron sequences in lower case. The deduced amino acid sequence of the exons is printed below the nucleotide sequence. Two predicted transcription start sites are shown in bold.

FIG. 17 presents an alignment of the amino acid sequences of human heparanase (SEQ ID NO: 11), mouse (SEQ ID NOS: 44, 45) and partial sequences of rat homologues (SEQ ID NOS: 46, 47). The human and the mouse sequences were determined by sequence analysis of the isolated cDNAs. The rat sequence is derived from two different EST clones, which represent two different regions (5' and 3') of the rat hpa cDNA. The human sequence and the amino acids in the mouse and rat homologues, which are identical to the human sequence, appear in bold.

DESCRIPTION OF THE PREFERRED EMBODIMENTS

Figure 2:
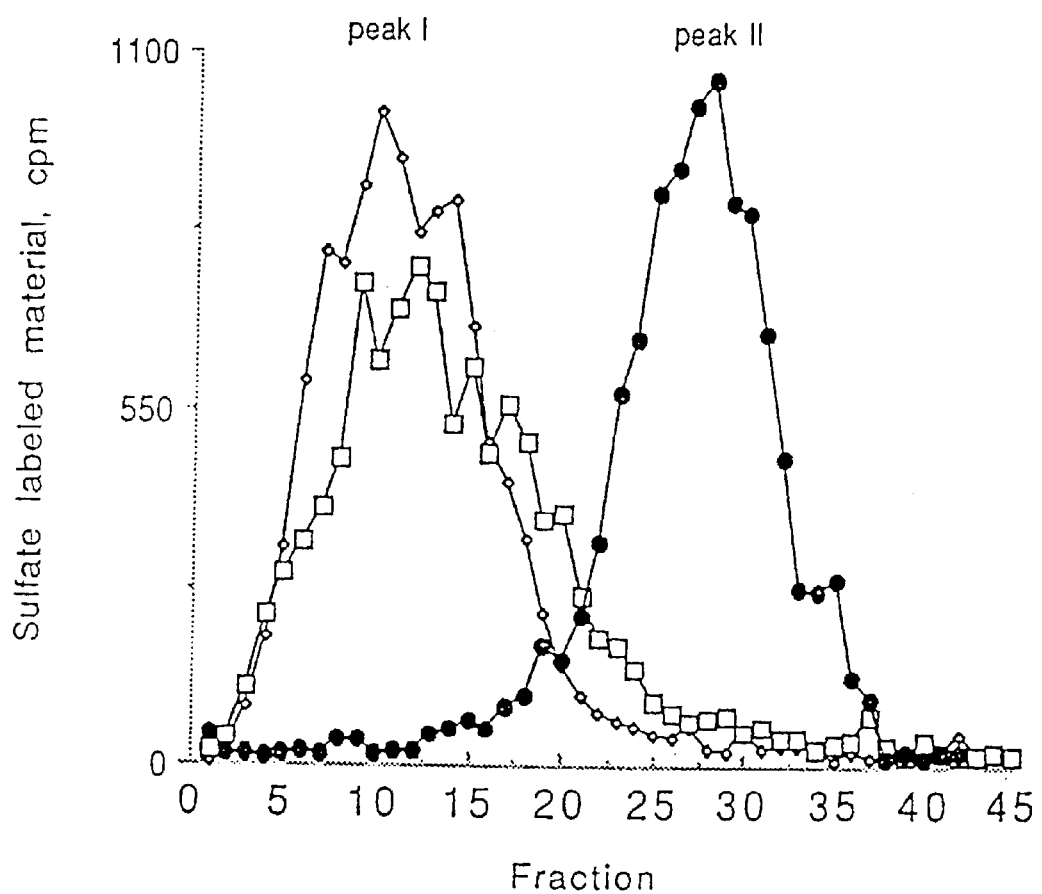
FIG. 2 demonstrates degradation of soluble sulfate labeled HSPG substrate by lysates of High Five cells infected with pFhpa2 virus. Lysates of High Five cells that were infected with pFhpa2 virus (●) or control pF2 virus (□) were incubated (18 h, 37° C.) with sulfate labeled ECM-derived soluble HSPG (peak I). The incubation medium was then subjected to gel filtration on Sepharose 6B. Low molecular weight HS degradation fragments (peak II) were produced only during incubation with the pFhpa2 infected cells, but there was no degradation of the HSPG substrate (◇) by lysates of pF2 infected cells.

The present invention is of a polynucleotide or nucleic acid, referred to hereinbelow interchangeably as hpa, hpa cDNA or hpa gene or identified by its SEQ ID NOs, encoding a polypeptide having heparanase activity, vectors or nucleic acid constructs including same and which are used for over-expression or antisense inhibition of heparanase, genetically modified cells expressing same, recombinant protein having heparanase activity, antisense oligonucleotides and ribozymes for heparanase modulation, and heparanase promoter sequences which can be used to direct the expression of desired genes.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Cloning of the human and mouse hpa genes, cDNAs and genomic sequence (for human), encoding heparanase and expressing recombinant heparanase by transfected cells is reported herein. These are the first mammalian heparanase genes to be cloned.

A purified preparation of heparanase isolated from human hepatoma cells was subjected to tryptic digestion and microsequencing.

The YGPDVGQPR (SEQ ID NO:8) sequence revealed was used to screen EST databases for homology to the corresponding back translated DNA sequences. Two closely related EST sequences were identified and were thereafter found to be identical.

Both clones contained an insert of 1020 bp which includes an open reading frame of 973 bp followed by a 3' untranslated region of 27 bp and a Poly A tail, whereas a translation start site was not identified.

Cloning of the missing 5' end was performed by PCR amplification of DNA from placenta Marathon RACE cDNA composite using primers selected according to the EST clones sequence and the linkers of the composite.

A 900 bp PCR fragment, partially overlapping with the identified 3' encoding EST clones was obtained. The joined cDNA fragment (hpa), 1721 bp long (SEQ ID NO:9), contained an open reading frame which encodes, as shown in FIG. 1 and SEQ ID NO:11, a polypeptide of 543 amino acids (SEQ ID NO:10) with a calculated molecular weight of 61,192 daltons.

A single nucleotide difference at position 799 (A to T) between the EST clones and the PCR amplified cDNA was observed. This difference results in a single amino acid substitution (Tyr to Phe) (FIG. 1). Furthermore, the published EST sequences contained an unidentified nucleotide, which following DNA sequencing of both the EST clones was resolved into two nucleotides (G and C at positions 1630 and 1631 in SEQ ID NO:9, respectively).

The ability of the hpa gene product to catalyze degradation of heparan sulfate in an in vitro assay was examined by expressing the entire open reading frame in insect cells, using the Baculovirus expression system.

Extracts and conditioned media of cells infected with virus containing the hpa gene, demonstrated a high level of heparan sulfate degradation activity both towards soluble ECM-derived HSPG and intact ECM, which was inhibited by heparin, while cells infected with a similar construct containing no hpa gene had no such activity, nor did non-infected cells.

The expression pattern of hpa RNA in various tissues and cell lines was investigated using RT-PCR. It was found to be expressed only in tissues and cells previously known to have heparanase activity.

Cloning an extended 5' sequence was enabled from the human SK-hep1 cell line by PCR amplification using the Marathon RACE. The 5' extended sequence of the SK-hep1 hpa cDNA was assembled with the sequence of the hpa cDNA isolated from human placenta (SEQ ID NO:9). The assembled sequence contained an open reading frame, SEQ ID NOs: 13 and 15, which encodes, as shown in SEQ ID NOs: 14 and 15, a polypeptide of 592 amino acids, with a calculated molecular weight of 66,407 daltons. This open reading frame was shown to direct the expression of catalytically active heparanase in a mammalian cell expression system. The expressed heparanase was detectable by anti heparanase antibodies in Western blot analysis.

A panel of monochromosomal human/CHO and human/ mouse somatic cell hybrids was used to localize the human heparanase gene to human chromosome 4. The newly isolated heparanase sequence can therefore be used to identify a chromosome region harboring a human heparanase gene in a chromosome spread.

The hpa cDNA was then used as a probe to screen a human genomic library. Several phages were positive. These phages were analyzed and were found to cover most of the hpa locus, except for a small portion which was recovered by bridging PCR. The hpa locus covers about 50,000 bp. The hpa gene includes 12 exons separated by 11 introns.

RT-PCR performed on a variety of cells revealed alternatively spliced hpa transcripts.

The amino acid sequence of human heparanase was used to search for homologous sequences in the DNA and protein databases. Several human EST's were identified, as well as mouse sequences highly homologous to human heparanase. The following mouse EST's were identified AA177901, AA674378, AA67997, AA047943, AA690179, AI122034, all sharing an identical sequence and correspond to amino acids 336–543 of the human heparanase sequence. The entire mouse heparanase cDNA was cloned, based on the nucleotide sequence of the mouse EST's using Marathon cDNA libraries. The mouse and the human hpa genes share an average homology of 78% between the nucleotide sequences and 81% similarity between the deduced amino acid sequences. hpa homologous sequences from rat were also uncovered (EST's AI060284 and AI237828).

Homology search of heparanase amino acid sequence against the DNA and the protein databases and prediction of its protein secondary structure enabled to identify candidate amino acids that participate in the heparanase active site.

Expression of hpa antisense in mammalian cell lines resulted in about five fold decrease in the number of recoverable cells as compared to controls.

Human Hpa cDNA was shown to hybridize with genomic DNAs of a variety of mammalian species and with an avian.

The human and mouse hpa promoters were identified and the human promoter was tested positive in directing the expression of a reporter gene.

Thus, according to the present invention there is provided an isolated nucleic acid comprising a genomic, complementary or composite polynucleotide sequence encoding a polypeptide having heparanase catalytic activity.

The phrase "composite polynucleotide sequence" refers to a sequence which includes exonal sequences required to encode the polypeptide having heparanase activity, as well as any number of intronal sequences. The intronal sequences can be of any source and typically will include conserved splicing signal sequences. Such intronal sequences may further include cis acting expression regulatory elements.

The term "heparanase catalytic activity" or its equivalent term "heparanase activity" both refer to a mammalian endoglycosidase hydrolyzing activity which is specific for heparan or heparan sulfate proteoglycan substrates, as opposed to the activity of bacterial enzymes (heparinase I, II and III) which degrade heparin or heparan sulfate by means of β-elimination (37).

According to a preferred embodiment of the present invention the polynucleotide or a portion thereof is hybridizable with SEQ ID NOs: 9, 13, 42, 43 or a portion thereof at 68° C. in 6×SSC, 1% SDS, 5×Denharts, 10% dextran sulfate, 100 μg/ml salmon sperm DNA, and $^{32}$p labeled probe and wash at 68° C. with 3, 2, 1, 0.5 or 0.1×SSC and 0.1% SDS.

According to another preferred embodiment of the present invention the polynucleotide or a portion thereof is at least 60%, preferably at least 65%, more preferably at least 70%, more preferably at least 75%, more preferably at least 80%, more preferably at least 85%, more preferably at least 90%, most preferably, 95–100% identical with SEQ ID NOs: 9, 13, 42, 43 or portions thereof as determined using the Bestfit procedure of the DNA sequence analysis software package developed by the Genetic Computer Group (GCG) at the university of Wisconsin (gap creation penalty—12, gap extension penalty—4—which are the default parameters).

According to another preferred embodiment of the present invention the polypeptide encoded by the polynucleotide sequence is as set forth in SEQ ID NOs:10, 14, 44 or portions thereof having heparanase catalytic activity. Such portions are expected to include amino acids Asp-Glu 224–225 (SEQ ID NO:10), which can serve as proton donors and glutamic acid 343 or 396 which can serve as a nucleophile.

According to another preferred embodiment of the present invention the polypeptide encoded by the polynucleotide sequence is at least 60%, preferably at least 65%, more preferably at least 70%, more preferably at least 75%, more preferably at least 80%, more preferably at least 85%, more preferably at least 90%, most preferably, 95–100% homologous (both similar and identical acids) to SEQ ID NOs: 10, 14, 44 or portions thereof as determined with the Smith-Waterman algorithm, using the Bioaccelerator platform developed by Compugene (gapop: 10.0, gapext: 0.5, matrix: blosum62, see also the description to FIG. 17).

Further according to the present invention there is provided a nucleic acid construct comprising the isolated nucleic acid described herein. The construct may and preferably further include an origin of replication and trans regulatory elements, such as promoter and enhancer sequences.

The construct or vector can be of any type. It may be a phage which infects bacteria or a virus which infects eukaryotic cells. It may also be a plasmid, phagemid, cosmid, bacmid or an artificial chromosome.

Further according to the present invention there is provided a host cell comprising the nucleic acid construct described herein. The host cell can be of any type. It may be a prokaryotic cell, an eukaryotic cell, a cell line, or a cell as a portion of an organism. The polynucleotide encoding heparanase can be permanently or transiently present in the cell. In other words, genetically modified cells obtained following stable or transient transfection, transformation or transduction are all within the scope of the present invention. The polynucleotide can be present in the cell in low copy (say 1–5 copies) or high copy number (say 5–50 copies or more). It may be integrated in one or more chromosomes at any location or be present as an extrachromosomal material.

The present invention is further directed at providing a heparanase over-expression system which includes a cell overexpressing heparanase catalytic activity. The cell may be a genetically modified host cell transiently or stably transfected or transformed with any suitable vector which includes a polynucleotide sequence encoding a polypeptide having heparanase activity and a suitable promoter and enhancer sequences to direct over-expression of heparanase. However, the overexpressing cell may also be a product of an insertion (e.g., via homologous recombination) of a promoter and/or enhancer sequence downstream to the endogenous heparanase gene of the expressing cell, which will direct over-expression from the endogenous gene.

The term "over-expression" as used herein in the specification and claims below refers to a level of expression which is higher than a basal level of expression typically characterizing a given cell under otherwise identical conditions.

According to another aspect the present invention provides an antisense oligonucleotide comprising a polynucleotide or a polynucleotide analog of at least 10, preferably 11–15, more preferably 16–17, more preferably 18, more preferably 19–25, more preferably 26–35, most preferably 35–100 bases being hybridizable in vivo, under physiological conditions, with a portion of a polynucleotide strand encoding a polypeptide having heparanase catalytic activity. The antisense oligonucleotide can be used for downregulating heparanase activity by in vivo administration thereof to a patient. As such, the antisense oligonucleotide according to the present invention can be used to treat types of cancers which are characterized by impaired (over) expression of heparanase, and are dependent on the expression of heparanase for proliferating or forming metastases.

The antisense oligonucleotide can be DNA or RNA or even include nucleotide analogs, examples of which are provided in the Background section hereinabove. The antisense oligonucleotide according to the present invention can be synthetic and is preferably prepared by solid phase synthesis. In addition, it can be of any desired length which still provides specific base pairing (eg., 8 or 10, preferably more, nucleotides long) and it can include mismatches that do not hamper base pairing under physiological conditions.

Further according to the present invention there is provided a pharmaceutical composition comprising the antisense oligonucleotide herein described and a pharmaceutically acceptable carrier. The carrier can be, for example, a liposome loadable with the antisense oligonucleotide.

According to a preferred embodiment of the present invention the antisense oligonucleofide further includes a ribozyme sequence. The ribozyme sequence serves to cleave a heparanase RNA molecule to which the antisense oligonucleotide binds, to thereby downregulate heparanase expression.

Further according to the present invention there is provided an anfisense nucleic acid construct comprising a promoter sequence and a polynucleotide sequence directing the synthesis of an antisense RNA sequence of at least 10 bases being hybridizable in vivo, under physiological conditions, with a portion of a polynucleotide strand encoding a polypeptide having heparanase catalytic activity. Like the antisense oligonucleotide, the antisense construct can be used for downregulating heparanase activity by in vivo administration thereof to a patient. As such, the antisense construct, like the antisense oligonucleotide, according to the present invention can be used to treat types of cancers which are characterized by impaired (over) expression of heparanase, and are dependent on the expression of heparanase for proliferating or forming metastases.

Thus, further according to the present invention there is provided a pharmaceutical composition comprising the antisense construct herein described and a pharmaceutically acceptable carrier. The carrier can be, for example, a liposome loadable with the antisense construct.

Formulations for topical administration may include, but are not limited to, lotions, ointments, gels, creams, suppositories, drops, liquids, sprays and powders. Conventional pharmaceutical carriers, aqueous, powder or oily bases, thickeners and the like may be necessary or desirable. Coated condoms, stents, active pads, and other medical devices may also be useful. Compositions for oral administration include powders or granules, suspensions or solutions in water or non-aqueous media, sachets, capsules or tablets. Thickeners, diluents, flavorings, dispersing aids, emulsifiers or binders may be desirable. Formulations for parenteral administration may include, but are not limited to, sterile aqueous solutions which may also contain buffers, diluents and other suitable additives.

Dosing is dependent on severity and responsiveness of the condition to be treated, but will normally be one or more doses per day, week or month with course of treatment lasting from several days to several months or until a cure is effected or a diminution of disease state is achieved. Persons ordinarily skilled in the art can easily determine optimum dosages, dosing methodologies and repetition rates.

Further according to the present invention there is provided a nucleic acid construct comprising a polynucleotide sequence functioning as a promoter, the polynucleotide sequence is derived from SEQ ID NO:42 and includes at least nucleotides 2135–2635, preferably 2235–2635, more preferably 2335–2635, more preferably 2435–2635, most preferably 2535–2635 thereof, or SEQ ID NO:43 and includes at least nucleotides 1–420, preferably 120–420, more preferably 220–420, most preferably 320–420, thereof These nucleotides are shown in the example section that follows to direct the synthesis of a reporter gene in transformed cells. Thus, further according to the present invention there is provided a method of expressing a polynucleotide sequence comprising the step of ligating the polynucleotide sequence downstream to either of the promoter sequences described herein. Heparanase promoters can be isolated from a variety of mammalian an other species by cloning genomic regions present 5' to the coding sequence thereof. This can be readily achievable by one ordinarily skilled in the art using the heparanase polynucleotides described herein, which are shown in the Examples section that follows to participate in efficient cross species hybridization.

Further according to the present invention there is provided a recombinant protein comprising a polypeptide having heparanase catalytic activity. The protein according to the present invention include modifications known as post translational modifications, including, but not limited to, proteolysis (e.g., removal of a signal peptide and of a pro- or preprotein sequence), methionine modification, glycosylation, alkylation (e.g., methylation), acetylation, etc. According to preferred embodiments the polypeptide includes at least a portion of SEQ ID NOs: 10, 14 or 44, the portion has heparanase catalytic activity. According to preferred embodiments of the present invention the protein is encoded by any of the above described isolated nucleic acids. Further according to the present invention there is provided a pharmaceutical composition comprising, as an active ingredient, the recombinant protein described herein.

The recombinant protein may be purified by any conventional protein purification procedure close to homogeneity and/or be mixed with additives. The recombinant protein may be manufactured using any of the genetically modified cells described above, which include any of the expression nucleic acid constructs described herein. The recombinant protein may be in any form. It may be in a crystallized form, a dehydrated powder form or in solution. The recombinant protein may be useful in obtaining pure heparanase, which in turn may be useful in eliciting anti-heparanase antibodies, either poly or monoclonal antibodies, and as a screening active ingredient in an anti-heparanase inhibitors or drugs screening assay or system.

Further according to the present invention there is provided a method of identifying a chromosome region harboring a human heparanase gene in a chromosome spread the method is executed implementing the following method steps, in which in a first step the chromosome spread (either interphase or metaphase spread) is hybridized with a tagged polynucleotide probe encoding heparanase. The tag is preferably a fluorescent tag. In a second step according to the method the chromosome spread is washed, thereby excess of non-hybridized probe is removed. Finally, signals associated with the hybridized tagged polynucleotide probe are searched for, wherein detected signals being indicative of a chromosome region harboring the human heparanase gene. One ordinarily skilled in the art would know how to use the sequences disclosed herein in suitable labeling reactions and how to use the tagged probes to detect, using in situ hybridization, a chromosome region harboring a human heparanase gene.

Further according to the present invention there is provided a method of in vivo eliciting anti-heparanase antibodies comprising the steps of administering a nucleic acid construct including a polynucleotide segment corresponding to at least a portion of SEQ ID NOs:9, 13 or 43 and a promoter for directing the expression of said polynucleotide segment in vivo. Accordingly, there is provided also a DNA vaccine for in vivo eliciting anti-heparanase antibodies comprising a nucleic acid construct including a polynucleotide segment corresponding to at least a portion of SEQ ID NOs:9, 13 or 43 and a promoter for directing the expression of said polynucleotide segment in vivo. The vaccine optionally further includes a pharmaceutically acceptable carrier, such as a virus, liposome or an antigen presenting cell. Alternatively, the vaccine is employed as a naked DNA vaccine.

The present invention can be used to develop treatments for various diseases, to develop diagnostic assays for these diseases and to provide new tools for basic research especially in the fields of medicine and biology.

Specifically, the present invention can be used to develop new drugs to inhibit tumor cell metastasis, inflammation and autoimmunity. The identification of the hpa gene encoding for the heparanase enzyme enables the production of a recombinant enzyme in heterologous expression systems.

Furthermore, the present invention can be used to modulate bioavailability of heparin-binding growth factors, cellular responses to heparin-binding growth factors (e.g., bFGF, VEGF) and cytokines (e.g., IL-8), cell interaction with plasma lipoproteins, cellular susceptibility to viral, protozoa and some bacterial infections, and disintegration of neurodegenerative plaques. Recombinant heparanase offers a potential treatment for wound healing, angiogenesis, restenosis, atherosclerosis, inflammation, neurodegenerative diseases (such as, for example, Genstmann-Straussler Syndrome, Creutzfeldt-Jakob disease, Scrape and Alzheimer's disease) and certain viral and some bacterial and protozoa infections. Recombinant heparanase can be used to neutralize plasma heparin, as a potential replacement of protamine.

As used herein, the term "modulate" includes substantially inhibiting, slowing or reversing the progression of a disease, substantially ameliorating clinical symptoms of a disease or condition, or substantially preventing the appearance of clinical symptoms of a disease or condition. A "modulator" therefore includes an agent which may modulate a disease or condition. Modulation of viral, protozoa and bacterial infections includes any effect which substantially interrupts, prevents or reduces any viral, bacterial or protozoa activity and/or stage of the virus, bacterium or protozoon life cycle, or which reduces or prevents infection by the virus, bacterium or protozoon in a subject, such as a human or lower animal.

As used herein, the term "wound" includes any injury to any portion of the body of a subject including, but not limited to, acute conditions such as thermal burns, chemical burns, radiation burns, burns caused by excess exposure to ultraviolet radiation such as sunburn, damage to bodily tissues such as the perineum as a result of labor and childbirth, including injuries sustained during medical procedures such as episiotomies, trauma-induced injuries including cuts, those injuries sustained in automobile and other mechanical accidents, and those caused by bullets, knives and other weapons, and post-surgical injuries, as well as chronic conditions such as pressure sores, bedsores, conditions related to diabetes and poor circulation, and all types of acne, etc.

Anti-heparanase antibodies, raised against the recombinant enzyme, would be useful for immunodetection and diagnosis of micrometastases, autoimmune lesions and renal failure in biopsy specimens, plasma samples, and body fluids. Such antibodies may also serve as neutralizing agents for heparanase activity.

The genomic heparanase sequences described herein can be used to construct knock-in and knock-out constructs. Such constructs include a fragment of 10–20 Kb of a heparanase locus and a negative and a positive selection markers and can be used to provide heparanase knock-in and knock-out animal models by methods known to the skilled artisan. Such animal models can be used for studying the function of heparanase in developmental processes, and in normal as well as pathological processes. They can also serve as an experimental model for testing drugs and gene therapy protocols. The complementary heparanase sequence (cDNA) can be used to derive transgenic animals, overexpressing heparanase for same. Alternatively, if cloned in the antisense orientation, the complementary heparanase sequence (cDNA) can be used to derive transgenic animals under-expressing heparanase for same.

The heparanase promoter sequences described herein and other cis regulatory elements linked to the heparanase locus can be used to regulated the expression of genes. For example, these promoters can be used to direct the expression of a cytotoxic protein, such as TNF, in tumor cells. It will be appreciated that heparanase itself is abnormally expressed under the control of its own promoter and other cis acting elements in a variety of tumors, and its expression is correlated with metastasis. It is also abnormally highly expressed in inflammatory cells. The introns of the heparanase gene can be used for the same purpose, as it is known that introns, especially upstream introns include cis acting element which affect expression. A heparanase promoter fused to a reporter protein can be used to study/monitor its activity.

The polynucleotide sequences described herein can also be used to provide DNA vaccines which will elicit in vivo anti heparanase antibodies. Such vaccines can therefore be used to combat inflammatory and cancer.

Antisense oligonucleotides derived according to the heparanase sequences described herein, especially such oligonucleotides supplemented with ribozyme activity, can be used to modulate heparanase expression. Such oligonucleotides can be from the coding region, from the introns or promoter specific. Antisense heparanase nucleic acid constructs can similarly function, as well known in the art.

The heparanase sequences described herein can be used to study the catalytic mechanism of heparanase. Carefully selected site directed mutagenesis can be employed to provide modified heparanase proteins having modified characteristics in terms of, for example, substrate specificity, sensitivity to inhibitors, etc.

While studying heparanase expression in a variety of cell types alternatively spliced transcripts were identified. Such transcripts if found characteristic of certain pathological conditions can be used as markers for such conditions. Such transcripts are expected to direct the synthesis of heparanases with altered functions.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturers' specifications. These techniques and various other techniques are generally performed according to Sambrook et al., Molecular Cloning—A Laboratory Manual, Cold Spring Harbor Laboratory, Cold Spring Harbor, N.Y. (1989), which is incorporated herein by reference. Other general references are provided throughout this document. The procedures therein are believed to be well known in the art and are provided for the convenience of the reader. All the information contained therein is incorporated herein by reference.

The following protocols and experimental details are referenced in the Examples that follow:

Purification and characterization of heparanase from a human hepatoma cell line and human placenta: A human hepatoma cell line (Sk-hep-1) was chosen as a source for purification of a human tumor-derived heparanase. Purification was essentially as described in U.S. Pat. No. 5,362,641 to Fuks, which is incorporated by reference as if fully set forth herein. Briefly, 500 liter, $5\times10^{11}$ cells were grown in suspension and the heparanase enzyme was purified about 240,000 fold by applying the following steps: (i) cation exchange (CM-Sephadex) chromatography performed at pH 6.0, 0.3–1.4 M NaCl gradient; (ii) cation exchange (CM-Sephadex) chromatography performed at pH 7.4 in the presence of 0.1% CHAPS, 0.3–1.1 M NaCl gradient; (iii) heparin-Sepharose chromatography performed at pH 7.4 in the presence of 0.1% CHAPS, 0.35–1.1 M NaCl gradient; (iv) ConA-Sepharose chromatography performed at pH 6.0 in buffer containing 0.1% CHAPS and 1 M NaCl, elution with 0.25 M α-methyl mannoside; and (v) HPLC cation exchange (Mono-S) chromatography performed at pH 7.4 in the presence of 0.1% CHAPS, 0.25–1 M NaCl gradient.

Active fractions were pooled, precipitated with TCA and the precipitate subjected to SDS polyacrylamide gel electrophoresis and/or tryptic digestion and reverse phase HPLC. Tryptic peptides of the purified protein were separated by reverse phase HPLC (C8 column) and homogeneous peaks were subjected to amino acid sequence analysis.

The purified enzyme was applied to reverse phase HPLC and subjected to N-terminal amino acid sequencing using the amino acid sequencer (Applied Biosystems).

Cells: Cultures of bovine corneal endothelial cells (BCECs) were established from steer eyes as previously described (19, 38). Stock cultures were maintained in DMEM (1 g glucose/liter) supplemented with 10% newborn calf serum and 5% FCS. bFGF (1 ng/ml) was added every other day during the phase of active cell growth (13, 14).

Preparation of dishes coated with ECM: BCECs (second to fifth passage) were plated into 4-well plates at an initial density of $2\times10^5$ cells/ml, and cultured in sulfate-free Fisher medium plus 5% dextran T-40 for 12 days. $Na_2{}^{35}SO_4$ (25 µCi/ml) was added on day 1 and 5 after seeding and the cultures were incubated with the label without medium change. The subendothelial ECM was exposed by dissolving (5 min., room temperature) the cell layer with PBS containing 0.5% Triton X-100 and 20 mM $NH_4OH$, followed by four washes with PBS. The ECM remained intact, free of cellular debris and firmly attached to the entire area of the tissue culture dish (19, 22).

To prepare soluble sulfate labeled proteoglycans (peak I material), the ECM was digested with trypsin (25 µg/ml, 6 h, 37° C. ), the digest was concentrated by reverse dialysis and the concentrated material was applied onto a Sepharose 6B gel filtration column. The resulting high molecular weight material (Kav<0.2, peak I) was collected. More than 80% of the labeled material was shown to be composed of heparan sulfate proteoglycans (11, 39).

Heparanase activity: Cells ($1\times10^6$/35-mm dish), cell lysates or conditioned media were incubated on top of $^{35}$S-labeled ECM (18 h, 37° C.) in the presence of 20 mM phosphate buffer (pH 6.2). Cell lysates and conditioned media were also incubated with sulfate labeled peak I material (10–20 µl). The incubation medium was collected, centrifuged (18,000×g, 4° C., 3 min.), and sulfate labeled material analyzed by gel filtration on a Sepharose CL-6B column (0.9×30 cm). Fractions (0.2 ml) were eluted with PBS at a flow rate of 5 ml/h and counted for radioactivity using Bio-fluor scintillation fluid. The excluded volume ($V_o$) was marked by blue 20 dextran and the total included volume ($V_t$) by phenol red. The latter was shown to comigrate with free sulfate (7, 11, 23). Degradation fragments of HS side chains were eluted from Sepharose 6B at 0.5<Kav<0.8 (peak II) (7, 11, 23). A nearly intact HSPG released from ECM by trypsin—and, to a lower extent, during incubation with PBS alone—was eluted next to $V_o$ (Kav<0.2, peak I). Recoveries of labeled material applied on the columns ranged from 85 to 95% in different experiments (11). Each experiment was performed at least three times and the variation of elution positions (Kav values) did not exceed +/–15%.

Cloning of hpa cDNA: cDNA clones 257548 and 260138 were obtained from the I.M.A.G.E Consortium (2130 Memorial Parkway SW, Hunstville, Ala. 35801). The cDNAs were originally cloned in EcoRI and NotI cloning sites in the plasmid vector pT3T7D-Pac. Although these clones are reported to be somewhat different, DNA sequencing demonstrated that these clones are identical to one another. Marathon RACE (rapid amplification of cDNA ends) human placenta (poly-A) cDNA composite was a gift of Prof. Yossi Shiloh of Tel Aviv University. This composite is vector free, as it includes reverse transcribed cDNA fragments to which double, partially single stranded adapters are attached on both sides. The construction of the specific composite employed is described in reference 39a.

Amplification of hp3 PCR fragment was performed according to the protocol provided by Clontech laboratories. The template used for amplification was a sample taken from the above composite. The primers used for amplification were:

First step: 5'-primer: AP1: 5'-CCATCCTAATACGACTCACTATAGGGC-3', SEQ ID

NO:1; 3'-primer: HPL229: 5'-GTAGTGATGCCATGTAACTGAATC-3', SEQ ID NO:2.

Second step: nested 5'-primer: AP2: 5'-ACTCACTATAGGGCTCGAGCGGC-3', SEQ ID NO:3; nested 3'- primer: HPL171: 5'-GCATCTTAGCCGTCTTTCTTCG-3', SEQ ID NO:4. The HPL229 and HPL171 were selected according to the sequence of the EST clones. They include nucleotides 933–956 and 876–897 of SEQ ID NO:9, respectively.

PCR program was 94° C.—4 min., followed by 30 cycles of 94° C.—40 sec., 62° C.—1 min., 72° C.—2.5 min. Amplification was performed with Expand High Fidelity (Boehringer Mannheim). The resulting ca. 900 bp hp3 PCR product was digested with BfrI and PvuII. Clone 257548 (phpa1) was digested with EcoRI, followed by end filling and was then further digested with BfrI. Thereafter the PvuII-BfrI fragment of the hp3 PCR product was cloned into the blunt end—BfrI end of clone phpa1 which resulted in having the entire cDNA cloned in pT3T7-pac vector, designated phpa2.

RT-PCR: RNA was prepared using TRI-Reagent (Molecular research center Inc.) according to the manufacturer instructions. 1.25 µg were taken for reverse transcription reaction using MuMLV Reverse transcriptase (Gibco BRL) and Oligo (dT)$_{15}$ primer, SEQ ID NO:5, (Promega). Amplification of the resultant first strand cDNA was performed with Taq polymerase (Promega). The following primers were used:

HPU-355: 5'-TTCGATCCCAAGAAGGAATCAAC-3', SEQ ID NO:6, nucleotides 372–394 in SEQ ID NOs:9 or 11.

HPL-229: 5'-GTAGTGATGCCATGTAACTGAATC-3', SEQ ID NO:7, nucleotides 933–956 in SEQ ID NOs:9 or 11.

PCR program: 94° C.—4 min., followed by 30 cycles of 94° C.—40 sec., 62° C.—1 min., 72° C.—1 min.

Alternatively, total RNA was prepared from cell cultures using Tri-reagent (Molecular Research Center, Inc.) according to the manufacturer recommendation. Poly A+ RNA was isolated from total RNA using mRNA separator (Clontech). Reverse transcription was performed with total RNA using Superscript II (GibcoBRL). PCR was performed with Expand high fidelity (Boehringer Mannheim). Primers used for amplification were as follows:

Hpu-685, 5'-GAGCAGCCAGGTGAGCCCAAGAT-3', SEQ ID NO:24

Hpu-355, 5'-TTCGATCCCAAGAAGGAATCAAC-3', SEQ ID NO:25

Hpu 565, 5'-AGCTCTGTAGATGTGCTATACAC-3', SEQ ID NO:26

Hpl 967, 5'-TCAGATGCAAGCAGCAACTTTGGC-3', SEQ ID NO:27

Hpl 171, 5'-GCATCTTAGCCGTCTTTCTTCG-3', SEQ ID NO:28

Hpl 229, 5'-GTAGTGATGCCATGTAACTGAATC-3', SEQ ID NO:29

PCR reaction was performed as follows: 94° C. 3 minutes, followed by 32 cycles of 94° C. 40 seconds, 64° C. 1 minute, 72° C. 3 minutes, and one cycle 72° C., 7 minutes.

Expression of recombinant heparanase in insect cells: Cells, High Five and Sf21 insect cell lines were maintained as monolayer cultures in SF900II-SFM medium (GibcoBRL).

Recombinant Baculovirus: Recombinant virus containing the hpa gene was constructed using the Bac to Bac system (GibcoBRL). The transfer vector pFastBac was digested with SalI and NotI and ligated with a 1.7 kb fragment of phpa2 digested with XhoI and NotI. The resulting plasmid was designated pFasthpa2. An identical plasmid designated pFasthpa4 was prepared as a duplicate and both independently served for further experimentations. Recombinant bacmid was generated according to the instructions of the manufacturer with pFasthpa2, pFasthpa4 and with pFastBac. The latter served as a negative control. Recombinant bacmid DNAs were transfected into Sf21 insect cells. Five days after transfection recombinant viruses were harvested and used to infect High Five insect cells, 3×10$^6$ cells in T-25 flasks. Cells were harvested 2–3 days after infection. 4×10$^6$ cells were centrifuged and resuspended in a reaction buffer containing 20 mM phosphate citrate buffer, 50 mM NaCl. Cells underwent three cycles of freeze and thaw and lysates were stored at −80° C. Conditioned medium was stored at 4° C.

Figure 10A:
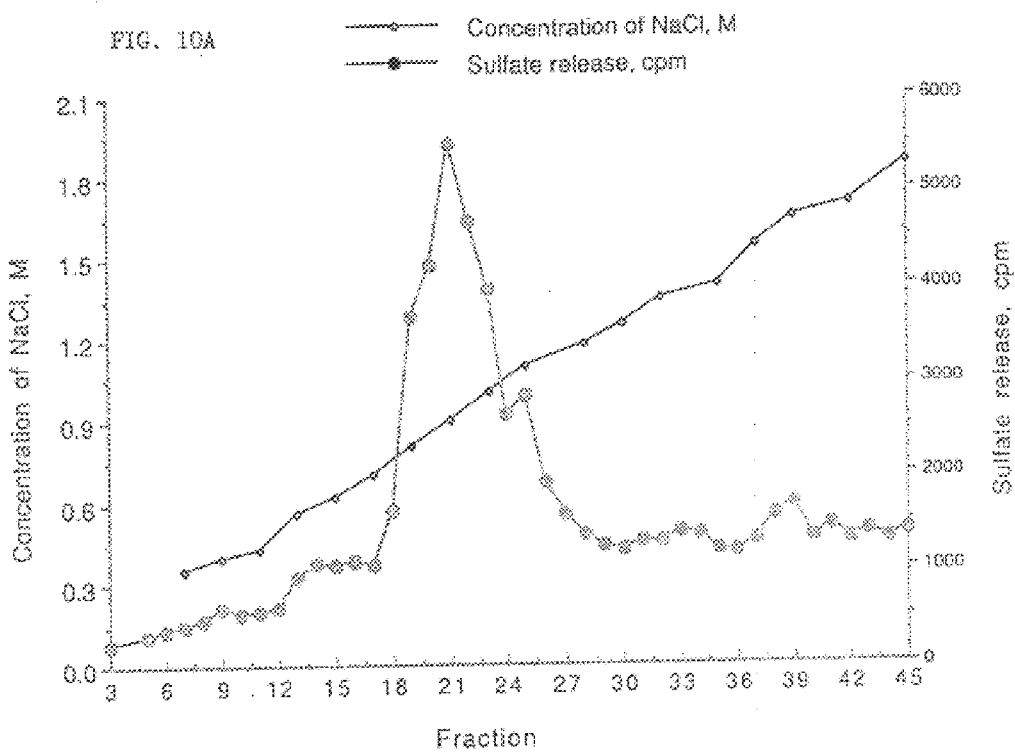
FIGS. 10a–b demonstrate purification of recombinant heparanase on heparin-Sepharose. Culture medium of Sf21 cells infected with pFhpa4 virus was subjected to heparin-Sepharose chromatography. Elution of fractions was performed with 0.35–2 M NaCl gradient (◊). Heparanase activity in the eluted fractions is demonstrated in FIG. 10a (●). Fractions 15–28 were subjected to 15% SDS-polyacrylamide gel electrophoresis followed by silver nitrate staining. A correlation is demonstrated between a major protein band (MW~63,000) in fractions 19–24 and heparanase activity.

Partial purification of recombinant heparanase: Partial purification of recombinant heparanase was performed by heparin-Sepharose column chromatography followed by Superdex 75 column gel filtration. Culture medium (150 ml) of Sf21 cells infected with pFhpa4 virus was subjected to heparin-Sepharose chromatography. Elution of 1 ml fractions was performed with 0.35–2 M NaCl gradient in presence of 0.1% CHAPS and 1 mM DTT in 10 mM sodium acetate buffer, pH 5.0. A 25 µl sample of each fraction was tested for heparanase activity. Heparanase activity was eluted at the range of 0.65–1.1 M NaCl (fractions 18–26, FIG. 10a). 5 µl of each fraction was subjected to 15% SDS-polyacrylamide gel electrophoresis followed by silver nitrate staining. Active fractions eluted from heparin-Sepharose (FIG. 10a) were pooled and concentrated (×6) on YM3 cut-off membrane. 0.5 ml of the concentrated material was applied onto 30 ml Superdex 75 FPLC column equilibrated with 10 mM sodium acetate buffer, pH 5.0, containing 0.8 M NaCl, 1 mM DTT and 0.1% CHAPS. Fractions (0.56 ml) were collected at a flow rate of 0.75 ml/min. Aliquots of each fraction were tested for heparanase activity and were subjected to SDS-polyacrylamide gel electrophoresis followed by silver nitrate staining (FIG. 11b).

PCR amplification of genomic DNA: 94° C. 3 minutes, followed by 32 cycles of 94° C. 45 seconds, 64° C. 1 minute, 68° C. 5 minutes, and one cycle at 72° C., 7 minutes. Primers used for amplification of genomic DNA included:

GHpu-L3 5'-AGGCACCCTAGAGATGTTCCAG-3', SEQ ID NO:30

GHpl-L6 5'-GAAGATTTCTGTTTCCATGACGTG-3', SEQ ID NO:31.

Screening of genomic libraries: A human genomic library in Lambda phage EMBLE3 SP6/T7 (Clontech, Paulo Alto, CA) was screened. 5×10$^5$ plaques were plated at 5×10$^4$ pfu/plate on NZCYM agar/top agarose plates. Phages were absorbed on nylon membranes in duplicates (Qiagen). Hybridization was performed at 65° C. in 5×SSC, 5×Denhart's, 10% dextran sulfate, 100 µg/ml Salmon sperm, $^{32}$p labeled probe (10$^6$ cpm/ml). A 1.6 kb fragment, containing the entire hpa cDNA was labeled by random priming (Boehringer Mannheim). Following hybridization membranes were washed once with 2×SSC, 0.1% SDS at 65° C. for 20 minutes, and twice with 0.2×SSC, 0.1% SDS at 65° C. for 15 minutes. Hybridizing plaques were picked, and plated at 100 pfu/plate. Hybridization was performed as above and single isolated positive plaques were picked.

Phage DNA was extracted using a Lambda DNA extraction kit (Qiagen). DNA was digested with XhoI and EcoRI, separated on 0.7% agarose gel and transferred to nylon membrane Hybond N+ (Amersham). Hybridization and washes were performed as above.

cDNA Sequence analysis: Sequence determinations were performed with vector specific and gene specific primers, using an automated DNA sequencer (Applied Biosystems, model 373A). Each nucleotide was read from at least two independent primers.

Genomic sequence analysis: Large-scale sequencing was performed by Commonwealth Biotechnology Incorporation.

Isolation of mouse hpa: Mouse hpa cDNA was amplified from either Marathon ready cDNA library of mouse embryo or from mRNA isolated from mouse melanoma cell line BL6, using the Marathon RACE kit from Clontech. Both procedures were performed according to the manufacturer's recommendation.

Primers used for PCR amplification of mouse hpa:

Mhpl773 5'-CCACACTGAATGTAATACTGAAGTG-3', SEQ ID NO:32

MHpl736 5'-CGAAGCTCTGGAACTCGGCAAG-3', SEQ ID NO:33

MHpl83 5'-GCCAGCTGCAAAGGTGTTGGAC-3', SEQ ID NO:34

Mhpl152 5'-AACACCTGCCTCATCACGACTTC-3', SEQ ID NO:35

Mhpl114 5'-GCCAGGCTGGCGTCGATGGTGA-3', SEQ ID NO:36

MHpl103 5'-GTCGATGGTGATGGACAGGAAC-3', SEQ ID NO:37

Ap1 5'-GTAATACGACTCACTATAGGGC-3', SEQ ID NO:38—(Genome walker)

Ap2 5'-ACTATAGGGCACGCGTGGT-3', SEQ ID NO:39—(Genome walker)

Ap1 5'-CCATCCTAATACGACTCACTATAGGGC-3', SEQ ID NO:40—(Marathon RACE)

Ap2 5'-ACTCACTATAGGGCTCGAGCGGC-3', SEQ ID NO:41—(Marathon RACE)

Southern analysis of genomic DNA: Genomic DNA was extracted from animal or from human blood using Blood and cell culture DNA maxi kit (Qiagene). DNA was digested with EcoRI, separated by gel electrophoresis and transferred to a nylon membrane Hybond N+ (Amersham). Hybridization was performed at 68° C. in 6×SSC, 1% SDS, 5×Denharts, 10% dextran sulfate, 100 μg/ml salmon sperm DNA, and $^{32}$p labeled probe. A 1.6 kb fragment, containing the entire hpa cDNA was used as a probe. Following hybridization, the membrane was washed with 3×SSC, 0.1% SDS, at 68° C. and exposed to X-ray film for 3 days. Membranes were then washed with 1×SSC, 0.1% SDS, at 68° C. and were reexposed for 5 days.

Construction of hpa promoter-GFP expression vector: Lambda DNA of phage L3, was digested with SacI and BglII, resulting in a 1712 bp fragment which contained the hpa promoter (877–2688 of SEQ ID NO:42). The pEGFP-1 plasmid (Clontech) was digested with BglII and SacI and ligated with the 1712 bp fragment of the hpa promoter sequence. The resulting plasmid was designated phpEGL. A second hpa promoter-GFP plasmid was constructed containing a shorter fragment of the hpa promoter region: phpEGL was digested with HindIII, and the resulting 1095 bp fragment (nucleotides 1593–2688 of SEQ ID NO:42) was ligated with HindIII digested pEGFP-1. The resulting plasmid was designated phpEGS.

Computer analysis of sequences: Homology searches were performed using several computer servers, and various databases. Blast 2.0 service, at the NCBI server was used to screen the protein database swplus and DNA databases such as GenBank, EMBL, and the EST databases. Blast 2.0 search was performed using the basic search option of the NCBI server. Sequence analysis and alignments were done using the DNA sequence analysis software package developed by the Genetic Computer Group (GCG) at the university of Wisconsin. Alignments of two sequences were performed using Bestfit (gap creation penalty—12, gap extension penalty—4). Protein homology search was performed with the Smith-Waterman algorithm, using the Bio-accelerator platform developed by Compugene. The protein database swplus was searched using the following parameters: gapop: 10.0, gapext: 0.5, matrix: blosum62. Blocks homology was performed using the Blocks WWW server developed at Fred Hutchinson Cancer Research Center in Seattle, Wash., USA. Secondary structure prediction was performed using the PHD server—Profile network Prediction Heidelberg. Fold recognition (threading) was performed using the UCLA-DOE structure prediction server. The method used for prediction was gonnet+predss. Alignment of three sequences was performed using the pileup application (gap creation penalty—5, gap extension penalty—1). Promoter analysis was performed using TSSW and TSSG programs (BCM Search Launcher Human Genome Center, Baylor College of Medicine, Houston Tex.).

Example 1

Cloning of Human hpa cDNA

Purified fraction of heparanase isolated from human hepatoma cells (SK-hep-1) was subjected to tryptic digestion and microsequencing. EST (Expressed Sequence Tag) databases were screened for homology to the back translated DNA sequences corresponding to the obtained peptides. Two EST sequences (accession Nos. N41349 and N45367) contained a DNA sequence encoding the peptide YGPD-VGQPR (SEQ ID NO:8). These two sequences were derived from clones 257548 and 260138 (I.M.A.G.E Consortium) prepared from 8 to 9 weeks placenta cDNA library (Soares). Both clones which were found to be identical contained an insert of 1020 bp which included an open reading frame (ORF) of 973 bp followed by a 3' untranslated region of 27 bp and a Poly A tail. No translation start site (AUG) was identified at the 5' end of these clones.

Cloning of the missing 5' end was performed by PCR amplification of DNA from a placenta Marathon RACE cDNA composite. A 900 bp fragment (designated hp3), partially overlapping with the identified 3' encoding EST clones was obtained.

The joined cDNA fragment, 1721 bp long (SEQ ID NO:9), contained an open reading frame which encodes, as shown in FIG. 1 and SEQ ID s NO:11, a polypeptide of 543 amino acids (SEQ ID NO:10) with a calculated molecular weight of 61,192 daltons. The 3' end of the partial cDNA inserts contained in clones 257548 and 260138 started at nucleotide $G^{721}$ of SEQ ID NO:9 and FIG. 1.

As further shown in FIG. 1, there was a single sequence discrepancy between the EST clones and the PCR amplified sequence, which led to an amino acid substitution from $Tyr^{246}$ in the EST to $Phe^{246}$ in the amplified cDNA. The nucleotide sequence of the PCR amplified cDNA fragment was verified from two independent amplification products. The new gene was designated hpa.

As stated above, the 3' end of the partial cDNA inserts contained in EST clones 257548 and 260138 started at nucleotide 721 of hpa (SEQ ID NO:9). The ability of the hpa cDNA to form stable secondary structures, such as stem and loop structures involving nucleotide stretches in the vicinity of position 721 was investigated using computer modeling. It was found that stable stem and loop structures are likely to be formed involving nucleotides 698–724 (SEQ ID NO:9). In addition, a high GC content, up to 70%, characterizes the 5' end region of the hpa gene, as compared to about only 40% in the 3' region. These findings may explain the immature termination and therefore lack of 5' ends in the EST clones.

To examine the ability of the hpa gene product to catalyze degradation of heparan sulfate in an in vitro assay the entire open reading frame was expressed in insect cells, using the Baculovirus expression system. Extracts of cells, infected with virus containing the hpa gene, demonstrated a high level of heparan sulfate degradation activity, while cells infected with a similar construct containing no hpa gene had no such activity, nor did non-infected cells. These results are further demonstrated in the following Examples.

Example 2

Degradation of Soluble ECM-derived HSPG

Monolayer cultures of High Five cells were infected (72 h, 28° C.) with recombinant Bacoluvirus containing the pFasthpa plasmid or with control virus containing an insert free plasmid. The cells were harvested and lysed in heparanase reaction buffer by three cycles of freezing and thawing. The cell lysates were then incubated (18 h, 37° C.) with sulfate labeled, ECM-derived HSPG (peak I), followed by gel filtration analysis (Sepharose 6B) of the reaction mixture.

As shown in FIG. 2, the substrate alone included almost entirely high molecular weight (Mr) material eluted next to $V_o$ (peak I, fractions 5–20, Kav<0.35). A similar elution pattern was obtained when the HSPG substrate was incubated with lysates of cells that were infected with control virus. In contrast, incubation of the HSPG substrate with lysates of cells infected with the hpa containing virus resulted in a complete conversion of the high Mr substrate into low Mr labeled degradation fragments (peak II, fractions 22–35, 0.5<Kav<0.75).

Fragments eluted in peak II were shown to be degradation products of heparan sulfate, as they were (i) 5- to 6-fold smaller than intact heparan sulfate side chains (Kav approx. 0.33) released from ECM by treatment with either alkaline borohydride or papain; and (ii) resistant to further digestion with papain or chondroitinase ABC, and susceptible to deamination by nitrous acid (6, 11). Similar results (not shown) were obtained with Sf21 cells. Again, heparanase activity was detected in cells infected with the hpa containing virus (pFhpa), but not with control virus (pF). This result was obtained with two independently generated recombinant viruses. Lysates of control not infected High Five cells failed to degrade the HSPG substrate.

In subsequent experiments, the labeled HSPG substrate was incubated with medium conditioned by infected High Five or Sf21 cells.

As shown in FIGS. 3a–b, heparanase activity, reflected by the conversion of the high Mr peak I substrate into the low Mr peak II which represents HS degradation fragments, was found in the culture medium of cells infected with the pFhpa2 or pFhpa4 viruses, but not with the control pF1 or pF2 viruses. No heparanase activity was detected in the culture medium of control non-infected High Five or Sf21 cells.

Figure 4:
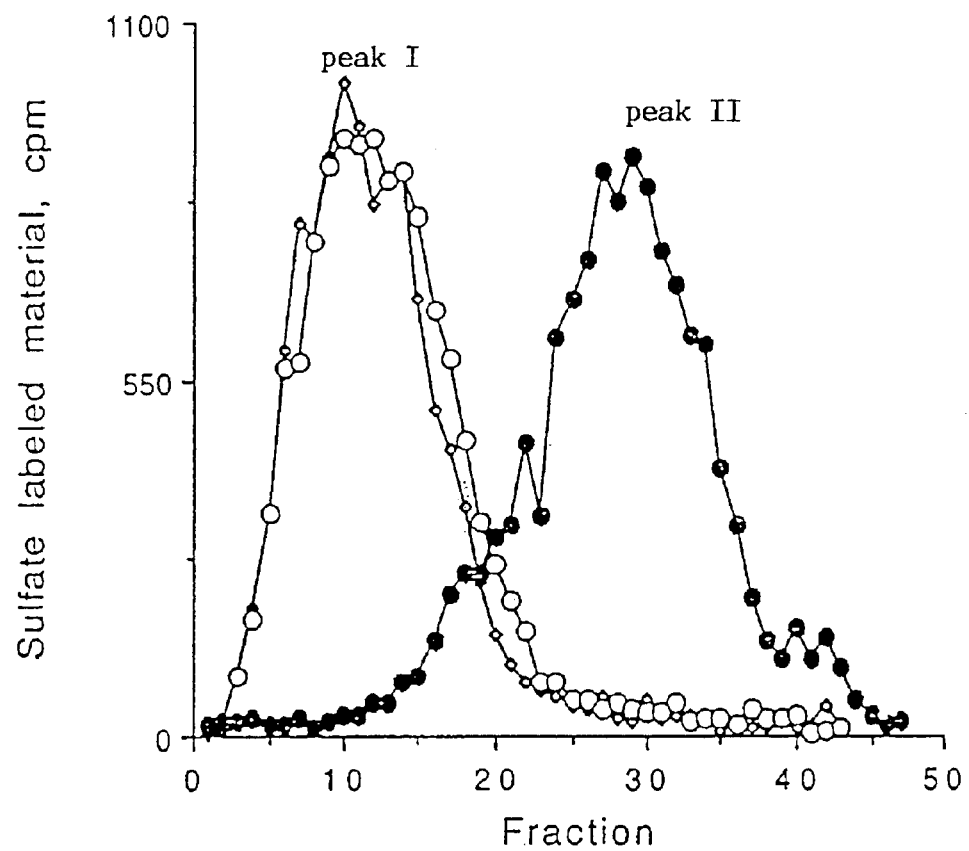
FIG. 4 presents size fractionation of heparanase activity expressed by pFhpa2 infected cells. Culture medium of pFhpa2 infected High Five cells was applied onto a 50 kDa cut-off membrane. Heparanase activity (conversion of the peak I substrate, (◇) into peak II HS degradation fragments) was found in the high (>50 kDa) (●),but not low (<50 kDa) (○) molecular weight compartment.

The medium of cells infected with the pFhpa4 virus was passed through a 50 kDa cut off membrane to obtain a crude estimation of the molecular weight of the recombinant heparanase enzyme. As demonstrated in FIG. 4, all the enzymatic activity was retained in the upper compartment and there was no activity in the flow through (<50 kDa) material. This result is consistent with the expected molecular weight of the hpa gene product.

In order to further characterize the hpa product the inhibitory effect of heparin, a potent inhibitor of heparanase mediated HS degradation (40) was examined.

Figure 5A:
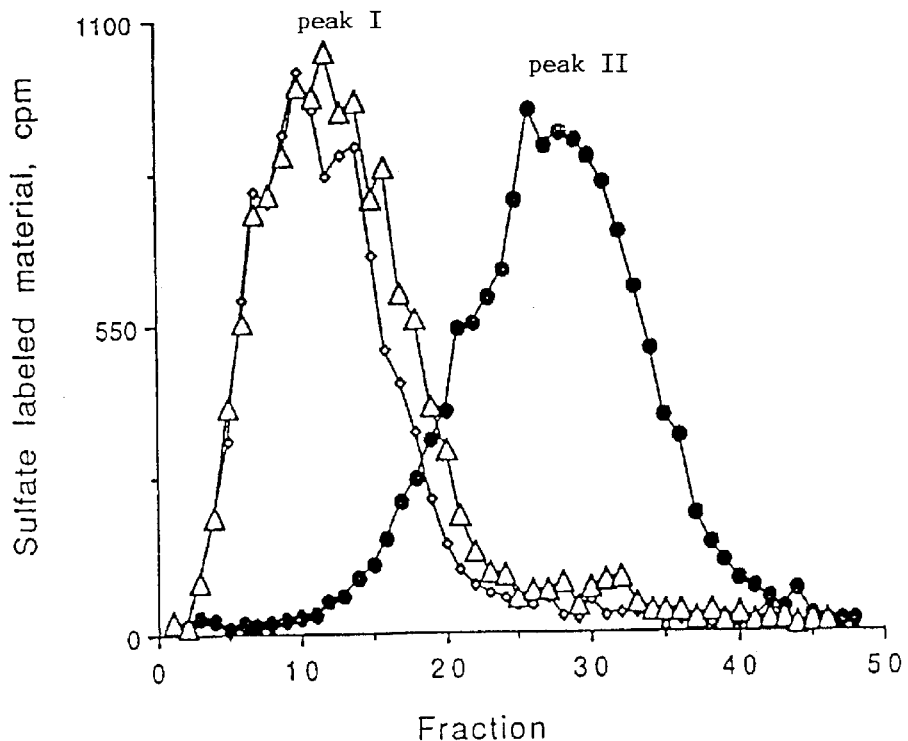
FIGS. 5a–b demonstrate the effect of heparin on heparanase activity expressed by pFhpa2 and pFhpa4 infected High Five cells. Culture media of pFhpa2 (5a) and pFhpa4 (5b) infected High Five cells were incubated (18 h, 37° C.) with sulfate labeled ECM-derived soluble HSPG (peak I, ◇) in the absence (●) or presence (Δ) of 10 μg/ml heparin. Production of low molecular weight HS degradation fragments was completely abolished in the presence of heparin, a potent inhibitor of heparanase activity (6, 7).
Figure 5B:
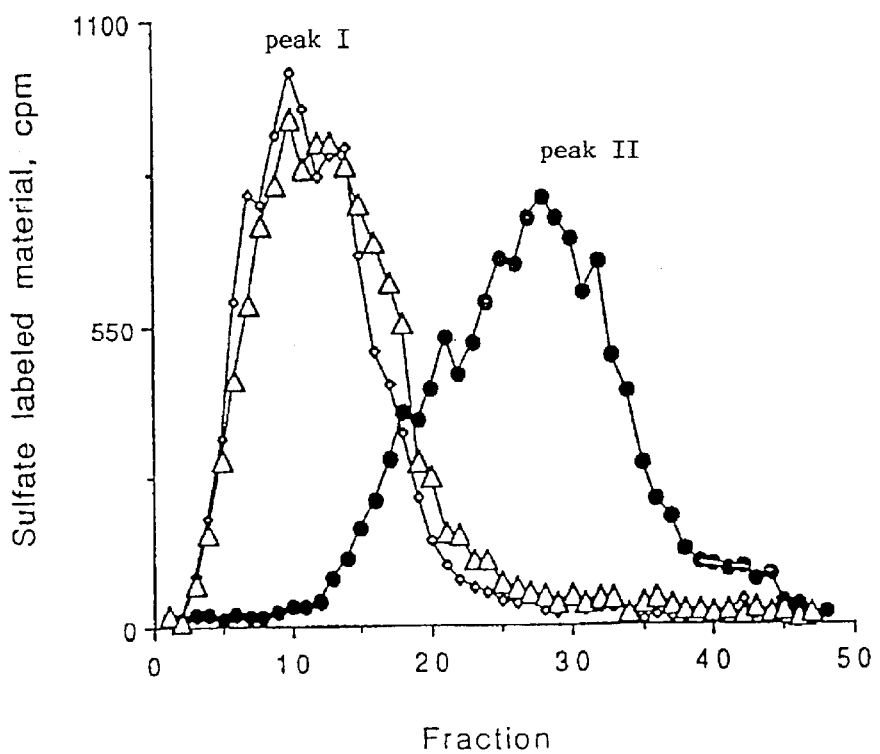
Figure 6A:
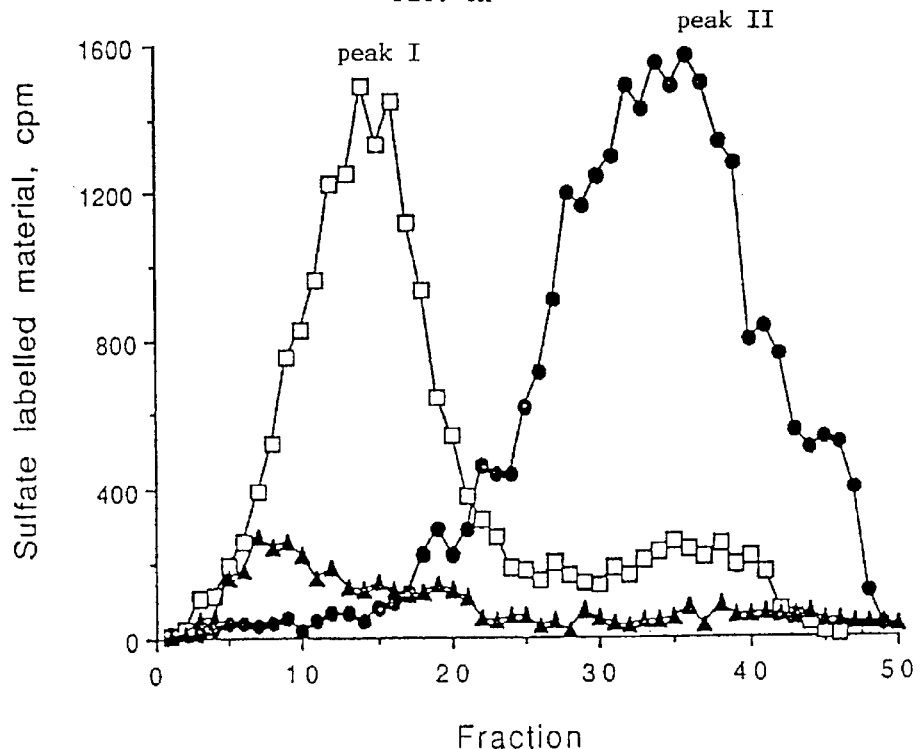
FIGS. 6a–b demonstrate degradation of sulfate labeled intact ECM by virus infected High Five and Sf21 cells. High Five (6a) and Sf21 (6b) cells were plated on sulfate labeled ECM and infected (48 h, 28° C.) with pFhpa4 (●) or control pF1 (□) viruses. Control non-infected Sf21 cells (▲) were plated on the labeled ECM as well. The pH of the cultured medium was adjusted to 6.0–6.2 followed by 24 h incubation at 37° C. Sulfate labeled material released into the incubation medium was analyzed by gel filtration on Sepharose 6B. HS degradation fragments were produced only by cells infected with the hpa containing virus.
Figure 6B:
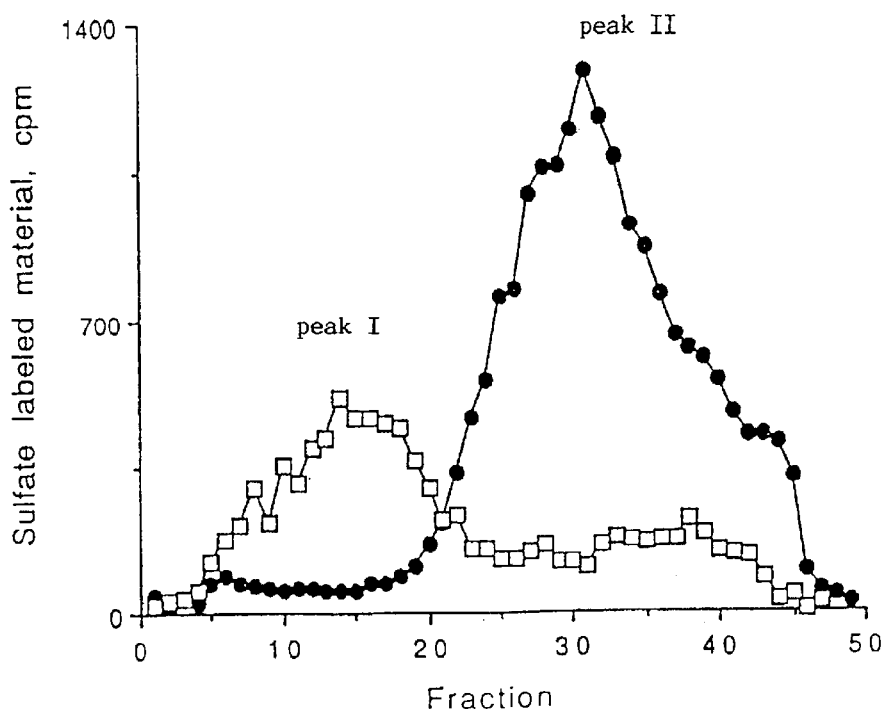
Figure 7A:
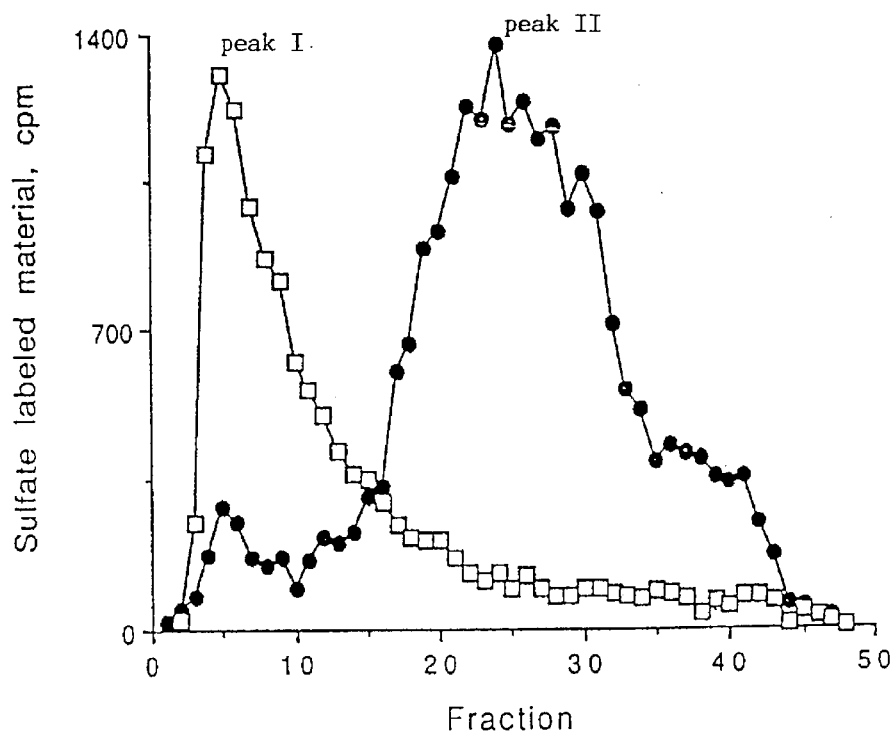
FIGS. 7a–b demonstrate degradation of sulfate labeled intact ECM by virus infected cells. High Five (7a) and Sf21 (7b) cells were plated on sulfate labeled ECM and infected (48 h, 28° C.) with pFhpa4 (●) or control pF1 (□) viruses. Control non-infected Sf21 cells (▲) were plate on labeled ECM as well. The pH of the cultured medium was adjusted to 6.0–6.2, followed by 48 h incubation at 28° C. Sulfate labeled degradation fragments released into the incubation medium was analyzed by gel filtration on Sepharose 6B. HS degradation fragments were produced only by cells infected with the hpa containing virus.
Figure 7B:
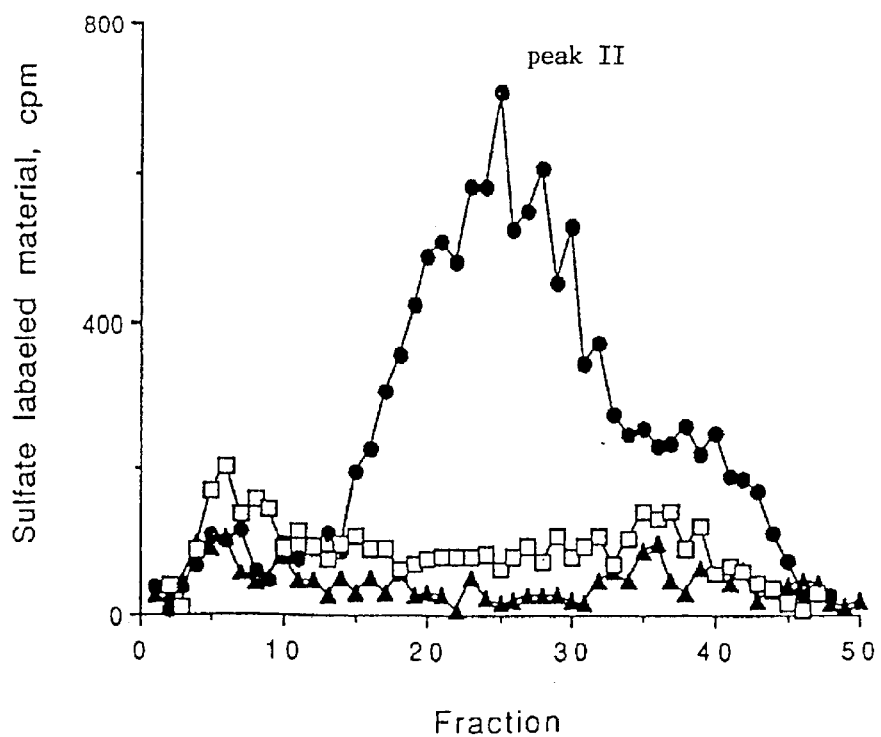

As demonstrated in FIGS. 5a–b, conversion of the peak I substrate into peak II HS degradation fragments was completely abolished in the presence of heparin.

Altogether, these results indicate that the heparanase enzyme is expressed in an active form by insect cells infected with Baculovirus containing the newly identified human hpa gene.

Example 3

Degradation of HSPG in Intact ECM

Next, the ability of intact infected insect cells to degrade HS in intact, naturally produced ECM was investigated. For this purpose, High Five or Sf21 cells were seeded on metabolically sulfate labeled ECM followed by infection (48 h, 28° C.) with either the pFhpa4 or control pF2 viruses. The pH of the medium was then adjusted to pH 6.2–6.4 and the cells further incubated with the labeled ECM for another 48 h at 28° C. or 24 h at 37° C. Sulfate labeled material released into the incubation medium was analyzed by gel filtration on Sepharose 6B.

As shown in FIGS. 6a–b and 7a–b, incubation of the ECM with cells infected with the control pF2 virus resulted in a constant release of labeled material that consisted almost entirely (>90%) of high Mr fragments (peak I) eluted with or next to $V_o$. It was previously shown that a proteolytic activity residing in the ECM itself and/or expressed by cells is responsible for release of the high Mr material (6). This nearly intact HSPG provides a soluble substrate for subsequent degradation by heparanase, as also indicated by the relatively large amount of peak I material accumulating when the heparanase enzyme is inhibited by heparin (6, 7, 12, FIG. 9). On the other hand, incubation of the labeled ECM with cells infected with the pFhpa4 virus resulted in release of 60–70% of the ECM-associated radioactivity in the form of low Mr sulfate-labeled fragments (peak II, 0.5<Kav<0.75), regardless of whether the infected cells were incubated with the ECM at 28° C. or 37° C. Control intact non-infected Sf21 or High Five cells failed to degrade the ECM HS side chains.

Figure 8A:
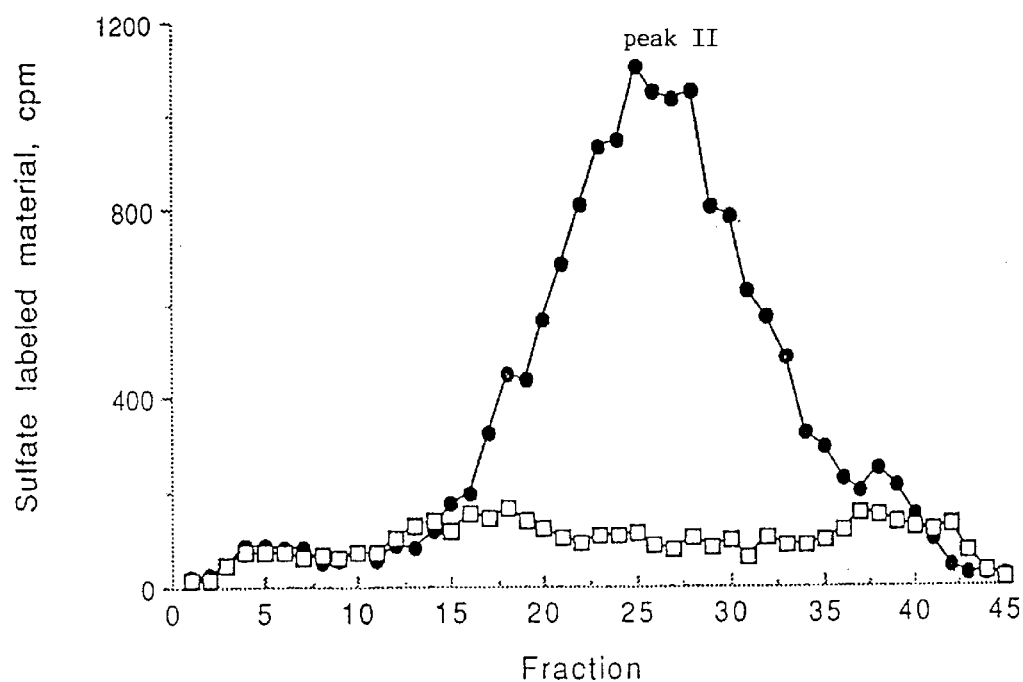
FIGS. 8a–b demonstrate degradation of sulfate labeled intact ECM by the culture medium of pFhpa4 infected cells. Culture media of High Five (8a) and Sf21 (8b) cells that were infected with pFhpa4 (●) or control pF1 (□) viruses were incubated (48 h, 37° C., pH 6.0) with intact sulfate labeled ECM. The ECM was also incubated with the culture medium of control non-infected Sf21 cells (▲). Sulfate labeled material released into the reaction mixture was subjected to gel filtration analysis. Heparanase activity was detected only in the culture medium of pFhpa4 infected cells.
Figure 8B:
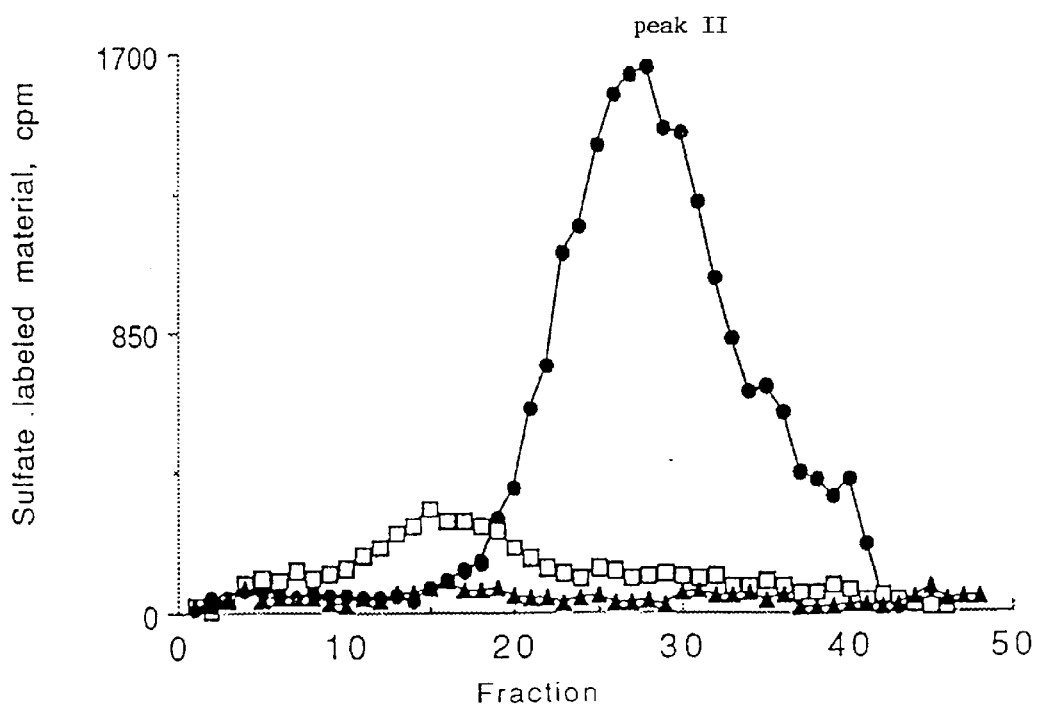
Figure 9A:
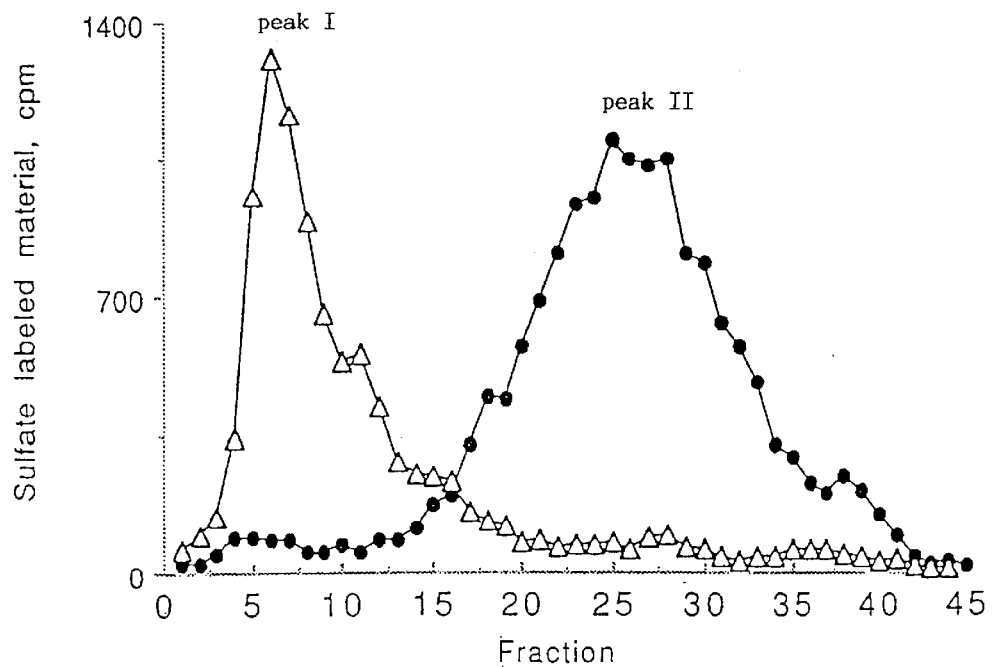
FIGS. 9a–b demonstrate the effect of heparin on heparanase activity in the culture medium of pFhpa4 infected cells. Sulfate labeled ECM was incubated (24 h, 37° C., pH 6.0) with culture medium of pFhpa4 infected High Five (9a) and Sf21 (9b) cells in the absence (●) or presence (Δ) of 10 μg/ml heparin. Sulfate labeled material released into the incubation medium was subjected to gel filtration on Sepharose 6B. Heparanase activity (production of peak II HS degradation fragments) was completely inhibited in the presence of heparin.
Figure 9B:
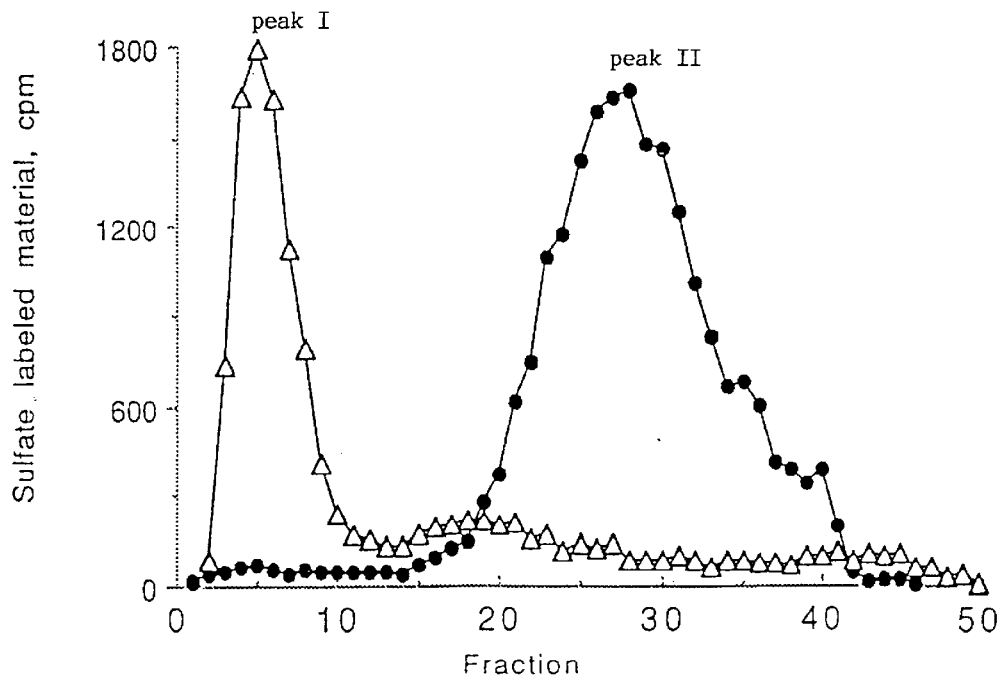

In subsequent experiments, as demonstrated in FIGS. 8a–b, High Five and Sf21 cells were infected (96 h, 28° C.) with pFhpa4 or control pF1 viruses and the culture medium incubated with sulfate-labeled ECM. Low Mr HS degradation fragments were released from the ECM only upon incubation with medium conditioned by pFhpa4 infected cells. As shown in FIG. 9, production of these fragments was abolished in the presence of heparin. No heparanase activity was detected in the culture medium of control, non-infected cells. These results indicate that the heparanase enzyme expressed by cells infected with the pFhpa4 virus is capable of degrading HS when complexed to other macromolecular constituents (i.e. fibronectin, laminin, collagen) of a naturally produced intact ECM, in a manner similar to that reported for highly metastatic tumor cells or activated cells of the immune system (6, 7).

Example 4

Purification of Recombinant Human Heparanase

Figure 10B:
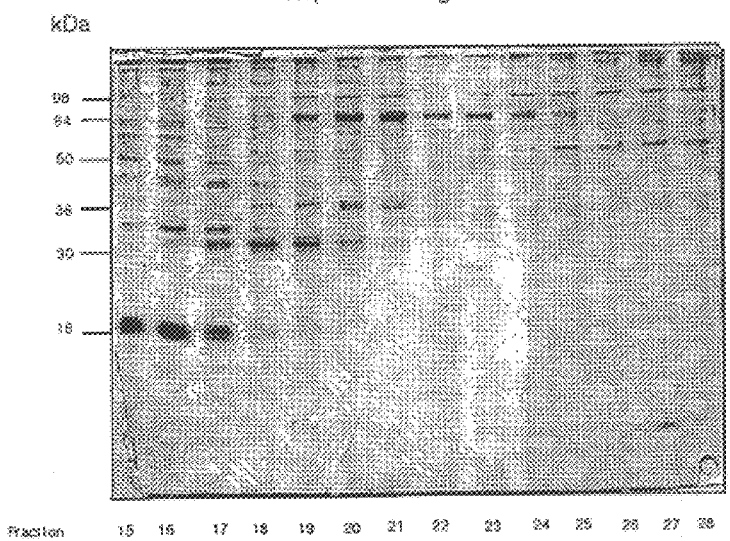
Figure 11A:
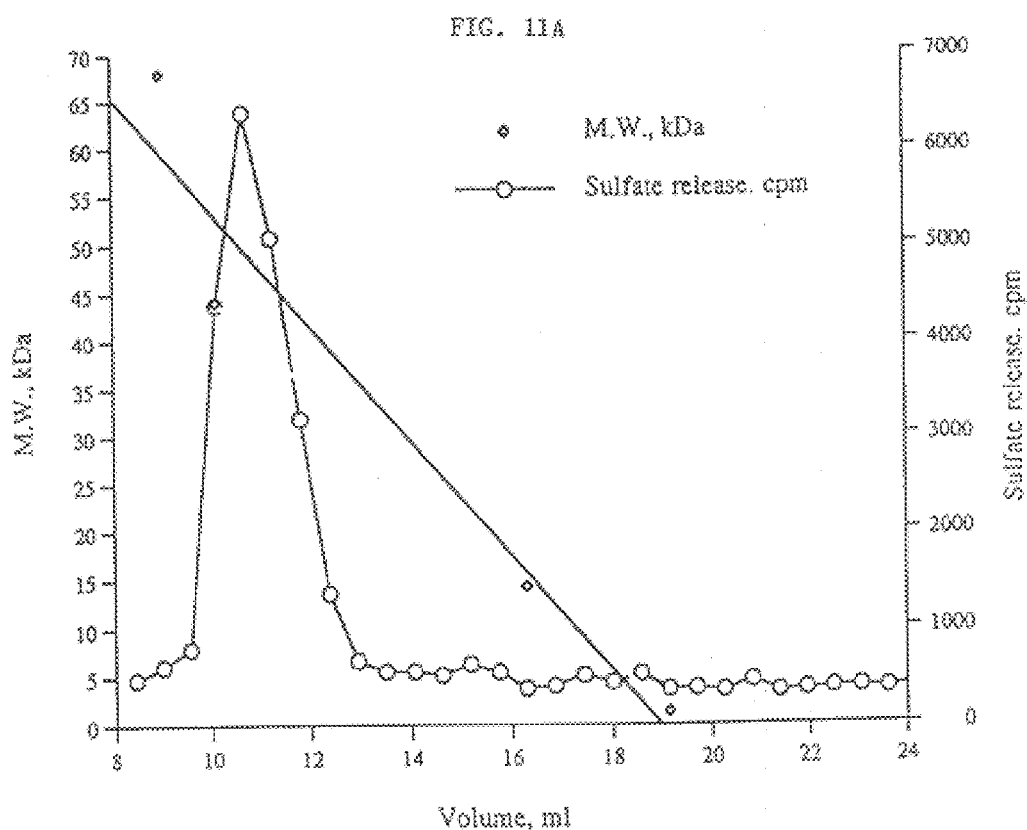
FIGS. 11a–b demonstrate purification of recombinant heparanase on a Superdex 75 gel filtration column. Active fractions eluted from heparin-Sepharose (FIG. 10a) were pooled, concentrated and applied onto Superdex 75 FPLC column. Fractions were collected and aliquots of each fraction were tested for heparanase activity (○, FIG. 11a) and analyzed by SDS-polyacrylamide gel electrophoresis followed by silver nitrate staining (FIG. 11b). A correlation is seen between the appearance of a major protein band (MW~63,000) in fractions 4–7 and heparanase activity.
Figure 11B:
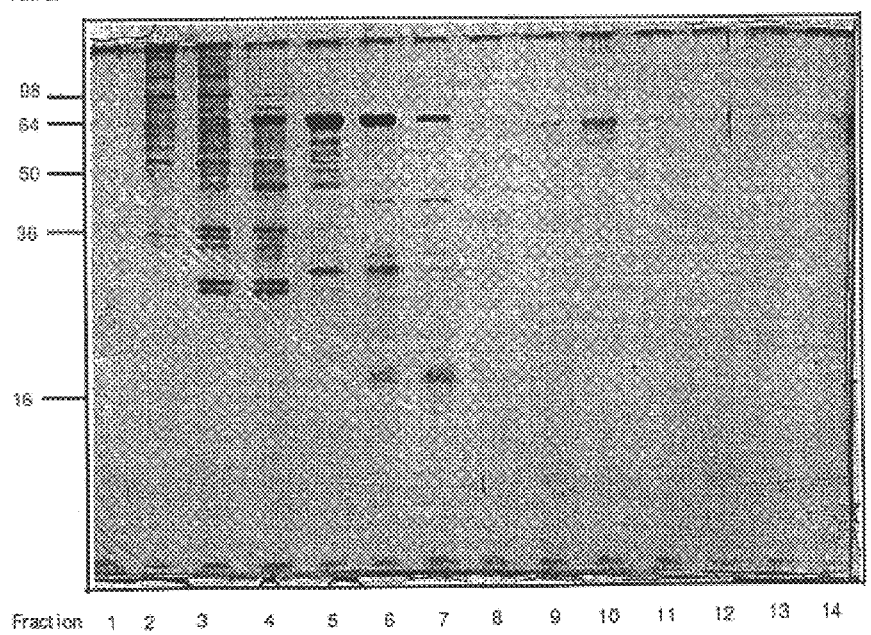

The recombinant heparanase was partially purified from medium of pFhpa4 infected Sf21 cells by Heparin- Sepharose chromatography (FIG. 10a) followed by gel filtration of the pooled active fractions over an FPLC Superdex 75 column (FIG. 11a). A ~63 kDa protein was observed, whose quantity, as was detected by silver stained SDS-polyacrylamide gel electrophoresis, correlated with heparanase activity in the relevant column fractions (FIGS. 10b and 11b, respectively). This protein was not detected in the culture medium of cells infected with the control pF1 virus and was subjected to a similar fractionation on heparin-Sepharose (not shown).

Example 5

Expression of the Human hpa cDNA in Various Cell Types, Organs and Tissues

Figure 12A:
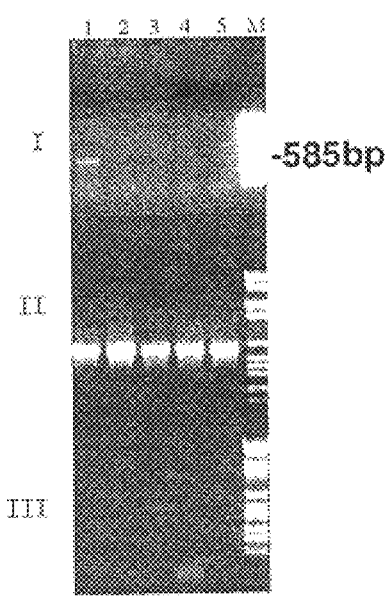
FIGS. 12a–e demonstrate expression of the hpa gene by RT-PCR with total RNA from human embryonal tissues (12a), human extra-embryonal tissues (12b) and cell lines from different origins (12c–e). RT-PCR products using hpa specific primers (I), primers for GAPDH housekeeping gene (II), and control reactions without reverse transcriptase demonstrating absence of genomic DNA or other contamination in RNA samples (III). M—DNA molecular weight marker VI (Boehringer Mannheim). For 12a: lane I—neutrophil cells (adult), lane 2—muscle, lane 3—thymus, lane 4—heart, lane 5—adrenal. For 12b: lane 1—kidney, lane 2—placenta (8 weeks), lane 3—placenta (11 weeks), lanes 4–7—mole (complete hydatidiform mole), lane 8—cytotrophoblast cells (freshly isolated), lane 9—cytotrophoblast cells (1.5 h in vitro), lane 10—cytotrophoblast cells (6 h in vitro), lane 11—cytotrophoblast cells (18 h in vitro), lane 12—cytotrophoblast cells (48 h in vitro). For 12c: lane 1—JAR bladder cell line, lane 2—NCITT testicular tumor cell line, lane 3—SW-480 human hepatoma cell line, lane 4—HTR (cytotrophoblasts transformed by SV40), lane 5—HPTLP-I hepatocellular carcinoma cell line, lane 6—EJ-28 bladder carcinoma cell line. For 12d: lane 1—SK-hep-1 human hepatoma cell line, lane 2—DAMI human megakaryocytic cell line, lane 3—DAMI cell line+PMA, lane 4—CHRF cell line+PMA, lane 5—CHRF cell line. For 12e: lane 1—ABAE bovine aortic endothelial cells, lane 2—1063 human ovarian cell line, lane 3—human breast carcinoma MDA435 cell line, lane 4—human breast carcinoma MDA231 cell line.
Figure 12B:
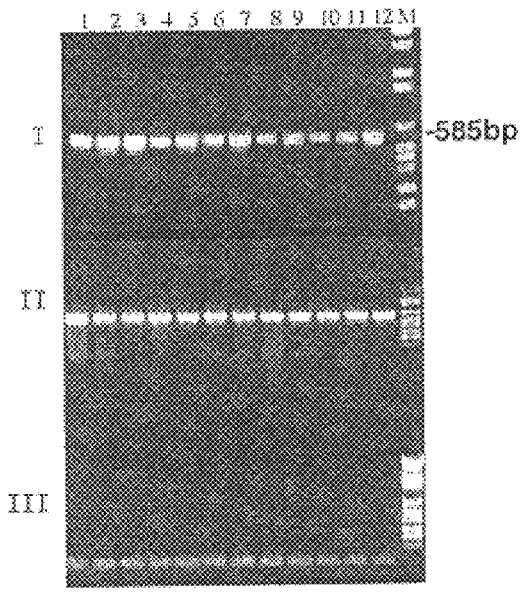
Figure 12C:
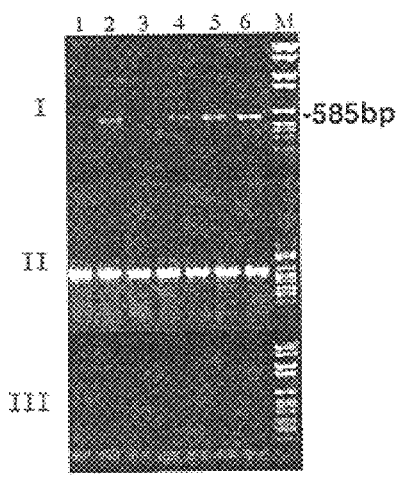
Figure 12D:
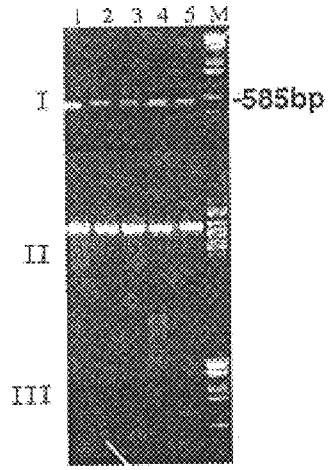
Figure 12E:
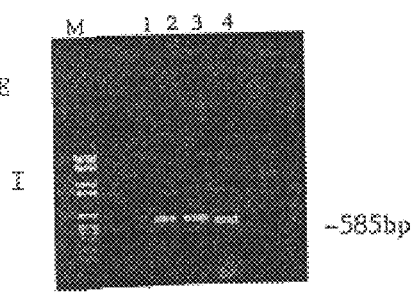

Referring now to FIGS. 12a–e, RT-PCR was applied to evaluate the expression of the hpa gene by various cell types and tissues. For this purpose, total RNA was reverse transcribed and amplified. The expected 585 bp long cDNA was clearly demonstrated in human kidney, placenta (8 and 11 weeks) and mole tissues, as well as in freshly isolated and short termed (1.5–48 h) cultured human placental cytotrophoblastic cells (FIG. 12a), all known to express a high heparanase activity (41). The hpa transcript was also expressed by normal human neutrophils (FIG. 12b). In contrast, there was no detectable expression of the hpa mRNA in embryonic human muscle tissue, thymus, heart and adrenal (FIG. 12b). The hpa gene was expressed by several, but not all, human bladder carcinoma cell lines (FIG. 12c), SK hepatoma (SK-hep-1), ovarian carcinoma (OV 1063), breast carcinoma (435, 231), melanoma and megakaryocytic (DAMI, CHRF) human cell lines (FIGS. 12d–e).

The above described expression pattern of the hpa transcript was determined to be in a very good correlation with heparanase activity levels determined in various tissues and cell types (not shown).

Example 6

Isolation of an Extended 5' End of hpa cDNA From Human SK-hep1 Cell Line

The 5' end of hpa cDNA was isolated from human SK-hep1 cell line by PCR amplification using the Marathon RACE (rapid amplification of cDNA ends) kit (Clontech). Total RNA was prepared from SK-hep1 cells using the TRI-Reagent (Molecular research center Inc.) according to the manufacturer instructions. Poly A+ RNA was isolated using the mRNA separator kit (Clonetech).

The Marahton RACE SK-hep1 cDNA composite was constructed according to the manufacturer recommendations. First round of amplification was performed using an adaptor specific primer AP1: 5'-CCATCCTAATACGACTCACTATAGGGC-3', SEQ ID NO:1, and a hpa specific antisense primer hpl-629: 5'-CCCCAGGAGCAGCAGCATCAG-3', SEQ ID NO:17, corresponding to nucleotides 119–99 of SEQ ID NO:9. The resulting PCR product was subjected to a second round of amplification using an adaptor specific nested primer AP2: 5'-ACTCACTATAGGGCTCGAGCGGC-3', SEQ ID NO:3, and a hpa specific antisense nested primer hpl-666 5'-AGGCTTCGAGCGCAGCAGCAT-3', SEQ ID NO:18, corresponding to nucleotides 83–63 of SEQ ID NO:9. The PCR program was as follows: a hot start of 94° C. for 1 minute, followed by 30 cycles of 90° C.—30 seconds, 68° C.—4 minutes. The resulting 300 bp DNA fragment was extracted from an agarose gel and cloned into the vector pGEM-T Easy (Promega). The resulting recombinant plasmid was designated pHPSK1.

The nucleotide sequence of the pHPSK1 insert was determined and it was found to contain 62 nucleotides of the 5' end of the placenta hpa cDNA (SEQ ID NO:9) and additional 178 nucleotides upstream, the first 178 nucleotides of SEQ ID NOs: 13 and 15.

A single nucleotide discrepancy was identified between the SK-hep1 cDNA and the placenta cDNA. The "T" derivative at position 9 of the placenta cDNA (SEQ ID NO:9), is replaced by a "C" derivative at the corresponding position 187 of the SK-hep1 cDNA (SEQ ID NO: 13).

The discrepancy is likely to be due to a mutation at the 5' end of the placenta cDNA clone as confirmed by sequence analysis of sevsral additional cDNA clones isolated from placenta, which like the SK-hep1 cDNA contained C at position 9 of SEQ ID NO:9.

The 5' extended sequence of the SK-hep1 hpa cDNA was assembled with the sequence of the hpa cDNA isolated from human placenta (SEQ ID NO:9). The assembled sequence contained an open reading frame which encodes, as shown in SEQ ID NOs: 14 and 15, a polypeptide of 592 amino acids with a calculated molecular weight of 66,407 daltons. The open reading frame is flanked by 93 bp 5' untranslated region (UTR).

Example 7

Isolation of the Upstream Genomic Region of the hpa Gene

The upstream region of the hpa gene was isolated using the Genome Walker kit (Clontech) according to the manufacturer recommendations. The kit includes five human genomic DNA samples each digested with a different restriction endonuclease creating blunt ends: EcoRV, ScaI, DraI, PvuII and SspI.

The blunt ended DNA fragments are ligated to partially single stranded adaptors. The Genomic DNA samples were subjected to PCR amplification using the adaptor specific primer and a gene specific primer. Amplification was performed with Expand High Fidelity (Boehringer Mannheim).

A first round of amplification was performed using the ap1 primer: 5'-G TAATACGACTCACTATAGGGC-3', SEQ ID NO:19, and the hpa specific antisense primer hpl-666: 5'-AGGCTTCGAGCGCAGCAGCAT-3', SEQ ID NO:18, corresponding to nucleotides 83–63 of SEQ ID NO:9. The PCR program was as follows: a hot start of 94° C.—3 minutes, followed by 36 cycles of 94° C.—40 seconds, 67° C.—4 minutes.

The PCR products of the first amplification were diluted 1:50. One μl of the diluted sample was used as a template for a second amplification using a nested adaptor specific primer ap2: 5'-ACTATAGGGCACGCGTGGT-3', SEQ ID NO:20, and a hpa specific antisense primer hpl-690, 5'-CTTGGGCTCACCTGGCTGCTC-3'; SEQ ID NO:21, corresponding to nucleotides 62–42 of SEQ ID NO:9. The resulting amplification products were analyzed using agarose gel electrophoresis. Five different PCR products were obtained from the five amplification reactions. A DNA fragment of approximately 750 bp which was obtained from the SspI digested DNA sample was gel extracted. The purified fragment was ligated into the plasmid vector pGEM-T Easy (Promega). The resulting recombinant plasmid was designated pGHP6905 and the nucleotide sequence of the hpa insert was determined.

A partial sequence of 594 nucleotides is shown in SEQ ID NO: 16. The last nucleotide in SEQ ID NO: 13 corresponds to nucleotide 93 in SEQ ID:13. The DNA sequence in SEQ ID NO: 16 contains the 5' region of the hpa cDNA and 501 nucleotides of the genomic upstream region which are predicted to contain the promoter region of the hpa gene.

Example 8

Expression of the 592 Amino Acids HPA Polypeptide in a Human 293 Cell Line

The 592 amino acids open reading frame (SEQ ID NOs:13 and 15) was constructed by ligation of the 110 bp corresponding to the 5' end of the SK-hep1 hpa cDNA with the placenta cDNA. More specifically the Marathon RACE-PCR amplification product of the placenta hpa DNA was digested with SacI and an approximately 1 kb fragment was ligated into a SacI-digested pGHP6905 plasmid. The resulting plasmid was digested with EarI and AatII. The EarI sticky ends were blunted and an approximately 280 bp EarI/blunt-AatII fragment was isolated. This fragment was ligated with pFasthpa digested with EcoRI which was blunt ended using Klenow fragment and further digested with AatII. The resulting plasmid contained a 1827 bp insert which includes an open reading frame of 1776 bp, 31 bp of 3' UTR and 21 bp of 5' UTR. This plasmid was designated pFastLhpa.

A mammalian expression vector was constructed to drive the expression of the 592 amino acids heparanase polypeptide in human cells. The hpa cDNA was excised prom pFastLhpa with BssHII and NotI. The resulting 1850 bp BssHII-NotI fragment was ligated to a mammalian expression vector pSI (Promega) digested with MluI and NotI. The resulting recombinant plasmid, pSIhpaMet2 was transfected into a human 293 embryonic kidney cell line.

Transient expression of the 592 amino-acids heparanase was examined by western blot analysis and the enzymatic activity was tested using the gel shift assay. Both these procedures are described in length in U.S. patent application Ser. No. 09/071,739, filed May 1, 1998, which is incorporated by reference as if fully set forth herein. Cells were harvested 3 days following transfection. Harvested cells were re-suspended in lysis buffer containing 150 mM NaCl, 50 mM Tris pH 7.5, 1% Triton X-100, 1 mM PMSF and protease inhibitor cocktail (Boehringer Mannheim). 40 μg protein extract samples were used for separation on a SDS-PAGE. Proteins were transferred onto a PVDF Hybond-P membrane (Amersham). The membrane was incubated with an affinity purified polyclonal anti heparanase antibody, as described in U.S. patent application Ser. No. 09/071,739. A major band of approximately 50 kDa was observed in the transfected cells as well as a minor band of approximately 65 kDa. A similar pattern was observed in extracts of cells transfected with the pShpa as demonstrated in U.S. patent application Ser. No. 09/071,739. These two bands probably represent two forms of the recombinant heparanase protein produced by the transfected cells. The 65 kDa protein probably represents a heparanase precursor, while the 50 kDa protein is suggested herein to be the processed or mature form.

The catalytic activity of the recombinant protein expressed in the pShpaMet2 transfected cells was tested by gel shift assay. Cell extracts of transfected and of mock transfected cells were incubated overnight with heparin (6 μg in each reaction) at 37° C., in the presence of 20 mM phosphate citrate buffer pH 5.4, 1 mM CaCl$_2$, 1 mM DTT and 50 mM NaCl. Reaction mixtures were then separated on a 10% polyacrylamide gel. The catalytic activity of the recombinant heparanase was clearly demonstrated by a faster migration of the heparin molecules incubated with the transfected cell extract as compared to the control. Faster migration indicates the disappearance of high molecular weight heparin molecules and the generation of low molecular weight degradation products.

Example 9

Chromosomal Localization of the hpa Gene

Chromosomal mapping of the hpa gene was performed utilizing a panel of monochromosomal human/CHO and human/mouse somatic cell hybrids, obtained from the UK HGMP Resource Center (Cambridge, England).

40 ng of each of the somatic cell hybrid DNA samples were subjected to PCR amplification using the hpa primers: hpu565 5'-AGCTCTGTAGATGTGCTATACAC-3', SEQ ID NO:22, corresponding to nucleotides 564–586 of SEQ ID NO:9 and an antisense primer hpl171 5'-GCATCTTAGCCGTCTTTCTTCG-3', SEQ ID NO:23, corresponding to nucleotides 897–876 of SEQ ID NO:9.

The PCR program was as follows: a hot start of 94° C.—3 minutes, followed by 7 cycles of 94° C.—45 seconds, 66° C.—1 minute, 68° C.—5 minutes, followed by 30 cycles of 94° C.—45 seconds, 62° C.—1 minute, 68 ° C.—5 minutes, and a 10 minutes final extension at 72° C.

Figure 14:
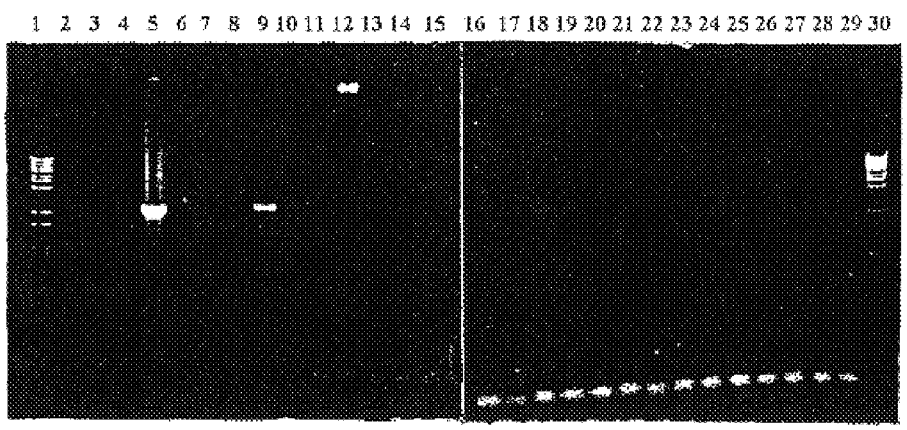
FIG. 14 demonstrates the chromosomal localization of the hpa gene. PCR products of DNA derived from somatic cell hybrids and of genomic DNA of hamster, mouse and human of were separated on 0.7% agarose gel following amplification with hpa specific primers. Lane 1—Lambda DNA digested with BstEII, lane 2—no DNA control, lanes 3–29, PCR amplification products. Lanes 3–5—human, mouse and hamster genomic DNA, respectively. Lanes 6–29, human monochromosomal somatic cell hybrids representing chromosomes 1–22 and X and Y, respectively. Lane 30—Lambda DNA digested with BstEII. An amplification product of approximately 2.8 Kb is observed only in lanes 5 and 9, representing human genomic DNA and DNA derived from cell hybrid carrying human chromosome 4, respectively. These results demonstrate that the hpa gene is localized in human chromosome 4.

The reactions were performed with Expand long PCR (Boehringer Mannheim). The resulting amplification products were analyzed using agarose gel electrophoresis. As demonstrated in FIG. 14, a single band of approximately 2.8 Kb was obtained from chromosome 4, as well as from the control human genomic DNA. A 2.8 kb amplification product is expected based on amplification of the genomic hpa clone (data not shown ). No amplification products were obtained neither in the control DNA samples of hamster and mouse nor in somatic hybrids of other human chromosome.

Example 10

Human Genomic Clone Encoding Heparanase

Five plaques were isolated following screening of a human genomic library and were designated L3-1, L5-1, L8-1, L10-1 and L6-1. The phage DNAs were analyzed by Southern hybridization and by PCR with hpa specific and vector specific primers. Southern analysis was performed with three fragments of hpa cDNA: a PvuII-BamHI fragment (nucleotides 32–450, SEQ ID NO:9), a BamHI-NdeI fragment (nucleotides 451–1102, SEQ ID NO:9) and an NdeI-XhoI fragment (nucleotides 1103–1721, SEQ ID NO:9).

Figure 15:
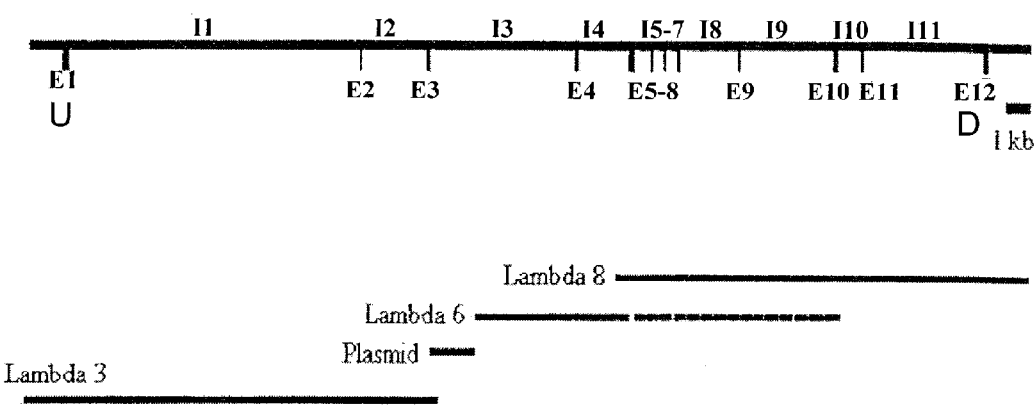
FIG. 15 demonstrates the genomic exon-intron structure of the human hpa locus (top) and the relative positions of the lambda clones used as sequencing templates to sequence the locus (below). The vertical rectangles represent exons (E) and the horizontal lines therebetween represent introns (I), upstream (U) and downstream (D) regions. Continuous lines represent DNA fragments, which were used for sequence analysis. The discontinuous line in lambda 6 represent a region, which overlaps with lambda 8 and hence was not analyzed. The plasmid contains a PCR product, which bridges the gap between L3 and L6.

Following Southern analysis, phages L3, L6, L8 were selected for further analysis. A scheme of the genomic region and the relative position of the three phage clones is depicted in FIG. 15. A 2 kb DNA fragment containing the gap between phages L6 and L3 was PCR amplified from human genomic DNA with two gene specific primers GHpuL3 and GHplL6. The PCR product was cloned into the plasmid vector pGEM-T-easy (Promega).

Large scale DNA sequencing of the three Lambda clones and the amplified fragment was performed with Lambda purified DNA by primer walking. A nucleotide sequence of 44,898 bp was analyzed (FIG. 16, SEQ ID NO:42). Comparison of the genomic sequence with that of hpa cDNA revealed 12 exons separated by 11 introns (FIGS. 15 and 16). The genomic organization of the hpa gene is depicted in FIG. 15 (top). The sequence include the coding region from the first ATG to the stop codon which spans 39,113 nucleotides, 2742 nucleotides upstream of the first ATG and 3043 nucleotides downstream of the stop codon. Splice site consensus sequences were identified at exon/intron junctions.

Example 11

Alternative Splicing

Several minor RT-PCR products were obtained from various cell types, following amplification with hpa specific primers. Each one found to contain a deletion of one or two exons. Some of these PCR products contain ORFs, which encode potential shorter proteins.

Table 1 below summarizes the alternative spliced products isolated from various cell lines.

Fragments of similar sizes were obtained following amplification with two cell lines, placenta and platelets.

| Cell type | Nucleotides deleted | Exons deleted | ORF |
|---|---|---|---|
| Platelets | 1047–1267 | 8, 9 | + |
| Platelets | 1154–1267 | 9 | − |
| Platelets | 289–435, 562–735 | 2, 4 | − |
| Sk-hep1, platelets, Zr75 | 562–735 | 4 | + |
| Sk-hep1 (hepatoma) | 561–904 | 4, 5 | − |
| Zr75 (breast carcinoma) | 96–203 | 1 (partial) | + |

Example 12

Mouse and Rat hpa

EST databases were screened for sequences homologous to the hpa gene. Three mouse EST's were identified (accession No. Aa177901, from mouse spleen, Aa067997 from mouse skin, Aa47943 from mouse embryo), assembled into a 824 bp cDNA fragment which contains a partial open reading frame (lacking a 5' end) of 629 bp and a 3' untranslated region of 195 bp (SEQ ID NO:12). As shown in FIG. 13, the coding region is 80% similar to the 3' end of the hpa cDNA sequence. These EST's are probably cDNA fragments of the mouse hpa homolog that encodes for the mouse heparanase.

Searching for consensus protein domains revealed an amino terminal S homology between the heparanase and several precursor proteins such as Procollagen Alpha 1 precursor, Tyrosine-protein kinase-RYK, Fibulin-1, Insulin-like growth factor binding protein and several others. The amino terminus is highly hydrophobic and contains a potential trans-membrane domain. The homology to known signal peptide sequences suggests that it could function as a signal peptide for protein localization.

The amino acid sequence of human heparanase was used to search for homologous sequences in the DNA and protein databases. Several human EST's were identified, as well as mouse sequences highly homologous to human heparanase. The following mouse EST's were identified AA177901, AA674378, AA67997, AA047943, AA690179, A122034, all sharing an identical sequence and correspond to amino acids 336–543 of the human heparanase sequence. The entire mouse heparanase cDNA was cloned, based on the nucleotide sequence of the mouse EST's. PCR primers were designed and a Marathon RACE was performed using a Marathon cDNA library from 15 days mouse embryo (Clontech) and from BL6 mouse melanoma cell line. The mouse hpa homologous cDNA was isolated following several amplification steps. A 1.1 kb fragment was amplified from mouse embryo Marathon cDNA library. The first cycle of amplification was performed with primers mhpl773 and Ap1 and the second cycle with primers mhpl736 and AP2. A 1.1 kb fragment was then amplified from BL6 Marathon cDNA library. The first cycle of amplification was performed with the primers mhpl152 and Ap1, and the second with mhpl83 and AP2. The combined sequence was homologous to nucleotides 157–1702 of the human hpa cDNA, which encode amino acids 33–543. The 5' end of the mouse hpa gene was isolated from a mouse genomic DNA library using the Genome Walker kit (Clontech). An 0.9 kb fragment was amplified from a DraI digested Genome walker DNA library. The first cycle of amplification was performed with primers mhpl114 and Ap1 and the second with primers mhpl103 and AP2. The assembled sequence (SEQ ID NOs:43, 45) is 2396 nucleotides long. It contains an open reading frame of 1605 nucleotides, which encode a polypeptide of 535 amino acids (SEQ ID NOs:44, 45), 196 nucleotides of 3' untranslated region (UTR), and an upstream sequence which includes the promoter region and the 5'-UTR of the mouse hpa cDNA. According to two promoter predicting programs TSSW and TSSG, the transcription start site is localized to nucleotide 431 of SEQ ID NOs:43, 45, 163 nucleotides upstream of the first ATG codon. The 431 upstream genomic sequence contains the promoter region. A TATA box is predicted at position 394 of SEQ ID NOs:43, 45. The mouse and the human hpa genes share an average homology of 78% between the nucleotide sequences and 81% similarity between the deduced amino acid sequences.

Search for hpa homologous sequences, using the Blast 2.0 server revealed two EST's from rat: AI060284 (385 nucleotides, SEQ ID NO:46) which is homologous to the amino terminus (68% similarity to amino acids 12–136) of human heparanase and AI237828 (541 nucleotides, SEQ ID NO:47) which is homologous to the carboxyl terminus (81% similarity to amino acids 500–543) of human heparanase, and contains a 3'-UTR. A comparison between the human heparanase and the mouse and rat homologous sequences is demonstrated in FIG. 17.

Example 13

Prediction of Heparanase Active Site

Homology search of heparanase amino acid sequence against the DNA and the protein databases revealed no significant homologies. The protein secondary structure as predicted by the PHD program consists of alternating alpha helices and beta sheets. The fold recognition server of UCLA predicted alpha/beta barrel structure, with under-threshold confidence.

Five of 15 proteins, which were predicted to have most similar folds, were glycosyl hydrolases from various organisms: lxyza—xylanase from Clostridium Thermocellum, lpbga—6-phospho-beta-δ-galactosidase from Lactococcus Lactis, 1amy—alpha-amylase from Barley, 1ecea—endocellulase from Acidothermus Cellulolyticus and 1qbc—hexosaminidase alpha chain, glycosyl hydrolase.

Protein homology search using the bioaccelerator pulled out several proteins, including glycosyl hydrolyses such as beta-fructofuranosidase from *Vicia faba* (broad bean) and from potato, lactase phlorizin hydrolase from human, xylanases from *Clostridium thermocellum* and from *Streptomyces halstedii* and cellulase from *Clostridium thermocellum*. Blocks 9.3 database pulled out the active site of glycosyl hydrolases family five, which includes cellulases from various bacteria and fungi. Similar active site motif is shared by several lysosomal acid hydrolases (63) and other glycosyl hydrolases. The common mechanism shared by these enzymes involves two glutamic acid residues, a proton donor and a nucleophile.

Despite the lack of an overall homology between the heparanase and other glycosyl hydolases, the amino acid couple Asp-Glu (NE), which is characteristic of the proton donor of glycosyl hydrolyses of the GH-A clan, was found at positions 224–225 of the human heparanase protein sequence. As in other clan members, this NE couple is located at the end of a β sheet.

Considering the relative location of the proton donor and the predicted secondary structure, the glutamic acid that functions as nucleophile is most likely located at position 343, or at position 396. Identification of the active site and the amino acids directly involved in hydrolysis opens the way for expression of the defined catalytic domain. In addition, it will provide the tools for rational design of enzyme activity either by modification of the microenviroment or catalytic site itself.

Example 14

Expression of hpa Antisense in Mammalian Cell Lines

A mammalian expression vector Hpa2Kepcdna3 was constructed in order to express hpa antisense in mammalian cells. hpa cDNA (1.7 kb EcoRI fragment) was cloned into the plasmid pcDNA3 in 3'>5' (antisense) orientation. The construct was used to transfect MBT2-T50 and T24P cell lines. $2 \times 10^5$ cells in 35 mm plates were transfected using the Fugene protocol (Boehringer Mannheim). 48 hours after transfection cells were trypsinized and seeded in six well plates. 24 hours later G418 was added to initiate selection. The number of colonies per 35 mm plate following 3 weeks:

|  | Antisense | No insert |
|---|---|---|
| T24P | 15 | 60 |
| MBT-T50 | 1 | 6 |

The lower number of colonies obtained after transfection with hpa antisense, as compared with the control plasmid suggests that the introduction of hpa antisense interfere with cell growth. This experiment demonstrates the use of complementary antisense hpa DNA sequence to control heparanase expression in cells. This approach may be used to inhibit expression of heparanase in vivo, in, for example, cancer cells and in other pathological processes in which heparanase is involved.

Example 15

Zoo Blot

Figure 18:
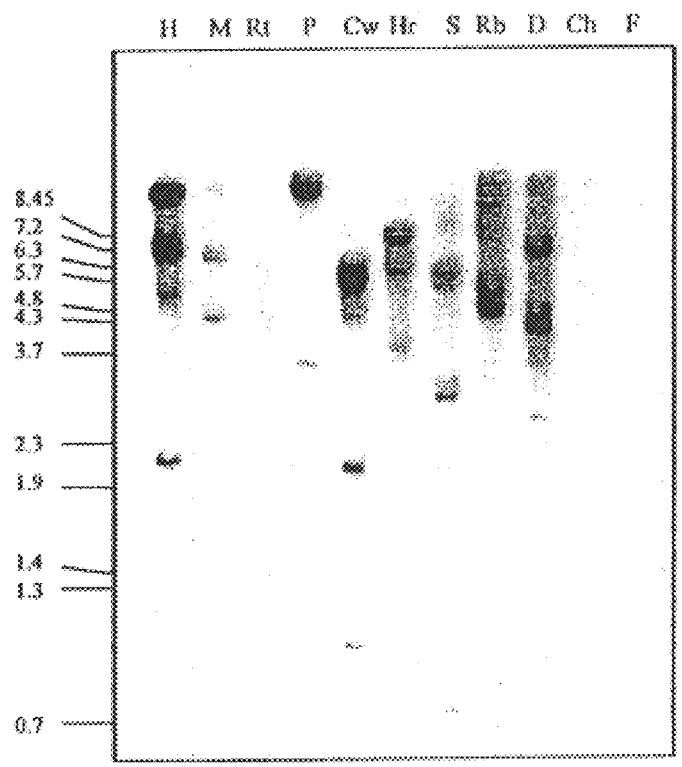
FIG. 18 presents a heparanase Zoo blot. Ten micrograms of genomic DNA from various sources were digested with EcoRI and separated on 0.7% agarose—TBE gel. Following electrophoresis, the was gel treated with HCl and than with NaOH and the DNA fragments were downward transferred to a nylon membrane (Hybond N+, Amersham) with 0.4 N NaOH. The membrane was hybridized with a 1.6 Kb DNA probe that contained the entire hpa cDNA. Lane order: H—Human; M—Mouse; Rt—Rat; P—Pig; Cw—Cow; Hr—Horse; S—Sheep; Rb—Rabbit; D—Dog; Ch—Chicken; F—Fish. Size markers (Lambda BstelI) are shown on the left FIG. 19 demonstrates the secondary structure prediction for heparanase performed using the PHD server—Profile network Prediction Heidelberg. H—helix, E—extended (beta strand), The glutamic acid predicted as the proton donor is marked by asterisk and the possible nucleophiles are underlined.

Hpa cDNA was used as a probe to detect homologous sequences in human DNA and in DNA of various animals. The autoradiogram of the Southern analysis is presented in FIG. 18. Several bands were detected in human DNA, which correlated with the accepted pattern according to the genomic hpa sequence. Several intense bands were detected in all mammals, while faint bands were detected in chicken. This correlates with the phylogenetic relation between human and the tested animals. The intense bands indicate that hpa is conserved among mammals as well as in more genetically distant organisms. The multiple bands patterns suggest that in all animals, like in human, the hpa locus occupy large genomic region. Alternatively, the various bands could represent homologous sequences and suggest the existence of a gene family, which can be isolated based on their homology to the human hpa reported herein. This conservation was actually found, between the isolated human hpa cDNA and the mouse homologue.

Example 16

Characterization of the hpa Promoter

The DNA sequence upstream of the hpa first ATG was subjected to computational analysis in order to localize the predicted transcription start site and to identify potential transcription factors binding sites. Recognition of human PolII promoter region and start of transcription were predicted using the TSSW and TSSG programs. Both programs identified a promoter region upstream of the coding region. TSSW pointed at nucleotide 2644 and TSSG at 2635 of SEQ ID NO:42. These two predicted transcription start sites are located 4 and 13 nucleotides upstream of the longest hpa cDNA isolated by RACE.

A hpa promoter-GFP reporter vector was constructed in order to investigate the regulation of hpa transcription. Two constructs were made, containing 1.8 kb and 1.1 kb of the hpa promoter region. The reporter vector was transfected into T50-mouse bladder carcinoma cells. Cells transfected with both constructs exhibited green fluorescence, which indicated the promoter activity of the genomic sequence upstream of the hpa-coding region. This reporter vector, enables the monitoring of hpa promoter activity, at various conditions and in different cell types and to characterize the factors involved regulation of hpa expression.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

LIST OF REFERENCES

1. Wight, T. N., Kinsella, M. G., and Qwarnstromn, E. E. (1992). The role of proteoglycans in cell adhesion, migration and proliferation. *Curr. Opin. Cell Biol.*, 4, 793–801.
2. Jackson, R. L., Busch, S. J., and Cardin, A. L. (1991). Glycosaminoglycans: Molecular properties, protein interactions and role in physiological processes. *Physiol. Rev.*, 71, 481–539.
3. Wight, T. N. (1989). Cell biology of arterial proteoglycans. *Arteriosclerosis*, 9, 1–20.
4. Kjellen, L., and Lindahl, U. (1991). Proteoglycans: structures and interactions. *Annu. Rev. Biochem.*, 60, 443–475.
5. Ruoslahti, E., and Yamaguchi, Y. (1991). Proteoglycans as modulators of growth factor activities. *Cell*, 64, 867–869.
6. Vlodavsky, I., Eldor, A., Haimovitz-Friedman, A., Matzner, Y., Ishai-Michaeli, R., Levi, E., Bashkin, P., Lider, O., Naparstek, Y., Cohen, I. R., and Fuks, Z. (1992). Expression of heparanase by platelets and circulating cells of the immune system: Possible involvement in diapedesis and extravasation. *Invasion & Metastasis*, 12, 112–127.

7. Vlodavsky, I., Mohsen, M., Lider, O., Ishai-Michaeli, R., Ekre, H.-P., Svahn, C. M., Vigoda, M., and Peretz, T. (1995). Inhibition of tumor metastasis by heparanase inhibiting species of heparin. *Invasion & Metastasis*, 14, 290–302.
8. Nakajima, M., Irimura, T., and Nicolson, G. L. (1988). Heparanase and tumor metastasis. *J. Cell. Biochem.*, 36, 157–167.
9. Nicolson, G. L. (1988). Organ specificity of tumor metastasis: Role of preferential adhesion, invasion and growth of malignant cells at specific secondary sites. *Cancer Met. Rev.*, 7, 143–188.
10. Liotta, L. A., Rao, C. N., and Barsky, S. H. (1983). Tumor invasion and the extracellular matrix. *Lab. Invest.*, 49, 639–649.
11. Vlodavsky, I., Fuks, Z., Bar-Ner, M., Ariav, Y., and Schirrmacher, V. (1983). Lymphoma cell mediated degradation of sulfated proteoglycans in the subendothelial extracellular matrix: Relationship to tumor cell metastasis. *Cancer Res.*, 43, 2704–2711.
12. Vlodavsky, I., Ishai-Michaeli, R., Bar-Ner, M., Fridman, R., Horowitz, A. T., Fuks, Z. and Biran, S. (1988). Involvement of heparanase in tumor metastasis and angiogenesis. Is. *J. Med.*, 24, 464–470.
13. Vlodavsky, I., Liu, G. M., and Gospodarowicz, D. (1980). Morphological appearance, growth behavior and migratory activity of human tumor cells maintained on extracellular matrix vs. plastic. *Cell*, 19, 607–616.
14. Gospodarowicz, D., Delgado, D., and Viodavsky, I. (1980). Permissive effect of the extracellular matrix on cell proliferation in-vitro. *Proc. Natl. Acad. Sci. USA.*, 77, 4094–4098.
15. Bashkin, P., Doctrow, S., Klagsbrun, M., Svahn, C. M., Folkman, J., and Vlodavsky, 1. (1989). Basic fibroblast growth factor binds to subendothelial extracellular matrix and is released by heparitinase and heparin-like molecules. *Biochemistry*, 28, 1737–1743.
16. Parish, C. R., Coombe, D. R., Jakobsen, K. B., and Underwood, P. A. (1987). Evidence that sulphated polysaccharides inhibit tumor metastasis by blocking tumor cell-derived heparanase. *Int. J. Cancer*, 40, 511–517.
16a. Vlodavsky, I., Hua-Quan Miao., Benezra, M., Lider, O., Bar-Shavit, R., Schmidt, A., and Peretz, T. (1997). Involvement of the extracellular matrix, heparan sulfate proteoglycans and heparan sulfate degrading enzymes in angiogenesis and metastasis. In: Tumor Angiogenesis. Eds. C. E. Lewis, R. Bicknell & N. Ferrara. Oxford University Press, Oxford UK, pp. 125–140.
17. Burgess, W. H., and Maciag, T. (1989). The heparin-binding (fibroblast) growth factor family of proteins. *Annu. Rev. Biochem.*, 58, 575–606.
18. Folkman, J., and Klagsbrun, M. (1987). Angiogenic factors. *Science*, 235, 442–447.
19. Vlodavsky, I., Folkman, J., Sullivan, R., Fridman, R., Ishai-Michaelli, R., Sasse, J., and Klagsbrun, M. (1987). Endothelial cell-derived basic fibroblast growth factor: Synthesis and deposition into subendothelial extracellular matrix. *Proc. Natl. Acad. Sci. USA*, 84, 2292–2296.
20. Folkman, J., Klagsbrun, M., Sasse, J., Wadzinski, M., Ingber, D., and Vlodavsky, I. (1980). A heparin-binding angiogenic protein—basic fibroblast growth factor—is stored within basement membrane. *Am. J. Pathol*, 130, 393–400.
21. Cardon-Cardo, C., Vlodavsky, I., Haimovitz-Friedman, A., Hicklin, D., and Fuks, Z. (1990). Expression of basic fibroblast growth factor in normal human tissues. *Lab. Invest.*, 63, 832–840.
22. Ishai-Michaeli, R., Svahn, C.-M., Chajek-Shaul, T., Komer, G., Ekre, H.-P., and Vlodavsky, I. (1992). Importance of size and sulfation of heparin in release of basic fibroblast factor from the vascular endothelium and extracellular matrix. *Biochemistry*, 31, 2080–2088.
23. Ishai-Michaeli, R., Eldor, A., and Vlodavsky, I. (1990). Heparanase activity expressed by platelets, neutrophils and lymphoma cells releases active fibroblast growth factor from extracellular matrix. *Cell Reg.*, 1, 833–842.
24. Vlodavsky, I., Bar-Shavit, R., Ishai-Michaeli, R., Bashkin, P., and Fuks, Z. (1991). Extracellular sequestration and release of fibroblast growth factor: a regulatory mechanism? *Trends Biochem. Sci.*, 16, 268–271.
25. Vlodavsky, I., Bar-Shavit, R., Komer, G., and Fuks, Z. (1993). Extracellular matrix-bound growth factors, enzymes and plasma proteins. In Basement membranes: Cellular and molecular aspects (eds. D. H. Rohrbach and R. Timpi), pp327–343. Academic press Inc., Orlando, Fla.
26. Yayon, A., Klagsbrun, M., Esko, J. D., Leder, P., and Omitz, D. M. (1991). Cell surface, heparin-like molecules are required for binding of basic fibroblast growth factor to its high affinity receptor. *Cell*, 64, 841–848.
27. Spivak-Kroizman, T., Lemmon, M. A., Dikic, I., Ladbury, J. E., Pinchasi, D., Huang, J., Jaye, M., Crumley, G., Schlessinger, J., and Lax, I. (1994). Heparin-induced oligomerization of FGF molecules is responsible for FGF receptor dimerization, activation, and cell proliferation. *Cell*, 79, 1015–1024.
28. Omitz, D. M., Herr, A. B., Nilsson, M., West, a., J., Svahn, C.-M., and Waksman, G. (1995). FGF binding and FGF receptor activation by synthetic heparan-derived di- and trisaccharides. *Science*, 268, 432–436.
29. Gitay-Goren, H., Soker, S., Vlodavsky, 1., and Neufeld, G. (1992). Cell surface associated heparin-like molecules are required for the binding of vascular endothelial growth factor (VEGF) to its cell surface receptors. *J. Biol. Chem.*, 267, 6093–6098.
30. Lider, O., Baharav, E., Mekori, Y., Miller, T., Naparstek, Y., Vlodavsky, I., and Cohen, I. R. (1989). Suppression of experimental autoimmune diseases and prolongation of allograft survival by treatment of animals with heparinoid inhibitors of T lymphocyte heparanase. *J. Clin. Invest.*, 83, 752–756.
31. Lider, O., Cahalon, L., Gilat, D., Hershkovitz, R., Siegel, D., Margalit, R., Shoseyov, O., and Cohn, I. R. (1995). A disaccharide that inhibits tumor necrosis factor α is formed from the extracellular matrix by the enzyme heparanase. *Proc. Natl. Acad. Sci. USA.*, 92, 5037–5041.
31a. Rapraeger, A., Krufka, A., and Olwin, B. R. (1991). Requirement of heparan sulfate for bFGF-mediated fibroblast growth and myoblast differentiation. *Science*, 252, 1705–1708.
32. Eisenberg, S., Sehayek, E., Olivecrona, T., and Vlodavsky, I. (1992). Lipoprotein lipase enhances binding of lipoproteins to heparan sulfate on cell surfaces and extracellular matrix. *J. Clin. Invest.*, 90, 2013–2021.
33. Shieh, M-T., Wundunn, D., Montgomery, R. I., Esko, J. D., and Spear, P. G. J. (1992). Cell surface receptors for herpes simplex virus are heparan sulfate proteoglycans. *J. Cell Biol.*, 116, 1273–1281.
33a. Chen, Y., Maguire, T., Hileman, R. E., Fromm, J. R., Esko, J. D., Linhardt, R. J., and Marks, R. M. (1997). Dengue virus infectivity depends on envelope protein binding to target cell heparan sulfate. *Nature Medicine* 3, 866–871.
33b. Putnak, J. R., Kanesa-Thasan, N., and Innis, B. L. (1997). A putative cellular receptor for dengue viruses. *Nature Medicine* 3, 828–829.

34. Narindrasorasak, S., Lowery, D., Gonzalez-DeWhitt, P., Poorman, R. A., Greenberg, B., Kisilevsky, R. (1991). High affinity interactions between the Alzheimer's beta-amyloid precursor protein and the basement membrane form of theparan sulfate proteoglycan. *J. Biol. Chem.*, 266, 12878–83.

35. Ross, R. (1993). The pathogenesis of atherosclerosis: a perspective for the 1990s. *Nature (Lond.).*, 362:801–809.

36. Zhong-Sheng, J., Walter, J., Brecht, R., Miranda, D., Mahmood Hussain, M., Innerarity, T. L. and Mahley, W. R. (1993). Role of heparan sulfate proteoglycans in the binding and uptake of apolipoprotein E-enriched remnant lipoproteins by cultured cells. *J. Biol. Chem.*, 268, 10160–10167.

37. Ernst, S., Langer, R., Cooney, Ch. L., and Sasisekharan, R. (1995). Enzymatic degradation of glycosaminoglycans. Critical Reviews in Biochemistry and Molecular Biology, 30(5), 387–444.

38. Gospodarowicz, D., Mescher, A L., Birdwell, C R. (1977). Stimulation of corneal endothelial cell proliferation in vitro by fibroblast and epidermal growth factors. *Exp Eye Res* 25, 75–89.

39. Haimovitz-Friedman, A., Falcone, D. J., Eldor, A., Schirrmacher, V., Vlodavsky, I., and Fuks, Z. (1991) Activation of platelet heparitinase by tumor cell-derived factors. *Blood*, 78, 789–796.

39a. Savitsky, K., Platzer, M., Uziel, T., Gilad, S., Sartiel, A., Rosental, A., Elroy-Stein, O., Siloh, Y. and Rotman, G. (1997). Ataxia-telangiectasia: structural diversity of untranslated sequences suggests complex post-translational regulation of ATM gene expression. Nucleic Acids Res. 25(9), 1678–1684.

40. Bar-Ner, M., Eldor, A., Wasserman, L., Matzner, Y., and Vlodavsky, I. (1987). Inhibition of heparanase mediated degradation of extracellular matrix heparan sulfate by modified and non-anticoagulant heparin species. *Blood*, 70, 551–557.

41. Goshen, R., Hochberg, A., Korner, G., Levi, E., Ishai-Michaeli, R., Elkin, M., de Grot, N., and Vlodavsky, 1. (1996). Purification and characterization of placental heparanase and its expression by cultured cytotrophoblasts. *Mol. Human Reprod.*, 2, 679–684.

42. Korb M., Ke Y. and Johnson L. F. (1993) Stimulation of gene expression by introns: conversion of an inhibitory intron to a stimulatory intron by alteration of the splice donor sequence. *Nucleic Acids Res.*, 25;21(25):5901–8.

43. Zheng B., Qiu X. Y., Tan M., Xing Y. N., Lo D., Xue J. L. and Qiu X. F. (1997) Increment of HFIX expression with endogenous intron 1 in vitro. *Cell Res.*, 7(1):21–29.

44. Kurachi S., Hitomi Y., Furukawa M. and Kurachi K. (1995) Role of intron 1 in expression of the human factor IX gene. *J. Biol. Chem.* 10, 270(10):5276–5281.

45. Shekhar P. V. and Miller F. R. (1994–5) Correlation of differences in modulation of ras expression with metastatic competence of mouse mammary tumor subpopulations. *Invasion Metastasis*, 14(1–6):27–37.

46. Zhou G., Garofalo S., Mukhopadhyay K., Lefebvre V., Smith C. N., Eberspaecher H. and de Crombrugghe B. (1995) A 182 bp fragment of the mouse pro alpha 1(II) collagen gene is sufficient to direct chondrocyte expression in transgenic mice. *J. Cell Sci.*, 108 (Pt 12):3677–3684.

47. Hormuzdi S. G., Penttinen R., Jaenisch R. and Bornstein P. (1998) A gene-targeting approach identifies a function for the first intron in expression of the alpha1(I) collagen gene. *Mol. Cell*, 18(6):3368–3375.

48. Kang Y. K., Lee C. S., Chung A. S. and Lee K. K. (1998) Prolactin-inducible enhancer activity of the first intron of the bovine beta-casein gene. *Mol. Cells*, 30;8(3):259–265.

49. Chow Y. H., O'Brodovich H., Plumb J., Wen Y., Sohn K. J., Lu Z., Zhang F., Lukacs G. L., Tanswell A. K., Hui C. C., Buchwald M. and Hu J. (1997) Development of an epithelium-specific expression cassette with human DNA regulatory elements for transgene expression in lung airways. *Proc. Natl. Acad. Sci. USA*, 23;94(26):14695–14700.

50. Gottschalk U. and Chan S. (1998) Somatic gene therapy. Present situation and future perspective. *Arzneimittelforschung*, 48(11):1111–1120.

51. Ye S., Cole-Strauss A. C., Frank B. and Kmiec E. B. (1998) Targeted gene correction: a new strategy for molecular medicine. *Mol. Med. Today*, 4(10):431–437.

52. Lai L., and Lien Y. (1999) Homologous recombination based gene therapy. *Exp. Nephrol.*, 7(1):11–14.

53. Yazaki N., Fujita H., Ohta M., Kawasaki T. and Itoh N. (1993) The structure and expression of the FGF receptor-1 mRNA isoforms in rat tissues. *Biochim. Biophys. Acta.*, 20;1172(1–2):37–42.

54. Le Fur N., Kelsall S. R., Silvers W. K. and Mintz B. (1997) Selective increase in specific alternative splice variants of tyrosinase in murine melanomas: a projected basis for immunotherapy. *Proc. Natl. Acad. Sci. USA*, 13;94(10):5332–5337.

55. Miyake H., Okamoto I., Hara I., Gohji K., Yamanaka K., Arakawa S., Kamidono S. and Saya H. (1998) Highly specific and sensitive detection of malignancy in urine samples from patients with urothelial cancer by CD44v8-10/CD44v10 competitive RT-PCR. *Int. J. Cancer*, 18;79(6):560–564.

56. Guriec N., Marcellin L., Gairard B., Calderoli H., Wilk A., Renaud R., Bergerat J. P. and Oberling F. (1996) CD44 exon 6 expression as a possible early prognostic factor in primary node negative breast carcinoma. *Clin. Exp. Metastasis*, 14(5):434–439.

57. Gewirtz A. M., Sokol D. L. and Ratajczak M. Z. (1998) Nucleic acid therapeutics: state of the art and future prospects. Blood, 1;92(3):712–736.

58. Hida K., Shindoh M., Yasuda M., Hanzawa M., Funaoka K., Kohgo T., Amemiya A., Totsuka Y., Yoshida K. and Fujinaga K (1997) Antisense EIAF transfection restrains oral cancer invasion by reducing matrix metalloproteinase activities. *Am. J. Pathol.* 150(6):2125–2132.

59. Shastry B. S. (1998) Gene disruption in mice: models of development and disease. *Mol. Cell. Biochem.* 1998 April; 181(1–2):163–179.

60. Carpentier A. F., Rosenfeld M. R., Delattre J. Y., Whalen R. G., Posner J. B. and Dalmau J. (1998) DNA vaccination with HuD inhibits growth of a neuroblastoma in mice. *Clin. Cancer Res.*, 4(11):2819–2824.

61. Lai W. C. and Bennett M. (1998) DNA vaccines. *Crit. Rev. Immunol.*, 18(5):449–484.

62. Welch P. J., Barber J. R., and Wong-Staal F. (1998) Expression of ribozymes in gene transfer systems to modulate target RNA levels. *Curr. Opin. Biotechnol.*, 9(5):486–496.

63. Durand P., Lehn P., Callebaunt I., Fabrega S., Henrissat B. and Mornon J.P. (1997) Active-site motifs of lysosomal acid hydrolyses: invariant features of clan GH-A glycosyl hydrolases deduced from hydrophobic cluster analysis. Glycobiology, 7(2):277–284.

64. Thuong and Helene (1993) Sequence specific recognition and modification of double helical DNA by oligonucleotides Angev. Chem. Int. Ed. Engl. 32:666

65. Dash P., Lotan I., Knapp M., Kandel E. R. and Goelet P. (1987) Selective elimination of mRNAs in vivo: complementary oligodeoxynucleotides promote RNA degradation by an RNase H-like activity. Proc. Natl. Acad. Sci. USA, 84:7896.
66. Chiang M. Y., Chan H., Zounes M. A., Freier S. M., Lima W. F. and Bennett C. F. (1991) Antisense oligonucleotides inhibit intercellular adhesion molecule 1 expression by two distinct mechanisms. J. Biol. Chem. 266:18162–71.
67. Paterson Paterson B. M, Roberts B. E and Kuff E L. (1977) Structural gene identification and mapping by DNA-mRNA hybrid-arrested cell-free translation. Proc. Natl. Acad. Sci. USA, 74:4370.
68. Cohen (1992) Oligonucleotide therapeutics. Trends in Biotechnology, 10:87.
69. Szczylik et al (1991) Selective inhibition of leukemia cell proliferation by BCR-ABL antisense oligodeoxynucleotides. Science 253:562.
70. Calabretta et al. (1991) Normal and leukemic hematopoietic cell manifest differential sensitivity to inhibitory effects of c-myc antisense oligodeoxynucleotides: an in vitro study relevant to bone marrow purging. Proc. Natl. Acad. Sci. USA 88:2351.
71. Heikhila et al. (1987) A c-myc antisense oligodeoxynucleotide inhibits entry into S phase but not progress from G(0) to G(1). Nature, 328:445.
72. Reed et al. (1990) Antisense mediated inhibition of BCL2 prooncogene expression and leukemic cell growth and survival: comparison of phosphodiester and phosphorothioate oligodeoxynucleotides. Cancer Res. 50:6565.
73. Burch and Mahan (1991) Oligodeoxynucleotides antisense to the interleukin I receptor m RNA block the effects of interleukin I in cultured murine and human fibroblasts and in mice. J. Clin. Invest. 88:1190.
74. Agrawal (1992) Antisense oligonucleotides as antiviral agents. TIBTECH 10:152.
75. Uhlmann et al. (1990) Chem. Rev. 90:544.
76. Cook (1991) Medicinal chemistry of antisense oligonucleotides—future opportunities. Anti-Cancer Drug Design 6:585.
77. Biotechnology research news (1993) Can DNA mimics improve on the real thing? Science 262:1647.

What is claimed is:

1. An antisense oligonucleotide comprising a polynucleotide of a least 10 bases which specifically targets and inhibits the expression of the polynucleotide of SEQ ID No: 9 or SEQ ID NO: 13, wherein the polynucleotides SEQ ID NO: 9 and 13 encode polypeptides having heparanase catalytic activity.

2. The antisense oligonucleotide of claim 1, wherein said polypeptide having heparanase catalytic activity is as set forth in SEQ ID NOs: 10 and 14.

3. An antisense nucleic acid construct comprising a promoter sequence operably-linked to a polynucleotide sequence encoding the antisense oligonucleotide of claim 1.

4. The antisense nucleic acid construct of claim 3, wherein said polypeptide having heparanase catalytic activity is as set forth in SEQ ID NOs: 10, or 14.

5. A nucleic acid construct comprising SEQ ID NO: 13, encoding a polypeptide having heparanase catalytic activity.

* * * * *

```
                            SEQUENCE LISTING

<160> NUMBER OF SEQ ID NOS: 47

<210> SEQ ID NO 1
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 1
ccatcctaat acgactcact atagggc                                         27

<210> SEQ ID NO 2
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 2
gtagtgatgc catgtaactg aatc                                            24

<210> SEQ ID NO 3
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 3
actcactata gggctcgagc ggc                                             23

<210> SEQ ID NO 4
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 4
gcatcttagc cgtctttctt cg                                              22
```

```
<210> SEQ ID NO 5
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 5
tttttttttt ttttt                                                      15

<210> SEQ ID NO 6
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 6
ttcgatccca agaaggaatc                                                 20

<210> SEQ ID NO 7
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 7
gtagtgatgc catgtaactg aatc                                            24

<210> SEQ ID NO 8
<211> LENGTH: 9
<212> TYPE: PRT
<213> ORGANISM: Homo sapiens

<400> SEQUENCE: 8

Tyr Gly Pro Asp Val Gly Gln Pro Arg
1               5

<210> SEQ ID NO 9
<211> LENGTH: 1721
<212> TYPE: DNA
<213> ORGANISM: Homo sapiens

<400> SEQUENCE: 9
ctagagcttt cgactctccg ctgcgcggca gctggcgggg ggagcagcca ggtgagccca      60
agatgctgct gcgctcgaag cctgcgctgc cgccgccgct gatgctgctg ctcctggggc     120
cgctgggtcc cctctcccct ggcgcccgtc cccgacctgc gcaagcacag gacgtcgtgg     180
acctggactt cttcacccag gagccgctgc acctggtgag ccctcgtttc ctgtccgtca     240
ccattgacgc caacctggcc acggacccgc ggttcctcat cctcctgggt tctccaaagc     300
ttcgtacctt ggccagaggc ttgtctcctg cgtacctgag gtttggtggc accaagacag     360
acttcctaat tttcgatccc aagaaggaat caacctttga agagaagt tactggcaat      420 ctcaagtcaa ccaggatatt tgcaaatatg gatccatccc tcctgatgtg gaggagaagt     480
tacggttgga atggcctac caggagcaat tgctactccg agaacactac cagaaaaagt      540
tcaagaacag cacctactca agaagctctg tagatgtgct atacactttt gcaaactgct     600
caggactgga cttgatcttt ggcctaaatg cgttattaag aacagcagat ttgcagtgga     660
acagttctaa tgctcagttg ctcctggact actgctcttc caagggtat aacatttctt      720
```

-continued

```
gggaactagg caatgaacct aacagtttcc ttaagaaggc tgatattttc atcaatgggt      780
cgcagttagg agaagattat attcaattgc ataaacttct aagaaagtcc accttcaaaa      840
atgcaaaact ctatggtcct gatgttggtc agcctcgaag aaagacggct aagatgctga      900
agagcttcct gaaggctggt ggagaagtga ttgattcagt tacatggcat cactactatt      960
tgaatggacg gactgctacc agggaagatt ttctaaaccc tgatgtattg gacatttttta    1020 tttcatctgt gcaaaaagtt ttccaggtgg ttgagagcac caggcctggc aagaaggtct    1080
ggttaggaga aacaagctct gcatatggag cggagcgcc cttgctatcc gacacctttg      1140
cagctggctt tatgtggctg ataaattgg gcctgtcagc ccgaatggga atagaagtgg      1200
tgatgaggca agtattcttt ggagcaggaa actaccattt agtggatgaa acttcgatc      1260 ctttacctga ttattggcta tctcttctgt tcaagaaatt ggtgggcacc aaggtgttaa    1320
tggcaagcgt gcaaggttca agagaagga agcttcgagt ataccttcat tgcacaaaca    1380
ctgacaatcc aagtataaa gaaggagatt taactctgta tgccataaac ctccataacg      1440
tcaccaagta cttgcggtta ccctatcctt tttctaacaa gcaagtggat aaataccttc      1500
taagaccttt gggacctcat ggattacttt ccaaatctgt ccaactcaat ggtctaactc    1560
taaagatggt ggatgatcaa accttgccac cttttaatgga aaaacctctc cggccaggaa    1620
gttcactggg cttgccagct ttctcatata gttttttttgt gataagaaat gccaaagttg    1680
ctgcttgcat ctgaaaataa aatatactag tcctgacact g                         1721
```

<210> SEQ ID NO 10
<211> LENGTH: 543
<212> TYPE: PRT
<213> ORGANISM: Homo sapiens

<400> SEQUENCE: 10

```
Met Leu Leu Arg Ser Lys Pro Ala Leu Pro Pro Leu Met Leu Leu
1               5                   10                  15

Leu Leu Gly Pro Leu Gly Pro Leu Ser Pro Gly Ala Leu Pro Arg Pro
            20                  25                  30

Ala Gln Ala Gln Asp Val Val Asp Leu Asp Phe Phe Thr Gln Glu Pro
        35                  40                  45

Leu His Leu Val Ser Pro Ser Phe Leu Ser Val Thr Ile Asp Ala Asn
    50                  55                  60

Leu Ala Thr Asp Pro Arg Phe Leu Ile Leu Leu Gly Ser Pro Lys Leu
65                  70                  75                  80

Arg Thr Leu Ala Arg Gly Leu Ser Pro Ala Tyr Leu Arg Phe Gly Gly
                85                  90                  95

Thr Lys Thr Asp Phe Leu Ile Phe Asp Pro Lys Lys Glu Ser Thr Phe
            100                 105                 110

Glu Glu Arg Ser Tyr Trp Gln Ser Gln Val Asn Gln Asp Ile Cys Lys
        115                 120                 125

Tyr Gly Ser Ile Pro Pro Asp Val Glu Lys Leu Arg Leu Glu Trp
    130                 135                 140

Pro Tyr Gln Glu Gln Leu Leu Leu Arg Glu His Tyr Gln Lys Lys Phe
145                 150                 155                 160

Lys Asn Ser Thr Tyr Ser Arg Ser Ser Val Asp Val Leu Tyr Thr Phe
                165                 170                 175

Ala Asn Cys Ser Gly Leu Asp Leu Ile Phe Gly Leu Asn Ala Leu Leu
            180                 185                 190

Arg Thr Ala Asp Leu Gln Trp Asn Ser Ser Asn Ala Gln Leu Leu Leu
```

```
                195                 200                 205
Asp Tyr Cys Ser Ser Lys Gly Tyr Asn Ile Ser Trp Glu Leu Gly Asn
    210                 215                 220
Glu Pro Asn Ser Phe Leu Lys Lys Ala Asp Ile Phe Ile Asn Gly Ser
225                 230                 235                 240
Gln Leu Gly Glu Asp Tyr Ile Gln Leu His Lys Leu Leu Arg Lys Ser
                245                 250                 255
Thr Phe Lys Asn Ala Lys Leu Tyr Gly Pro Asp Val Gly Gln Pro Arg
            260                 265                 270
Arg Lys Thr Ala Lys Met Leu Lys Ser Phe Leu Lys Ala Gly Gly Glu
        275                 280                 285
Val Ile Asp Ser Val Thr Trp His His Tyr Tyr Leu Asn Gly Arg Thr
    290                 295                 300
Ala Thr Arg Glu Asp Phe Leu Asn Pro Asp Val Leu Asp Ile Phe Ile
305                 310                 315                 320
Ser Ser Val Gln Lys Val Phe Gln Val Val Glu Ser Thr Arg Pro Gly
                325                 330                 335
Lys Lys Val Trp Leu Gly Glu Thr Ser Ser Ala Tyr Gly Gly Gly Ala
            340                 345                 350
Pro Leu Leu Ser Asp Thr Phe Ala Ala Gly Phe Met Trp Leu Asp Lys
        355                 360                 365
Leu Gly Leu Ser Ala Arg Met Gly Ile Glu Val Val Met Arg Gln Val
    370                 375                 380
Phe Phe Gly Ala Gly Asn Tyr His Leu Val Asp Glu Asn Phe Asp Pro
385                 390                 395                 400
Leu Pro Asp Tyr Trp Leu Ser Leu Leu Phe Lys Lys Leu Val Gly Thr
                405                 410                 415
Lys Val Leu Met Ala Ser Val Gln Gly Ser Lys Arg Arg Lys Leu Arg
            420                 425                 430
Val Tyr Leu His Cys Thr Asn Thr Asp Asn Pro Arg Tyr Lys Glu Gly
        435                 440                 445
Asp Leu Thr Leu Tyr Ala Ile Asn Leu His Asn Val Thr Lys Tyr Leu
    450                 455                 460
Arg Leu Pro Tyr Pro Phe Ser Asn Lys Gln Val Asp Lys Tyr Leu Leu
465                 470                 475                 480
Arg Pro Leu Gly Pro His Gly Leu Leu Ser Lys Ser Val Gln Leu Asn
                485                 490                 495
Gly Leu Thr Leu Lys Met Val Asp Asp Gln Thr Leu Pro Pro Leu Met
            500                 505                 510
Glu Lys Pro Leu Arg Pro Gly Ser Ser Leu Gly Leu Pro Ala Phe Ser
        515                 520                 525
Tyr Ser Phe Phe Val Ile Arg Asn Ala Lys Val Ala Ala Cys Ile
    530                 535                 540

<210> SEQ ID NO 11
<211> LENGTH: 1721
<212> TYPE: DNA
<213> ORGANISM: Homo sapiens
<220> FEATURE:
<221> NAME/KEY: CDS
<222> LOCATION: (63)..(1691)

<400> SEQUENCE: 11
ctagagcttt cgactctccg ctgcgcggca gctggcgggg ggagcagcca ggtgagccca      60 ag atg ctg ctg cgc tcg aag cct gcg ctg ccg ccg ccg ctg atg ctg        107
```

-continued

```
    Met Leu Leu Arg Ser Lys Pro Ala Leu Pro Pro Leu Met Leu
     1               5                  10                 15 ctg ctc ctg ggg ccg ctg ggt ccc ctc tcc cct ggc gcc ctg ccc cga   155
Leu Leu Leu Gly Pro Leu Gly Pro Leu Ser Pro Gly Ala Leu Pro Arg
             20                  25                  30 cct gcg caa gca cag gac gtc gtg gac ctg gac ttc ttc acc cag gag   203
Pro Ala Gln Ala Gln Asp Val Val Asp Leu Asp Phe Phe Thr Gln Glu
         35                  40                  45 ccg ctg cac ctg gtg agc ccc tcg ttc ctg tcc gtc acc att gac gcc   251
Pro Leu His Leu Val Ser Pro Ser Phe Leu Ser Val Thr Ile Asp Ala
     50                  55                  60 aac ctg gcc acg gac ccg cgg ttc ctc atc ctc ctg ggt tct cca aag   299
Asn Leu Ala Thr Asp Pro Arg Phe Leu Ile Leu Leu Gly Ser Pro Lys
 65                  70                  75 ctt cgt acc ttg gcc aga ggc ttg tct cct gcg tac ctg agg ttt ggt   347
Leu Arg Thr Leu Ala Arg Gly Leu Ser Pro Ala Tyr Leu Arg Phe Gly
 80                  85                  90                  95 ggc acc aag aca gac ttc cta att ttc gat ccc aag aag gaa tca acc   395
Gly Thr Lys Thr Asp Phe Leu Ile Phe Asp Pro Lys Lys Glu Ser Thr
                100                 105                 110 ttt gaa gag aga agt tac tgg caa tct caa gtc aac cag gat att tgc   443
Phe Glu Glu Arg Ser Tyr Trp Gln Ser Gln Val Asn Gln Asp Ile Cys
            115                 120                 125 aaa tat gga tcc atc cct cct gat gtg gag gag aag tta cgg ttg gaa   491
Lys Tyr Gly Ser Ile Pro Pro Asp Val Glu Glu Lys Leu Arg Leu Glu
        130                 135                 140 tgg ccc tac cag gag caa ttg cta ctc cga gaa cac tac cag aaa aag   539
Trp Pro Tyr Gln Glu Gln Leu Leu Leu Arg Glu His Tyr Gln Lys Lys
    145                 150                 155 ttc aag aac agc acc tac tca aga agc tct gta gat gtg cta tac act   587
Phe Lys Asn Ser Thr Tyr Ser Arg Ser Ser Val Asp Val Leu Tyr Thr
160                 165                 170                 175 ttt gca aac tgc tca gga ctg gac ttg atc ttt ggc cta aat gcg tta   635
Phe Ala Asn Cys Ser Gly Leu Asp Leu Ile Phe Gly Leu Asn Ala Leu
                180                 185                 190 tta aga aca gca gat ttg cag tgg aac agt tct aat gct cag ttg ctc   683
Leu Arg Thr Ala Asp Leu Gln Trp Asn Ser Ser Asn Ala Gln Leu Leu
            195                 200                 205 ctg gac tac tgc tct tcc aag ggg tat aac att tct tgg gaa cta ggc   731
Leu Asp Tyr Cys Ser Ser Lys Gly Tyr Asn Ile Ser Trp Glu Leu Gly
        210                 215                 220 aat gaa cct aac agt ttc ctt aag aag gct gat att ttc atc aat ggg   779
Asn Glu Pro Asn Ser Phe Leu Lys Lys Ala Asp Ile Phe Ile Asn Gly
    225                 230                 235 tcg cag tta gga gaa gat tat att caa ttg cat aaa ctt cta aga aag   827
Ser Gln Leu Gly Glu Asp Tyr Ile Gln Leu His Lys Leu Leu Arg Lys
240                 245                 250                 255 tcc acc ttc aaa aat gca aaa ctc tat ggt cct gat gtt ggt cag cct   875
Ser Thr Phe Lys Asn Ala Lys Leu Tyr Gly Pro Asp Val Gly Gln Pro
                260                 265                 270 cga aga aag acg gct aag atg ctg aag agc ttc ctg aag gct ggt gga   923
Arg Arg Lys Thr Ala Lys Met Leu Lys Ser Phe Leu Lys Ala Gly Gly
            275                 280                 285 gaa gtg att gat tca gtt aca tgg cat cac tac tat ttg aat gga cgg   971
Glu Val Ile Asp Ser Val Thr Trp His His Tyr Tyr Leu Asn Gly Arg
        290                 295                 300 act gct acc agg gaa gat ttt cta aac cct gat gta ttg gac att ttt  1019
Thr Ala Thr Arg Glu Asp Phe Leu Asn Pro Asp Val Leu Asp Ile Phe
    305                 310                 315
```

-continued

| | | | | |
|---|---|---|---|---|
| att tca tct gtg caa aaa gtt ttc cag gtg gtt gag agc acc agg cct<br>Ile Ser Ser Val Gln Lys Val Phe Gln Val Val Glu Ser Thr Arg Pro<br>320                          325                          330                          335 | 1067 |

```
att tca tct gtg caa aaa gtt ttc cag gtg gtt gag agc acc agg cct    1067
Ile Ser Ser Val Gln Lys Val Phe Gln Val Val Glu Ser Thr Arg Pro
320                 325                 330                 335 ggc aag aag gtc tgg tta gga gaa aca agc tct gca tat gga ggc gga    1115
Gly Lys Lys Val Trp Leu Gly Glu Thr Ser Ser Ala Tyr Gly Gly Gly
                340                 345                 350 gcg ccc ttg cta tcc gac acc ttt gca gct ggc ttt atg tgg ctg gat    1163
Ala Pro Leu Leu Ser Asp Thr Phe Ala Ala Gly Phe Met Trp Leu Asp
            355                 360                 365 aaa ttg ggc ctg tca gcc cga atg gga ata gaa gtg gtg atg agg caa    1211
Lys Leu Gly Leu Ser Ala Arg Met Gly Ile Glu Val Val Met Arg Gln
        370                 375                 380 gta ttc ttt gga gca gga aac tac cat tta gtg gat gaa aac ttc gat    1259
Val Phe Phe Gly Ala Gly Asn Tyr His Leu Val Asp Glu Asn Phe Asp
385                 390                 395 cct tta cct gat tat tgg cta tct ctt ctg ttc aag aaa ttg gtg ggc    1307
Pro Leu Pro Asp Tyr Trp Leu Ser Leu Leu Phe Lys Lys Leu Val Gly
400                 405                 410                 415 acc aag gtg tta atg gca agc gtg caa ggt tca aag aga agg aag ctt    1355
Thr Lys Val Leu Met Ala Ser Val Gln Gly Ser Lys Arg Arg Lys Leu
                420                 425                 430 cga gta tac ctt cat tgc aca aac act gac aat cca agg tat aaa gaa    1403
Arg Val Tyr Leu His Cys Thr Asn Thr Asp Asn Pro Arg Tyr Lys Glu
            435                 440                 445 gga gat tta act ctg tat gcc ata aac ctc cat aac gtc acc aag tac    1451
Gly Asp Leu Thr Leu Tyr Ala Ile Asn Leu His Asn Val Thr Lys Tyr
        450                 455                 460 ttg cgg tta ccc tat cct ttt tct aac aag caa gtg gat aaa tac ctt    1499
Leu Arg Leu Pro Tyr Pro Phe Ser Asn Lys Gln Val Asp Lys Tyr Leu
465                 470                 475 cta aga cct ttg gga cct cat gga tta ctt tcc aaa tct gtc caa ctc    1547
Leu Arg Pro Leu Gly Pro His Gly Leu Leu Ser Lys Ser Val Gln Leu
480                 485                 490                 495 aat ggt cta act cta aag atg gtg gat gat caa acc ttg cca cct tta    1595
Asn Gly Leu Thr Leu Lys Met Val Asp Asp Gln Thr Leu Pro Pro Leu
                500                 505                 510 atg gaa aaa cct ctc cgg cca gga agt tca ctg ggc ttg cca gct ttc    1643
Met Glu Lys Pro Leu Arg Pro Gly Ser Ser Leu Gly Leu Pro Ala Phe
            515                 520                 525 tca tat agt ttt ttt gtg ata aga aat gcc aaa gtt gct gct tgc atc    1691
Ser Tyr Ser Phe Phe Val Ile Arg Asn Ala Lys Val Ala Ala Cys Ile
        530                 535                 540 tgaaaataaa atatactagt cctgacactg                                   1721

<210> SEQ ID NO 12
<211> LENGTH: 824
<212> TYPE: DNA
<213> ORGANISM: Mus musculus

<400> SEQUENCE: 12
ctggcaagaa ggtctggttg ggagagacga gctcagctta cggtggcggt gcacccttgc      60
tgtccaacac ctttgcagct ggctttatgt ggctggataa attgggcctg tcagcccaga     120
tgggcataga agtcgtgatg aggcaggtgt tcttcggagc aggcaactac cacttagtgg     180
atgaaaactt tgagccttta cctgattact ggctctctct tctgttcaag aaactggtag     240
gtcccagggt gttactgtca agagtgaaag gcccagacag gagcaaactc cgagtgtatc     300
tccactgcac taacgtctat cacccacgat atcaggaagg agatctaact ctgtatgtcc     360
tgaacctcca taatgtcacc aagcacttga aggtaccgcc tccgttgttc aggaaaccag     420
```

```
tggatacgta ccttctgaag ccttcggggc cggatggatt actttccaaa tctgtccaac      480
tgaacggtca aattctgaag atggtggatg agcagaccct gccagctttg acagaaaaac      540
ctctccccgc aggaagtgca ctaagcctgc ctgcctttc ctatggtttt tttgtcataa       600
gaaatgccaa aatcgctgct tgtatatgaa aataaaaggc atacggtacc cctgagacaa      660
aagccgaggg gggtgttatt cataaaacaa acccctagtt taggaggcca cctccttgcc      720
gagttccaga gcttcgggag ggtggggtac acttcagtat tacattcagt gtggtgttct      780
ctctaagaag aatactgcag gtggtgacag ttaatagcac tgtg                      824

<210> SEQ ID NO 13
<211> LENGTH: 1899
<212> TYPE: DNA
<213> ORGANISM: Homo sapiens

<400> SEQUENCE: 13
gggaaagcga gcaaggaagt aggagagagc cgggcaggcg gggcgggtt ggattgggag       60 cagtgggagg gatgcagaag aggagtggga gggatggagg gcgcagtggg aggggtgagg     120
aggcgtaacg gggcggagga aaggagaaaa gggcgctggg gctcggcggg aggaagtgct     180
agagctctcg actctccgct gcgcggcagc tggcgggggg agcagccagg tgagcccaag     240
atgctgctgc gctcgaagcc tgcgctgccg ccgccgctga tgctgctgct cctggggccg     300
ctgggtcccc tctcccctgg cgccctgccc gacctgcgc aagcacagga cgtcgtggac      360
ctggacttct tcacccagga gccgctgcac ctggtgagcc cctcgttcct gtccgtcacc     420
attgacgcca acctggccac ggacccgcgc ttcctcatcc tcctgggttc tccaaagctt     480
cgtaccttgg ccagaggctt gtctcctgcg tacctgaggt ttggtggcac caagacagac     540
ttcctaattt tcgatcccaa gaggaatca acctttgaag agagaagtta ctggcaatct      600
caagtcaacc aggatatttg caaatatgga tccatccctc ctgatgtgga ggagaagtta     660
cggttggaat ggccctacca ggagcaattg ctactccgag aacactacca gaaaaagttc     720
aagaacagca cctactcaag aagctctgta gatgtgctat acactttttgc aaactgctca    780 ggactggact tgatctttgg cctaaatgcg ttattaagaa cagcagattt gcagtggaac     840
agttctaatg ctcagttgct cctggactac tgctcttcca aggggtataa catttcttgg     900
gaactaggca tgaacctaa cagtttcctt aagaaggctg atattttcat caatgggtcg     960
cagttaggag aagattatat tcaattgcat aaacttctaa gaaagtccac cttcaaaaat    1020
gcaaaactct atggtcctga tgttggtcag cctcgaagaa agacggctaa gatgctgaag    1080
agcttcctga aggctggtgg agaagtgatt gattcagtta catggcatca ctactatttg    1140
aatggacgga ctgctaccag ggaagatttt ctaaaccctg atgtattgga catttttatt    1200
tcatctgtgc aaaagttttt ccaggtggtt gagagcacca ggcctggcaa gaaggtctgg    1260
ttaggagaaa caagctctgc atatggaggc ggagcgccct tgctatccga cacctttgca    1320
gctggcttta tgtggctgga taattgggc ctgtcagccc gaatgggaat agaagtggtg     1380
atgaggcaag tattctttgg agcaggaaac taccatttag tggatgaaaa cttcgatcct    1440
ttacctgatt attggctatc tcttctgttc aagaaattgg tgggcaccaa ggtgttaatg    1500
gcaagcgtgc aaggttcaaa gagaaggaag cttcgagtat accttcattg cacaaacact    1560
gacaatccaa ggtataaaga aggagattta actctgtatg ccataaacct ccataacgtc    1620
accaagtact tgcggttacc ctatccttttt tctaacaagc aagtggataa ataccttcta    1680
```

```
agacctttgg gacctcatgg attactttcc aaatctgtcc aactcaatgg tctaactcta    1740
aagatggtgg atgatcaaac cttgccacct ttaatggaaa aacctctccg gccaggaagt    1800
tcactgggct tgccagcttt ctcatatagt tttttttgtga taagaaatgc caaagttgct    1860
gcttgcatct gaaaataaaa tatactagtc ctgacactg                           1899
```

<210> SEQ ID NO 14
<211> LENGTH: 592
<212> TYPE: PRT
<213> ORGANISM: Homo sapiens

<400> SEQUENCE: 14

```
Met Glu Gly Ala Val Gly Gly Val Arg Arg Asn Gly Ala Glu Glu
1               5                   10                  15

Arg Arg Lys Gly Arg Trp Gly Ser Ala Gly Gly Ser Ala Arg Ala Leu
            20                  25                  30

Asp Ser Pro Leu Arg Gly Ser Trp Arg Gly Glu Gln Pro Gly Glu Pro
        35                  40                  45

Lys Met Leu Leu Arg Ser Lys Pro Ala Leu Pro Pro Pro Leu Met Leu
    50                  55                  60

Leu Leu Leu Gly Pro Leu Gly Pro Leu Ser Pro Gly Ala Leu Pro Arg
65                  70                  75                  80

Pro Ala Gln Ala Gln Asp Val Val Asp Leu Asp Phe Phe Thr Gln Glu
                85                  90                  95

Pro Leu His Leu Val Ser Pro Ser Phe Leu Ser Val Thr Ile Asp Ala
            100                 105                 110

Asn Leu Ala Thr Asp Pro Arg Phe Leu Ile Leu Leu Gly Ser Pro Lys
        115                 120                 125

Leu Arg Thr Leu Ala Arg Gly Leu Ser Pro Ala Tyr Leu Arg Phe Gly
130                 135                 140

Gly Thr Lys Thr Asp Phe Leu Ile Phe Asp Pro Lys Lys Glu Ser Thr
145                 150                 155                 160

Phe Glu Glu Arg Ser Tyr Trp Gln Ser Gln Val Asn Gln Asp Ile Cys
                165                 170                 175

Lys Tyr Gly Ser Ile Pro Pro Asp Val Glu Glu Lys Leu Arg Leu Glu
            180                 185                 190

Trp Pro Tyr Gln Glu Gln Leu Leu Leu Arg Glu His Tyr Gln Lys Lys
        195                 200                 205

Phe Lys Asn Ser Thr Tyr Ser Arg Ser Ser Val Asp Val Leu Tyr Thr
    210                 215                 220

Phe Ala Asn Cys Ser Gly Leu Asp Leu Ile Phe Gly Leu Asn Ala Leu
225                 230                 235                 240

Leu Arg Thr Ala Asp Leu Gln Trp Asn Ser Ser Asn Ala Gln Leu Leu
                245                 250                 255

Leu Asp Tyr Cys Ser Ser Lys Gly Tyr Asn Ile Ser Trp Glu Leu Gly
            260                 265                 270

Asn Glu Pro Asn Ser Phe Leu Lys Lys Ala Asp Ile Phe Ile Asn Gly
        275                 280                 285

Ser Gln Leu Gly Glu Asp Tyr Ile Gln Leu His Lys Leu Leu Arg Lys
    290                 295                 300

Ser Thr Phe Lys Asn Ala Lys Leu Tyr Gly Pro Asp Val Gly Gln Pro
305                 310                 315                 320

Arg Arg Lys Thr Ala Lys Met Leu Lys Ser Phe Leu Lys Ala Gly Gly
                325                 330                 335
```

```
Glu Val Ile Asp Ser Val Thr Trp His His Tyr Tyr Leu Asn Gly Arg
            340                 345                 350

Thr Ala Thr Arg Glu Asp Phe Leu Asn Pro Asp Val Leu Asp Ile Phe
            355                 360                 365

Ile Ser Ser Val Gln Lys Val Phe Gln Val Val Glu Ser Thr Arg Pro
        370                 375                 380

Gly Lys Lys Val Trp Leu Gly Glu Thr Ser Ala Tyr Gly Gly Gly
385                 390                 395                 400

Ala Pro Leu Leu Ser Asp Thr Phe Ala Ala Gly Phe Met Trp Leu Asp
                405                 410                 415

Lys Leu Gly Leu Ser Ala Arg Met Gly Ile Glu Val Val Met Arg Gln
            420                 425                 430

Val Phe Phe Gly Ala Gly Asn Tyr His Leu Val Asp Glu Asn Phe Asp
        435                 440                 445

Pro Leu Pro Asp Tyr Trp Leu Ser Leu Leu Phe Lys Lys Leu Val Gly
        450                 455                 460

Thr Lys Val Leu Met Ala Ser Val Gln Gly Ser Lys Arg Arg Lys Leu
465                 470                 475                 480

Arg Val Tyr Leu His Cys Thr Asn Thr Asp Asn Pro Arg Tyr Lys Glu
                485                 490                 495

Gly Asp Leu Thr Leu Tyr Ala Ile Asn Leu His Asn Val Thr Lys Tyr
            500                 505                 510

Leu Arg Leu Pro Tyr Pro Phe Ser Asn Lys Gln Val Asp Lys Tyr Leu
            515                 520                 525

Leu Arg Pro Leu Gly Pro His Gly Leu Leu Ser Lys Ser Val Gln Leu
        530                 535                 540

Asn Gly Leu Thr Leu Lys Met Val Asp Asp Gln Thr Leu Pro Pro Leu
545                 550                 555                 560

Met Glu Lys Pro Leu Arg Pro Gly Ser Ser Leu Gly Leu Pro Ala Phe
                565                 570                 575

Ser Tyr Ser Phe Phe Val Ile Arg Asn Ala Lys Val Ala Ala Cys Ile
            580                 585                 590

<210> SEQ ID NO 15
<211> LENGTH: 1899
<212> TYPE: DNA
<213> ORGANISM: Homo sapiens
<220> FEATURE:
<221> NAME/KEY: CDS
<222> LOCATION: (94)..(1869)

<400> SEQUENCE: 15
gggaaagcga gcaaggaagt aggagagagc cgggcaggcg ggcgggggtt ggattgggag      60
cagtgggagg gatgcagaag aggagtggga ggg atg gag ggc gca gtg gga ggg     114
                                     Met Glu Gly Ala Val Gly Gly
                                       1               5 gtg agg agg cgt aac ggg gcg gag gaa agg aga aaa ggg cgc tgg ggc      162
Val Arg Arg Arg Asn Gly Ala Glu Glu Arg Arg Lys Gly Arg Trp Gly
        10                  15                  20 tcg gcg gga gga agt gct aga gct ctc gac tct ccg ctg cgc ggc agc      210
Ser Ala Gly Gly Ser Ala Arg Ala Leu Asp Ser Pro Leu Arg Gly Ser
    25                  30                  35 tgg cgg ggg gag cag cca ggt gag ccc aag atg ctg ctg cgc tcg aag      258
Trp Arg Gly Glu Gln Pro Gly Glu Pro Lys Met Leu Leu Arg Ser Lys
40                  45                  50                  55 cct gcg ctg ccg ccg ccg ctg atg ctg ctg ctc ctg ggg ccg ctg ggt      306
Pro Ala Leu Pro Pro Pro Leu Met Leu Leu Leu Leu Gly Pro Leu Gly
```

```
                 60              65              70
ccc ctc tcc cct ggc gcc ctg ccc cga cct gcg caa gca cag gac gtc      354
Pro Leu Ser Pro Gly Ala Leu Pro Arg Pro Ala Gln Ala Gln Asp Val
             75              80              85 gtg gac ctg gac ttc ttc acc cag gag ccg ctg cac ctg gtg agc ccc      402
Val Asp Leu Asp Phe Phe Thr Gln Glu Pro Leu His Leu Val Ser Pro
         90              95             100 tcg ttc ctg tcc gtc acc att gac gcc aac ctg gcc acg gac ccg cgg      450
Ser Phe Leu Ser Val Thr Ile Asp Ala Asn Leu Ala Thr Asp Pro Arg
        105             110             115 ttc ctc atc ctc ctg ggt tct cca aag ctt cgt acc ttg gcc aga ggc      498
Phe Leu Ile Leu Leu Gly Ser Pro Lys Leu Arg Thr Leu Ala Arg Gly
120             125             130             135 ttg tct cct gcg tac ctg agg ttt ggt ggc acc aag aca gac ttc cta      546
Leu Ser Pro Ala Tyr Leu Arg Phe Gly Gly Thr Lys Thr Asp Phe Leu
                140             145             150 att ttc gat ccc aag aag gaa tca acc ttt gaa gag aga agt tac tgg      594
Ile Phe Asp Pro Lys Lys Glu Ser Thr Phe Glu Glu Arg Ser Tyr Trp
            155             160             165 caa tct caa gtc aac cag gat att tgc aaa tat gga tcc atc cct cct      642
Gln Ser Gln Val Asn Gln Asp Ile Cys Lys Tyr Gly Ser Ile Pro Pro
        170             175             180 gat gtg gag gag aag tta cgg ttg gaa tgg ccc tac cag gag caa ttg      690
Asp Val Glu Glu Lys Leu Arg Leu Glu Trp Pro Tyr Gln Glu Gln Leu
185             190             195 cta ctc cga gaa cac tac cag aaa aag ttc aag aac agc acc tac tca      738
Leu Leu Arg Glu His Tyr Gln Lys Lys Phe Lys Asn Ser Thr Tyr Ser
200             205             210             215 aga agc tct gta gat gtg cta tac act ttt gca aac tgc tca gga ctg      786
Arg Ser Ser Val Asp Val Leu Tyr Thr Phe Ala Asn Cys Ser Gly Leu
                220             225             230 gac ttg atc ttt ggc cta aat gcg tta tta aga aca gca gat ttg cag      834
Asp Leu Ile Phe Gly Leu Asn Ala Leu Leu Arg Thr Ala Asp Leu Gln
            235             240             245 tgg aac agt tct aat gct cag ttg ctc ctg gac tac tgc tct tcc aag      882
Trp Asn Ser Ser Asn Ala Gln Leu Leu Leu Asp Tyr Cys Ser Ser Lys
        250             255             260 ggg tat aac att tct tgg gaa cta ggc aat gaa cct aac agt ttc ctt      930
Gly Tyr Asn Ile Ser Trp Glu Leu Gly Asn Glu Pro Asn Ser Phe Leu
    265             270             275 aag aag gct gat att ttc atc aat ggg tcg cag tta gga gaa gat tat      978
Lys Lys Ala Asp Ile Phe Ile Asn Gly Ser Gln Leu Gly Glu Asp Tyr
280             285             290             295 att caa ttg cat aaa ctt cta aga aag tcc acc ttc aaa aat gca aaa     1026
Ile Gln Leu His Lys Leu Leu Arg Lys Ser Thr Phe Lys Asn Ala Lys
            300             305             310 ctc tat ggt cct gat gtt ggt cag cct cga aga aag acg gct aag atg     1074
Leu Tyr Gly Pro Asp Val Gly Gln Pro Arg Arg Lys Thr Ala Lys Met
        315             320             325 ctg aag agc ttc ctg aag gct ggt gga gaa gtg att gat tca gtt aca     1122
Leu Lys Ser Phe Leu Lys Ala Gly Gly Glu Val Ile Asp Ser Val Thr
    330             335             340 tgg cat cac tac tat ttg aat gga cgg act gct acc agg gaa gat ttt     1170
Trp His His Tyr Tyr Leu Asn Gly Arg Thr Ala Thr Arg Glu Asp Phe
345             350             355 cta aac cct gat gta ttg gac att ttt att tca tct gtg caa aaa gtt     1218
Leu Asn Pro Asp Val Leu Asp Ile Phe Ile Ser Ser Val Gln Lys Val
360             365             370             375 ttc cag gtg gtt gag agc acc agg cct ggc aag aag gtc tgg tta gga     1266
```

```
Phe Gln Val Val Glu Ser Thr Arg Pro Gly Lys Lys Val Trp Leu Gly
                380                 385                 390 gaa aca agc tct gca tat gga ggc gga gcg ccc ttg cta tcc gac acc    1314
Glu Thr Ser Ser Ala Tyr Gly Gly Gly Ala Pro Leu Leu Ser Asp Thr
            395                 400                 405 ttt gca gct ggc ttt atg tgg ctg gat aaa ttg ggc ctg tca gcc cga    1362
Phe Ala Ala Gly Phe Met Trp Leu Asp Lys Leu Gly Leu Ser Ala Arg
        410                 415                 420 atg gga ata gaa gtg gtg atg agg caa gta ttc ttt gga gca gga aac    1410
Met Gly Ile Glu Val Val Met Arg Gln Val Phe Phe Gly Ala Gly Asn
    425                 430                 435 tac cat tta gtg gat gaa aac ttc gat cct tta cct gat tat tgg cta    1458
Tyr His Leu Val Asp Glu Asn Phe Asp Pro Leu Pro Asp Tyr Trp Leu
440                 445                 450                 455 tct ctt ctg ttc aag aaa ttg gtg ggc acc aag gtg tta atg gca agc    1506
Ser Leu Leu Phe Lys Lys Leu Val Gly Thr Lys Val Leu Met Ala Ser
                460                 465                 470 gtg caa ggt tca aag aga agg aag ctt cga gta tac ctt cat tgc aca    1554
Val Gln Gly Ser Lys Arg Arg Lys Leu Arg Val Tyr Leu His Cys Thr
            475                 480                 485 aac act gac aat cca agg tat aaa gaa gga gat tta act ctg tat gcc    1602
Asn Thr Asp Asn Pro Arg Tyr Lys Glu Gly Asp Leu Thr Leu Tyr Ala
        490                 495                 500 ata aac ctc cat aac gtc acc aag tac ttg cgg tta ccc tat cct ttt    1650
Ile Asn Leu His Asn Val Thr Lys Tyr Leu Arg Leu Pro Tyr Pro Phe
    505                 510                 515 tct aac aag caa gtg gat aaa tac ctt cta aga cct ttg gga cct cat    1698
Ser Asn Lys Gln Val Asp Lys Tyr Leu Leu Arg Pro Leu Gly Pro His
520                 525                 530                 535 gga tta ctt tcc aaa tct gtc caa ctc aat ggt cta act cta aag atg    1746
Gly Leu Leu Ser Lys Ser Val Gln Leu Asn Gly Leu Thr Leu Lys Met
                540                 545                 550 gtg gat gat caa acc ttg cca cct tta atg gaa aaa cct ctc cgg cca    1794
Val Asp Asp Gln Thr Leu Pro Pro Leu Met Glu Lys Pro Leu Arg Pro
            555                 560                 565 gga agt tca ctg ggc ttg cca gct ttc tca tat agt ttt ttt gtg ata    1842
Gly Ser Ser Leu Gly Leu Pro Ala Phe Ser Tyr Ser Phe Phe Val Ile
        570                 575                 580 aga aat gcc aaa gtt gct gct tgc atc tgaaaataaa atatactagt          1889
Arg Asn Ala Lys Val Ala Ala Cys Ile
    585                 590 cctgacactg                                                          1899

<210> SEQ ID NO 16
<211> LENGTH: 594
<212> TYPE: DNA
<213> ORGANISM: Homo sapiens

<400> SEQUENCE: 16
attactatag ggcacgcgtg gtcgacggcc cgggctggta ttgtcttaat gagaagttga     60
taaagaattt tgggtggttg atctctttcc agctgcagtt tagcgtatgc tgaggccaga    120 tttttttcagg caaaagtaaa atacctgaga aactgcctgg ccagaggaca atcagatttt   180
ggctggctca agtgacaagc aagtgtttat aagctagatg ggagaggaag ggatgaatac    240
tccattggag gctttactcg agggtcagag ggatacccgg cgccatcaga atgggatctg    300
ggagtcggaa acgctgggtt ccacgagag cgcgcagaac acgtgcgtca ggaagcctgg     360
tccgggatgc ccagcgctgc tccccgggcg ctcctccccg ggcgctcctc cccaggcctc    420
```

-continued

```
ccgggcgctt ggatcccggc catctccgca cccttcaagt gggtgtgggt gatttcgtaa    480
gtgaacgtga ccgccaccgg ggggaaagcg agcaaggaag taggagagag ccgggcaggc    540
ggggcggggt tggattggga gcagtgggag ggatgcagaa gaggagtggg aggg          594
```

<210> SEQ ID NO 17
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 17

```
ccccaggagc agcagcatca g                                              21
```

<210> SEQ ID NO 18
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 18

```
aggcttcgag cgcagcagca t                                              21
```

<210> SEQ ID NO 19
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 19

```
gtaatacgac tcactatagg gc                                             22
```

<210> SEQ ID NO 20
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 20

```
actatagggc acgcgtggt                                                 19
```

<210> SEQ ID NO 21
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 21

```
cttgggctca cctggctgct c                                              21
```

<210> SEQ ID NO 22
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 22

```
agctctgtag atgtgctata cac                                            23
```

```
<210> SEQ ID NO 23
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 23
gcatcttagc cgtctttctt cg                                        22

<210> SEQ ID NO 24
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 24
gagcagccag gtgagcccaa gat                                       23

<210> SEQ ID NO 25
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 25
ttcgatccca agaaggaatc aac                                       23

<210> SEQ ID NO 26
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 26
agctctgtag atgtgctata cac                                       23

<210> SEQ ID NO 27
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 27
tcagatgcaa gcagcaactt tggc                                      24

<210> SEQ ID NO 28
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 28
gcatcttagc cgtctttctt cg                                        22

<210> SEQ ID NO 29
<211> LENGTH: 24
<212> TYPE: DNA
<213> ORGANISM: Artificial Sequence
<220> FEATURE:
<223> OTHER INFORMATION: synthetic oligonucleotide
```

<400> SEQUENCE: 29
gtagtgatgc catgtaactg aatc                                      24

<210> SEQ ID NO 30
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 30
aggcacccta gagatgttcc ag                                        22

<210> SEQ ID NO 31
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 31
gaagatttct gtttccatga cgtg                                      24

<210> SEQ ID NO 32
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 32
ccacactgaa tgtaatactg aagtg                                     25

<210> SEQ ID NO 33
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 33
cgaagctctg gaactcggca ag                                        22

<210> SEQ ID NO 34
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 34
gccagctgca aaggtgttgg ac                                        22

<210> SEQ ID NO 35
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 35
aacacctgcc tcatcacgac ttc                                       23

<210> SEQ ID NO 36
<211> LENGTH: 22

```
<212> TYPE: DNA
<213> ORGANISM: Artificial Sequence
<220> FEATURE:
<223> OTHER INFORMATION: synthetic oligonucleotide

<400> SEQUENCE: 36
gccaggctgg cgtcgatggt ga                                              22

<210> SEQ ID NO 37
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 37
gtcgatggtg atggacagga ac                                              22

<210> SEQ ID NO 38
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 38
gtaatacgac tcactatagg gc                                              22

<210> SEQ ID NO 39
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 39
actatagggc acgcgtggt                                                  19

<210> SEQ ID NO 40
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 40
ccatcctaat acgactcact atagggc                                         27

<210> SEQ ID NO 41
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 41
actcactata gggctcgagc ggc                                             23

<210> SEQ ID NO 42
<211> LENGTH: 44848
<212> TYPE: DNA
<213> ORGANISM: Homo sapiens

<400> SEQUENCE: 42
ggatcttggc tcactgcaat ctctgcctcc catgcaattc ttatgcatca gcctcctgag    60
```

-continued

```
tagcttggat tataggtctg cgccaccact cctggctaca ccatgttgcc caggctggtc    120
ttgaactctt gggctctagt gatccacccg ccttggcctc ccaaagtgct gggattacag    180
gtgtgagcca tcacacccgg cccccgtttt ccatattagt aactcacatg tagaccacaa    240
ggatgcacta tttagaaaac ttgcaatggt ccacttttca aatcacccaa acatgttaaa    300
gaaattggta tgactgggca tggcacagtg gctcatgcct gcaatcctag cattttgtga    360
ggctgagacg ggcagatcac gaggtcagga gattgagacc atcctgacag acatggtgaa    420
atcccatctc tactaaaaat acaaaacaat tagccggggg tgatggcagg ccctgtagt     480 cccagctact cgggaggctg aggcaggaga atggcgtgaa tccaggaggc agagcttgca    540
gtgagccgag atggtgccac tgcactccag cctgggcgac agagcgagac tccgtctcaa    600
aaaaaaaaaa aagaaagaa attggtatga ctgttgactc acaacaggag tcagggcat     660 ggggtggggt gtaagattaa tgtcatgaca aatgtggaaa agaaacttct gttttttccaa   720 ctccacgtct gctaccatat tattacactc ttctggtagt gtggtgttta tgtgtgaatt    780 tttttttcata tgtatacagt aattgtagga tatgaacctg attctagttg caaaactcac    840
tatgagctta gcttttaagt tgcttaagaa taggtagatc tatgcaaata atgataatta    900
ttattattat tttaagagag ggtctcactt tgtcacccag gctggagtgc agtggtgtga    960
ttaagggtca ctgcaacctc cacctcccag gctcaaataa acctcccacc tcagcctccc   1020
cagtagctgg aaccacaggc acgggccacc acgcctggct aattttttgt attttttgta   1080
gagatggggt ttcatcatgt tgcccaggct gttcttgaat tcctcggctc aagcaatcct   1140
cccaccttgg cctcccaaaa tgctggcatc acaggcatga tggcatcact ggcatcacat   1200
accatgcctg gcctgattta tgcaaattag atatgcattt caaaataatc tattttat     1260 tgttgcctta ttggtggtac aatctcaagt ggaaaaatct aagggttttg gtgttatttg   1320
cttactcaac caatatttat tagactctta ctaagcacca acatgatcac atgcctgagc   1380
tatggctagc atagcgtgtg agacaaactt aatctctgtt ttggtggagc atataatcta   1440
gtagatgaag ccaatgttga gcaacatcac aatactaaca aattgaggat gctacgagag   1500
tgtctaacaa attgaggatg ctacgagagt gtctaacaaa ttgaggatgc tatgagagtg   1560
tgtcatggag agctgcctgg agattgagag aaagcttcct tgagggaagt tacatttcag   1620
ctgaaacaca ctgccatctg ctcgaggttt tgtaactgca ttcacatccc gattctgaca   1680
cttcacatcc cgattctgac acttcaccca gttactgtct cagagcttgg gtccgcatgt   1740
gtaaaacaag gacagtatgc acttggcagg gttgtgagaa gggaagagaa cacaagtaaa   1800
gcacctgtat caggcataca gtaggcacta agcgtgcgat gcttgctatg attatacatc   1860
agtgtaagca tcaaggaaaa gctgaagaaa agtctgacca acagcgaaag ataaatgcgc   1920
agaggagaaa tttggcaaag gctccaaatt caggggcagt ccgtactcta cactttgtat   1980
gggggcttca ggtcctgagt tccagacatt ggagcaacta acccctttaag attgctaaat  2040 attgtcttaa tgagaagttg ataaagaatt tgggtggtt gatctctttc cagctgcagt    2100
ttagcgtatg ctgaggccag attttttcaa gcaaaagtaa aatacctgag aaactgcctg   2160
gccagaggac aatcagattt tggctggctc aagtgacaag caagtgttta taagctagat   2220
gggagaggaa gggatgaata ctccattgga ggttttactc gagggtcaga gggatacccg   2280
gcgccatcag aatgggatct gggagtcgga aacgctgggt tcccacgaga gcgcgcagaa   2340
cacgtgcgtc aggaagcctg gtccgggatg cccagcgctg ctcccggggc gctcctcccc   2400
gggcgctcct ccccaggcct cccgggcgct tggatcccgg ccatctccgc acccttcaag   2460
```

```
tgggtgtggg tgatttcgta agtgaacgtg accgccaccg aggggaaagc gagcaaggaa    2520
gtaggagaga gccgggcagg cggggcgggg ttggattggg agcagtggga gggatgcaga    2580
agaggagtgg gagggatgga gggcgcagtg ggaggggtga ggaggcgtaa cggggcggag    2640
gaaaggagaa aagggcgctg gggctcggcg ggaggaagtg ctagagctct cgactctccg    2700
ctgcgcggca gctggcgggg ggagcagcca ggtgagccca agatgctgct gcgctcgaag    2760
cctgcgctgc cgccgccgct gatgctgctg ctcctggggc cgctgggtcc cctctcccct    2820
ggcgccctgc cccgacctgc gcaagcacag gacgtcgtgg acctggactt cttcacccag    2880
gagccgctgc acctggtgag cccctcgttc ctgtccgtca ccattgacgc caacctggcc    2940
acggacccgc ggttcctcat cctcctgggg taagcgccag cctcctggtc ctgtcccctt    3000
tcctgtcctc ctgacaccta tgtctgcccc gccagcggct ctccttcttt tgcgcggaaa    3060
caacttcaca ccgaacctc cccgcctgtc tctccccacc ccacttcccg cctctcattc    3120
tccctctccc tcccttactc tcagacccca aaccgctttt tgggggtat catttaaaaa    3180 atagatttag gggttacaag tgcagttctg ttccatgggt atattgcatt gtggtggcat    3240
ctgggctctt agtgtaactg tcacccgaat gttgtacatt gtatctaata ggtaatttct    3300
catccctcat ccctctccca ccctcccacc ttttggagtc tccagtgtct actattccac    3360
taagtccatg tgtacacatt gtttagcgcc cactctaaat gagcctttt gtttcattca    3420 ttctgtaagt gttgaatagg caccacctaa ggtcaggtat aagtgaaat ttgaaaaaga    3480 aactgcccac ttgccccagt acttccctag ccaagaggag ggaaaccagg caggtgcacc    3540
tgaaggcctg tgagtgcttg atttgctgtg cagtgtagga caagtaagat tgtgcatagc    3600
cttctgtatt taagactgtg ttaggaagat ttctcttctct tttcttttct tttctttttt    3660
tcttttcttt ttttttttta ggcagatgaa aagggcgtca cagaacagga ataaaaatct    3720
aaatattcaa taaatgagac ctaggagact actgcagtga cttacaaagt cctaataaaa    3780
agatgtctct ccaaaatggg gctgcaaaat gtggtgctgc cttatcagct ctaagttttt    3840
tccttacctg agaaagaagg aacctgatgc aggttcaggg ctcctgcccc atgaatgcag    3900
gctgactcca agatggggag ctacagggac aatcccaggt cttctaggcc tcttatttag    3960
gccctgggag cctccagaga tggccacatc ttgaccagcc cagatagagg gaaagatcac    4020
cattatctca cctctgtgtc aaataccctag atgctgtcct ccctgagccc acactatagt    4080
tgccagcgct aatttaatgg gtagtgtact ggttaagaga tggacagacc atcctggctt    4140
gactctcagc tctggcaaag atgagtgact tggttttcc atatctcttg gccacaccaa    4200
ccttgatttc ttcagctgta gaatggaatt tctcaagctt gcctcaagga ttattgcccg    4260
aggatttgat gatatggtaa gagcttctca gtgtttgacc catagtaagt gtttgacgtt    4320
tcaaacgaat tgtttctttc taggacatgg tgagcatttg gtagccattc accgttttc    4380 tgtttctttg gatcatagtt aacctctcct tttccttctg gcactacaat ttctggtgg    4440 ggaagaatcc ttactttctg cccttcccct taaggatagg aagctgatac taggcagcaa    4500
ctagttgggg gataggaaga ttgttccaga gaaatgctga accataggc tccagatcac    4560 aggaccccag tcttagcttg ctgggtgtg ggtggggg gggcggttac tgaacatggg    4620
tatgaagtag atgtccattt actgaaatgt gaggacctga ggcctcttct attgctgtag    4680
ccagcatatt ccccaacctc tccccaagaa aggacagatg ggggttcccc cctggagtaa    4740
caggtccaaa agaaaaaaca tacagtggga cttccaggat ctgggcctga tcacccagca    4800
```

-continued

| | |
|---|---|
| gtcaagctcc ccgcaattga ctaacacccc cctaacacgt agaaattcca atctgcaatt | 4860 |
| tagtgaggat gataccttta ttcttcttaa atacatctct tcatttccca gagcacccct | 4920 |
| ttttcccctc ctctgcacct ttttgttaaa gactggagta taatgaaata ccaagagagc | 4980 |
| ataacatgtg atacataaaa cttttttttct ggtttacaaa acagttcatt cttgtccata | 5040 |
| cgtgcttctc tccaaggctg gctgctgtct gttccagccc gcttcgcttg gagaggccat | 5100 |
| ctgccatacc tgctccccag acgcatcgac aagcacaccc agagtgttat ctgctaagac | 5160 |
| ctaaaagagg gaggaacccc ctctcctcat ctaagaccta gcttctaaat tagagtgtga | 5220 |
| gggtccatct ccccaggagg ggcacagggc ccaaacagcc cagccatctc agaagacaac | 5280 |
| actaagcttt gtaggggtcc acagtagagg agagtaagac gcctgttgtt taatttatta | 5340 |
| cagttcctca aaagtgaaga tgtgtgggcg ggatggcaag agctgagcag acgaaagctg | 5400 |
| aaggaataag gaaagagagg aggacacaaa cagctgacac ttcctcagtt cttgtcattt | 5460 |
| gcctggccct gttctaagca ccttctaggt attaatccat ttagtcttgg ctacaacact | 5520 |
| gtgagtaact agttttgtca cccccatttt aaaaatgaag aaagtgaggc tcagggaggt | 5580 |
| taagtaactt ggccacagtt tgaaactaga ctctgatcac atgagataat agtgcccata | 5640 |
| aaaagggaaa gcagattata tttttttaaag gaaagagagt aggatatggt agaaaaagat | 5700 |
| tgtttggaaa ggaattgaga gattgatata atgaaaagaa gcattcacat gagagtaaca | 5760 |
| gtatcagggc ccaaaccttc atctaaggta cttcaaagag gcctaagcaa acttagtcac | 5820 |
| tggcgtggtt ctagtctcca tgatggcaaa tacattgtgt acagcccaac tccacacaaa | 5880 |
| acttaaatac caatgataga gcaatctaaa atttgaaaga aaaatctttt caatttgtcg | 5940 |
| tcttcccaga gggacttaat caagaaacca atcaaaatac ttcctaagcc taactgtgtg | 6000 |
| cagaactcca aagagagccc agccctaaat caacactgtc caatggaaat ataatataat | 6060 |
| gtgggcctca tatgcaaggt catatgtaat tttaaatttt ctagtagcca tattaaaaag | 6120 |
| gtaaaaagaa acaagtgaaa ttaattttaa taatttttatt tagttcaata gatccaaaat | 6180 |
| gttttctcag catgtaatca atataaaaat attaatgagg tatttattat tccttttctc | 6240 |
| aaaccaagtc tattctataa tctggcgtgt attatttaca gcacttctca gactatattt | 6300 |
| cttttctttct tttttttttc cgagacaatt ttgctcttgt cacccaagct agagtacaat | 6360 |
| ggcgttacct cggctcactg caacctccgc ctcccgggtt caagttattc tcctgcctca | 6420 |
| gtctcccaag tagctgggac tagaggcatg caccaccacg cctggctaat tgtgtatttt | 6480 |
| tagtagagac agggtttcac catgttggcc aggctaatct caaactcctg agctcaggtg | 6540 |
| atatgcccac ctcggcctcc caaagtgttg ggattacagg cgtgagccac tgcacccggc | 6600 |
| ctcagattaa ctatatttca agcgttcagt agccacatgt agctagtgct atggtagtgg | 6660 |
| acagtacaga tctgcatttc aattaagaca cgtatacaag catagttcac taatgcacgg | 6720 |
| taaaaaaaag tatagtgctg agtcggtggt agaaatccta aatactgcag agcaaaagtg | 6780 |
| gtacgaacag caatctcagt gataatgcaa ccatgcttgc ttttcattgc aatttgctta | 6840 |
| ttttccttca gcaaagttca tccatttttg ccaattcaat aaatatttac tgataaaaac | 6900 |
| tttcaatatt agattcttgc atcttcatag acagagttgc ttttcacatt tagaaaatta | 6960 |
| cttatcaatg ttaaacacac gttttgataa ccagtgttgg aaagaggtgc agactcccca | 7020 |
| tgtgcctatt gatggcagaa atattcacag ccaaagggaa acaaagggct ggggacaatc | 7080 |
| acacacctca tgtctcctaa ctcctgggaa gtgctgtccc tctgattgag ctcttattat | 7140 |
| tgccttcccc actaaccctg tccactgtgc cctggagccc tttgcagggt tacctgctct | 7200 |

```
gtcctcctca cagaatatct cctctacctc cttgtccaag ctacaacttg gctattctct   7260
gatgacactg tcttccctgt agcccttttg agtaatggct gcatattctc ccatagtcca   7320
gttcttttcc tgttctccag tctggcttct ggatgacagc ccactagttt gaactccata   7380
ctgctatagt tcaagtccct tttgacttgt taccttgggc aaattacctc cttttgttca   7440
ggttccttgt ttgtaaaatg acgataataa tgccatttgc ttcagtgggt tattttgaaa   7500
ttgagtgaaa gaaggcgggt agcttcccta cacgctcagt gtagactagc ctgatgtgca   7560
ttacgggtga tgccatgact cagtgtgttt cctcatctc cacatctggc tctcatccag    7620
tgctcctgct tacggcactc tgtccccctc ttacttactc cccttatta actgaagact    7680 ggcactgatc tcacagtttc ctctccactt cctagtctca ccatcatcct agatgacttc   7740
aagtcaccta gataaactgt ctcagtttct tcactcacat tttttataa cagataatgt    7800 tacactcaag ttgtaacaga accagcttat ccagctcatg aaatgtatgc atttcatctc   7860
aactctgtat tcagtgacat cctgtgggta tctggaaatc agccatggtg agaatattta   7920
ccatggaaat tggcaaatac taaaaagcag agcacctttt tttctgagag ccagaccata   7980
gctcttctac tccatagcac ccatcataac aatttttaaa tacctccact gaacagcttc   8040
ttcctctctc tacttcttcc atatctgatt tgagcttctt aatttatcat gtgaaccact   8100
cttgtaataa taaccccaaa tccctgttcc attgttcttc ctgctaaaat actaaacctg   8160
gtttagtcca accatatttt ctctctttgg aatctacagg gtggcccaaa aacctggaaa   8220
tggaaaaata ttacttatta attttaatgt atattaataa gccatttaa tgcttcattt     8280 ccagtctcag tggccaccct gtatagctgg gctattgagc tcttgcggga ggagggagtg   8340
gacagtctcc cagccacaca gactgatgtt gcaccaaaca ttttttagct tccagacttc   8400
cctggccctt agtgttaccc ttaactctcc atttctctgc cttcacatt ctctactttt    8460 taaaaatctc tgactccacc ttcaccttat cattcttagc acatgaccat acttctgctt   8520
cccaaagaaa atgagcaatt acttcctttt ccttttcctc ctgtcatcaa atctgcagac   8580
atgtcatgcc taagtccagc tttcctcctt tctctgatct cagtctgctt cttccatttc   8640
tgccctgaat cccgtcccct ccccaacccc caaggacttc gctctatcag tcacctcttc   8700
cctctcctgt atcttcaact cctcccattt tactggcttc ttcctcaagc ctttccccaa   8760
gcctttccca tctcaattac ctcctcgcac atgcctctgc agaaaccacc ccgtttcttc   8820
cctcccctcg gcagcctgtt cttcctgttc tgccctcatg atggcaccat cattgtgtca   8880
ctaaaatcaa tctctccgac atcatcaatg gccttccttt gttgggaaac ctaataaaca   8940
ctttatctta tttggtcttt gttatgggtt gaatgaggtt accccgaaat ccatattaga   9000
agtcctaacc cccagtacct cagaatgtga ctttatttgg gaatagggtc attgcagacg   9060
ttattagtta ggatgaggtc atactggaat gtgatgggc gcttatctaa tatgactgat    9120
gtccttataa caaggagaaa tttggagaca gacacgcaca tagggagaat accatgtgat   9180
gacaggagtt atggagttgg agtcaaaaag ctatgggaac ttaggagaaa gacctggaac   9240
aaatcctttc ctgcgcctag agagggagta tggccctgcc actaccttga attcaacgtt   9300
tcggcttttc aaaactgtaa gacaatacat ttctgttgtt caaaccaatt agtttgcagt   9360
actctgcgac tgcagcccta acaaactaat acagtctctt ggaggcattt ggcaaggttg   9420
acaatggaag cactttctta cccctttagg tctgtcgcct ttcttgttgg ggggtgtttt   9480
ctaacaattc ctctccatct ctctctctct agtttgtctt aaacattggt gttcttcaga   9540
```

```
cttctgacct aggccttctt ttcacttcac atattcccct gggtggtctc acccacttcc    9600
agaaattact taaattactg ctcatgcagt actgtgctgg aaactgttta caactggct     9660 ctctgggaag aggggagact ggttgatggt ttttgctgat ttctgtggtg taaatactcc    9720
ctccatggcc aattccaaac tgccaacagt ttaacaactg gctcacaaat tttctccaaa    9780
tttaacattt ggctttcaca ggccaacaac gtggtacagc caactccagc acacctctgc    9840
ttttgtgtca gagagaagta acttattttt gtacaaaagg taaaataaaa acacctgcag    9900
gccccctttt tttccttaac aaactgctct agaaatagaa tagctgaagc ttcttttatg    9960
cattcatctg ttatttccat gtcactgtgg tggtgggatt attttttcctt tattttttctt   10020 gtatatggtt gaaatactgt accttttgatc agttttagtt ttatggcatg ttttgcaccc   10080
atattaaatc tagtttttgt cagagggcgt caatattatt ttctcaaaac aagaaaatat    10140
ttcattgcaa aggagacaaa caaaaaggtc cttaatacca aaactttgaa atgtgatttc    10200
ttgtacttgg cagtgtccaa gtggtaaacc caaacagtat tgggttttca ttttgttcag    10260
gaaagtcttt gtctggcagc gacttaccct tacatcaggc gggccttgct cattcattca    10320
cttaagtatt tattaaacac cagcggtgtg ccaagtactt atctaggtat cgggtagatt    10380
ctgataagtc agtcaggtcc ctgctctcag ggagcttgca gcagagatgg gggctgcaat    10440
agagagtaag ccaaggaaat gaaaaaggaa gttgatttca gagagtgatg aatgctatga    10500
agaaaatgaa ggcagcgcag tgtgatggag agtgacccaa ggtggtacag tttgtacctc    10560
taaggaccag actgtgaccc aggtcactca cagatgcccg tcatgtgatg ccacagcaac    10620
ttttccaggt gctcgtttcc tcccacttcc cagtctcttg cccagccgcg actgcttaca    10680
aatacagcta gaggaatcta aatgaggttc ctctatcatc aaacccaatc aaaatgccaa    10740
ggaacagaat cagtgcctgg ctgaaggcag tggaacaggg ccagcctgga gtggttctct    10800
ctgaggaagt tcctcatctt ggttttaggg ccataccttg tgacctgtga gctagggggtt   10860 gccagtccct gacatttcta ctgaggactc gcctgtctat attcccggcc tgtatgtgtc    10920
tcctgagttc cagacacaca gggcgaagcg cctgatggat ggaagtatgt ttttttggtgt   10980 tccattggta tctcaaattc tacaaaactt agtgccccctt ctcctccctg ttcctcccca   11040
tcttcagtct atcacctgtt cctcatccag caaatgatat taccatcttc caaggagctt   11100
cccaggagta atccttgact cctcctcaac atccaattaa taatcaaatc taggccaggt   11160
acaatagctc acgcctataa tcccagcact ttgggaggct gaggcaggtg gatcatttga   11220
ggccaggagt tcaagaccag cctggccaac aaggtgaaac ctgtctcatt taaaaaaagt   11280
tattttaaaa actcaaatct attatttcta cctctaagtg tgtcttgaat ttatccatct    11340
ctctccatct ctgagctgtt accttacctc agtccatcac gttttgtcta cgttaacatg   11400
accagagtct tgttcttagt ctggtgaggt cactccagct gcttcagatc cttccatggc   11460
tcaccgttgc cctcatataa agttggcact cctggacatg tggcttacgg ggccctccgt   11520
gatgtggccc tatttgcttc tccattctgt tctctcccag cctctctgcc cccatctcta    11580
ggcaccaacc acacccttct gctcgtcaat ggtgccagct tctcttctat ctctggtctt    11640
tggacagact tttcccttca cctggaatgc tttcttcaat cctacccac tctctttaat    11700 ctagataagg tttattcttt ttgaatgtct agcagtgaaa ccatttcccc tgaaaaacct    11760
tctctaacca accccctacc ctcagcccaa ggtctagatt aggagtccct ctgaatgttt    11820
ccatagcatt tttaaagaat tgcctattta cttgttcgta tctatcacta aactacaaat    11880
tgtatgagaa cagccactat ctctgcctgg ttcaccattc atctccagca actagcataa    11940
```

```
tgcctggcag agtcagcctg caacaaatat ttgttgaata aattaacaga tggctttatc   12000
tccttaagta aatcttgctt ttttcaccta ttaaaacaga cgcacaggcc aggtgtggtg   12060
gcccatgcct gtaatcccag cactttggca ggctgaggtg ggcggatcac ctgaggtcag   12120
gagttcaaga ccagcctggc caacatggtg aaaccccatc tctaataaaa atacaaaaat   12180
tagctgggca tggtggtggg tgcgtatagt cccagctact agggaggctg aggcaagaga   12240
atcgcttgaa cccaggaggc agaggtggca gtgagccgag atcatgccac tgtactccag   12300
cctggatgac agagaccctg tctcaaaaca cacacacaca cacacacaca cacacacaca   12360
cacacacaca cacacacacc aagttgtata atttaaaata taacgtgctt gttatggaac   12420
acttgtaaaa tacaggaaag taatgaaaaa gtctaccatc tagctcacca cataatgacc   12480
attgctatca tcctggcata attctctcct gtatataaat atatattctt ttattgttaa   12540
aattacacta tgagtactat ttatttattt tactgtggca aaatgcgcaa aacataaaat   12600
cttgccattt taaggtatgc agtttggtgc attcaccaca ctcacattgt tgtgcaaata   12660
tcaccactat ctatctcaga acttcttcgt cttcccaaac tgaaactctg tacccattaa   12720
acaatagtgc atcctctgtt ttcccctccc tacaatttat ttttatttgg gtttgtacca   12780
aactgaaaat agctgcttct tccttactta gttcagatta gcatttccat ttatttagcc   12840
gtggttttga ggatgccatg acagatgcca tccttcctag agctctttgg ggctgtcagg   12900
tatttcagtc agggtgaatt cgggttgata acatttaaaa atctcacttt attctgaggt   12960
tcctagtgtc agagcccacc gtattttag ggactcccaa gttacaaaca aaaatatggt   13020
gaggaggaat cactgaagtt ttaacacaag agacttacat tttgttcaat ttctatcttt   13080
tagtttattt cctaagcata aagaaatact ttgaaaattt tacatagcat tatacatatt   13140
taattaagca tgagcacatc ttaaaacttt aaattttaga tcagatcttt aattcctagg   13200
atattaagag gtactggcaa tttggccagg tgtggtggtt cacgcctata atcccaacac   13260
tttgggaggg tgaagtgggc gaattgctag agcccaggag gtggaggctg caatggcctg   13320
agatcacgcc atcgtactcc agcctggatg atgagaatga aatcctgtct caaaaaaaaa   13380
aaaaaaaaaa aaagaagaa gaagaagtat tggcaatcag tgctccagga ataatttcct   13440
gacttgaaat aaacctacat gtagacaaac taattaggcc attccaagag ttgctagcat   13500
tggtttaata tgttttcaga gcattccagg aagcagtgtg gccagcattg catgtttgat   13560
acttcagaaa tgtatgacag gtgtttctct tacccaggtc ttctgttttc ttagttttgc   13620
tcatgtaaat atttatgaac atcctcatct ttttgaggga agggattata gatcattcta   13680
attccatttt ctagcatttg gtaccattct aagcacatga taggcaccca tttggagcat   13740
ttttggcttg acagaatatg catttagaat tgttcaaatt agaggtgtca gtgatgggaa   13800
ttagaatact atataattct aagtcatttg acttaaatac aaaagaatga ttttccttgg   13860
tggggaatgg tgaagggagg caggagttaa gaagaggaga agagatccta agtcatttat   13920
aaacttctct ggaaagacag gtgtgtgaag actttttaaa aagtcattca ccaaattgtg   13980
tgtgtgtgtg tgtgtgtgtt ttaaatagac tttatttttt agagcagttt taggttcaca   14040
gcaaaattga atgcaaggac agagatttcc cataaacccc ctgccacac acatgcatag    14100 cctccctcat tatcaacatc cccaccagag aggtgtttgt tctagttgat gaacctacac   14160
tgacacatca ttatcaccca aagtccatag ttcacggcag ggttcactgt cggtgtacat   14220
tctatgggtt tgagcaaatg tataatgaca tgtatccacc attatagtaa catacagagt   14280
```

-continued

```
attttcagtg ccctgcaaat ccctgttct ccacctattc atccctcct ctctgcattt    14340 ccaccccag ccctggtaa ccgctgatct tttactgtc ccatagttc ggacgatcta     14400 ttttcagac agacacagag ctgtcttcc cttagtttct attctatcat ttctttctcc    14460
ccatccatca taaaaggcta tgagtttttt ttaagtgttg aacaccatcc tacttgtcaa   14520
gttaaaacat aagctcctgg ctgggtacag tggctcatgc ctgtaatctc agcattttgg   14580
gaggctgtgg cagaagcatc acttgaagcc agaagtttga gaccagcctg ggcaacatag   14640 caagaccca tcctccaca cacaaacaca cacacacaca cacacacaca cacacacaca    14700
cacacacaca cacaaaaaca agctcttgcc agaattagag ctacaaattg ccctcaggtt   14760
cctagaagat cagtccttca attagattca gattgagatg cttcctcttt taaacaatga   14820
ttccctttct atcatgccca ataagaaaac aaataaaaat taaacaatac tgcctgtaat   14880
ctcagctacc caggaggcag aagcagaact gcttcaaccc ggcaagcaga agttgcagtg   14940
aagtgagatc gcgccactgc actccagcct gggaaacaga gcaagattct gtctcaaaaa   15000 caaacaatg tgatttcctc ctctaagtcc tgcacaggga aatgttaaga aataggtcca    15060
ccaggaaaga aggaagtaag aatgtttgac tagattgtct tggaaaaaat agttatactt   15120
tcttgcttgt cttcctaaca gttctccaaa gcttcgtacc ttggccagag gcttgtctcc   15180
tgcgtacctg aggtttggtg gcaccaagac agacttccta atttcgatc ccaagaagga    15240 atcaaccttt gaagagagaa gttactggca atctcaagtc aaccagggtg aaaatttta    15300 aagattcact ctatatttta attaacgtca gtccgtcatg agaatgcttt gagaaaactg   15360
ttatttctca cacctaacaa ttaatgagat taacttcctc tccctcatc tgacctgtgg    15420 aggaatctga acaagaggag gaggcagtgg gcaggtttcc ttatcatgat gtttgtcatg   15480
ttcagtgtga ggcctcacaa aaaaaaaaa aaaaaaaaa ggcgtcctgg atataactga    15540
gagctcattg tacagtaaat attaataaaa cagtgattgt agctgaagga tagaactgct   15600
tggagggagc aagtgggtag aatcgcgtca aactaaagag catttctagc caaagacaca   15660
atgatagatt gaaggatatt tattctaaat atagaatatg ggtgaacgag atctgtggac   15720
ttctgggctc caacgttaga ttctgatttt agcaagcttg tcagggatt ctgatattga    15780 aaggctgtgg ccttcacctg agaaacctgc cctaggggc catgaaaatt tgtcctgtct    15840
ttcagaagtg ctatcagaca tcaaatggaa gttaaatcgt atcttaacaa ttactaggat   15900
gggcgcagtg actcacacct gtaatcccaa cactttggga ggctgaggca ggaggatcac   15960
ttgagcccag gagttcggga ccagcctggg caacatagag agacgttgtc tctatttttt   16020
aataatttaa agagaaaaaa atactgaaaa tattgtatac accactgaat tataataatg   16080
tgtatataat gtatatattc attatgagga atatttgatt atttcatata ttatatcttt   16140
tccttctgtt tatttatcc agttatgaag tatttagaac aattcatcag taattggggc    16200
taaattgaca gaatagtaat cagagaaaat agaaaaagac agatgggtta tctttgaata   16260
ccaggttgga gttgtttatg ggtttgtttt ttgtttgggg ggcgtttttt tagacagagt   16320
cccactctgt tgcccaggct ggagtgcagt ggcacaagca tgcccactg catccttgac     16380 ctcttgggct caagcaatct tcccacctta gcctcctgag tagctgggac acaggtgca    16440 tgtcaccaca cccagctaat ttttttattt tttgtagaga cagtctttct atgttatcca   16500
ggctgatctc aaactcctgc actcaagtga tcccctgcc ttggcgtccc aaagtattgg    16560
gattataggc atagccacca cacccaacct agtttctatt tagacttggc ccttccccac   16620
cagtcatttg tgtccaaaag atctcataaa tgtagacagg aaactgtcct ttgctcatca   16680
```

-continued

```
gttttcttca tcctgtgtct aggggatgg tcggtggggg aaactggggt tatgcaagtt    16740
cctctgaaac atcctctgtg agcccaggga tggatgaggc accagccgcc agcgagtcag    16800
tgtgcagctt tccagaaagg aagtcatcag ccagtcagcc ggccctggca gccagcaccc    16860
ggcaaccctg ctgtcttgtg ataaagaaat ggtctgcctg acaggatggt gtggattttt    16920 ctttttttctt tttttttttt ttgagacagg gtctggctct gtcgcccagg ctggagtgca    16980
atggcgggat cttggctcac tgcagcctct gcctcccagg ctcaaggcat cctcccacct    17040
cggtctcccg agtagctggg accacaggca cacaccacca cgcccaacta agttttcgta    17100
tttttagtag aggcagggtt ttactatgtt gtccaggcta gtctcaaact cctgagctca    17160
agctatccat ctgccttggc ctcccaaaga gctggaatta caagcgtgag ccactgtgcc    17220
tgaccagggt ggattttttc aagtgcacat gttgtggtcc cagaagctct gatggtacca    17280
aattccaagc gaaaaaaagt caatggttcc cacccatcct acctcccatg atggcaagag    17340
gaaatcacca cactgcagat acagtccatg taaaacaaat tgctatggat tttgaaagtg    17400
aaccttaaga gaactgcact atgttttctt cattagagtt ctctggtaat ttccagcttt    17460
tttttttttt tttttttagac agtgtctcgc tttgtcgccc agtgtcaccc aggctggagt    17520
gcagtgacgt gatctcggct cactgcaacc tccgcctcgt gggttgaagt gattctcctg    17580
cctcagcctc ctgagtagct gtattttagt agagacgagg tttcaccatt tggccaggct    17640
ggtctcgaac tcctgacctc aagtgattcg cccatctcag cctcccaaag tgctgggatt    17700
acaggtgtga gccactgcac ccggccagta atttcaagct tctgaggagc cctttgaatt    17760
gttaaataac ttgtagctat gtccaacata tccatgttca gtgtatgttc gatatttctt    17820
aggaaacctg cccttggttg ttttctttgt ggtaattcat gagccggcaa atttgacatg    17880
tgttacagaa tatacctttt tctgctctc ctacctcata accagaactt aattatcctg    17940
ctttagtcac ataaatagct aactaaataa atatatgaga tttcagtctg ctcactgtga    18000
aaatagacct tctaaatgat ctcttccact tgcagatatt tgcaaatatg gatccatccc    18060
tcctgatgtg gaggagaagt tacggttgga atggccctac caggagcaat tgctactccg    18120
agaacactac cagaaaaagt tcaagaacag cacctactca agtaagaaat gaaaggcacc    18180
ctagagatgt tccagccca aagatatttg aataggttgg actcgggcac caatctagca    18240
agtcctacgg aagttgtata aagctgaaaa tactgaagca tttcccaaat gggaaatcct    18300
aaactcaaaa cttgcttttt ggtttttttg tttgtttgtt ttttcttcat ctgacattgc    18360
ttagtagtca cagaatgaaa gataaatcaa tcattcatga tctaacaatg accttcagtg    18420
ctctaaaaaa ctacggagtc aaggaaaaca tgaatatatt cctcatgtaa aattaaaata    18480
cagacatata aagggcaaaa catgaacatc attcatacct tgaggtccgt cccccctccca    18540 gaaataaccc ccagtatgcc ttggtttaga gcattaagca ggagggccct gagtcactcc    18600
agacagtctt gaccaccaag cagcattctc ttttgtttc ctctgtggct tttgcaaaca    18660
cagggctagc tcagctaccc attagtatgt tttcagtcac taaaacagtc ttccagtctt    18720
caaattagga tgacattgtc acatggggct ttaaagcaag tgaaacaagg aacccccttt    18780
tttttttttt ttgagatgga atctcactct tgtcgcccag cctggagtgc aatggcgcaa    18840
tcttggctca ctgcaaccctc cacctcccag gttcaagaga ttctcctgcc ttagcctcct    18900
attcattatg aggaatattt gattattcag ttcctgtagg gtaaagatat tacccccgat    18960
catattattg attattgagt agctgagatt acaggtgcct gccaccacga ccggctaatt    19020
```

```
ttttgtattt tttagtagag acagggtttc accatgttgg ccaggctcca ggctcgtctc   19080
gaactcctga cctcaggtga tccacccacc tcagcctccc aaagttctgg gattacaggc   19140
gtgagccacc actcctggcc acaatccttt tttaactatg aaatatattt ttatctgaag   19200
tttgatgttt atacccaact gagggatgat gttcccatat ctcagttaaa gaaataacct   19260
gctcagatac ttcaagctct tcttttgact tttgaaaata aatgatcttg aagttactat   19320
actttgtttg ggttagttaa cattatttaa agtatattat tttaattaat tatctttgta   19380
agattttact gtatactacc tggagttcaa tgtatcagat ggatttcaaa tttatgtaca   19440 tttttttatgt atatggtaca gaaaaaaatg tgatccataa gaaatcagaa aatagcgcat   19500
atgctaatag ctaatgttgt cctctaaaaa acttattttt gcatttttaa gagggggata   19560
tactctgaca ctttaataag tgtaattaat tattgactgg aatttggcat gaggcagggc   19620
catttcagat cccattaaag gaatgacaca taccagagaa ccacagaagt aaggccacat   19680
ttgtaataaa tcattatagc tctgctagga gaagacccag ttgtattagg taattaatgg   19740
atttgctctt aaaacacatg tcccggaaga tataggtgag tcttgggggg ccgcattaaa   19800
cattatacca atgtatctta catttctaag aaagttttac tactttacag gatctttctg   19860
ttaccaaaat ggaaggtttc caactccagg acttggcttt catagttcct acaccagggg   19920
aaatgccttc ctttgctaac tatgcaacca ggttagttag tgtaagtcca gccaccctgt   19980
tggcaatgct aaaaggtaca acaaacacag aattttattt gcatttgtaa acatttgatt   20040
tctggctcga aattttcagt tttcatgggc acgtcatgga aacagaaatc ttctgtgttt   20100
agtttgggca cctactcatt gtagtgacaa atatttcaga agccaatagg ggattccaca   20160
aattgttctg aacctgtggc tgagactggt aatggctgag tgacatgggg acataccaca   20220
aaagaagagg tagcaaaagg ctgctgagat aaggacatgt tcattgctta gctagtggcc   20280
tgcaccctta aaacacatgt cccaggctgg gtgctgtggc tcacgcctgt aatcccagca   20340
ctttgggagg ctgaggcggg tggattacct gaggtcagga gttcgagacc aacctggcca   20400
acatagtgaa acctcatttc tactaaaaat acaaaaatta gccaggcatg gtggcgggcg   20460
cctgtagtcc cagctactca ggaggcaggc aggagaatta cttgaatctg ggaggcagag   20520
gttgtggtga gccgagattg cgccaccgca cgctagcctg ggcgacaaag tgagactctg   20580
tctcaaaaaa acaaaaacaa aaacaaaca aacaaaaaac aacaacaaca aaaaacggg    20640 tatcccagaa gatacaggta agttttctaa cacaggtcct cttgtatggt gcgttccact   20700
taagtagaag atgacaaaaa catttgtcat gagaatatag actcacattt taaacctgtt   20760
tgagcaggaa aaggaagcaa tgttacagat gtaattctgg gtgtgactgc agaaaggatg   20820
actcccttat taaagtagtc atcctgagtg agctaactct ttgtacttcc tcttctcctc   20880
ctgttcccct catcacccca ttcttccgtt gcctacaccc aggcccacat tggatgctga   20940
catagactta catggtacag tccaagggaa agatctgcca ttttttttcaa tgtgtcatct   21000 tggttatctt cattccaagg atctctccac tctttataca gtaagagatg agagtctgga   21060
aaggattggg aataagataa tgaattgtaa gttttaaatt gttcttcgta ttttggggaa   21120
ggagtaggct agtggtcct tctgtttttt ttttgttttt tttttaaag tagatgtggc    21180 cagacgtggt ggctcacgcc tgtaatccca gcactttgag aggctgaggc aggtggatca   21240
cttgatgtca ggagttcaag accagcctgg ccaacacagt gaaaccccgt ctttactaaa   21300
aatacaaaaa ctagccgggc ttggtggcgt ccacctgtag tcccagctac tgcagaggtg   21360
gaggcaggag aatcacttga acccgggagg tggaggttgc agtgagccaa gatcatgcca   21420
```

```
ttgtactcca gcctgggcga cagaacaata ctctgtctca aaaaaaaaga gaaaagaaaa    21480
gaaaaaaaga atggatttga actcagtcgt caatagcctc tattccagga gatgttacag    21540
ttgattatgt tataggaggt gtataataga atttcgagct atgtaaattc caagtgcatt    21600
tggaagaatg aagaaatgga ggaagggtaa agtatgagtg caagcattcc aggtttttg     21660 aaaatgctat aatctttgtt cagggctagt acaaagtgct atttagctgt aagggttttt    21720
tgtgatttac agacagtttt cacatgtgtc atttcaacct tggttttatg gcgaaggcat    21780
gtgatggtgc ttgtcccagg actttagatc catatctgag gttcctgtcg ggcaaagata    21840 ttaccccctga tcatattata gtctataagt gggagagttg tgcctggagc tcaagtctta    21900
tgatttctga tccagggcac ttcctacaac atgattttgc aatataaaag cctataatgt    21960
gtgactaaag caggtcactc accccttgta acagactcta gtaatggtac tgccaccaaa    22020
cggctgcgtg atattgggca aagacttacc ttatttgaat ctcagtttcc tcctagaaaa    22080
atgagggtgg aggttaagca taggctgatg atcctaaagc ctccatactg ccctaaactg    22140
tggctctaag atccagtaga atgctgggtc acaggactct agggagcttt tcaaacccaa    22200
atgtctgtca ttccttgatg gtaggcagca gtttatggaa gtgggcgaca cagcaaatat    22260
caaaatacct aaagcagctt gcaagagttg tttctgccta gtggtctttta tagttaatat    22320 taaatagtta attttttttt tttttgagac agagtcttgc tctgttaccc aggctgcagt    22380
gcagtggcac aatctcggct cactgcaacc tccacctccc gggtttgagc aattctgtct    22440
cagcctccca gtagctggg actacaggtg catgccactg cacccagcta ttttttgtat     22500
ttttagtaga cacggggttt caccatattg gcaggctgg tctcgaactc ttgacctcag     22560
gtgatccacc tgcctcagcc tcccaaagtg ctgggattac aggcatgagc cactgcaccc    22620
agcttaaata gctaatattt aatattattc tatagttatt caagtaattc aggccaaaga    22680
cttagaaaca aaacaaaag ccacttttaa ggagaaaggg tgtaagtttg ccagatagat      22740
agagatcttt ctttttttaac tacaagagtt caggaatgaa ttactcttta acaaacgact   22800
atagatatac atgaaaattg gaaggactta ttatgcatat gataatcaat ttaaagacaa    22860
cacttaaaat tatattgttg ccactctcaa aaagtggtaa tagaacagct aatggtttaa    22920
aaagcagagt acagaagttc ccaaacttat ggcaccttaa tatcgcagaa aactttttaa    22980
agcatgccta ggccacaaaa aatacctgta ttttgattat taaattgtaa ggtctacaca    23040
acctaatagt aataggtcca atagtaatgc tgtccaatag atgttgatgt ttttttcctt    23100
gcaaacttaa aagatcctac agtgcctctg taaatagcac tgcctggtta gagttgaatt    23160
tcagataaat aattttttc atgttaatta tttttctttt ctttactttt tttttgttt      23220 ttttgttttt ttgttttttt ttttgagaca gggtctcatt ctgttccca ggctgctgtg     23280 caatggcatg atcatggctc actgcagcct tgacctccct gggctcaggt gatcctccca    23340
cctcagcctc ccaagtagct agctgggact acaggtgctt accatcatgc ccggctaatt    23400
tttgtgtttt ttgtagagat gtggttttgc catgttgccc aggctggtct tgaactcctg    23460
ggctcaagtg atccgcccgc ctcggcctcc caaagtgcta ggatgacagg catgagccac    23520
tgcacctggc ccctgggcga agtatttctt aatggttaca taggacatac actaaacatt    23580
atttattgtc tatatgaagt tcaagtttaa ctaggtgccc tgcactttta gttgctaaat    23640
cctgtagctg tacccatgca ttcactggtg ctccccagct tgccttgcac agagtttgga    23700
aaccatagtc ctataactct aggccaattt tttaatgtaa aatttgattc atttttaaatt   23760
```

```
aataaataat aacaggaatt tttttaaaaa ttgttttaaa tataattaaa attatcaaaa   23820
tatttttaa ctgaacttgt gactagagat atttagatta tgaagagtgg ggtttatgct    23880
aactaatgac agtctggcta tgcatgtgga gcactgagct ataaattgtg gcttccccaa   23940
ttctcctgat gtcacttgaa caaaacctaa gtgtcagacc agagcttctg gtatcttcca   24000
tgggatttca ttcaacagct ggagcaaatg aagtcagatt gatttttttt aatttgtcca   24060
attttgttgt ctcaaaaaca taattataat catttattag aactagaatt tcttcagttt   24120
aacaacagaa atagttattc attatgaaaa gcgaatctgg aggccttcat tgtggtgcca   24180
atctaaccat taaattgtga cgttttctt ttaggaagct ctgtagatgt gctatacact    24240
tttgcaaact gctcaggact ggacttgatc tttggcctaa atgcgttatt aagaacagca   24300
gatttgcagt ggaacagttc taatgctcag ttgctcctgg actactgctc ttccaagggg   24360
tataacattt cttgggaact aggcaatggt gagtaccca gggaacaatt cattaataag    24420
gagattcccc actagcatta tttcttttct tttcttttt ttttcttttt tttttttttt    24480
gagacagagt ctcgcactgc tgcccaggct ggagtgcagt ggcgccacct cggctcactt   24540
gaagctctgc ctcccaaaac gccattctcc tgcctcagcc tcccgagtag ctgggactac   24600
aggcacccgc caccgcgccc ggctaatttt tttttttttt tttttttttt tttttttgca   24660
ttttagtag agacggggtt tcaccgtgtt agccaggatg gtcttgatct cctgacctcg    24720
tgatctgccc tcctcggcct cccaaagtgc tgggattaca ggcgtgagcc accaggcccg   24780
gctagcatta tttcttatga cacttttttt ttttttttga cacggagtct cgctctgtcg   24840
cccaggctgg agtgcagtgg cgccatctcg gctcactgca agctccacct cccaggttca   24900
cgccattctc ctgcctcagc ctcccgagta gctgggacta cacgcacccg ccaccacgcc   24960
cggctaattt ttttgtattt ttagtagaga cggggtttca ccgtgttagc caggatggtc   25020
tctatatcct gacccatga tctgcccgcc tcggcctccc aaagtggtgg gattacaggc    25080
gtgagccact gcgcccggcc aacactcttt ttattattag caaatatact tctgcctggg   25140
cacattcttg caagtgctca acaatgcaac ttttggaagt gcatgtggca gaaactcctg   25200
ctgtatttat tccagaacct attattgcta atcccagttt atgttacatt tgaagtgaga   25260
accagttgga gccagcaacg ttcccagctc caaagttccc ttgagatttt cagaatcact   25320
taacccctatt atgcttggca acctggactc agcaaaactg ggaagtcagc agtttgtttt   25380
attcatccct tcctttctca gtttctcaaa tgtgtcagtt aatctcagta accccattgc   25440
aaccttcatt acctgcccaa gcggtctaga acttgccagt atagaatcct acgtgggtca   25500
agctcctgac tgtctccttc ttcactcttt ttttgcaaag aacttgtaaa ttttaactat   25560
aagtattcat gattcgccac atttattcaa aacatagagt gcttttccca catatcagcc   25620
aatggaaata aggattaaat gggaaatgaa atgtagtaat aggataagca caagtcttct   25680
tcctgctcaa acttttttt tttttttttt cagacaagat cttgctctgt tacccaggct    25740
ggagtgcagt ggcgtgttca tagctcaatg taacctccaa ctcctgggct catgcaatct   25800
ctcacacctc agccccctga ttagctagga ctacactatg cctagccaat tttttttctt   25860
ttgtctggtt gtgttgccca ggctgtctcg atctcctggc tcaagtaat cctcctgcct    25920
cggccttcta aagtgctggg attataggca tgagccactg tgcccggtct caaacctttt   25980
tttccaaagt aaatgaagtt attagatatg gaatatagtc tagttcccag atatccatat   26040
ccattggttt attaccctca ttattaactt caaattgttt aatagaccct catatctcag   26100
ttatacagtt aaaattttg ttttgttttt ctggagtatc ttatttataa ctatgagttt    26160
```

```
tactttactt atttattta tttttgaga cagacgcttg ctctgtcact caggctggag   26220
tgcggttgcg tgatcatggc tcactatggc ctcgaccttc tgggctcaag tgatcctctc   26280
cctcagcctc ccaagctgag actacaggca tgcaccacca catctagcta atttttttt   26340 ttccccatgg aacaaggctt tactatgtta cccagagtgg tctcaaactc ctggcctcag   26400
gggatcctcc tgtctcagcc taccaaaatg ctgggattac aggcatgagc catagcgcca   26460
gacctggttt tacttttctt gactttgaat tacaagtttt tgtaatttgg aaaatgtttt   26520
gttgctttta aatactgctg tatgtttgct tttaaataca acatttctcg atatatattt   26580
tgagaattgc tgtctttcag aacctaacag tttccttaag aaggctgata ttttcatcaa   26640
tgggtcgcag ttaggagaag atttattca attgcataaa cttctaagaa agtccacctt   26700
caaaaatgca aaactctatg gtcctgatgt tggtcagcct cgaagaaaga cggctaagat   26760
gctgaagagg taggaactag aggatgcaga atcacttac ttttcttctt tttcctttg   26820 agacagagtc tcactctgtc agccagactg gagtgcagtg gtacaatcat ggctcactgc   26880
aacttcgacc tcccaggctc aagcaatcct cccatctcag tcccacaaat agctgggact   26940
acaggtgcac atcaccacac ctggctactt taaaaaaatt tttttgtaga gatggggtct   27000
ccctgtgttg cccaggctgg tctcttgaat tcctgtgctc aagccatcct tccacctcag   27060
cctcccagag tgccaggatt acaggcatga gccaccacac ccagccacca ctttcttaa   27120 aaaaaaaaaa agattctctc tggtagacaa tcctcaatag tccacatgtt attaaacaat   27180
ctgctgcctg aatacatgat ttaccaaaaa aaggaaattt tgacgggttc agaatatcaa   27240 gggatcgag gcaaatgtca cctatgataa aatttgctat caaaattagg aagtttgtgt   27300
ttacctgatc ctaaagcagt aaccagccca tttctaggga ataaaactct catgcgtata   27360
ttgtgcatat atatgtatta tatgactgag tgataataaa atttttttc tagcttcctg   27420 aaggctggtg gagaagtgat tgattcagtt acatggcatc agtaagtatg tctcctattc   27480
ttaatactag gaaagtaagg ctagctttat ttattaccta gtattcaaaa agttagttca   27540
tttaactgcc aattgactgc agttcaaata agaaacaaat agtgtctcaa gtagcactgt   27600
actccaattt taatattaat aaaaaaaatt ttaagttatt ttaaataatg tagtggtttc   27660
tataaagatc actttataca gaagaacagt gccaattaac ccatggaaca tataagtagc   27720
taaaaccaat tgcttgccaa agaaccagta acccaggagt acatgtcctt gccactgtgt   27780
tttttcaaga cagagtaact gatttctagt tacttgcata gaatggactc ctcctcataa   27840
ctcccttcca tcttggtctt tccctagtag aacttctacc ttttttagt aacaggtgag   27900 tgggagaggt aagaaggaga ataaggtcag caattaacct aaaagcagaa agtaaaattt   27960
gttatttttt ttctgaatat tttctgtgta atttagctac tatttgaatg gacggactgc   28020
taccagggaa gattttctaa accctgatgt attggacatt tttatttcat ctgtgcaaaa   28080
agttttccag gtaatagtct ttttaaactt tttaatgtaa aaccagaatc cttattttat   28140
agtctagcta gttctaaatt ctataggtat gtatatttac atgttttct aattttagag   28200 aacaagcact atgacttatc cactgttagt tttccctta gcattgggtc ttaccccatg   28260
tacgtgatta gaaatttgaa atatttccaa tagcctttag tagaattaac tcacatagat   28320
gataagaatg ggttggttca cttcatgttc cttccacagc ctactatttc aataaaagaa   28380
agtttcccaa gacctaaatg actatgaaca tattttataa ctatataggga ggggtgggtc   28440 taggaataca aagttttgaa tgctgttaat cttcaacacc acagttgaaa ccacaggtca   28500
```

```
gctttttgc aattaccatg gatacttttc tgttctatag gtggttgaga gcaccaggcc   28560
tggcaagaag gtctggttag gagaaacaag ctctgcatat ggaggcggag cgcccttgct   28620
atccgacacc tttgcagctg gctttatgtg agtgaagcag cgctggcctt agggqtcaga   28680 gtgcagctct tctccatcct tctattctgc tgaaatagct ccccagccaa aaagcagatc   28740
aaagaccgtt tcagtggctg agccccaaaa ttcatgccag attttgcaag aaatgatttt   28800
actaaagctt gagggacatc tttaacaagt gttccaaatt aatcactata aggatgaatt   28860
gtttcagaaa ttttggcctt taattatggc ccataaatat gtcaagtagt ccttactcta   28920
aagaagtaca ctgtaaaaga atgcatatag ccggatatgg tagttccctg taatcccaat   28980
actttgggag gccaaggtgg gaggattgct tgagcccagg agtttgaggc tgcagtgagt   29040
tatgatggtg ccactgcact ctagactggg caacagagtg agactgtctt ttttttttccc   29100 ctctgtcacc cagactggag ggcagtggca cgatctcacc tcactgcaac ctctgcctcc   29160
cggattgaag cgattctcct gcctcagcgt cctgagtagc tgggactaca ggagtatcac   29220
cgcactgggc taattttttgt attttagta gagacgggt tttgacatgt tgcccaggct   29280
ggtctgaaac ccatgagctc aagtgatctg cctacctcag ccttccaaaa tgctgggatt   29340
acggacatga gctaccacgc ccggccacac cctgtctctt aaaaaaaaaa aaaatgcaag   29400
ttagagcata ttacagcttt gtctctcagg aggatactta gtgtatgtag ctataattca   29460
tagattccca agaagtttag agcctaaagt atgaggtccc accagagggg ctatcattaa   29520
atttaaagat ttgttaaatc atctcattgt ccaacaccac aaacttgatt gctttaaaat   29580
actggtttag ttacatttag taactctatt agtgctttta atctatactg ctatatcctc   29640
acattgagat ttttttttctt ttctcttcca tcttcattct ttttctctc atcctcattc   29700 ttataagcct agaatacatc acaaatcctt tatgcccatg gaagcaagag gaataaagaa   29760
tggagatgtt tgttttgcca ttaactaaag atctggggtg tcggggagaa ggggatga   29820 gaaggagaag tgggaagagg tgtccataat agcttaggtg caattctgct tattttacat   29880
tttacccccg ctgactgcca cttttttcttc agccctcaca cattgtttgt gcagggacct   29940
cataggacca ggaattgtct atagaggtgg gaatttgtct caccctgaaa gggatacctc   30000
tagcatggta atagtcttct aggattgtt atcatatgga aagatgtaaa gggagggatt   30060
ctgctgctgc tgctgctgct gcatgcagtt gccatttcat ttaaatgact tatttataat   30120
tgatgacact tttctggctt cctgttaatt cctccctcaa agatcaataa accagaacca   30180
ggcatggtgg catgcacttg tggtcctgta accacccaac aggttcacct tgcctgctgt   30240
ctagatagag ccaattatca agacaggga attgcaaagg agaaagagta atttatgcag   30300
agccagctgt gcaggagacc agagttttat tattactcaa atcagtctcc ccgaacattc   30360
gaggatcaga gcttttaagg ataatttggc cggtagggc ttaggaagtg gagagtgctg   30420
gttggtcagg ttggagatgg aatcacaggg agtggaagtg aggttttctt gctgtcttct   30480
gttcctggat gggatggcag aactggttgg gccagattac cggtctgggt ggtctcaaat   30540
gatccaccca gttcagggtc tgcaagatat ctcaagcact gatcttaggt tttacaacag   30600
tgatgttatc cccaggaaca atttggggag gttcagactc ttggagccag aggctgcatt   30660
atccctaaac cgtaatctct aatgttgtag ctaatttgtt agtcctgcaa aggtagactt   30720
gtccccaggc aagaagggg tcttttcaga aagggctat tatcatttt gtttcagagt   30780 caaaccatga actgaatttc ttcccaaagt tagttcagcc tacacccagg aatgaagaag   30840
gacagcttaa aggttagaag caagatggag tcaatgaggt ctgatctctt tcactgtcat   30900
```

```
aatttcctca gttataattt ttgcaaaggc ggtttcagtc ccagctactt gggaggctga    30960
gacaggagga ttaatggagc ccaggagttt gaggttgcag agagctatga tcacgccact    31020
gcactccagc ctgggtgaca gagtgagacc ctgtctctaa ataaataaat aagtaaataa    31080
ataaatacat aaataaaatc aagatggtgt gcaattagaa ttgagcgatt ttgtttccaa    31140
acctcaagaa agcttggtct tgctctgtcc caggtggctg ataaattgg gcctgtcagc    31200 ccgaatggga atagaagtgg tgatgaggca agtattcttt ggagcaggaa actaccattt    31260
agtggatgaa aacttcgatc ctttacctgt aagtgaccat tattttccta attctagtgg    31320
agtagattaa agtcaactca ggacctctgg tgttaacctc ctatgaacag tcagtcctct    31380
cagtaactag ccaaatcatg agatgatgaa ttagaaggag ccttagatag catccaatct    31440
aacatttttt tgtgtgtttg aagagaagaa atcaagagct aggaataact ttttaaaggt    31500
aagccatttg cagtatagtg tggattttgt ttaaaagggg ataatttgaa attttatgac    31560
tcattataca agacaaaata agttggattt tcaaatgttt tacaaagtaa atcaaagtta    31620
taattgccta cagtacgcaa agcttcaaaa cattttttat gttatgaaat tgtaattttat   31680 ttaaccttaa aatgagccag taccatgtgt ttgcttaaaa atctcatgct aagaatttac    31740
tatgttgtta ataatcttca agatatttat gaataaagtc ttatttctaa tccttcctcc    31800
aactgtatct ggtgctaaat caggaaatgt ttcttcccaa aaagcctcgt ggaagatctg    31860
tatgtctaaa tatatgtcag ggataataca gatgtagccc tgcgaagcat gaccttgatt    31920
tttatagtct aaaatgtcat ttgcagatat ctattttcta agaataattc ctaaaagaat    31980
tatttgaatg ttgtaggaaa gctaagaaat tttgcaaaga gcgtacgtga aaatataagc    32040
taggcttttg tggtttgtgg atagacttcc caacaaaatt gcttttatc tatagtgatc     32100 caagcttgtg gaacatatta gtcatctttt tttagaaaat tcttagaaaa gtgatcttgc    32160
aaaaatggaa tttatctttc cccaagtata ttctgtcatg tatagagtta aactaagcat    32220
agtaatttca ccagacaaac attcaaaatc tactcctgac cttttatct catccaaatt     32280 ttcccagggc ccagacataa acctttgcct tacgaactct ttgtatatgc actaaatatg    32340
cttctccttc aaggttctca gtcagctaga aaaatgtgca agagtaaatg gtacccttct    32400
cacttgtaga tccaagagaa ttagacttaa actcactcta catgtctgtg actttatttt    32460
atttgcatga cagtcctgtg aggtggcaag gcaggtatct tggatccatt ttttagataa    32520
ggaagttcaa attgagaaga ggttgcatga tttacaggaa gccatactgt agtcctatgt    32580
tactcttaaa aatcccattc aaatcctgct tctgaggcct gcatacttc taccctacca     32640 gtcattgacc catgcttatg tctcctttga aaacattgat tccactcttg tctccagtga    32700
aaaagtggaa tttaagcaga gaaacaaaag ccattgtct tgttaagtct actttccctc     32760
tactttcaag aaggaaagtt ggggtatgtg ttgaatggta atttatttat ttatttatta    32820
ttttaaaaat tgatacaagg tcttactgta ttgtgcaggc tggtctcaaa ctcctgggct    32880
caagtgatca tcccacctca gcctcccagt gttgggatta cagcatgaac cattgtgccc    32940
accaccgatc cgcagttttt taagaaaaac ttttactata gaaattttta atcatataca    33000
aaatacagag gaaagtatat gaacccactt taggagacta gaatatgcca ccccaaaata    33060
tgccactttg gcataaggat tatttcgagc taaaggcaac tgggaagaaa cacatagaag    33120
aaaagttctc tgtccttctc catttgccta aagcaggac atgaatctta aaagtccccc      33180
tccttccctt tctaccagga aaaacaagag ttaatcactg aagataactt cagaccctta    33240
```

-continued

```
tcagtgtaga gatggcacta gaagaatcta tattacatac tcatttattt tccttcccac    33300
aacttgccac cccagagact aaaaatcctt ttcctttgtc atgtctcttg tccaaaaatt    33360
tgctctataa gctggagttc taagccacct ctttgagaat tacttgttcc ctggtatttt    33420
ctgttaacat acatgtatta atatacatgt taacaagctt ctgtttgttt ttctcctgtt    33480
ttctgtcttg ttacagaggt ccatcccaac taagaactaa agagtaggag gaaaatataa    33540
tttcctcctg catactttga tcttgtttaa tccgtaaccc ttcccacttt tcacctccta    33600
cctattagat tactttgaag caaatttcag atatattact ttatctataa atatttcagt    33660
atgtgctagg tgtggtggct cacacctgta atcccaacac tttgggaagc tgaggcagga    33720
ggatcacttg agcccaggag ttcaagacca gctacggcaa caaaaaatca aaaacttatc    33780
tgggcatggt ggcacatgcc tgtggtccca gctacatgag aggctgaggc aggaggatcg    33840
ctttagccca ggaggttgag gctgcagtaa gctgcattca caccactgca ctccagcctg    33900
ggtgacagag taagaccatg tctcaaaaaa atacatattt tagtatgtat ccttttttgta   33960 aaaacacaat acttttatca tactttaaat aataacaata attccttagt atcaccaaat    34020
attttgtcag tgtctcacat tttccttatt gtctaaaata ttgttgatag ttattcaaat    34080
cagaatccaa acaaggtcca tatattcat ttggttgaca agtctcttaa gtttgttcat     34140
ctttaagttc ttcctccctc tctttcatct cttgtaattt attaatgtga aaaaacaggt    34200
aatttgttct atagtatttc ctacattata gagtttgcta catttattcc ctatgatatc    34260
atttagcatg ttcctctgtc ccctgtgttt cctgtaaact ggtagttata cctagaagct    34320
tgagtttatt caggttttta attgtatttt ttttgcaaga attctttatt atctgcttct    34380
ggaagcacag aatgtctggt tgtgtctggt tttgatcttg acagctactg atgaccattg    34440
cctaatccat tactttattg gggtgggggg aataaggttt taaaataaat ttttttttaaa  34500 gatttttta actgttattt tgagacagtg tctcatttcg tttcccaggc tggagtgcag     34560
tggcacaatc acggctcact gcagccttga cctcctggga tcaggtgatc ttctcacctc    34620
agcctcctgg gtacctggaa ctacaggtgc acaccaccac acctggctaa ttttttgtat    34680
tttgtgtaca gaagggggttt catcatgttt cccagactgg tcttgaactc ctgggttcaa    34740
gtgatctacc cacttcagct tcccaaaatc ctgggattac actttggcca ccgtgcctgg   34800
cctaaatgaa attatttgtc tctaaacaga cagaagtttt actttaaaaa tttgtctttg    34860
tgtgtacatg tgtttgtgta tgtgtgtgtg tctaaaagtt tggctttgag ctttgctttg    34920
aattcttgga tgaacaataa ccaagaatac ttaaactctg atcattcttg acagatatcc    34980
cctacaggct atggccttttt gaattgtgtc ctccagtgat aaaaagcagc aagcacgata    35040
ctgctctcag attcatggtg gtcacatgtg aggtgaaaaa aaaaaaaaag atgaatccta   35100
tttaaatgcc cccaggataa cagtgatact cttttgtagga taactatttg cttgccactg   35160
gtttcattaa ataaggacat aagtaaagat ctattttttgt ctctttctcc ccaaccacca   35220
caactaggat tattggctat ctcttctgtt caagaaattg gtgggcacca aggtgttaat    35280
ggcaagcgtg caaggttcaa agagaaggaa gcttcgagta taccttcatt gcacaaacac    35340
tgacaagtaa gtatgaaaca cacccttac caatcatcaa gttttagtgg gtaagcctgt     35400
aactttactc aaacaccctg ttgcatgtgt ctatacattg cataagtata ggcagttgca    35460
atttagtaaa gttttataca acgattttat tttattttat ttttagaaga aaatgctac    35520 ttttgttgtt gttgtttttt gagacggggc ctcgctcgtc acccaggctg gagtgcagtg   35580
gtgcaatctc agctcactgc aacctccgcc tcccgggttc aagtgattct tgaagaggag   35640
```

```
aacaataata acaacaatat tattttcaaa agttgtgacc gcagtttctg gagttgagaa    35700
gacatcgaga tttttgtagc ctcatactct tgctttaggt agcaaaaaat gttcctaaat    35760
ctcaggaata ttctctagat aggtttcaat ctatcattcc tgataagatg atgctgaaat    35820
actaattcta gccaaaaaag accagctacc atttccgatt gttggggact gggaactctg    35880
gatagtgagg accccagtag gaagtagcga ggggaatggt ttgaatggat aaattcataa    35940
aaaatgtcag tagatttaat tttcttatac atttcagtct ttttataagg ctaggaaaag    36000
cccctgtttt tatggtttat aatttgaatt cacatgaacc cacaaaattt gccttttacc    36060
ttcctatgtc tgaaaatgga tagtctggct ggcctcttaa caacccagct ggcagagctg    36120
tgaggatctc agtgtgctct agcccagaca ttggtagcat gaacggcaac atttttaatt    36180
gtgttttcaa ataggagca cactagcggt ctaaaacgat cataaagaa ggatactaag      36240 agggcccact gtcattatgg atcctaatac ttaggatgca ttatgattg tcattatgga     36300 tactaatact taggatcaca tttgtaattg agttttaat tgcttaaatt agatacatat     36360
ttctattaag ttaacctctt tgcttttagt ccaaggtata aagaaggaga tttaactctg    36420
tatgccataa acctccataa tgtcaccaag tacttgcggt taccctatcc tttttctaac    36480
aagcaagtgg ataaatacct tctaagacct ttgggacctc atggattact ttccaagtaa    36540
gtaattttcc ttgttcattc caaactttca ataaatttat tggtgtttat cagaatagag    36600
agtttggaca gggagcaaaa gacaaagtca actatatcaa gttctaataa ttcttaatat    36660
tcaggaaatt tatgtatgaa tacttactaa tatgagtata actcatccta agagtctaaa    36720
gcaaaaggat gtgaacacaa actagcagtt atcttagaga ataagtttgc atttcaaaat    36780
aacttgacat atcaagatcc actcaacgca tttaaattat ttactctaaa aagacataat    36840
tcttggtaac acattcacta aagcaaaata tacctttata taattgctat caaaggtatg    36900
tgggttggta taaatatca taccatgtga gatcagtgtg attcctttac agcattaatt     36960
tttattggtt agagtaagaa aaagaatagc tagagtatat ttcttaagta gattctcata    37020
cactttggtt tcaaaaacca attattgact acatcttata aaagcctgta ttcaatggag    37080
tgccaaaaaa tgactatgag tcttaaagag ttaggcatat aaatatttta aggtttctgt    37140
tcaatgtatg ttgaaggag ttcctttctc atgactattc tcatattgga gcataaaaag     37200
agtttacagg cttggcgcag tggctcatgc ctgtaatccc aatactttgg gaagctgaag    37260
caggcagatc acttcagccc aggagtttga gaccagcctg gcaatatgg caaaactctc     37320 tctacaaaat ataccaaaat tagccaggcg tggtggtgca tgcctgtagt cccagctact    37380
tgggaagctg aggtgggagg attgcttgag cccaggggg tcatggctgc agtgagctgt     37440
gatggtgcct ctgtcaccca gcctgggtga cagagtgaga ccctgtctca aaaaaataaa    37500
taaataaaaa ttaagagttt acaaaattct caccatctcc tcccatcttt gcaaatgcca    37560
cataagtgat gtgttccagg actattagcc tcggaacctg aggcagtaca gtaagcacgc    37620
tttctccaaa gtcctgtccc ccacagacaa acattattta cactgggtac tgctctttta    37680 tttttttcccc tctatgcttt attttactat aactataatc atataacatg taataggaaa   37740
aaggcagggt cggggagag atccagaagt cttcccaaga gcctttccaa catagcctct     37800
gtagacattt tttctttctt cttttttttt tttttttttt ttctgagaca gagtctcact    37860
ctgttgtcca ggctagagtg cagtggcgtg atctaggctc actgcaacct ccgcctcctg    37920
ggttcaagca attctcccac ctcagcctcc ctagtagctg ggattagagg catgcatcac    37980
```

```
cacgcctggc taatttttgt attttttagta gagatgaggt ttcaccatgt gggccaggct   38040
ggtcttgaac tcctgacctc aagtgatcca cctgccttag cctcccaaag tgctaggatt   38100
acacgagtga gccaccgtgc cctgcccta ttacattctg atcacacatt tcatgtttta    38160
taattggaaa actggtgaaa ttatagacaa tgttttgttc ccctaaattc tctttgatga   38220
gtatatatta cttacactct tctgtcttta aattttgca aaatagtatc ctagataagt    38280
ttatgagtgc acagtctgta cgcttactca tattaatgac ctcggagagt taaacaacag   38340
tcacctttaa aaattattac tatcattatc attattttg aggcgggggt ctcattctgt    38400
ctcccaggct ggagagtagt ggtgcggtca cagctcactg cagccaccgc tacctgggct   38460
caagtgatcc ttcctcctca gccttctgag tagctgagac cacaggctta tgctaccaca   38520
cctggctaat ttttttaactt tttgtagaga cgatgtctca ttatgttgcc caggctggtc   38580
tcaaactcct aagctcaagt gatcttcctc agcctcccaa agtgctggga ttacaggcat   38640
gaaaaactgc acccagccct aaaaattatt agggtcctgc atagtaagac tttaataaat   38700
atttaaatga acatctggtt tttttaaaaa aaaaatagag acaaggtctc actatattgc    38760
ccaagctggt ctcgaactcc tggactcacg caatcctgct gccttagccg cccaaagtgc   38820
tgggattaca ggcatgaccc acctcatctg ggctgagtga acatattttt aacataaagg   38880
ccgtatttta tatttatctc atacattttg cccagcatcc ccatttccgc cgaatctgtt   38940
gcttgctaat tccttccagc ttcatttcat ctgaaatttg acaaacatct tctatttctt   39000
tgtcgtcatg ttattgactt cagaatataa aataaaacac tatacccaaa ttaaaccca   39060 ccctcattgc ccagcctgat gtgaaaataa tcagcataca ttaagcttac ccttgatata   39120
tgtgtagcat cttttagata aatatacagc tgattaagca atatagcctg atggtataat   39180
atcttgccca tgtacctcat cttatctcca gcaggattaa ttcacagtga tcagatttac   39240 cttaacttt tgtagcaaaa tatcctctcc aaaagcatat ctaaaacttt tgtgtgtact     39300
cttgcaagtt tcttaatttc atgcagaaca ggctcttacc actgttagct ggagatattt    39360
tcaagaccta tttttgtttg tggtttcctg atgatggtca tggcatttcc cccttcactc   39420
catctaaaaa ttgaggtgat acaggctttt aaacaaaacc aactcatata gactgagtac   39480
aactgcaatg caggcatgct aacctctgct acaatcatgg gcgtgctatt gatatgtctt   39540
aagttacaga acacagggct gagcgtctca ttaggtcaaa atgtaaacca gttttctgc    39600 tcactgatgc ttaatgagga cagggtgtga gagatttctt taaggaaaac aaatatataa   39660
taatgctaca tggaaaaata tctaacatta gagaattaag taaataaact aatatactca   39720
caccatggaa tcttgtgcag acattaaaat tatgtagtgg atggatgttt aatggtgtga   39780 gaaaagtta ggatgtgctg gggtgggggg aagaatcaag ttttaagaaa atacagtata    39840
cccatactta agtaaaaaaa aaaaaaaggg tatgtacagt catgtgttgc ttaatgatgg   39900
ggatacattc cgagaaatgt gtcgataggt gatttcatcc ttgtgtgaac atcatagagt   39960
gaacttacac aaacctagat ggtctagcct actatgtatc taggctatat gactagcctg   40020
ttgctcctag gctacaaacc tgtaaagcat gttactgtag cgaatataca aatacttaac   40080
acaatggcaa gctatcattg tgttaagtag ttgtgtatct aaacatatct aaaacataga   40140
aaactaatgt gttgtgctac aatgttacaa tgactatgac attgctaggc aataggaatt   40200
ataattttat ccttttatgg aaccacactt atatatgcgg tccatggtgg accaaaacat   40260
ccttatgtgg catatgactg tatacatgta cacaaaaaat agatgaaaga atgaatatac   40320
atcaaaatat ttaaaatggt tataatgact taggttactt ttatttatct tagtaataat   40380
```

```
aatgatgata gataatactt ttatagtgtt tactatataa aagacactgt tataagtgtt      40440
ctacatactt tacatgtatt acctaaatga tataaatata actctgacag taactaatct      40500
tatacgttct cttttctttt ttttttttt cttttttag acagaatctt gctctaccag       40560
gctggagtgc agggtgcaat ctcggctcac tgcaacctcc gcctcccagg ttcaaacgat      40620
tctcatgtct cagcctcctg agtagctggg actacaggca cacaccacca tgcccggcta     40680 attttttgtat ttttgggtag agatggagtt ttgccatgtt ggccaggctg atcttgaact    40740
cctggcctca agtgatctgc ctgcctcagc ctcccaaagt gctgggatta caggtgtgaa     40800
ccactgtgct cggcctaatc ttacaagttt tcaatattta aagagtgcta actttgttga     40860
caatataaaa catatttgag aaaagagat ataagcatct tatttagaat tatgaaaata      40920
tcaatagacc tacagccgac taaagctttt cttcataagc tcttgcctat attgattcgc     40980
tcctgtgaat atgcattaat ttgatttaaa taataagtat gtataagaaa taacactttt    41040 ccttaattt taagaacgtt caacagtttt taatttgaat tccaatagtg aaatacatag      41100
aaaatataaa attttctgta gtttagccaa attgttttg tttcaccaca gcattctacc     41160
aaaatttctt aataacagta agaaaatgaa tgcatacctc ctgcagggag aggggagtta    41220
ggcagtttat gggcatagtt acaagtgaga aatttcattg gctaccattt acgctaaatt    41280
cataaaaact gcattcaatt ctatatatct attttcttta cataaaaaag gtttcaatta    41340
ttggccatta aataaaatag ccaccattcc agaagttgtg tcatgtttat ccttttata    41400 ccaccatcat attgcctatt atatagattg tgtgtgttcc attttctgta atgggccaga    41460
cagtaagtat ttctggcttt ggagtccata tggtctctat cataactact catctctgcc    41520
attgtagctt aaagattatc taggtcaaat gcctaagtga tatagtgttg aaatacaagt    41580 tatataat aggctgccac aaaaaaaaat ttatttggtc taaaaagat ttcatgactt       41640 ttgtagcagc atgggtgggg catgcaccac ttggttaact cggtgtatct ttctcctttg    41700
cagatctgtc caactcaatg gtctaactct aaagatggtg gatgatcaaa ccttgccacc    41760
tttaatggaa aaacctctcc ggccaggaag ttcactgggc ttgccagctt tctcatatag    41820 ttttttttgtg ataagaaatg ccaaagttgc tgcttgcatc tgaaaataaa atatactagt  41880
cctgacactg aattttttcaa gtatactaag agtaaagcaa ctcaagttat aggaaaggaa   41940 gcagataccct tgcaaagcaa ctagtgggtg cttgagagac actgggacac tgtcagtgct   42000
agatttagca cagtattttg atctcgctag gtagaacact gctaataata atagctaata   42060
ataccttgtt ccaaatactg cttagcattt tgcatgtttt acttttatct aaagttttgt   42120
tttgttttat tatttattta tttatttatt ttgagacaga atctctctct gtcacccagg   42180
ctggagtgcc atggtgcgat cttggctcac tgcaacttta agcaattctc ctgcctcagc   42240
ttcctgagta gctgggatta taggcgtgtg ccaccacgcc cagctacttt ctatatttt    42300 tgtagagatg gagtttcgcc atattggcca agctggtctc gaactcctgt cctcgaactc   42360
ctgtcctcaa gtgatccacc cgcctcagcc tctcaaagtg ctgggattac aggtgtgagc   42420
caccacaccc agcagtgttt tattttgag acagggtatc attctgttgc ccaggcttga   42480
gtgcagtggt gcaatcatag atcactgcag cctttaact cctgggctca agtcatcctc    42540
ctgcttagcc tcccaagtag ctaggaccac agacacatgc catcacactt ggctattttt   42600
aaaaaatttt ttgtagagat ggggtctcgc tatgttaccc aaactggtcc tgaactcctg   42660
gactcaattg atcctcccac cttggccttc caggtgctgg gatttctttg ggagtacagc    42720
```

```
atggtacagc aggagatcat ttgatgttac ctctgtgcag tgttgctagt cagcgaaaga      42780
ctataatacc tgtggggaca gcgattagcc accacaacca gtctttattt aaagttatta      42840
aaaatggctg ggcgcagtgg ctcacacctg taatcctagc actttgggag gccgaggcag      42900
atggatcacc tgacgtgagg aatttgagac cagcctggcc aacatggtga acccccatct      42960
ctactaaaaa atacaaaaat tagctgggtg tggtcctgta gtcccagcta cttgggaggc      43020 tgggcagga gaattacttg aacccaggag gcagaggttg cagtgagccg agattgtgcc       43080
actgcactcc agcctgggtg acagagagag attccatctc aaaaaaacaa gttattaaaa      43140
atgtatatga atgctcctaa tatggtcagg aagcaaggaa gcgaaggata tattatgagt      43200
tttaagaagg tgcttagctg tatatttatc tttcaaaatg tattagaaga ttttagaatt      43260 cttccttca tgtgccatct ctacaggcac ccatcagaaa aagcatactg ccgttaccgt        43320
gaaactggtt gtaaaagaga aactatctat ttgcacctta aaagacagct agattttgct      43380
gattttcttc tttcggtttt ctttgtcagc aataatatgt gagaggacag attgttagat      43440
atgatagtat aaaaaatggt taatgacaat tcagaggcga ggagattctg taaacttaaa      43500
attactataa atgaaattga tttgtcaaga ggataaattt tagaaaacac ccaataccct      43560
ataactgtct gttaatgctt gcttttctc taccttcctt ccttgtttca gttgggaagc       43620
ttttggctgc aagtaacaga aactcctaat tcaaatggct taagcaataa ggaaatgtat      43680
attcccacat aactagacgt tcaaacaggc caggctccag cacttcagta cgtcaccagg      43740
gatctgggtt cttcccagct ctctgctctg ccatctttag cgctggcttc attctcagac      43800
tctggtagca tgatggctgt agctgtttca tgggcccctt caaacctcat agcaaccaga      43860
ggaagaaaat gagccatttt ttgagtctcc ttcatagact tgaataactc tttttcagag      43920
cttctcacag caaacctctc ctcatgtctc ctcatgtctt attgttcaga aatgggtaat      43980
gtggccattt caccagtcac tgccaacaac aacgaggttc ctataattgt ctctgagtaa      44040 cccttggaa tggagagggt gttggtcagt ctacaaactg aacactgcag ttctgcgctt       44100
tttaccagtg aaaaaatgta attattttcc cctcttaagg attaatattc ttcaaatgta      44160
tgcctgttat ggatatagta tctttaaaat ttttattttt aatagcttta ggggtacaca      44220 cttttttgctt acagggggtga attgtgtagt ggtgaagact cggcttttaa tgtacttgtc     44280
acctgagtga tgtacattgt acccaatagg taattttca tccattaccc tccttccgcc       44340
ctcttccctt ctgagtctcc aacatcccctt ataccactgt gtatgttctt gtgtacctac     44400
agctaagctt ccacttataa gtgagaacat gcagtatttg gttttccatt cctgagttac      44460
ttcccttagg ataacagccc ccagttccgt ccaagttgct gcaaaataca ttattcttct     44520
ttatggctga gtaatagtcc atggtacata tataccacat tttctttatc cacttatcag     44580
ttgatggaca cttaggttaa ttccattcaa tttcattcaa tttaagtata tttgtaagga     44640
gctaaagctg aaaattaaat tttagatctt tcaatactct taaattttat atgtaagtgg     44700
tttttatatt ttcacatttg aaataaagta atttttataa ccttgatatt gtatgactat     44760
tcttttagta atgtaaagcc tacagactcc tacatttgga accactagtg tgttgtttca     44820 cccccttgtta tactatcagg atcctcga                                        44848
```

<210> SEQ ID NO 43
<211> LENGTH: 2396
<212> TYPE: DNA
<213> ORGANISM: Mus musculus

<400> SEQUENCE: 43

-continued

```
tttctagttg cttttagcca atgtcggatc aggtttttca agcgacaaag agatactgag      60
atcctgggca gaggacatcc tagctcggtc agatttgggc aggctcaagt gaccagtgtc     120
ttaaggcaga agggagtcgg ggtagggtct ggctgaaccc tcaaccgggg cttttaactc     180
aggtctagt  cctggcgcca aatggatggg acctagaaaa ggtgacagag tgcgcaggac     240
accaggaagc tggtcccacc cctgcgcggc tcccgggcgc tccctcccca ggcctccgag     300
gatcttggat tctggccacc tccgcaccct ttggatgggt gtggatgatt caaaagtgg      360
acgtgaccgc ggcggagggg aaagccagca cggaaatgaa agagagcgag gaggggaggg     420
cggggagggg agggcgctag ggagggactc ccgggagggg tgggagggat ggagcgctgt     480
gggagggtac tgagtcctgg cgccagaggc gaagcaggac cggttgcagg gggcttgagc     540
cagcgcgccg gctgccccag ctctcccggc agcgggcggt ccagccaggt gggatgctga     600
ggctgctgct gctgtggctc tgggggccgc tcggtgccct ggcccagggc gccccgcgg      660
ggaccgcgcc gaccgacgac gtggtagact tggagtttta caccaagcgg ccgctccgaa     720
gcgtgagtcc ctcgttcctg tccatcacca tcgacgccag cctggccacc gacccgcgct     780
tcctcacctt cctgggctct ccaaggctcc gtgctctggc tagaggctta tctcctgcat     840
acttgagatt tggcggcaca aagactgact tccttatttt tgatccggac aaggaaccga     900
cttccgaaga aagaagttac tggaaatctc aagtcaacca tgatatttgc aggtctgagc     960
cggtctctgc tgcggtgttg aggaaactcc aggtggaatg gccttccag gagctgttgc     1020
tgctccgaga gcagtaccaa aaggagttca agaacagcac ctactcaaga agctcagtgg    1080
acatgctcta cagttttgcc aagtgctcgg ggttagacct gatctttggt ctaaatgcgt    1140
tactacgaac cccagactta cggtggaaca gctccaacgc ccagcttctc cttgactact    1200
gctcttccaa gggttataac atctcctggg aactgggcaa tgagcccaac agtttctgga    1260
agaaagctca cattctcatc gatgggttgc agttaggaga gactttgtg  gagttgcata    1320
aacttctaca aggtcagct  ttccaaaatg caaaactcta tggtcctgac atcggtcagc    1380
ctcgagggaa gacagttaaa ctgctgagga gtttcctgaa ggctggcgga gaagtgatcg    1440
actctcttac atggcatcac tattacttga atggacgcat cgctaccaaa gaagattttc    1500
tgagctctga tgcgctggac acttttattc tctctgtgca aaaaattctg aaggtcacta    1560
aagagatcac acctggcaag aaggtctggt gggagagac  gagctcagct tacggtggcg    1620
gtgcacccct gctgtccaac acctttgcag ctggctttat gtggctggat aaattgggcc    1680
tgtcagccca gatgggcata gaagtcgtga tgaggcaggt gttcttcgga gcaggcaact    1740
accacttagt ggatgaaaac tttgagcctt acctgattac ctggctctct cttctgttca    1800
agaaactggt aggtcccagg gtgttactgt caagagtgaa aggcccagac aggagcaaac    1860
tccgagtgta tctccactgc actaacgtct atcacccacg atatcaggaa ggagatctaa    1920
ctctgtatgt cctgaacctc cataatgtca ccaagcactt gaaggtaccg cctccgttgt    1980
tcaggaaacc agtggatacg taccttctga agccttcggg gccggatgga ttactttcca    2040
aatctgtcca actgaacggt caaattctga agatggtgga tgagcagacc ctgccagctt    2100
tgacagaaaa acctctcccc gcaggaagtg cactaagcct gctgccttt  tcctatggtt    2160
tttttgtcat aagaaatgcc aaaatcgctg cttgtatatg aaaataaaag gcatacggta    2220
cccctgagac aaaagccgag gggggtgtta ttcataaaac aaaaccctag tttaggaggc    2280
cacctccttg ccgagttcca gagcttcggg agggtggggt acacttcagt attacattca    2340
```

-continued

```
gtgtggtgtt ctctctaaga agaatactgc aggtggtgac agttaatagc actgtg        2396
```

<210> SEQ ID NO 44
<211> LENGTH: 535
<212> TYPE: PRT
<213> ORGANISM: Mus musculus

<400> SEQUENCE: 44

```
Met Leu Arg Leu Leu Leu Trp Leu Trp Gly Pro Leu Gly Ala Leu
1               5                   10                  15

Ala Gln Gly Ala Pro Ala Gly Thr Ala Pro Thr Asp Asp Val Val Asp
                20                  25                  30

Leu Glu Phe Tyr Thr Lys Arg Pro Leu Arg Ser Val Ser Pro Ser Phe
            35                  40                  45

Leu Ser Ile Thr Ile Asp Ala Ser Leu Ala Thr Asp Pro Arg Phe Leu
        50                  55                  60

Thr Phe Leu Gly Ser Pro Arg Leu Arg Ala Leu Ala Arg Gly Leu Ser
65                  70                  75                  80

Pro Ala Tyr Leu Arg Phe Gly Gly Thr Lys Thr Asp Phe Leu Ile Phe
                85                  90                  95

Asp Pro Asp Lys Glu Pro Thr Ser Glu Glu Arg Ser Tyr Trp Lys Ser
            100                 105                 110

Gln Val Asn His Asp Ile Cys Arg Ser Glu Pro Val Ser Ala Ala Val
        115                 120                 125

Leu Arg Lys Leu Gln Val Glu Trp Pro Phe Gln Glu Leu Leu Leu Leu
    130                 135                 140

Arg Glu Gln Tyr Gln Lys Glu Phe Lys Asn Ser Thr Tyr Ser Arg Ser
145                 150                 155                 160

Ser Val Asp Met Leu Tyr Ser Phe Ala Lys Cys Ser Gly Leu Asp Leu
                165                 170                 175

Ile Phe Gly Leu Asn Ala Leu Leu Arg Thr Pro Asp Leu Arg Trp Asn
            180                 185                 190

Ser Ser Asn Ala Gln Leu Leu Leu Asp Tyr Cys Ser Ser Lys Gly Tyr
        195                 200                 205

Asn Ile Ser Trp Glu Leu Gly Asn Glu Pro Asn Ser Phe Trp Lys Lys
    210                 215                 220

Ala His Ile Leu Ile Asp Gly Leu Gln Leu Gly Glu Asp Phe Val Glu
225                 230                 235                 240

Leu His Lys Leu Leu Gln Arg Ser Ala Phe Gln Asn Ala Lys Leu Tyr
                245                 250                 255

Gly Pro Asp Ile Gly Gln Pro Arg Gly Lys Thr Val Lys Leu Leu Arg
            260                 265                 270

Ser Phe Leu Lys Ala Gly Gly Glu Val Ile Asp Ser Leu Thr Trp His
        275                 280                 285

His Tyr Tyr Leu Asn Gly Arg Ile Ala Thr Lys Glu Asp Phe Leu Ser
    290                 295                 300

Ser Asp Ala Leu Asp Thr Phe Ile Leu Ser Val Gln Lys Ile Leu Lys
305                 310                 315                 320

Val Thr Lys Glu Ile Thr Pro Gly Lys Lys Val Trp Leu Gly Glu Thr
                325                 330                 335

Ser Ser Ala Tyr Gly Gly Gly Ala Pro Leu Leu Ser Asn Thr Phe Ala
            340                 345                 350

Ala Gly Phe Met Trp Leu Asp Lys Leu Gly Leu Ser Ala Gln Met Gly
        355                 360                 365
```

```
Ile Glu Val Val Met Arg Gln Val Phe Phe Gly Ala Gly Asn Tyr His
    370                 375                 380
Leu Val Asp Glu Asn Phe Glu Pro Leu Pro Asp Tyr Trp Leu Ser Leu
385                 390                 395                 400
Leu Phe Lys Lys Leu Val Gly Pro Arg Val Leu Leu Ser Arg Val Lys
                405                 410                 415
Gly Pro Asp Arg Ser Lys Leu Arg Val Tyr Leu His Cys Thr Asn Val
                420                 425                 430
Tyr His Pro Arg Tyr Gln Glu Gly Asp Leu Thr Leu Tyr Val Leu Asn
                435                 440                 445
Leu His Asn Val Thr Lys His Leu Lys Val Pro Pro Leu Phe Arg
    450                 455                 460
Lys Pro Val Asp Thr Tyr Leu Leu Lys Pro Ser Gly Pro Asp Gly Leu
465                 470                 475                 480
Leu Ser Lys Ser Val Gln Leu Asn Gly Gln Ile Leu Lys Met Val Asp
                485                 490                 495
Glu Gln Thr Leu Pro Ala Leu Thr Glu Lys Pro Leu Pro Ala Gly Ser
                500                 505                 510
Ala Leu Ser Leu Pro Ala Phe Ser Tyr Gly Phe Phe Val Ile Arg Asn
                515                 520                 525
Ala Lys Ile Ala Ala Cys Ile
                530                 535
```

<210> SEQ ID NO 45
<211> LENGTH: 2396
<212> TYPE: DNA
<213> ORGANISM: Mus musculus
<220> FEATURE:
<221> NAME/KEY: CDS
<222> LOCATION: (594)..(2198)

<400> SEQUENCE: 45

```
tttctagttg cttttagcca atgtcggatc aggttttca agcgacaaag agatactgag      60
atcctgggca gaggacatcc tagctcggtc agatttgggc aggctcaagt gaccagtgtc     120
ttaaggcaga agggagtcgg ggtagggtct ggctgaaccc tcaaccgggg cttttaactc     180
aggtctagt cctggcgcca aatggatggg acctagaaaa ggtgacagag tgcgcaggac      240
accaggaagc tggtcccacc cctgcgcggc tcccgggcgc tccctcccca ggcctccgag     300
gatcttggat tctggccacc tccgcaccct ttggatgggt gtggatgatt tcaaaagtgg     360
acgtgaccgc ggcggagggg aaagccagca cggaaatgaa agagagcgag gaggggaggg     420
cggggagggg agggcgctag ggagggactc ccggagggg tgggagggat ggagcgctgt      480
gggagggtac tgagtcctgg cgccagaggc gaagcaggac cggttgcagg gggcttgagc     540
cagcgcgccg gctgccccag ctctcccggc agcgggcggt ccagccaggt ggg atg        596
                                                              Met
                                                               1 ctg agg ctg ctg ctg ctg tgg ctc tgg ggg ccg ctc ggt gcc ctg gcc      644
Leu Arg Leu Leu Leu Leu Trp Leu Trp Gly Pro Leu Gly Ala Leu Ala
        5                   10                  15 cag ggc gcc ccc gcg ggg acc gcg ccg acc gac gac gtg gta gac ttg      692
Gln Gly Ala Pro Ala Gly Thr Ala Pro Thr Asp Asp Val Val Asp Leu
    20                  25                  30 gag ttt tac acc aag cgg ccg ctc cga agc gtg agt ccc tcg ttc ctg      740
Glu Phe Tyr Thr Lys Arg Pro Leu Arg Ser Val Ser Pro Ser Phe Leu
35                  40                  45 tcc atc acc atc gac gcc agc ctg gcc acc gac ccg cgc ttc ctc acc      788
```

-continued

```
Ser Ile Thr Ile Asp Ala Ser Leu Ala Thr Asp Pro Arg Phe Leu Thr
 50              55                  60                  65 ttc ctg ggc tct cca agg ctc cgt gct ctg gct aga ggc tta tct cct     836
Phe Leu Gly Ser Pro Arg Leu Arg Ala Leu Ala Arg Gly Leu Ser Pro
             70                  75                  80 gca tac ttg aga ttt ggc ggc aca aag act gac ttc ctt att ttt gat     884
Ala Tyr Leu Arg Phe Gly Gly Thr Lys Thr Asp Phe Leu Ile Phe Asp
                 85                  90                  95 ccg gac aag gaa ccg act tcc gaa gaa aga agt tac tgg aaa tct caa     932
Pro Asp Lys Glu Pro Thr Ser Glu Glu Arg Ser Tyr Trp Lys Ser Gln
                100                 105                 110 gtc aac cat gat att tgc agg tct gag ccg gtc tct gct gcg gtg ttg     980
Val Asn His Asp Ile Cys Arg Ser Glu Pro Val Ser Ala Ala Val Leu
115                 120                 125 agg aaa ctc cag gtg gaa tgg ccc ttc cag gag ctg ttg ctg ctc cga    1028
Arg Lys Leu Gln Val Glu Trp Pro Phe Gln Glu Leu Leu Leu Leu Arg
130                 135                 140                 145 gag cag tac caa aag gag ttc aag aac agc acc tac tca aga agc tca    1076
Glu Gln Tyr Gln Lys Glu Phe Lys Asn Ser Thr Tyr Ser Arg Ser Ser
                150                 155                 160 gtg gac atg ctc tac agt ttt gcc aag tgc tcg ggg tta gac ctg atc    1124
Val Asp Met Leu Tyr Ser Phe Ala Lys Cys Ser Gly Leu Asp Leu Ile
                165                 170                 175 ttt ggt cta aat gcg tta cta cga acc cca gac tta cgg tgg aac agc    1172
Phe Gly Leu Asn Ala Leu Leu Arg Thr Pro Asp Leu Arg Trp Asn Ser
            180                 185                 190 tcc aac gcc cag ctt ctc ctt gac tac tgc tct tcc aag ggt tat aac    1220
Ser Asn Ala Gln Leu Leu Leu Asp Tyr Cys Ser Ser Lys Gly Tyr Asn
        195                 200                 205 atc tcc tgg gaa ctg ggc aat gag ccc aac agt ttc tgg aag aaa gct    1268
Ile Ser Trp Glu Leu Gly Asn Glu Pro Asn Ser Phe Trp Lys Lys Ala
210                 215                 220                 225 cac att ctc atc gat ggg ttg cag tta gga gaa gac ttt gtg gag ttg    1316
His Ile Leu Ile Asp Gly Leu Gln Leu Gly Glu Asp Phe Val Glu Leu
                230                 235                 240 cat aaa ctt cta caa agg tca gct ttc caa aat gca aaa ctc tat ggt    1364
His Lys Leu Leu Gln Arg Ser Ala Phe Gln Asn Ala Lys Leu Tyr Gly
                245                 250                 255 cct gac atc ggt cag cct cga ggg aag aca gtt aaa ctg ctg agg agt    1412
Pro Asp Ile Gly Gln Pro Arg Gly Lys Thr Val Lys Leu Leu Arg Ser
            260                 265                 270 ttc ctg aag gct ggc gga gaa gtg atc gac tct ctt aca tgg cat cac    1460
Phe Leu Lys Ala Gly Gly Glu Val Ile Asp Ser Leu Thr Trp His His
        275                 280                 285 tat tac ttg aat gga cgc atc gct acc aaa gaa gat ttt ctg agc tct    1508
Tyr Tyr Leu Asn Gly Arg Ile Ala Thr Lys Glu Asp Phe Leu Ser Ser
290                 295                 300                 305 gat gcg ctg gac act ttt att ctc tct gtg caa aaa att ctg aag gtc    1556
Asp Ala Leu Asp Thr Phe Ile Leu Ser Val Gln Lys Ile Leu Lys Val
                310                 315                 320 act aaa gag atc aca cct ggc aag aag gtc tgg ttg gga gag acg agc    1604
Thr Lys Glu Ile Thr Pro Gly Lys Lys Val Trp Leu Gly Glu Thr Ser
                325                 330                 335 tca gct tac ggt ggc ggt gca ccc ttg ctg tcc aac acc ttt gca gct    1652
Ser Ala Tyr Gly Gly Gly Ala Pro Leu Leu Ser Asn Thr Phe Ala Ala
            340                 345                 350 ggc ttt atg tgg ctg gat aaa ttg ggc ctg tca gcc cag atg ggc ata    1700
Gly Phe Met Trp Leu Asp Lys Leu Gly Leu Ser Ala Gln Met Gly Ile
        355                 360                 365
```

-continued

```
gaa gtc gtg atg agg cag gtg ttc ttc gga gca ggc aac tac cac tta      1748
Glu Val Val Met Arg Gln Val Phe Phe Gly Ala Gly Asn Tyr His Leu
370                 375                 380                 385 gtg gat gaa aac ttt gag cct tta cct gat tac tgg ctc tct ctt ctg      1796
Val Asp Glu Asn Phe Glu Pro Leu Pro Asp Tyr Trp Leu Ser Leu Leu
                390                 395                 400 ttc aag aaa ctg gta ggt ccc agg gtg tta ctg tca aga gtg aaa ggc      1844
Phe Lys Lys Leu Val Gly Pro Arg Val Leu Leu Ser Arg Val Lys Gly
            405                 410                 415 cca gac agg agc aaa ctc cga gtg tat ctc cac tgc act aac gtc tat      1892
Pro Asp Arg Ser Lys Leu Arg Val Tyr Leu His Cys Thr Asn Val Tyr
        420                 425                 430 cac cca cga tat cag gaa gga gat cta act ctg tat gtc ctg aac ctc      1940
His Pro Arg Tyr Gln Glu Gly Asp Leu Thr Leu Tyr Val Leu Asn Leu
    435                 440                 445 cat aat gtc acc aag cac ttg aag gta ccg cct ccg ttg ttc agg aaa      1988
His Asn Val Thr Lys His Leu Lys Val Pro Pro Pro Leu Phe Arg Lys
450                 455                 460                 465 cca gtg gat acg tac ctt ctg aag cct tcg ggg ccg gat gga tta ctt      2036
Pro Val Asp Thr Tyr Leu Leu Lys Pro Ser Gly Pro Asp Gly Leu Leu
                470                 475                 480 tcc aaa tct gtc caa ctg aac ggt caa att ctg aag atg gtg gat gag      2084
Ser Lys Ser Val Gln Leu Asn Gly Gln Ile Leu Lys Met Val Asp Glu
            485                 490                 495 cag acc ctg cca gct ttg aca gaa aaa cct ctc ccc gca gga agt gca      2132
Gln Thr Leu Pro Ala Leu Thr Glu Lys Pro Leu Pro Ala Gly Ser Ala
        500                 505                 510 cta agc ctg cct gcc ttt tcc tat ggt ttt ttt gtc ata aga aat gcc      2180
Leu Ser Leu Pro Ala Phe Ser Tyr Gly Phe Phe Val Ile Arg Asn Ala
    515                 520                 525 aaa atc gct gct tgt ata tgaaaataaa aggcatacgg taccoctgag             2228
Lys Ile Ala Ala Cys Ile
530                 535 acaaaagccg aggggggtgt tattcataaa acaaaccct agtttaggag gccacctcct     2288
tgccgagttc cagagcttcg ggagggtggg gtacacttca gtattacatt cagtgtggtg    2348
ttctctctaa gaagaatact gcaggtggtg acagttaata gcactgtg                 2396
```

<210> SEQ ID NO 46
<211> LENGTH: 385
<212> TYPE: DNA
<213> ORGANISM: Rattus norvegicus

<400> SEQUENCE: 46

```
cggccgctgc tgctgctgtg gctctggggg cggctccgtg ccctgaccca aggcactccg      60
gcggggaccg cgccgaccaa agacgtggtg gacttggagt tttacaccaa gaggctattc     120
caaagcgtga gtccctcgtt cctgtccatc accatcgacg ccagtctggc caccgacccct    180 cggttcctca ccttcctgag ctctccacgg cttcgagccc tgtctagagg cttatctcct     240
gcgtacttga gatttggcgg caccaagact gacttcctta tttttgatcc caacaacgaa     300
cccacctctg aagaagaag ttactggcaa tctcaagaca acaatgatat ttgcgggtct      360
gaccgggtct ccgctgacgt gttga                                           385
```

<210> SEQ ID NO 47
<211> LENGTH: 541
<212> TYPE: DNA
<213> ORGANISM: Rattus norvegicus
<220> FEATURE:
<221> NAME/KEY: misc_feature -continued

```
<222> LOCATION: (507)..()
<223> OTHER INFORMATION: any nucleotide

<400> SEQUENCE: 47
aaatcaggac atatccttca cttatttgcc tcttggtcat attggaggca tttgtattca        60
tttttaataa ccctcaaaat agtgcatgca aagtgctaag cgtcatttgc cacatggtgc       120
cattaactgt caccacctgc agtggtctac ttagagaaca ccgcactgga tgttaacact       180
gaagcgcgtg ccccgccctc ccgaggctct ggatccagcg ttgaagcttg ccccgccctc       240
ccgaggctct ggatccagca ctggagcatg ccccgccctc ccgaggctct ggagcttgct       300
aaggagtccg ctccctaccg ctggggtttt gctttattct tatgaatgac acccctgacc       360
gctttcgtct caggggtact gtaatgcctt ttattttcat atacaagctg cgattttggc       420
atttcttatg acaaaaaacc cataggaaaa ggcgggcacg cttagtgagc ttcctgcggg       480
gagaggtttt tctgttagag ctggcanggt ctgctcatcg accatcttca ggcctcgtgc       540
c                                                                      541
```